US011832953B1

(12) United States Patent
Shanechi et al.

(10) Patent No.: US 11,832,953 B1
(45) Date of Patent: Dec. 5, 2023

(54) PREFERENTIAL SYSTEM IDENTIFICATION (PSID) FOR JOINT DYNAMIC MODELING OF SIGNALS WITH DISSOCIATION AND PRIORITIZATION OF THEIR SHARED DYNAMICS, WITH APPLICABILITY TO MODELING BRAIN AND BEHAVIOR DATA

(71) Applicant: UNIVERSITY OF SOUTHERN CALIFORNIA, Los Angeles, CA (US)

(72) Inventors: Maryam M. Shanechi, Los Angeles, CA (US); Omid Ghasem Sani, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 245 days.

(21) Appl. No.: 17/069,510

(22) Filed: Oct. 13, 2020

Related U.S. Application Data

(60) Provisional application No. 63/070,752, filed on Aug. 26, 2020, provisional application No. 62/914,666, filed on Oct. 14, 2019.

(51) Int. Cl.
*A61B 5/00* (2006.01)
(52) U.S. Cl.
CPC ............ *A61B 5/4064* (2013.01); *A61B 5/725* (2013.01); *A61B 5/7264* (2013.01); *A61B 5/7275* (2013.01)
(58) Field of Classification Search
CPC ..... A61B 5/4064; A61B 5/725; A61B 5/7264; A61B 5/7275
See application file for complete search history.

(56) References Cited

U.S. PATENT DOCUMENTS

| 10,365,340 | B1* | 7/2019 | Lou | G01R 33/4806 |
|---|---|---|---|---|
| 2014/0316217 | A1* | 10/2014 | Purdon | A61B 5/7275 600/300 |
| 2016/0242690 | A1* | 8/2016 | Principe | A61B 5/316 |
| 2018/0192936 | A1* | 7/2018 | Widge | G16H 50/20 |
| 2021/0065066 | A1* | 3/2021 | Xue | G06F 17/16 |
| 2022/0237454 | A1* | 7/2022 | Jain | G06N 3/082 |

OTHER PUBLICATIONS

Vrhel, "Rapid Computation of the Continuous Wavelet transform by Oblique Projection", (Apr. 1997), IEEE, vol. 45 Issue 4, pp. 891-900 (Year: 1997).*

* cited by examiner

*Primary Examiner* — Linda C Dvorak
*Assistant Examiner* — Abigail Bock
(74) *Attorney, Agent, or Firm* — Snell & Wilmer LLP

(57) ABSTRACT

A method for preferential system identification (PSID) for modeling neural dynamics of a brain includes extracting behaviorally relevant latent brain states via a projection of future behavior onto past neural activity. The method further includes identifying, based on the extracted latent brain states, model parameters for a linear state space dynamic model of neural activity. An extension of PSID includes accounting for an effect of external inputs to the brain by using oblique projections along the external inputs instead of orthogonal projections. PSID may be extended to apply to any primary signals and secondary signals in place of the neural activity and the behavior. In some embodiments, the extracting and the identifying may be performed using a numerical optimization of recurrent neural networks (RNN) instead of the projection.

22 Claims, 51 Drawing Sheets

PREFERENTIAL SYSTEM IDENTIFICATION (PSID) FOR JOINT DYNAMIC MODELING OF SIGNALS WITH DISSOCIATION AND PRIORITIZATION OF THEIR SHARED DYNAMICS, WITH APPLICABILITY TO MODELING BRAIN AND BEHAVIOR DATA

CROSS-REFERENCE TO RELATED APPLICATIONS

This application claims the benefit and priority of U.S. Provisional Application No. 62/914,666, entitled "MODELING BEHAVIORALLY RELEVANT NEURAL DYNAMICS ENABLED BY A NOVEL PREFERENTIAL SUBSPACE IDENTIFICATION (PSID) PROCESS," filed on Oct. 14, 2019, and U.S. Provisional Application No. 63/070,752, entitled "MODELING BEHAVIORALLY RELEVANT NEURAL DYNAMICS ENABLED BY PREFERENTIAL SUBSPACE IDENTIFICATION," filed on Aug. 26, 2020, the entire disclosures of both being hereby incorporated by reference in their entirety.

STATEMENT AS TO FEDERALLY SPONSORED RESEARCH

This invention was made with government support under contract number W911NF-16-1-0368 awarded by the Army Research Office. The government has certain rights in this invention.

BACKGROUND

1. Field

The present disclosure relates to systems and methods for joint dynamic modeling of signals simultaneous with dissociation and prioritization of their shared dynamics enabled by preferential system identification (PSID), and its application to modeling behaviorally relevant neural dynamics.

2. Description of the Related Art

Modeling of how behavior is encoded in the dynamics of neural activity over time is a central challenge in neuroscience. Scientists refer to the dynamics of neural activity regardless of the signal type—whether neural population spiking activity or local field potentials (LFP)—as neural dynamics. Modeling neural dynamics is essential for investigating or decoding behaviorally measurable brain functions such as movement planning, initiation and execution, speech and language, mood, decision making, as well as neurological dysfunctions such as movement tremor. However, building such models is challenging for two main reasons. First, in addition to the specific behavior being measured and studied (hereon referred to simply as "behavior"), the dynamics in recorded neural activity also encode other brain functions, inputs from other neurons, as well as internal states with brain-wide representations such as thirst. If these other dynamics do not influence the behavior of interest for the duration of neural recordings, they would constitute behaviorally irrelevant neural dynamics. Second, many natural behaviors such as movements or speech are temporally structured. Thus, understanding their neural representation is best achieved by learning a dynamic model, which explicitly characterizes the temporal evolution of neural population activity. Given these two challenges, answering increasingly sought-after and fundamental questions about neural dynamics such as their dimensionality and important temporal features such as rotations requires a novel dynamic modeling framework that can prioritize extracting those neural dynamics that are related to a specific behavior of interest. This would ensure that behaviorally relevant neural dynamics are not masked or confounded by behaviorally irrelevant ones and will broadly impact the study of diverse brain functions. Developing such a dynamic modeling framework has remained elusive to date.

Thus, there is a need in the art for developing a dynamic modeling framework for modeling neural dynamics while dissociating and prioritizing those dynamics relevant to another signal, for example behavioral measurements.

SUMMARY

Described herein is a method for preferential system identification (PSID) for modeling neural dynamics of a brain. The method includes extracting behaviorally relevant latent brain states via a projection of future behavior onto past neural activity. The method further includes identifying, based on the extracted latent brain states, model parameters for a linear state space dynamic model of neural activity.

Also described is a method for preferential system identification (PSID) for modeling neural dynamics of a brain. The method includes extracting behaviorally relevant latent brain states. The method further includes identifying, based on the extracted latent brain states, model parameters for a state space dynamic model of neural activity. In this method, the extracting and the identifying are performed using a numerical optimization of recurrent neural networks (RNN).

Also described is a method for preferential system identification (PSID) for modeling neural dynamics of a brain in presence of external inputs to the brain. The method includes extracting behaviorally relevant latent brain states via a non-orthogonal projection of future behavior onto the past neural activity data along the external input data. The method further includes identifying, based on the extracted latent brain states, model parameters for a linear state space dynamic model of neural activity.

Also described is a system for preferential system identification (PSID) for modeling neural dynamics of a brain. The system includes an input device configured to detect or receive past neural activity data. The system further includes a machine learning processor coupled to the input device. The machine learning processor is designed to extract behaviorally relevant latent brain states via a projection of future behavior onto the past neural activity data. The machine learning processor is further designed to identify, based on the extracted latent brain states, model parameters for a linear state space dynamic model of neural activity.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Figure 4:
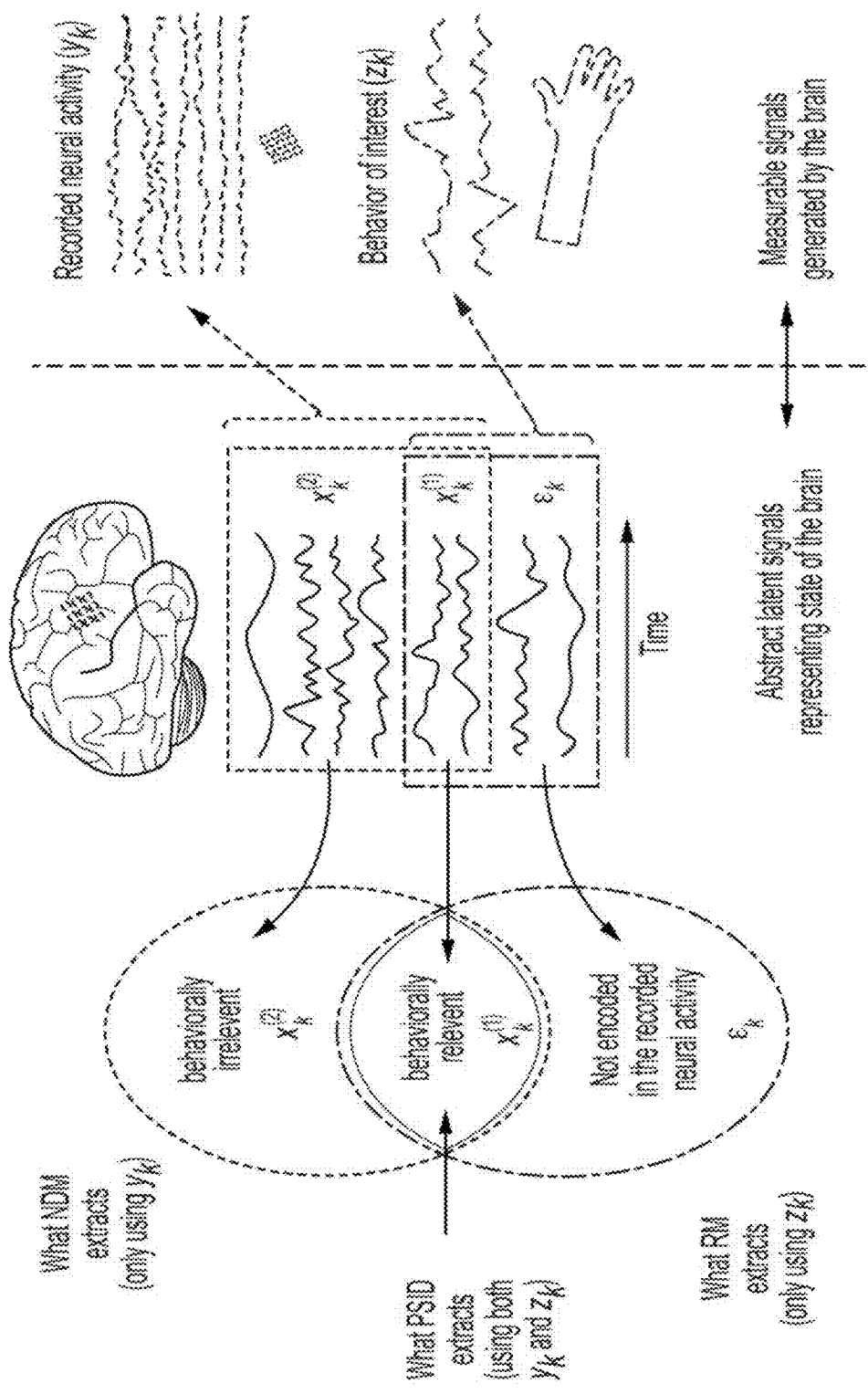
FIG. 4 is a drawing illustrating an outline for PSID according to an embodiment of the present invention.
Figure 4:
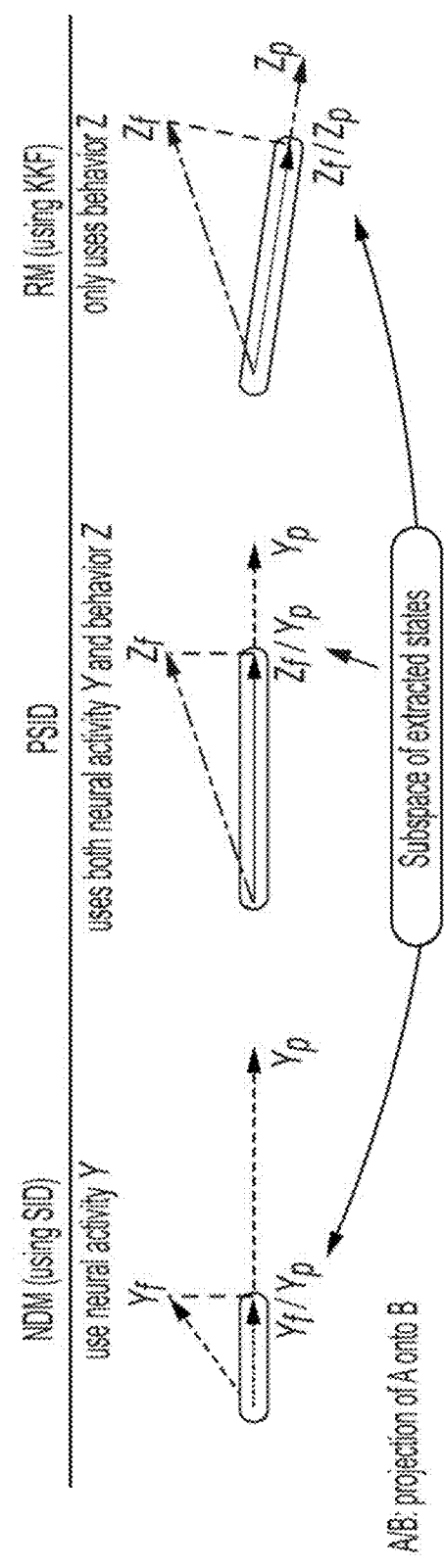
Figure 4:
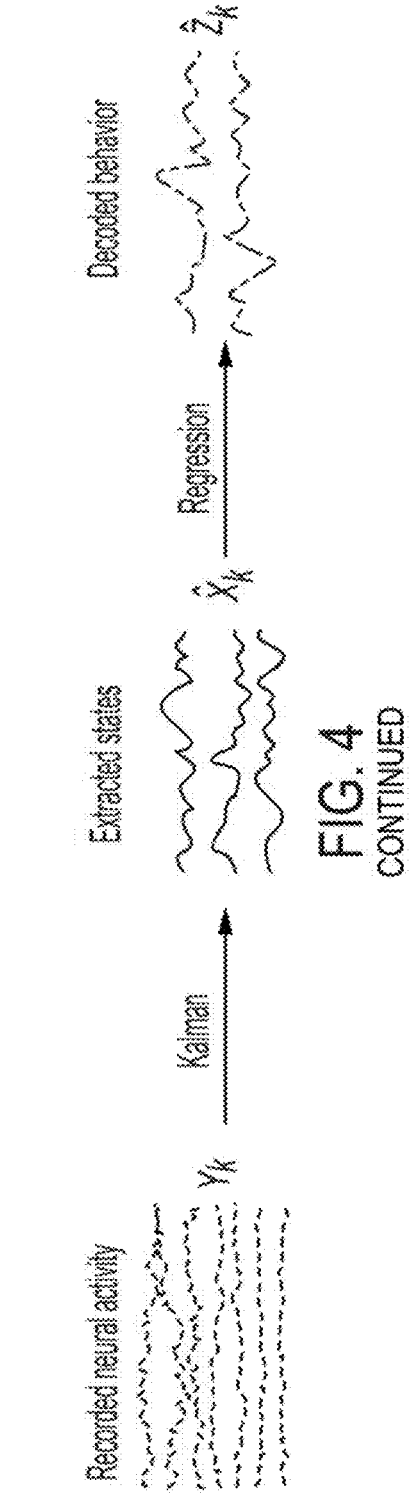

Currently, dynamic modeling of neural activity, regardless of the signal type, is largely performed according to two alternative conceptual frameworks. In both frameworks, a state-space model formulation is used but these frameworks differ in which elements within the brain state—a latent signal describing the overall state of the brain—they can learn and model as their state. In the first framework, often termed representational modeling (RM), behavioral measurements such as movement kinematics, mood, decision choices or tremor intensity at each time are assumed to be directly represented in the neural activity at that time. By making this assumption, RM implicitly assumes that the dynamics of neural activity are the same as those in the behavior of interest; the RM framework thus takes behavior as the state in the model and learns its dynamics without considering the neural activity (as shown in FIG. 4, a, and discussed below). This assumption, however, may not hold since neural activity in many cortical regions, including the prefrontal, motor and visual cortices and other brain structures such as amygdala, often contains components that are responsive to different behavioral and task parameters and thus is not fully explained by the RM framework. Motivated by this complex neural response, a second framework known as neural dynamic modeling (NDM) has received growing attention and has led to recent findings for example about movement generation and mood. In NDM, the dynamics of neural activity are modeled in terms of a latent variable that constitutes the state in the model and is learned purely using the recorded neural activity and agnostic to the behavior (shown in FIG. 4, a). When modeling the relationship between neural dynamics and behavioral measurements such as movement kinematics or mood variations is of interest, a second step is needed to relate the already learned latent state to the behavior. Because NDM does not use behavior to guide the learning of neural dynamics, it may miss or less accurately learn some of the behaviorally relevant neural dynamics, which are masked or confounded by behaviorally irrelevant ones. Uncovering behaviorally relevant neural dynamics requires a new modeling framework to directly learn the dynamics that are shared between the recorded neural activity and behavior of interest, rather than learning the prominent dynamics present in one or the other as done by current dynamic models (shown in FIG. 4, a).

The inventors have developed a novel general modeling and learning algorithm, termed preferential system identification (PSID), for extracting and modeling shared dynamics between signal sources which can for example be generated from dynamical systems or the like. The signals each can be multi-dimensional or high-dimensional. One signal source can be considered primary and one can be considered secondary. When the signal sources are taken to be the neural activity and the behavior measurement, respectively, PSID extracts and models behaviorally relevant dynamics in high-dimensional neural activity. In this case the primary signal is neural activity and the secondary signal is behavior as detailed below. The inventors thus describe the invention in the context of this example to model behaviorally relevant neural dynamics but the invention can be applied to any signal sources. The mathematical derivation of PSID and numerical simulations illustrated in the Figures herewith do not depend on the nature of the two signals. For example, PSID could be applied to neural signals from two brain areas, in which case it will prioritize and dissociate their shared dynamics from those that are exclusive to one area. The signals in PSID could even be from different sources. For example, when studying interpersonal neural and behavioral synchrony and social behavior, applying PSID to neural and/or behavioral signals that are synchronously recorded from different individuals may enable extraction and modeling of common dynamics between them. In general, when signals acquired from different systems are suspected to have shared dynamics (e.g. because they may be driven by common dynamic inputs), PSID can be used to extract and model the shared dynamics.

PSID uses both neural activity and behavior together to learn (i.e. identify) a dynamic model that describes neural activity in terms of latent states while prioritizing the extraction and characterization of behaviorally relevant neural dynamics. A key insight of PSID is to identify the subspace shared between neural activity and behavior through a projection, and then extract the latent states within this subspace and model their temporal structure and dynamics (all described below in more detail). For this reason, the PSID algorithm in this projection implementation can also be referred to as "preferential subspace identification", which has the same acronym (i.e. PSID) as the alternative name for "preferential system identification".

The disclosure first shows with extensive numerical simulations that PSID learns the behaviorally relevant neural dynamics with greater accuracy, with markedly lower-dimensional latent states, and with orders of magnitude fewer training samples compared with conventional methods. The disclosure demonstrates the new functionalities that PSID enables by applying it to existing datasets consisting of multi-regional motor and premotor cortical activity recorded in two non-human primates (NHP) performing a rich 3D reach, grasp, and return task to diverse locations. PSID uniquely uncovers several new features of neural dynamics underlying motor behavior. First, PSID reveals that the dimension of behaviorally relevant neural dynamics is markedly lower than what standard methods conclude, and learns these dynamics more accurately. Second, while both NDM and PSID find rotational neural dynamics during the 3D task, PSID uncovers rotations that are in the opposite directions in reach vs. return epochs and are significantly more predictive of behavior compared with NDM, which in contrast finds rotations in the same direction. Third, compared with NDM and RM, PSID more accurately learns behaviorally relevant neural dynamics for almost all of the 27 arm and finger joint angles, for 3D end-point kinematics, and for almost all individual channels across the multi-regional recordings. Finally, the disclosure applies PSID to existing datasets consisting of raw local field potentials (LFP) prefrontal activity during a different saccadic eye movement task to demonstrate that PSID generalizes to other behavioral tasks, brain regions and neural signal types.

Figure 1:
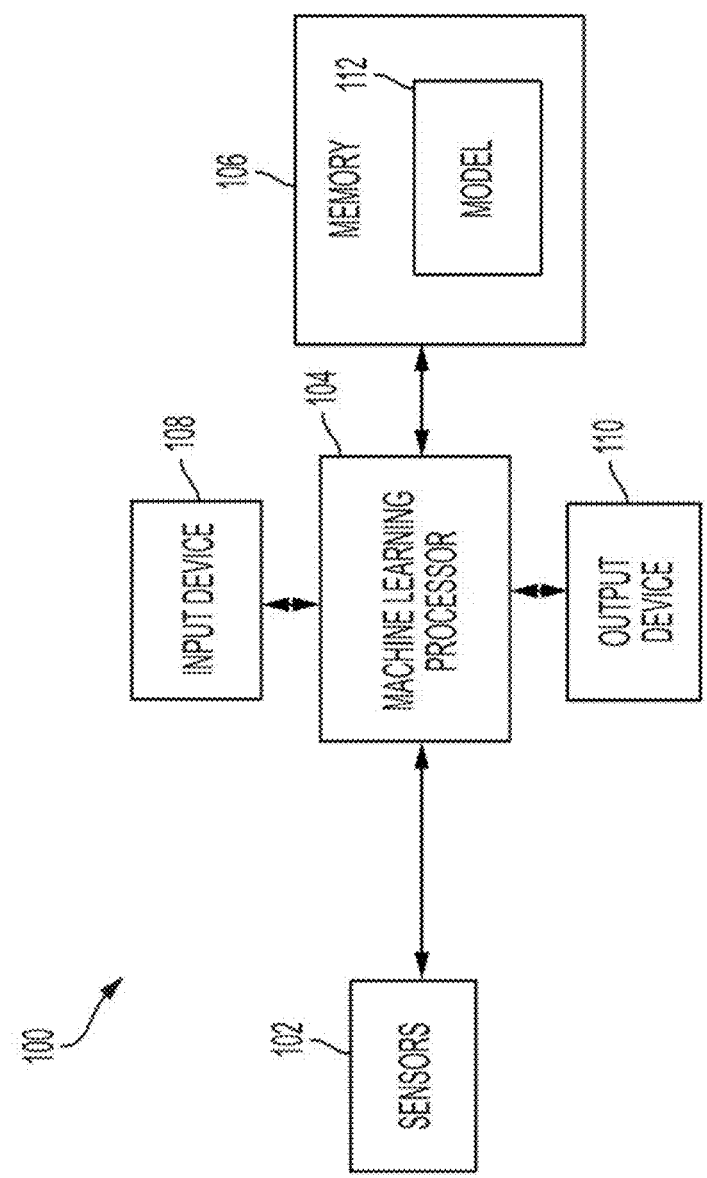
FIG. 1 is a block diagram illustrating a system for creating a model of neural activity using preferential system identification (PSID) according to an embodiment of the present invention.

Referring now to FIG. 1, a system 100 for creating a model 112 of neural response to stimulation is shown. The system 100 may include one or more sensor 102, a machine learning processor 104, a non-transitory memory 106, an input device 108, and an output device 110. The one or more sensor 102 may include any sensors such as sensors capable of detecting electrical brain wave data. In that regard, the sensor 102 may be directly or indirectly coupled to a brain and may detect data corresponding to electrical activity of the brain.

The machine learning processor 104 may include one or more processors or controllers, which may be specifically designed for functions related to PSID. For example, the machine learning processor 104 may include an application specific integrated circuit (ASIC), a digital signal processor (DSP), a general-purpose processor, a field programmable gate array (FPGA), or the like. The machine learning processor 104 may perform logic functions based on instructions, such as instructions stored in the memory 106. The machine learning processor 104 may perform various functions. In some embodiments, each function may be performed by a separate and dedicated piece of hardware. In some embodiments, each function may be performed by a single multifunction piece of hardware.

The memory 106 may include any non-transitory memory capable of storing data usable by the machine learning processor 104. For example, the memory 106 may store instructions usable by the processor to perform functions. As another example, the memory 106 may store data as instructed by the machine learning processor 104. The memory 106 may further store the model 112.

The input device 108 may include any input device such as a mouse, keyboard, button, a touchscreen, or the like. In some embodiments, the input device 108 may include a data port capable of receiving data from a separate device (e.g., a universal serial bus (USB) port, a Wi-Fi port, a Bluetooth port, an Ethernet port, or the like).

The output device 110 may include any output device such as a speaker, a display, a touchscreen, or the like. In some embodiments, the output device 110 may include a data port capable of transmitting data to a separate device.

The machine learning processor 104 may receive signals from the sensors 102 (or previously recorded signals from the input device 108). The signals may include past neural activity related to a brain. The machine learning processor 104 may perform processing functions on the received signals. For example, the machine learning processor 104 may extract behaviorally relevant latent brain states via a projection of future behavior onto past neural activity, and may identify model parameters for a linear state space dynamic model (i.e., the model 112) of neural activity. The machine learning processor 104 may perform additional functions as described throughout the present disclosure.

The output device 110 may output data, such as data related to the model 112 or data the machine learning processor 104 provides. For example, the output device 110 may output the model parameters determined by the machine learning processor 104.

Figure 2:
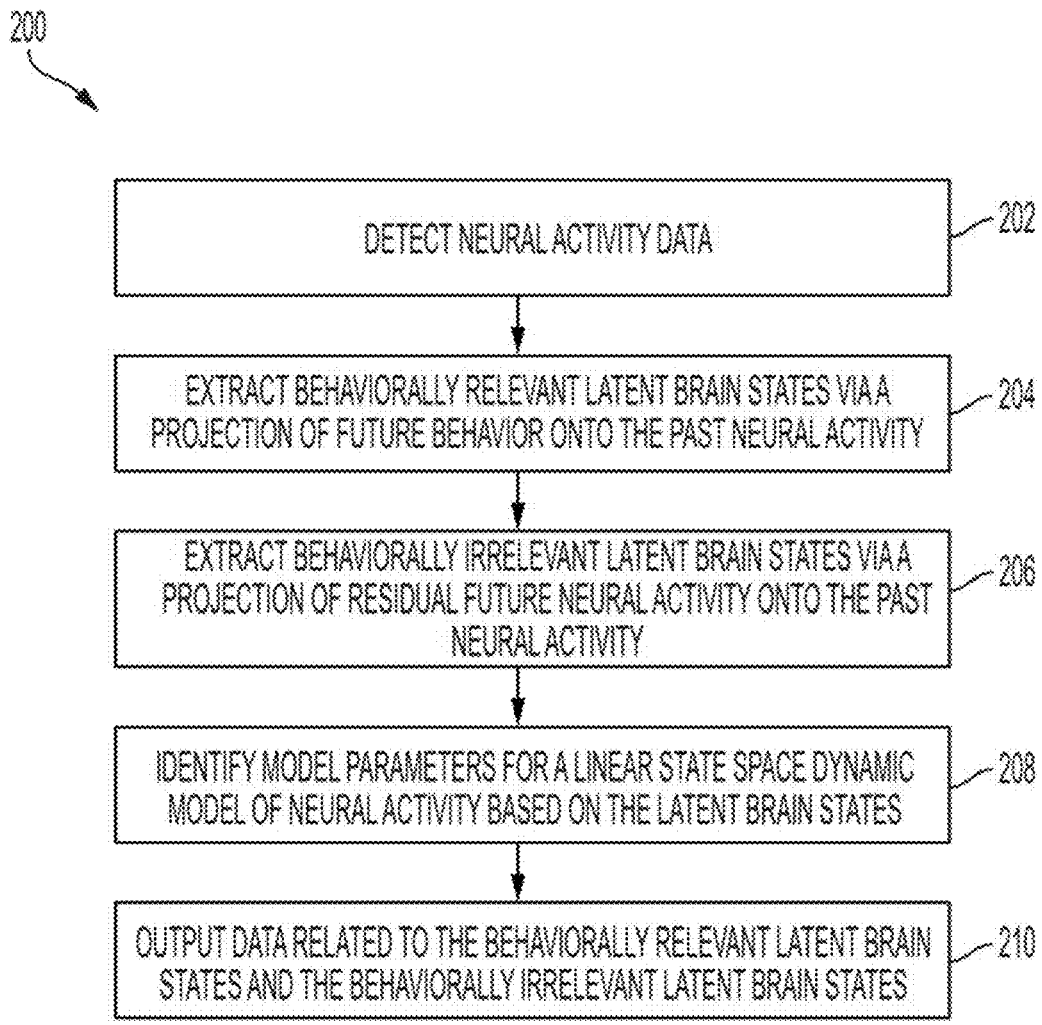
FIG. 2 is a flowchart illustrating a method for PSID for modeling neural dynamics of a brain according to an embodiment of the present invention.

Referring now to FIG. 2, a method 200 for PSID for modeling neural dynamics of a brain is shown. The method 200 may be performed by a system similar to the system 100 of FIG. 1. The various blocks may be performed by components similar to the components of the system 100 of FIG. 1. In block 202, one or more sensor may detect neural activity data. In some embodiments, the system may further receive related data such as behavior or any measured external input to the brain associated with the neural activity data. In some embodiments, the data may be provided via an input device (e.g., via a universal serial bus (USB) key or other electronic input device) rather than via sensors.

In block 204, a machine learning processor may extract behaviorally relevant latent brain states via a projection of future behavior onto the past neural activity.

In block 206, the machine learning processor may also extract behaviorally irrelevant latent brain states via a projection of residual future neural activity onto the past neural activity.

In block 208, the machine learning processor may identify model parameters for a linear state space dynamic model of the neural activity based on the extracted latent brain states.

In block 210, an output device may output data related to the behaviorally relevant latent brain states, the behaviorally irrelevant latent brain states, and the dynamic model.

Figure 3:
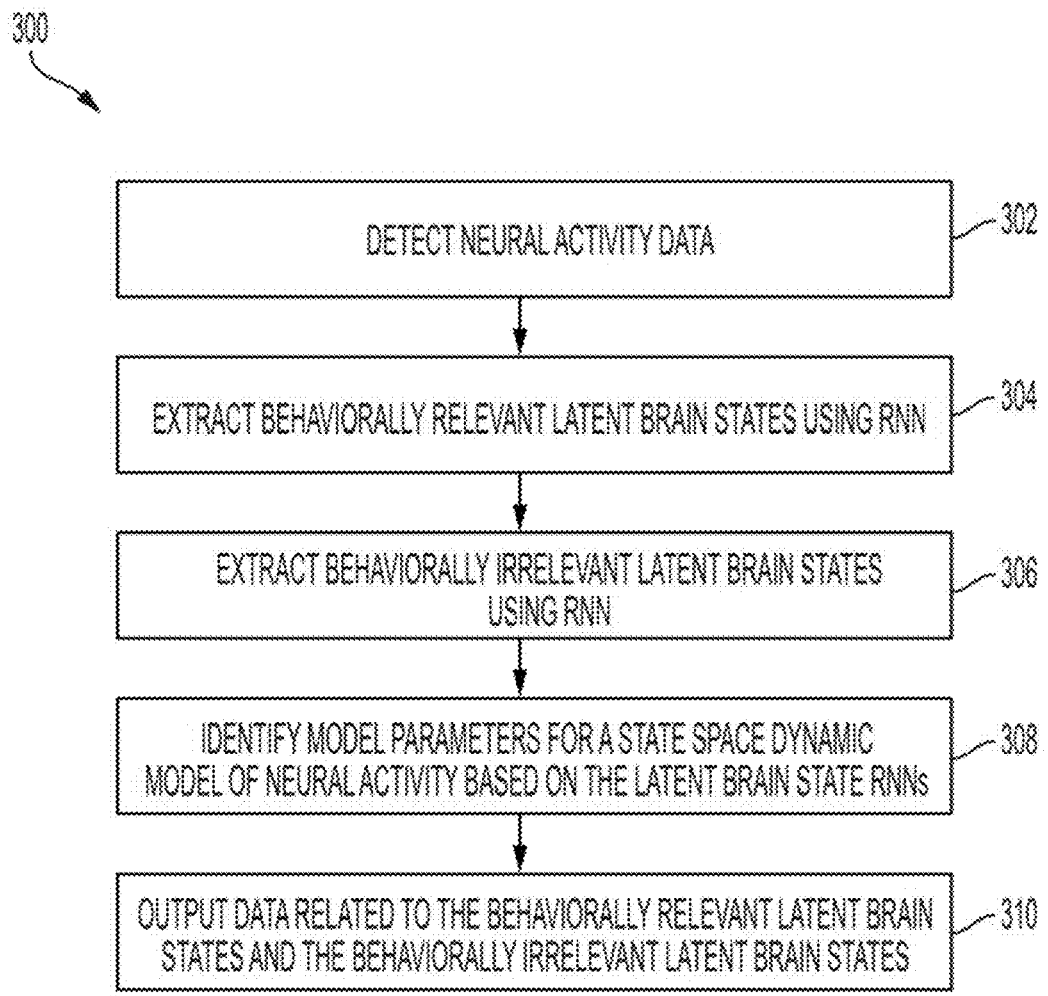
FIG. 3 is a flowchart illustrating a method for PSID for modeling neural dynamics of a brain using a recurrent neural network (RNN) according to an embodiment of the present invention.

Referring now to FIG. 3, another method 300 for PSID for modeling neural dynamics of a brain is shown. The method 300 may be performed by a system similar to the system 100 of FIG. 1. The various blocks may be performed by components similar to the components of the system 100 of FIG. 1. The method 300 may begin in block 302 where neural activity data is detected or received.

In block 304, a machine learning processor may extract behaviorally relevant latent brain states using a recurrent neural network (RNN). In block 306, the machine learning processor may extract behaviorally irrelevant latent brain states using a recurrent neural network (RNN).

In block 308, the machine learning processor may identify model parameters for a state space dynamic model of neural activity based on the latent brain state recurrent neural networks (RNNs).

In block 310, an output device may output data relevant to the behaviorally relevant latent brain states, the behaviorally irrelevant latent brain states, and the dynamic model.

Figure 11:
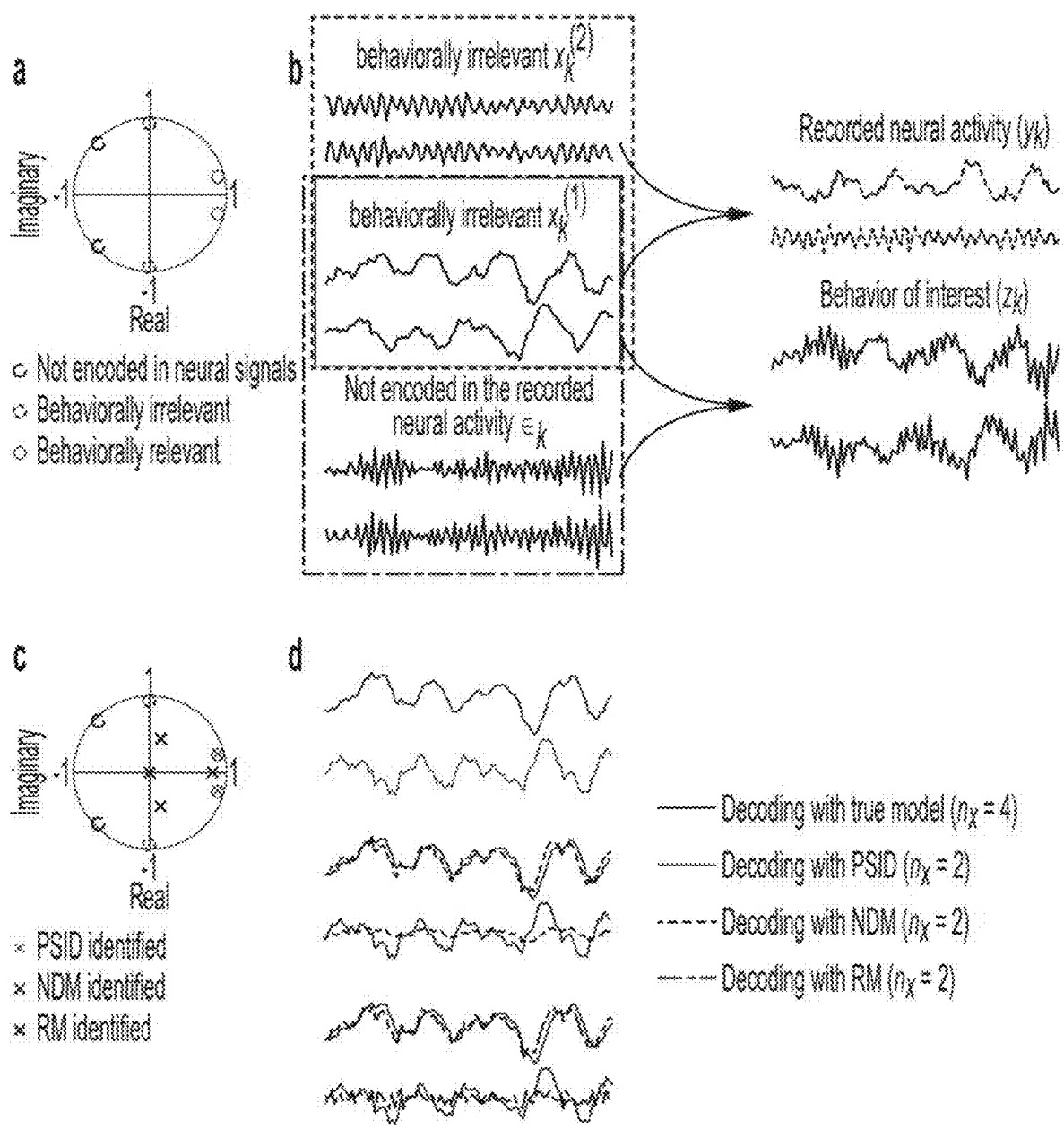
FIG. 11 illustrates an example numerical simulation that shows how brain states may be related to behavior, neural activity or both and which states are identified by PSID, neural dynamic modeling (NDM), and representational modeling (RM) according to an embodiment of the present invention.

Turning now to FIG. 4, an outline of PSID is shown. FIG. 4, a, illustrates a schematic view of how a state of a brain can be thought of as a high-dimensional time varying variable of which some dimensions ($x_k^{(1)}$ and $x_k^{(2)}$) drive the recorded neural activity ($y_k$), some dimensions ($x_k^{(1)}$ and $\epsilon_k$) drive the measured behavior ($z_k$), and some dimensions ($x_k^{(1)}$) drive both and are thus shared between them (a numerical simulation is shown in FIG. 11). The choice of the learning method affects which elements of the brain states can be extracted from neural activity. NDM extracts states regardless of their relevance to behavior and RM extracts states regardless of their relevance to recorded neural activity. PSID enables extraction of states that are related to both the recorded neural activity and a specific behavior.

FIG. 4, b, illustrates schematics of how PSID achieves its goal in learning the dynamic model (also see FIG. 10) in comparison with a representative NDM method (i.e. SID) and an RM method (i.e. kinematic-state Kalman filter (KKF)). A/B denotes projecting A onto B (discussed in more detail below). The key idea in PSID is to project future behavior $z_k$ (denoted by $Z_f$) onto past neural activity $y_k$ (denoted by $Y_p$). This is unlike NDM using SID, which instead projects future neural activity (denoted by $Y_f$) onto the past neural activity $Y_p$. It is also unlike RM using KKF, which projects future behavior onto past behavior (denoted by $Z_p$).

FIG. 4, c, illustrates that for all three methods, after the model parameters are learned, the procedures for state extraction and neural decoding of behavior may be similar. A Kalman filter operating on the neural activity alone may extract the states, and behavior may be decoded by applying a linear regression to these extracted states (discussed in more detail below).

A summary of PSID will now be provided. The inventors considered the state of the brain at each point in time as a high-dimensional latent variable of which some dimensions may drive the recorded neural activity, some may drive the observed behavior, and some may drive both (FIG. 4, a, FIG. 11). The present disclosure thus models the recorded neural activity ($y_k \in \mathbb{R}^{n_y}$) and behavior ($z_k \in \mathbb{R}^{n_z}$) using the following general dynamic linear state-space model (SSM) formulation:

$$\begin{cases} x_{k+1} = A x_k + w_k \\ y_k = C_y x_k + v_k, \quad x_k = \begin{bmatrix} x_k^{(1)} \\ x_k^{(2)} \end{bmatrix} \\ z_k = C_z x_k + \epsilon_k \end{cases} \quad \text{Equation 1}$$

In Equation 1, $x_k \in \mathbb{R}^{n_x}$ is the latent state that drives the recorded neural activity, and $x_k^{(1)} \in \mathbb{R}^{n_1}$ and $x_k^{(2)} \in \mathbb{R}^{n_2}$ (with $n_2 = n_x - n_1$) are its behaviorally relevant and behaviorally irrelevant components, respectively. To illustrate the idea, this model structure is depicted to include both $x_k^{(1)}$ and $x_k^{(2)}$; but PSID has a novel two-stage identification approach that allows it to learn $x_k^{(1)}$ directly from training data in its first stage without the need to also learn $x_k^{(2)}$ until an optional second stage (Table 1, FIG. 10). This allows PSID to prioritize learning of behaviorally relevant dynamics, which is key in learning these dynamics more accurately and with very low-dimensional states (i.e. only $x_k^{(1)}$). Finally, $\epsilon_k$ represents the behavior dynamics that are not present in the recorded neural activity, and $w_k$ and $v_k$ are noises. A, $C_y$, $C_z$, and noise statistics are model parameters to be learned using PSID given training samples from neural activity and behavior. PSID therefore provides a general mathematical framework whose special cases also include standard NDM (if states are not dissociated to $x_k^{(1)}$ and $x_k^{(2)}$, Methods) and RM (if $C_z$ is identity and $\epsilon_k = 0$).

The goal of PSID is to model how neural activity evolves in time while prioritizing the behaviorally relevant neural dynamics, which are the ones driven by the behaviorally relevant latent states (i.e. $x_k^{(1)}$). The key idea for achieving this goal is that the behaviorally relevant latent states lie in the intersection of the space spanned by the past neural activity and the space spanned by the future behavior. Using this idea, during learning, the behaviorally relevant latent states can be extracted via an orthogonal projection of future behavior onto the past neural activity in the first stage (FIG. 4, b). The remaining neural dynamics correspond to the latent states that do not directly drive behavior (i.e. $x_k^{(2)}$). Optionally, once behaviorally relevant latent states are extracted, these remaining behaviorally irrelevant latent states can then be extracted by an additional orthogonal projection from the residual neural activity (i.e. the part not predicted by the extracted behaviorally relevant latent states) onto past neural activity in the second stage during learning (Table 1, FIG. 10). Finally, model parameters that describe the temporal evolution can be learned based on the extracted latent states. Thus, PSID solves two challenges. It builds a dynamic model of how high-dimensional neural activity evolves in time (temporal structure); it simultaneously dissociates behaviorally relevant and irrelevant dynamics and can prioritize the former with its novel two-stage structure to learn them more accurately and with lower-dimensional latent states.

The inventors compared PSID with NDM and RM. Standard NDM describes neural activity using a latent SSM (Equation (1)), but in terms of a latent state that is learned agnostic (i.e., unsupervised) with respect to behavior; these latent states are then regressed onto the behavior. Since NDM methods extract the latent states and learn their dynamics without using the observed behavior, unlike PM, they do not prioritize the behaviorally relevant neural dynamics. The disclosure uses the standard subspace identification (SID) algorithm to learn the latent SSM in linear NDM. SID extracts the latent states by projecting future neural activity onto past neural activity (FIG. 4, b), unlike PSID that projects future behavior onto past neural activity (FIG. 4, b). As control analyses, PSID was also compared with example nonlinear NDMs (e.g. using recurrent neural networks (RNN)) as well as with linear NDMs learned with expectation-maximization (EM). To implement RM, the disclosure uses the commonly used RM method (sometimes termed Kinematic-state Kalman Filter (KKF)), which builds an auto-regressive model for the behavior and directly relates the behavior to the neural activity using linear regression. RM learns the state and its dynamics agnostic to the observed neural activity (FIG. 4, b) and thus, as will be shown, may learn state dynamics that are not encoded in the observed neural activity.

Importantly, all three linear methods (RM, NDM, PSID) describe the neural activity using the same model structure, which is a linear SSM. The critical difference is how model parameters are learned, i.e., how states and their dynamics are learned from neural data (NDM), from behavior data (RM) or from both (PSID), and thus which brain states are extracted (FIG. 4, a). After SSM parameters are learned in each of these three methods, in all of them, the extraction of the state from neural activity and the decoding of behavior are done using a Kalman filter and linear regression, respectively (FIG. 4, c), and are evaluated with cross-validation. The disclosure uses the cross-validated correlation coefficient (CC) of decoding behavior using neural activity as the measure for how accurately the behaviorally relevant neural dynamics are learned. The inventors emphasize that in PSID behavior is only seen in the training set to learn the dynamic model; in the test set, behavior is in no way seen by the learned dynamic model and similar to other methods the extraction of latent states and decoding are done purely using neural activity.

The inventors first validated PSID using extensive and general numerical simulations and then used PSID to uncover the behaviorally relevant neural dynamics in three neural signal types across two existing experimental datasets employing different behavioral tasks. The first existing experimental dataset consisted of recorded neural activity in motor cortices of two adult Rhesus macaque monkeys as they performed 3D reach, grasp, and return movements to diverse random locations within a 50 cm×50 cm×50 cm workspace and continuously in time, i.e., without any timing cues. The angles of 27 (monkey J) or 25 (monkey C) joints on the right shoulder, elbow, wrist, and fingers at each point in time were tracked via retroreflective markers and were taken as the main behavior of interest. The inventors also studied joint angular velocities and 3D end-point position of hand and elbow. The existing experimental dataset consisted of recorded neural activity from 137 (monkey J) or 128 (monkey C) electrodes covering primary motor cortex (M1), dorsal premotor cortex (PMd), ventral premotor cortex (PMv), and prefrontal cortex (PFC) in monkey J and bilateral PMd and PMv in monkey C. The inventors modeled the neural dynamics in two neural signal types in this dataset separately: 1) local field potential (LFP) power in 7 frequency bands, 2) multi-unit spiking activity. The second existing experimental dataset consisted of recorded neural activity in PFC using 32 electrodes in two adult Rhesus macaque monkeys performing saccadic eye movements to visually presented targets on a display. Here, in this existing dataset, the inventors took the 2D eye position as the behavior of interest and modelled the raw LFP activity, which is different from LFP powers, constituting the third neural signal type.

Figure 12:
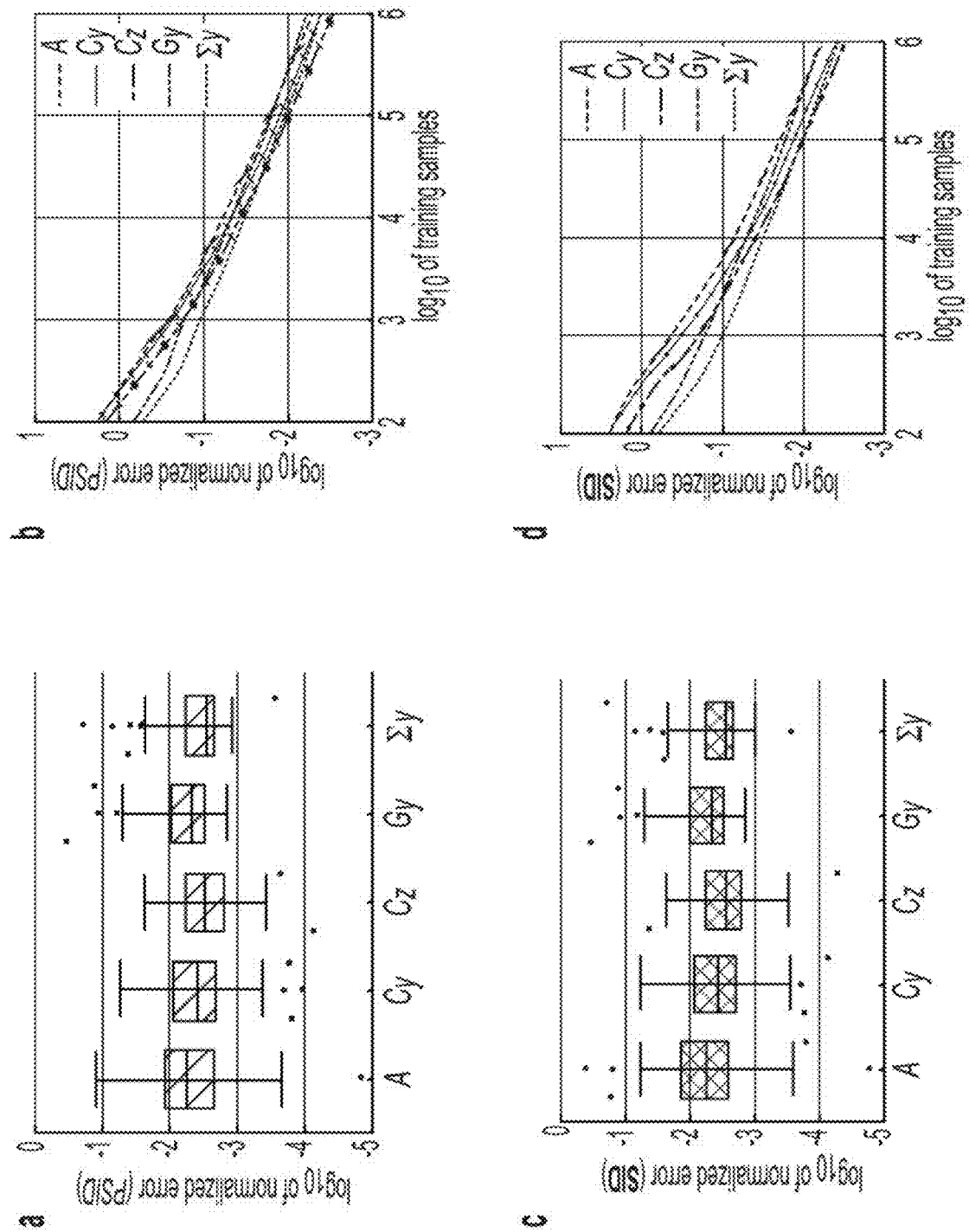
FIG. 12 illustrates that PSID correctly learns model parameters at a rate of convergence similar to that of standard subspace identification (SID) while also being able to prioritize behaviorally relevant dynamics according to an embodiment of the present invention.
Figure 13:
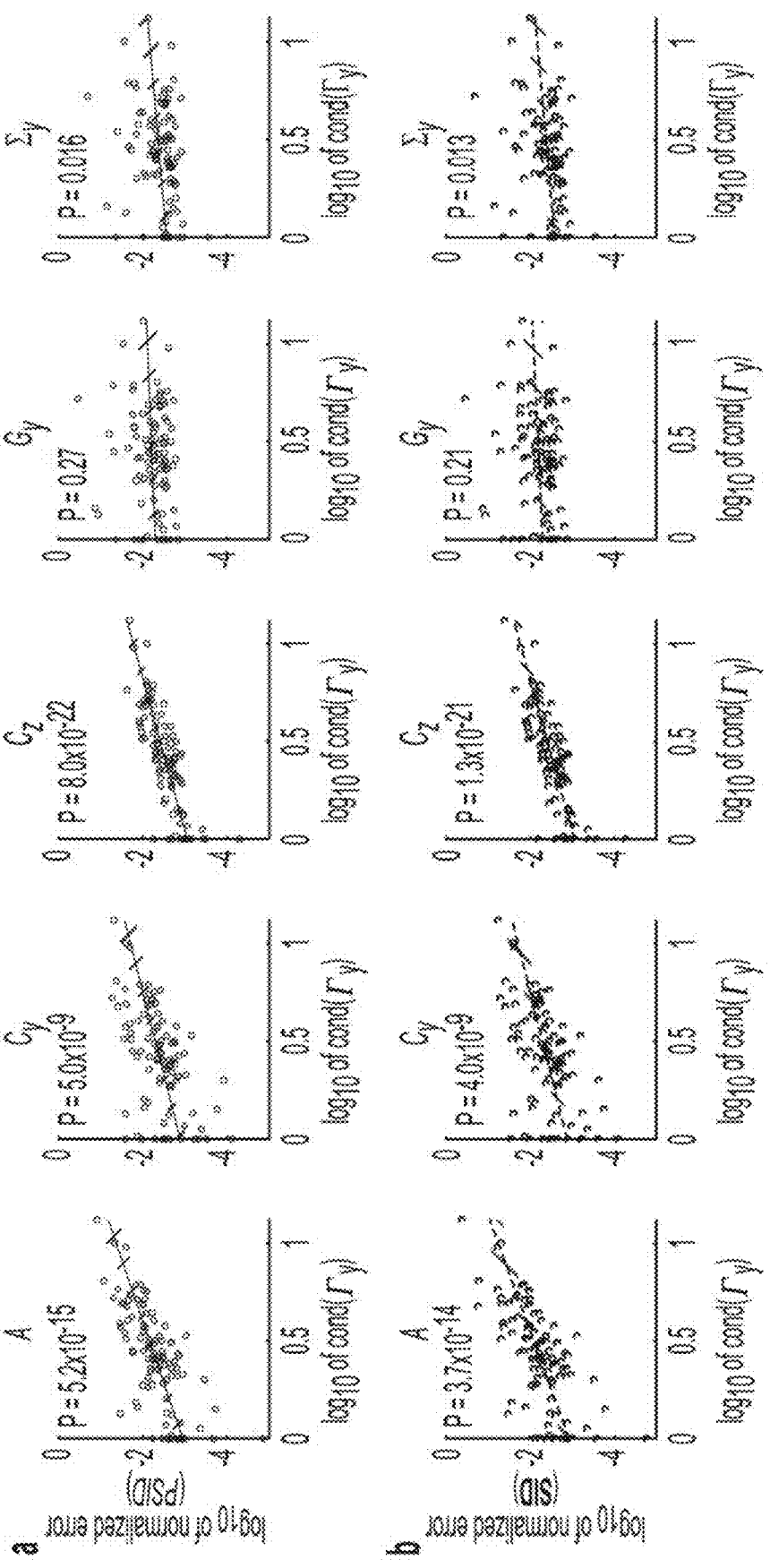
FIG. 13 illustrates that identification error is greater for models that are closer to unobservability and thus inherently more difficult to identify according to an embodiment of the present invention.
Figure 14:
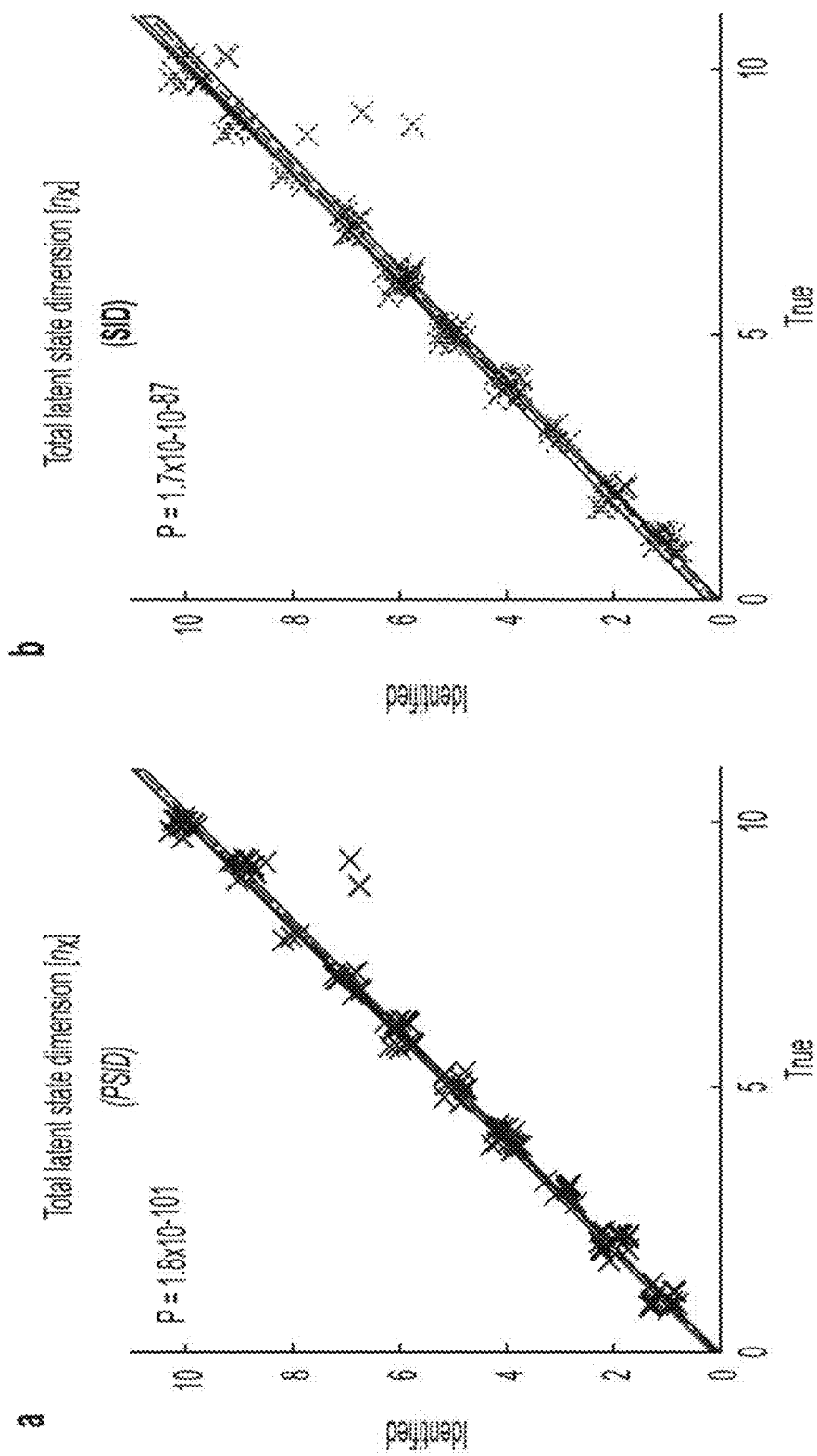
FIG. 14 illustrates that model structure parameters can be accurately identified using cross-validation according to an embodiment of the present invention.
Figure 14:
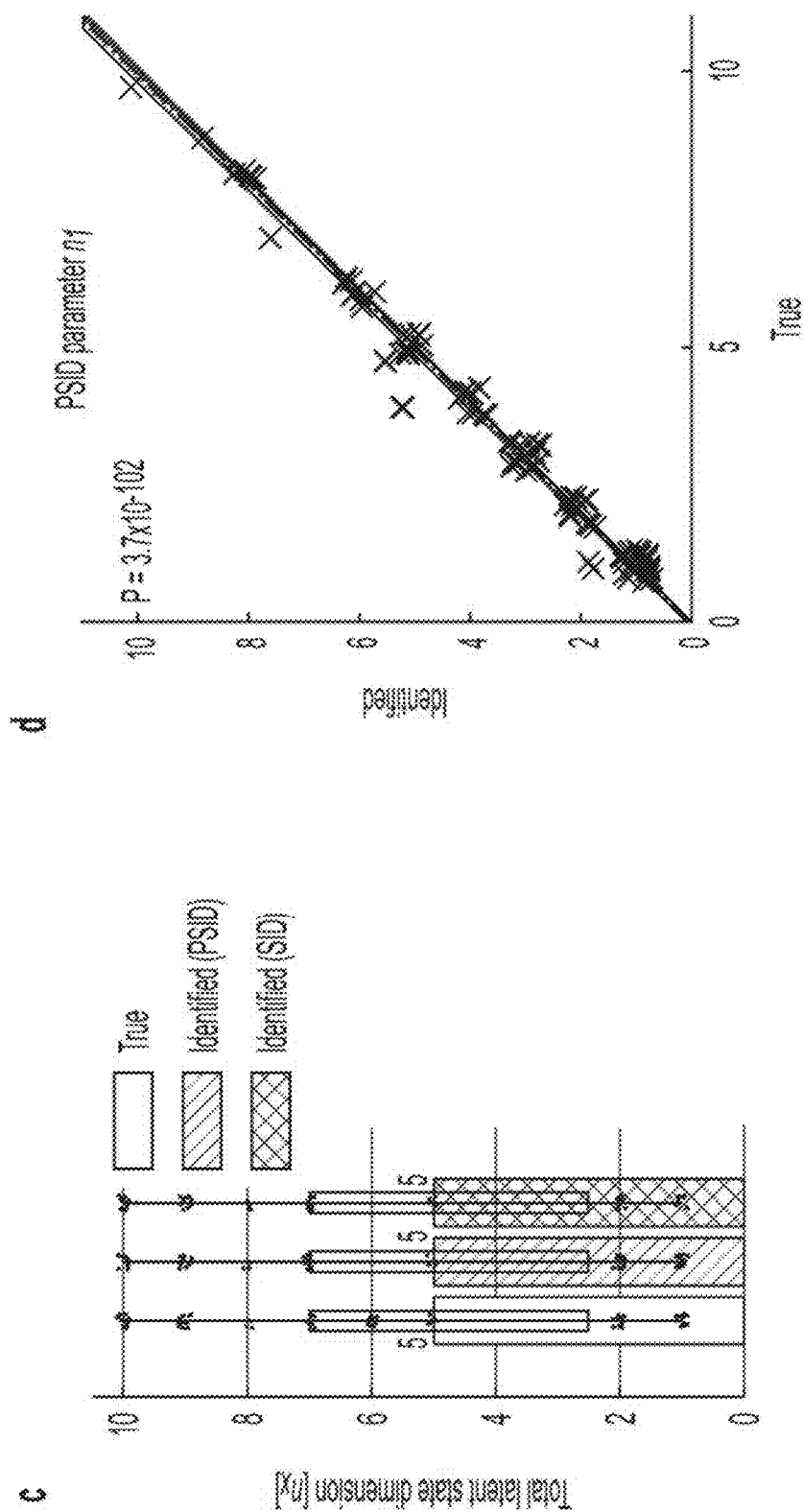
Figure 14:
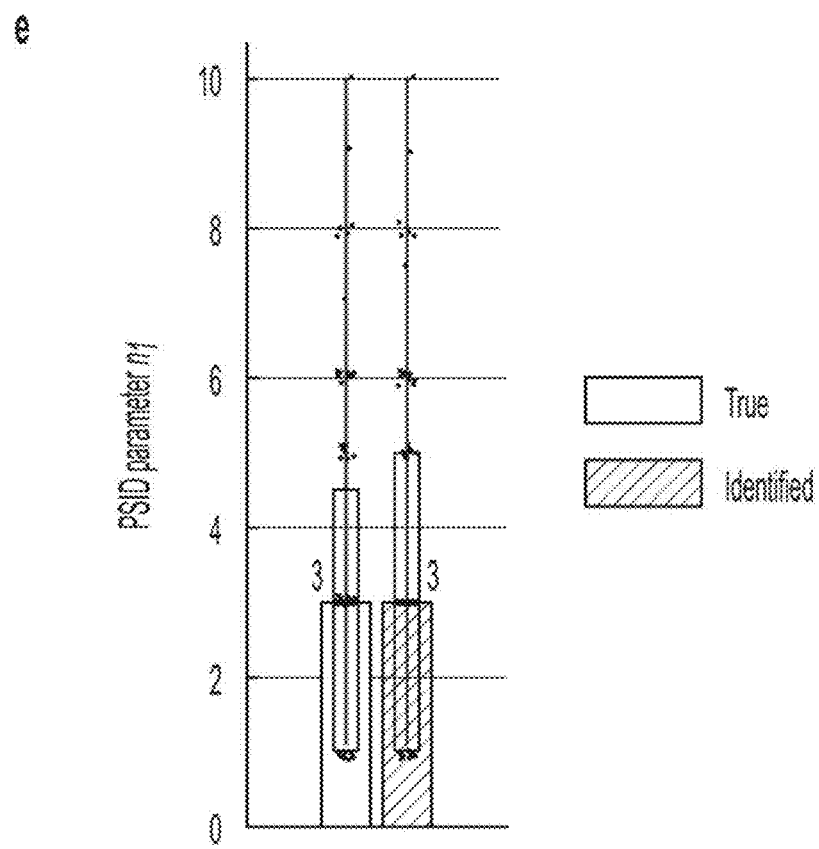

In addition to the two existing experimental datasets, the inventors generated extensive general simulated data and applied PSID to this simulated data. The inventors applied PSID to simulated data generated from 100 models with random parameters and found that it correctly identified all model parameters in Equation 1 with less than one percent (1%) normalized error (FIG. 12, a), with a trend toward lower errors given more training samples (FIG. 12, b). Moreover, compared with standard SID, PSID showed a similar error and rate of convergence (FIG. 12, c, d), indicating that even when learning of all latent states is of interest rather than just the behaviorally relevant ones, PSID performs as well as SID. Further, the identification error of both PSID and SID was correlated with a mathematical measure of how inherently difficult it was to extract the latent states for a given random model (FIG. 13). Finally, using cross-validation, the model structure parameters $n_x$ and $n_1$ could also be accurately identified (FIG. 14).

The inventors found that, unlike standard methods, PSID correctly prioritizes identification of behaviorally relevant dynamics even when performing dimensionality reduction, i.e., identifying models with fewer latent states than the total number of latent states in the true model. The inventors applied PSID to simulated data from 100 random models with 16 latent state dimensions ($n_x$=16) out of which 4 were behaviorally relevant ($n_1$=4, FIG. 5). The inventors evaluated the accuracy for learning the behaviorally relevant eigenvalues within the state transition matrix A, which characterize the behaviorally relevant dynamics. Overall, using a minimal total state dimension of 4, PSID could learn all 4 behaviorally relevant eigenvalues whereas the standard methods could not achieve similar accuracy as PSID even when they used higher dimensional latent states (FIG. 5), even as high as that of the true model (FIG. 5, b when for NDM $n_x$=16 and for PSID $n_x$=4).

Figure 5:
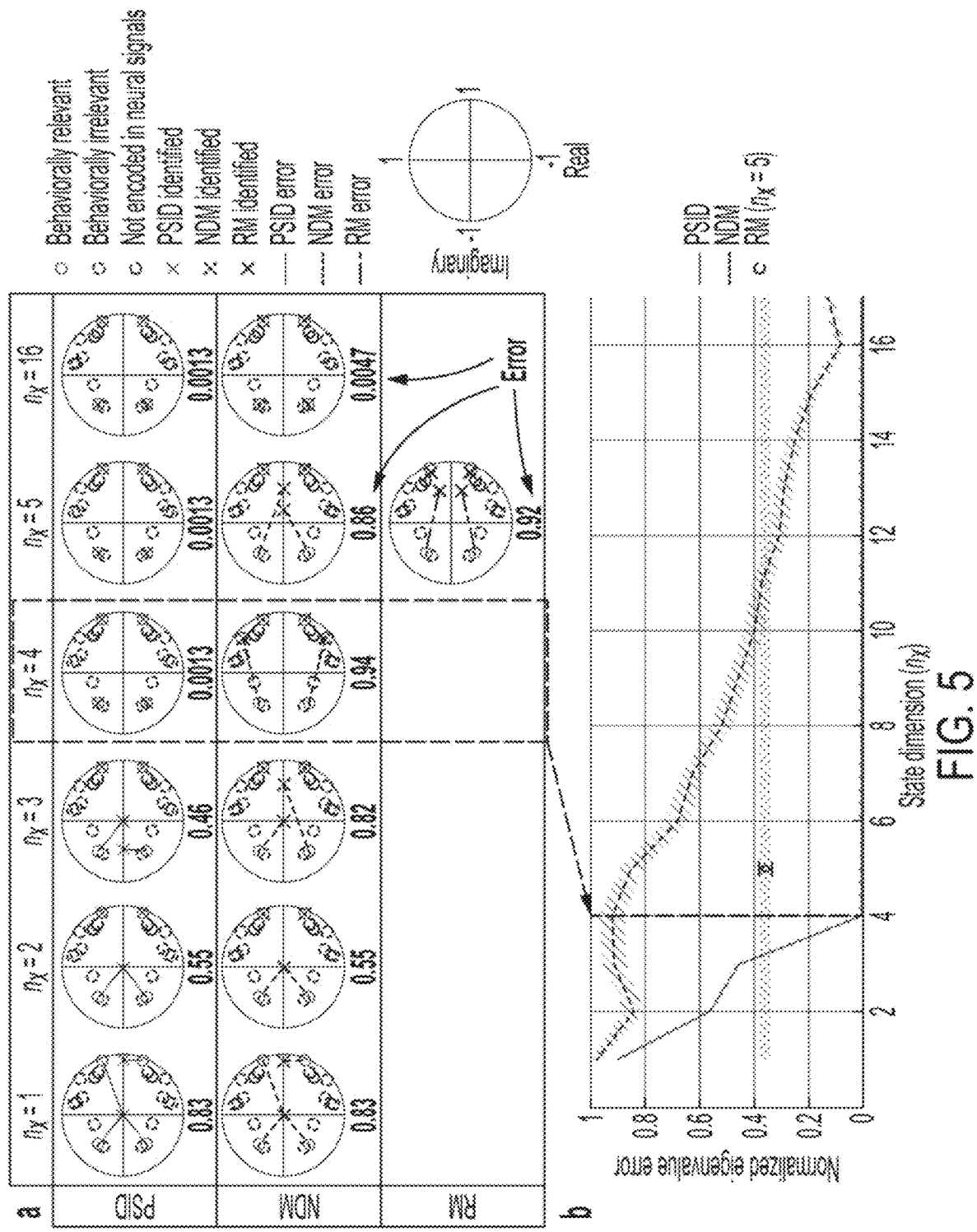
FIG. 5 illustrates results of a model using PSID according to an embodiment of the present invention.

In particular, FIG. 5, a shows, for one simulated model, the identified behaviorally relevant eigenvalues for PSID, NDM, and RM and for different latent state dimensions. For RM, the state dimension can only be equal to the behavior dimension (here $n_z$=5). Eigenvalues are shown on the complex plane, i.e. real part on the horizontal axis and imaginary part on the vertical axis. The unit circle is shown towards the bottom right. True model eigenvalues are shown as patterned circles, with patterns indicating their relevance to neural activity, behavior, or both. Crosses show the identified behaviorally relevant eigenvalues. When the state dimension $n_x$ is less than the true dimension of behaviorally relevant states ($n_1$=4), missing eigenvalues are taken as 0, representing an equivalent model for which some (i.e. $n_1 - n_x$) latent state dimensions are always 0. Thus, all cases have 4 crosses indicating 4 identified eigenvalues ($n_1 - n_x$ of which are zero when $n_x < n_1$). Lines indicate the identified eigenvalue error whose normalized value—average line length normalized by the average true eigenvalue magnitude—is noted below each plot. Unlike PSID, NDM may learn latent states that are unrelated to behavior and RM may learn latent states that are not encoded in the observed neural activity.

FIG. 5, b illustrates the normalized eigenvalue error given $10^6$ training samples when using PSID, NDM and RM, averaged over 100 random models. For all random models, the total dimension of latent states ($n_x$=16), the dimension of behaviorally relevant states ($n_1$=4), and the number of behavior dimensions not encoded in neural activity (i.e. 4) is as in FIG. 5, a. Solid lines show the average error and shaded areas show the s.e.m. For NDM and PSID, total state dimension is changed from 1 to 16 (for PSID $n_1$=4). Since for RM the state dimension can only be equal to the behavior dimension ($n_z$=5), for easier comparison, the RM s.e.m. is shown as error bars and also a horizontal shaded area.

Figure 15:
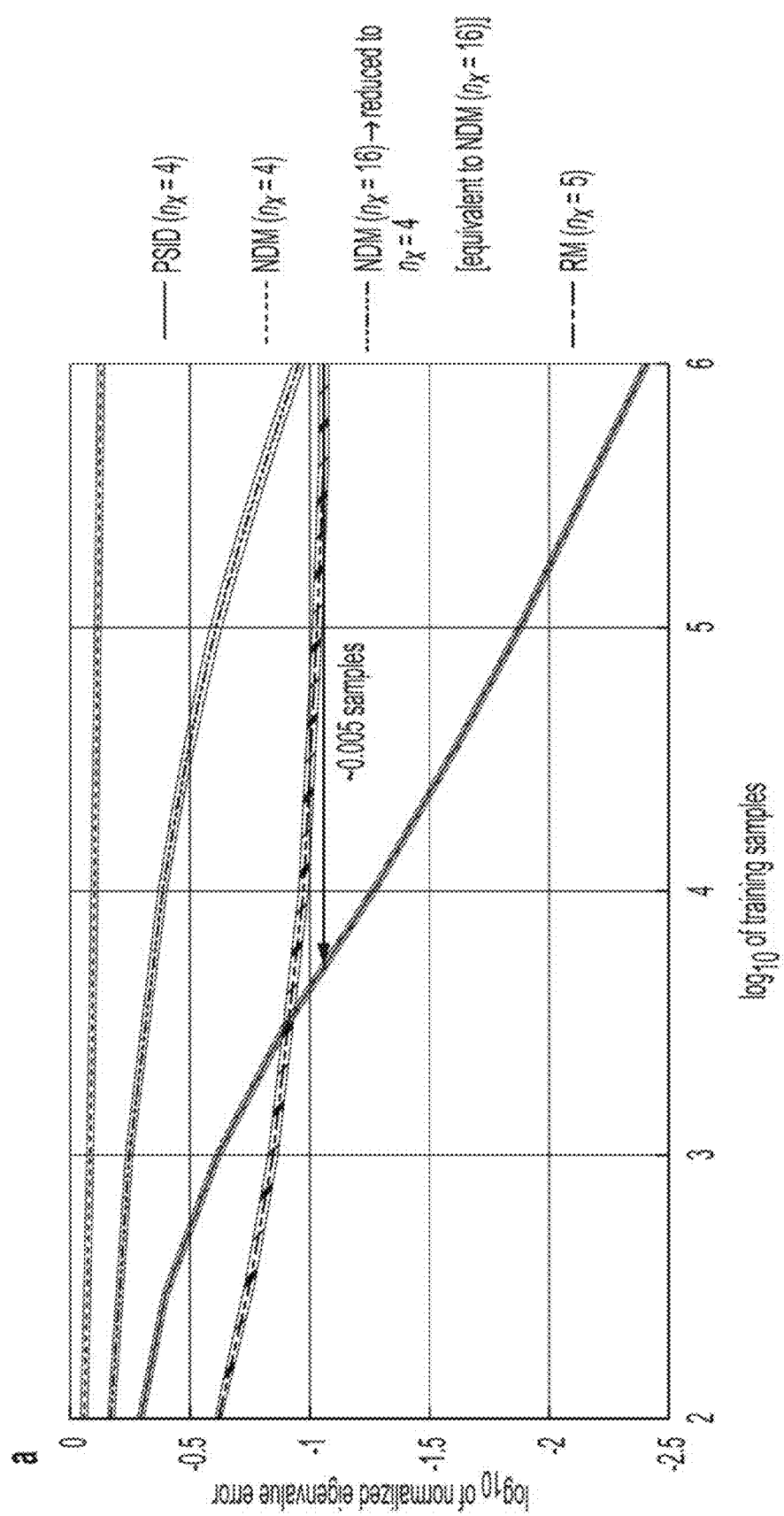
FIG. 15 illustrates that PSID requires orders of magnitude fewer training samples to achieve the same performance as an NDM with a larger latent state dimension, and NDM with the same latent state dimension as PSID or RM do not achieve a comparable performance to PSID even with orders of magnitude more samples according to an embodiment of the present invention.
Figure 15:
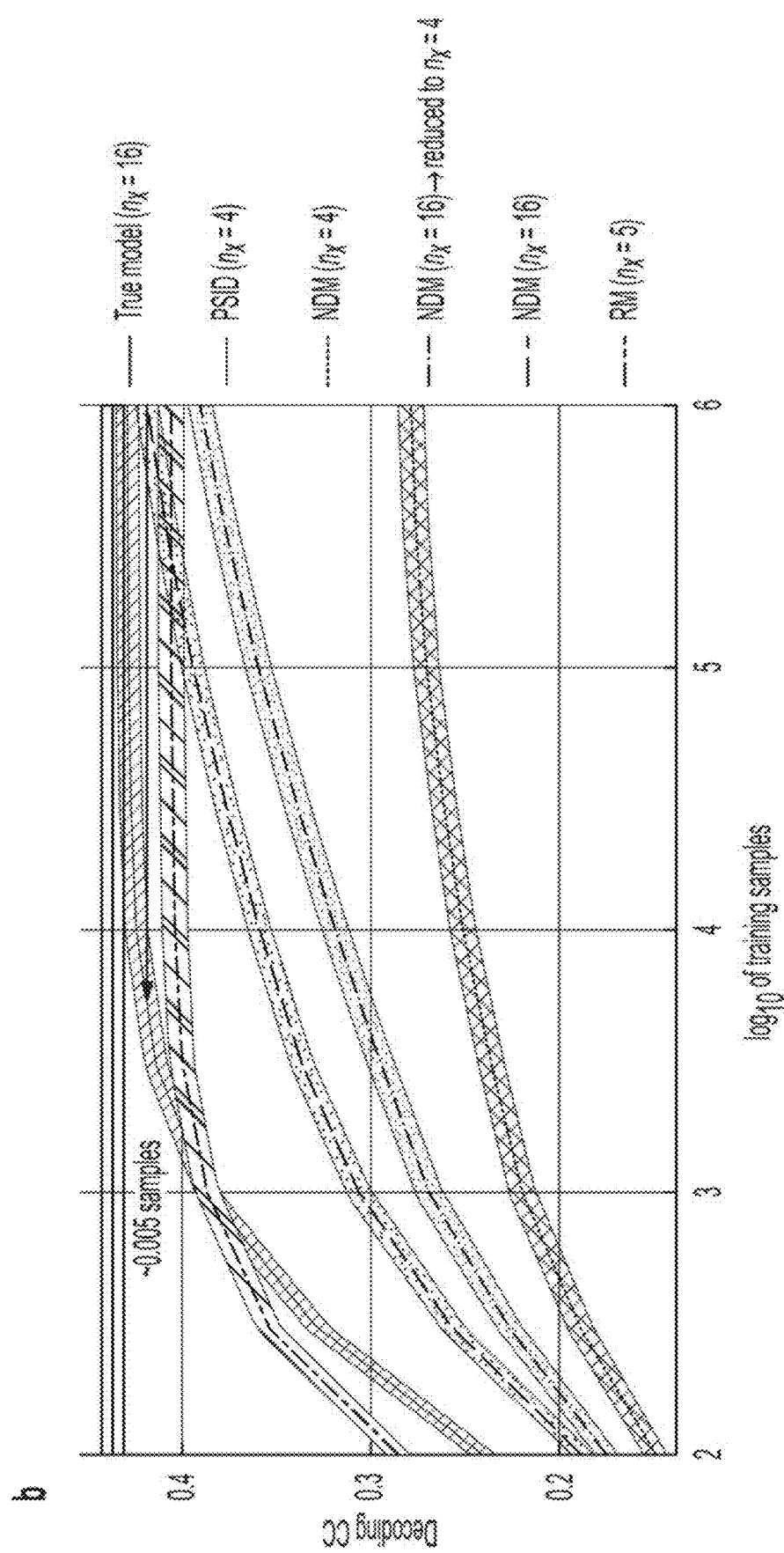

The inventors investigated the PSID advantage in learning behaviorally relevant dynamics as a function of the training sample size. The inventors found that RM and NDM in the dimensionality reduction regime could not learn behaviorally relevant dynamics even when training samples increased significantly (FIG. 15, a, b). Also, importantly, even compared with NDM with a latent state dimension as high as the actual model, PSID achieved a similar eigenvalue and decoding accuracy but with orders of magnitude fewer training samples (i.e. 200 times fewer; FIG. 15). This result suggests that unlike NDM, PSID is suitable for dimensionality reduction while preserving behavior information. Since experimental data is always limited, this data efficiency is another important advantage of PSID over NDM.

Figure 6:
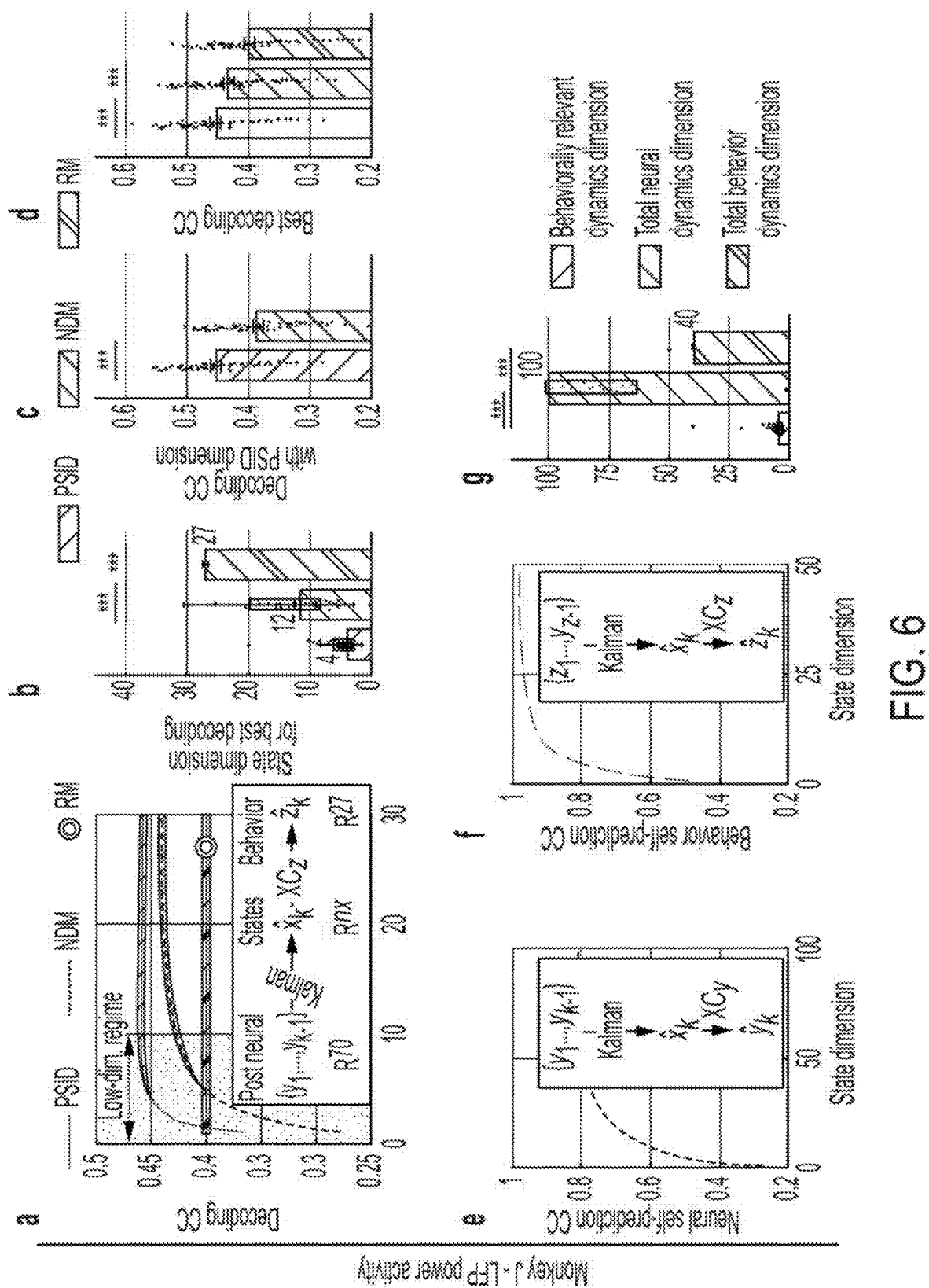
FIG. 6 illustrates that PSID reveals a markedly lower dimension for behaviorally relevant neural dynamics and extracts them more accurately in existing datasets consisting of motor cortex LFP activity during 3D reach, grasp, and return movements according to an embodiment of the present invention.
Figure 6:
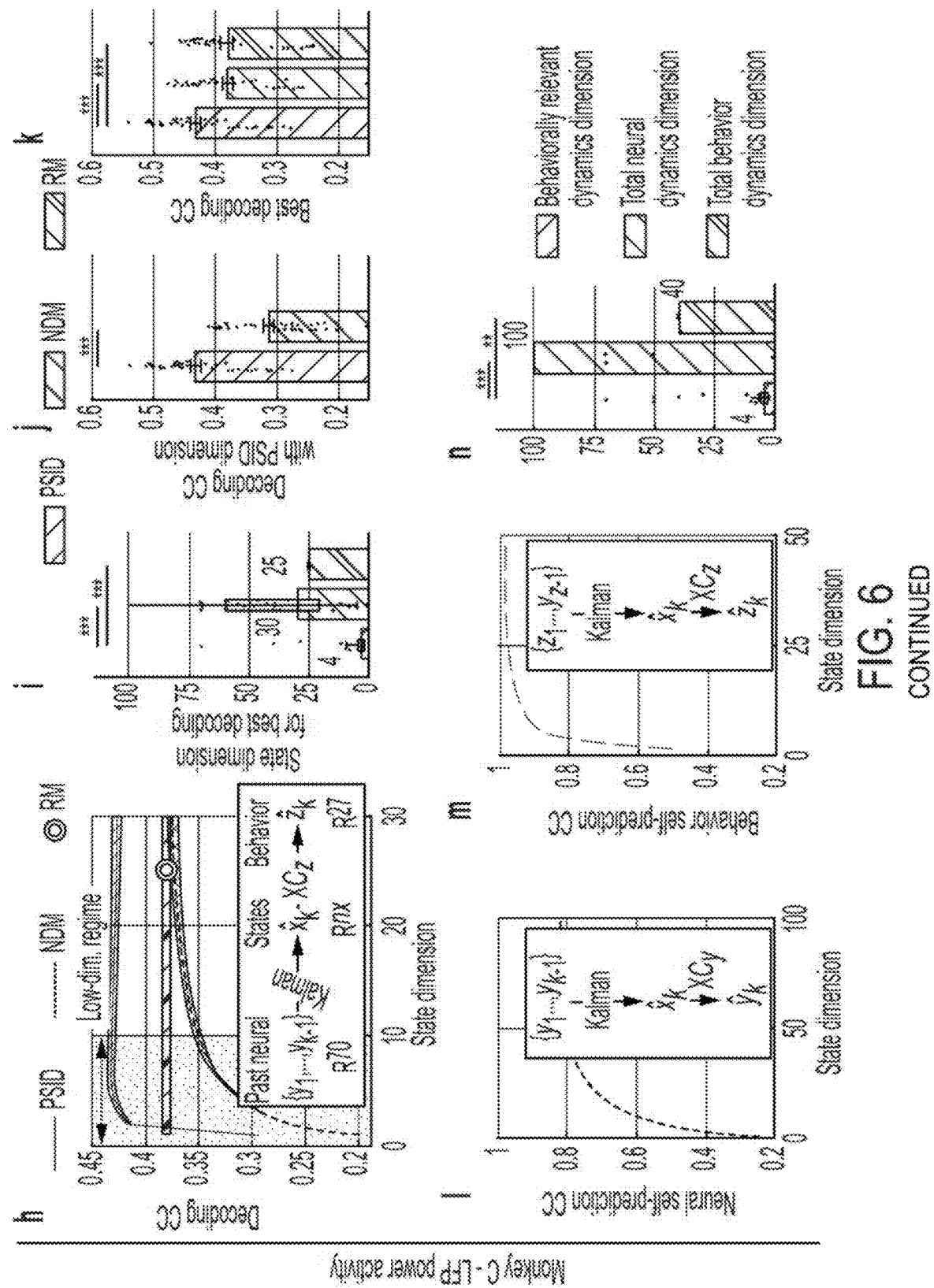
Figure 16:
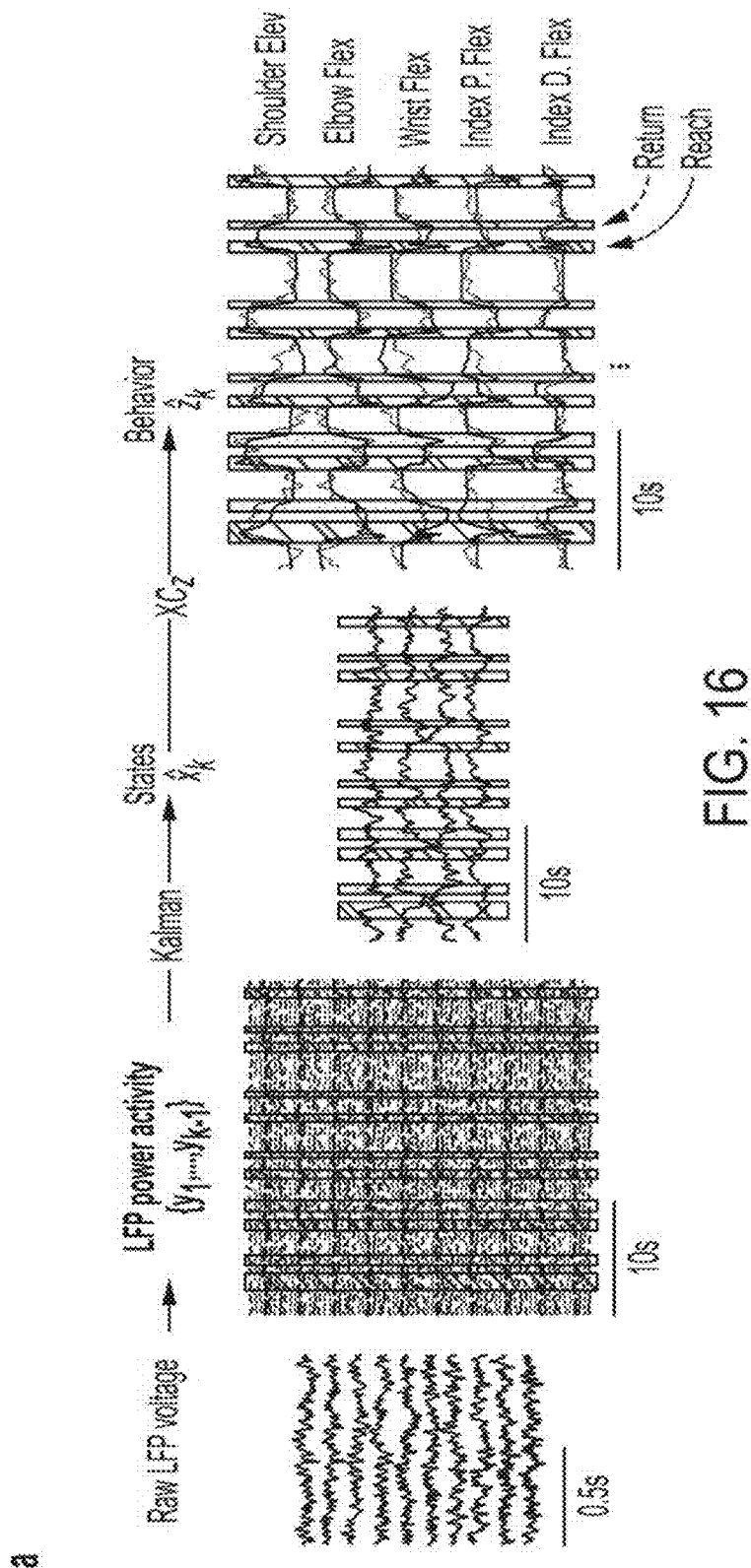
FIG. 16 illustrates that PSID can be used to model neural activity for different neural signal types including LFP power activity and population spiking activity according to an embodiment of the present invention.
Figure 16:
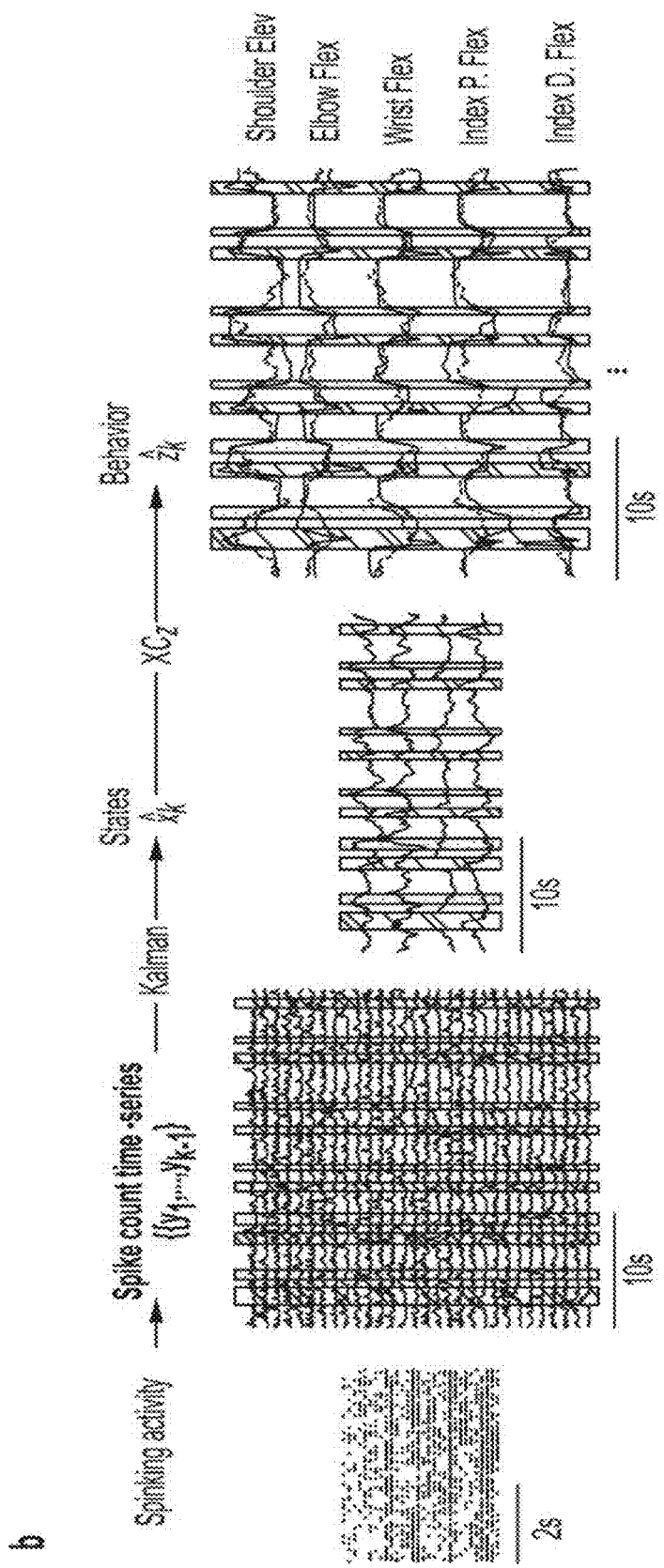

Given that PSID can prioritize and dissociate behaviorally relevant neural dynamics, the inventors used it to investigate these dynamics and their true dimensionality in existing data consisting of multi-regional motor cortical recordings during reach, grasp and return movements to diverse 3D locations with behavior being all arm-hand joint angles (FIG. 6, FIG. 16, a). The inventors first examined the LFP power activity in this data.

Figure 17:
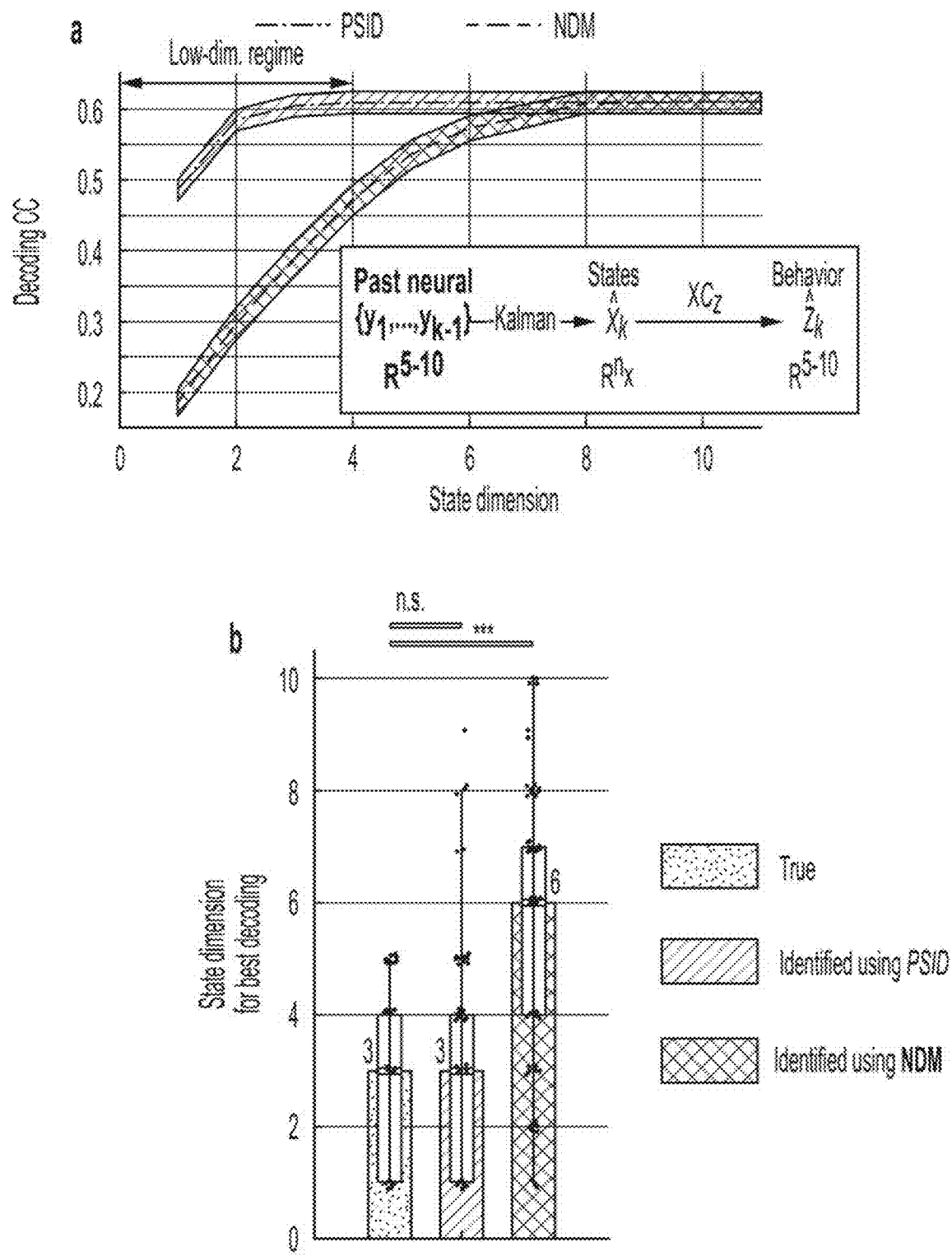
FIG. 17 illustrates that PSID can accurately estimate the behaviorally relevant dynamics dimension, as well as the total neural dynamics dimension and the total behavior dynamics dimension in simulations according to an embodiment of the present invention.
Figure 17:
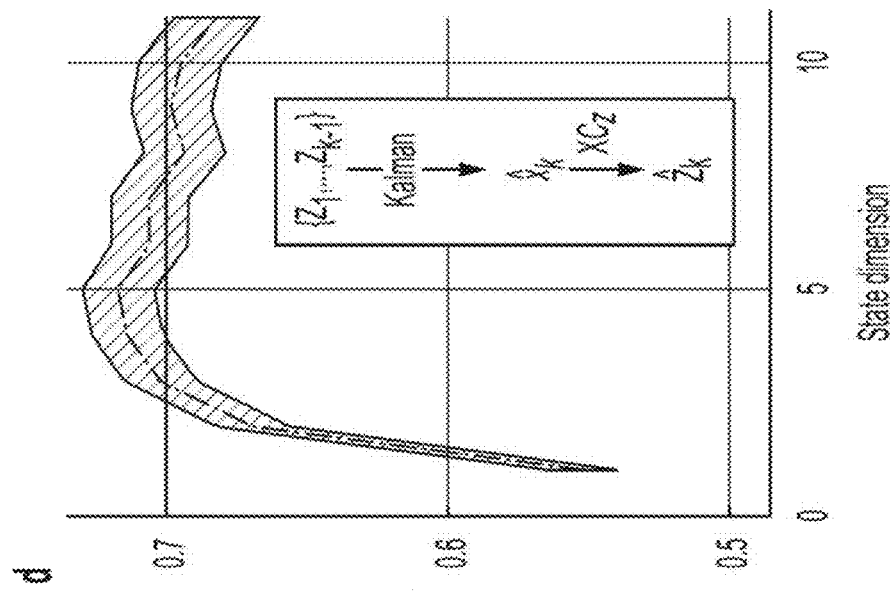
Figure 17:
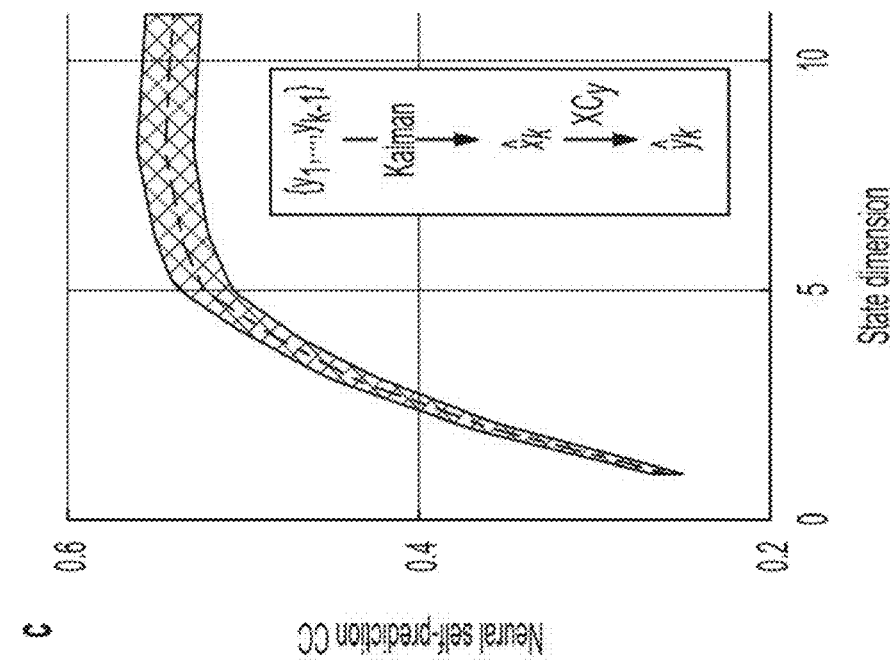
Figure 17:
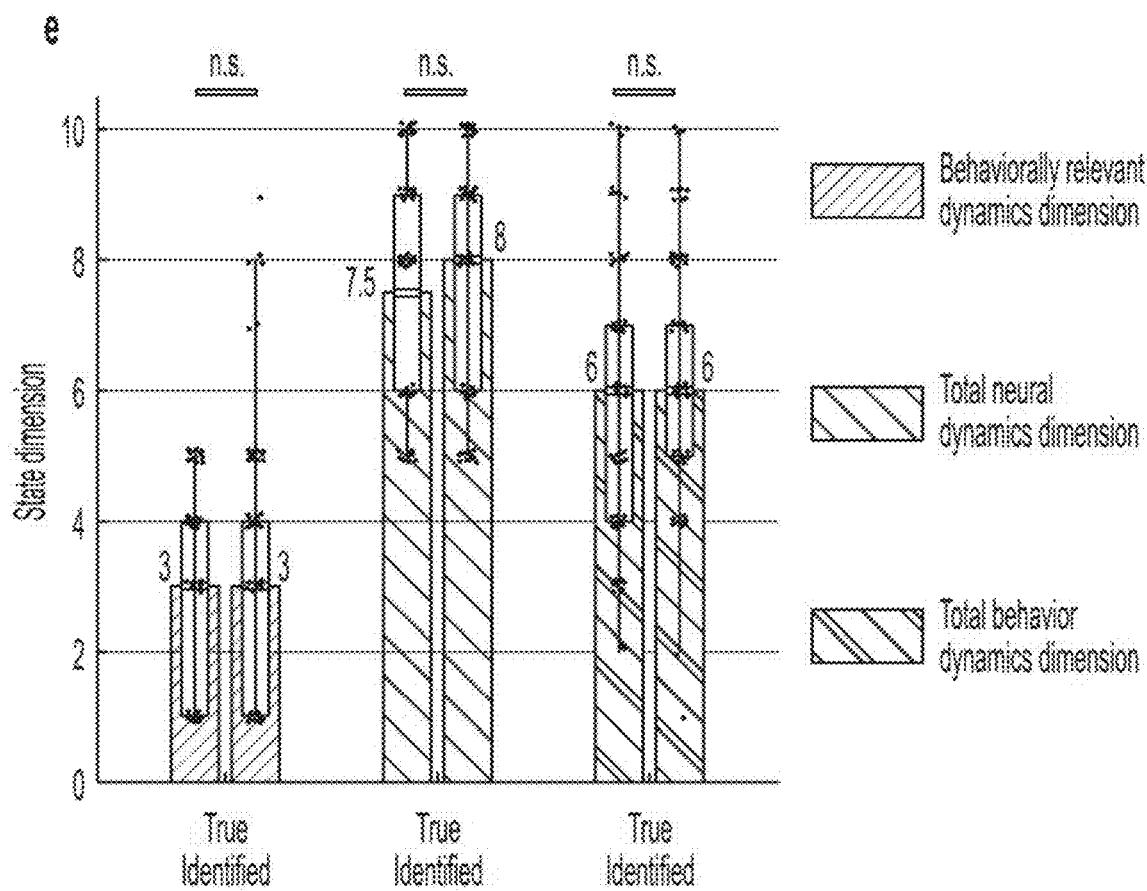

The inventors found that PSID reveals that the behaviorally relevant neural dynamics are much lower-dimensional than would otherwise be concluded using standard methods (FIG. 6, b, i). Further, PSID identifies these dynamics more accurately than standard methods both at that dimension (FIG. 6, c, j) and even when standard methods used much higher-dimensional latent states (FIG. 6, d, k). The dimension of behaviorally relevant neural dynamics is defined as the minimal state dimension required to best explain behavior using neural activity. To find this dimension from data with each method, the inventors modeled the neural activity with various state dimensions in each dataset (FIG. 6, a, h) and found the smallest state dimension at which the best behavior decoding performance was achieved (averaged across all joints). First, the inventors found that the best decoding performance for PSID was significantly higher than both NDM and RM in both monkeys, suggesting that PSID more accurately learns behaviorally relevant neural dynamics (FIG. 6, d, k; $P<10^{-5}$; one-sided signed-rank; $N_s \geq 48$). Second, importantly, this best performance was achieved using a significantly smaller state dimension with PSID compared with NDM and RM—a median dimension of only 4 in both monkeys versus 12-30, or at least 3 times smaller (FIG. 6, b, i; $P<10^{-9}$; one-sided signed-rank; $N_s \geq 48$). Third, the inventors confirmed with numerical simulations that PSID accurately estimates the true dimension of behaviorally relevant neural dynamics, whereas NDM overestimates it (FIG. 17, a, b). Fourth, at the dimension estimated by PSID, the NDM state had a significantly lower decoding accuracy (FIG. 6, c, j; $P<10^{-9}$; one-sided signed-rank; $N_s \geq 48$), suggesting that PSID more accurately identifies the low-dimensional behaviorally relevant state; this comparison and the fact that PSID achieved more accurate decoding for all latent state dimensions (FIG. 6, a, h) also show the significant advantage of PSID for dynamic dimensionality reduction while preserving behavior information.

Figure 18:
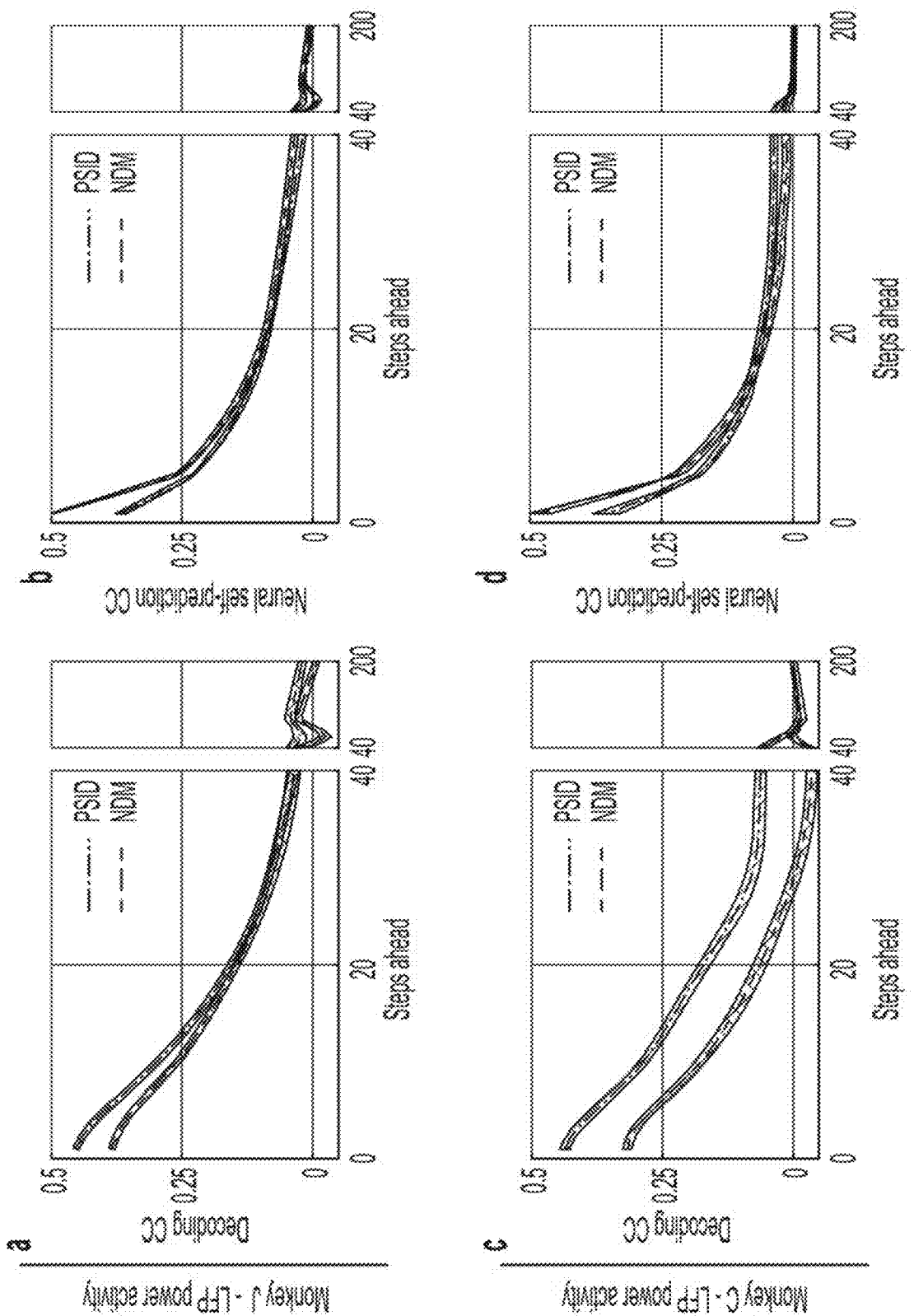
FIG. 18 illustrates that PSID is more predictive of behavior than NDM for multiple-step-ahead prediction of behavior from neural activity according to an embodiment of the present invention.
Figure 19:
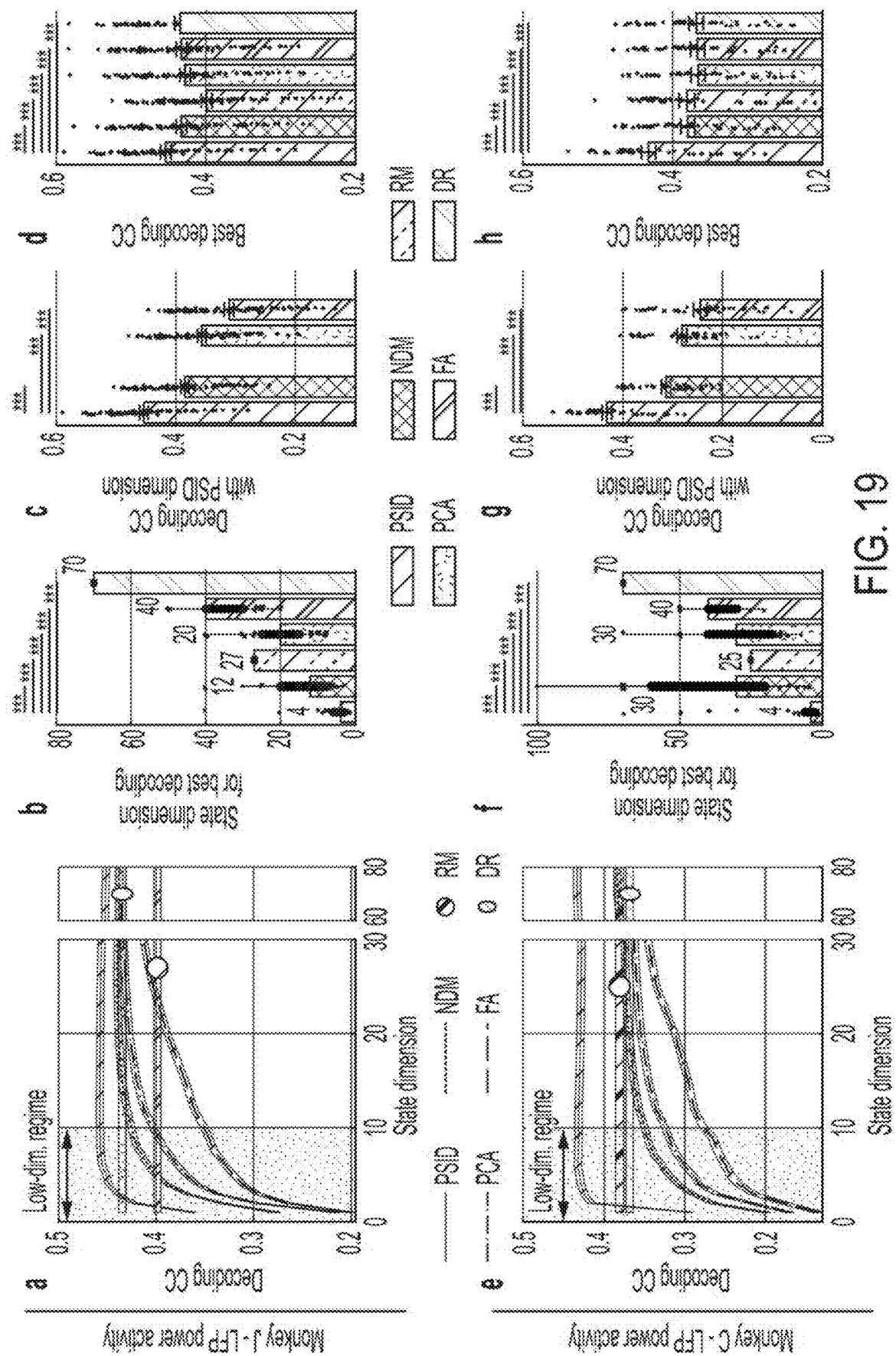
FIG. 19 illustrates that PSID also reveals a markedly lower behaviorally relevant neural dimension and does better decoding compared with non-dynamic dimension reduction using principal component analysis (PCA), factor analysis (FA) and direct regression (DR) (i.e. PSID extracts the behaviorally relevant dynamics more accurately) according to an embodiment of the present invention.
Figure 20:
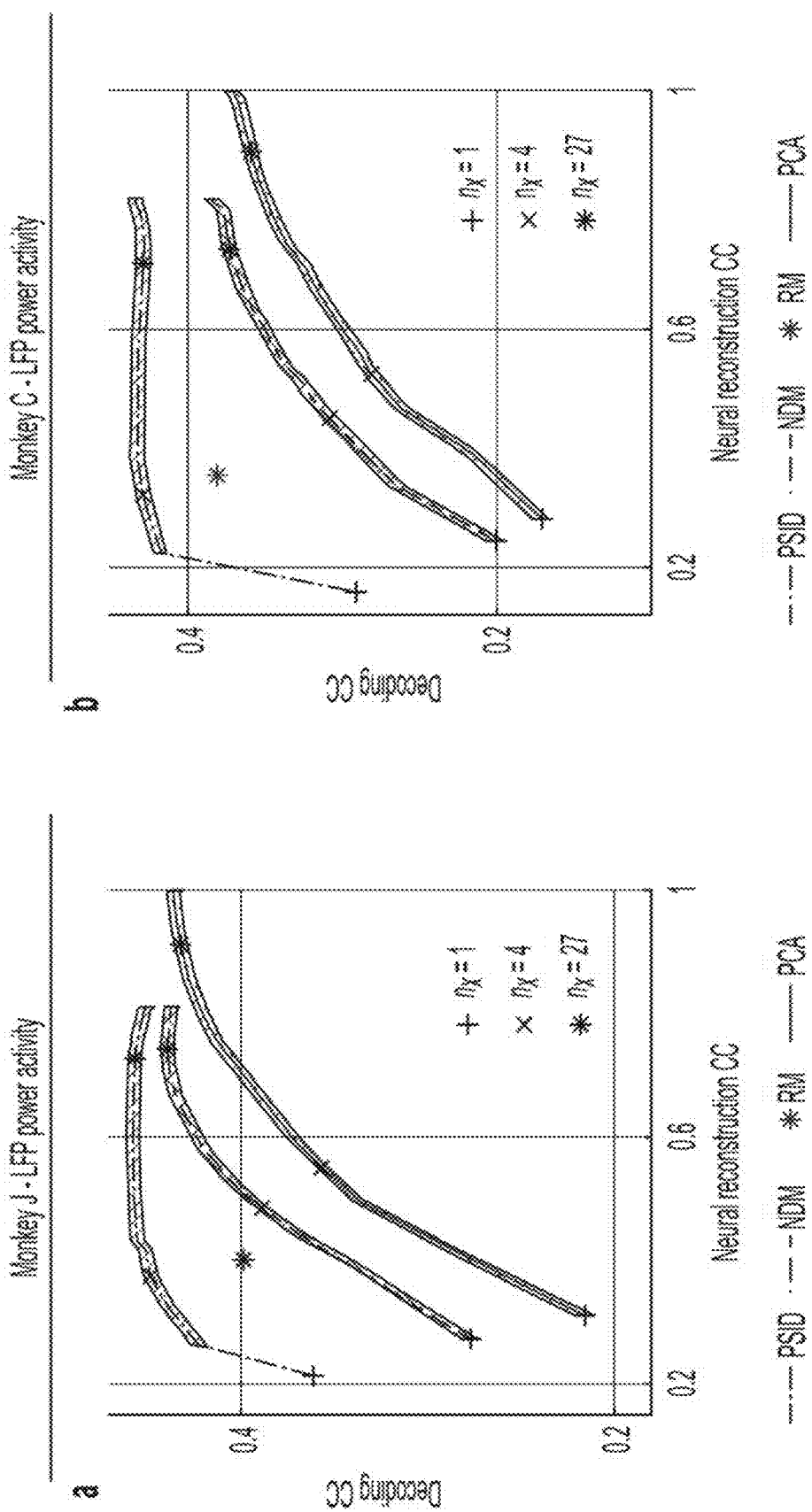
FIG. 20 illustrates that as the dimension of the latent state extracted by PSID increases, it first covers the subspace of neural dynamics that are behaviorally relevant and then covers the subspace of residual neural dynamics according to an embodiment of the present invention.

Next, in three control analyses, the inventors confirmed that these results still hold if (i) explained variance is used instead of CC as performance measure, (ii) 1-4 Hz is added to the original 7 LFP power bands, and (iii) NDM is implemented using expectation maximization (EM) instead of SID, with PSID revealing markedly lower dimension for behaviorally relevant dynamics ($P<10^{-6}$; one-sided signed-rank; $N_s \geq 48$) and achieving better decoding even compared with the best decoding of NDM/RM using much higher-dimensional states ($P<10^{-9}$; one-sided signed-rank; $N_s \geq 48$). Further, PSID achieved more accurate decoding than NDM for neural prediction of behavior multiple time steps into the future (FIG. 18). The inventors also compared with non-dynamic dimension reduction using principal component analysis (PCA) and factor analysis (FA), and with direct regression (DR) from neural activity without any dimension reduction and again found similar results with PSID achieving better decoding using lower-dimensional states (FIG. 19). Comparing the decoding accuracy versus neural reconstruction accuracy for different methods as the dimension of the latent state increased, the inventors found that PSID uniquely prioritizes the extraction of behaviorally relevant dynamics in low-dimensional states and leaves the extraction of any residual dynamics for the higher dimensions of states (FIG. 20).

Figure 21:
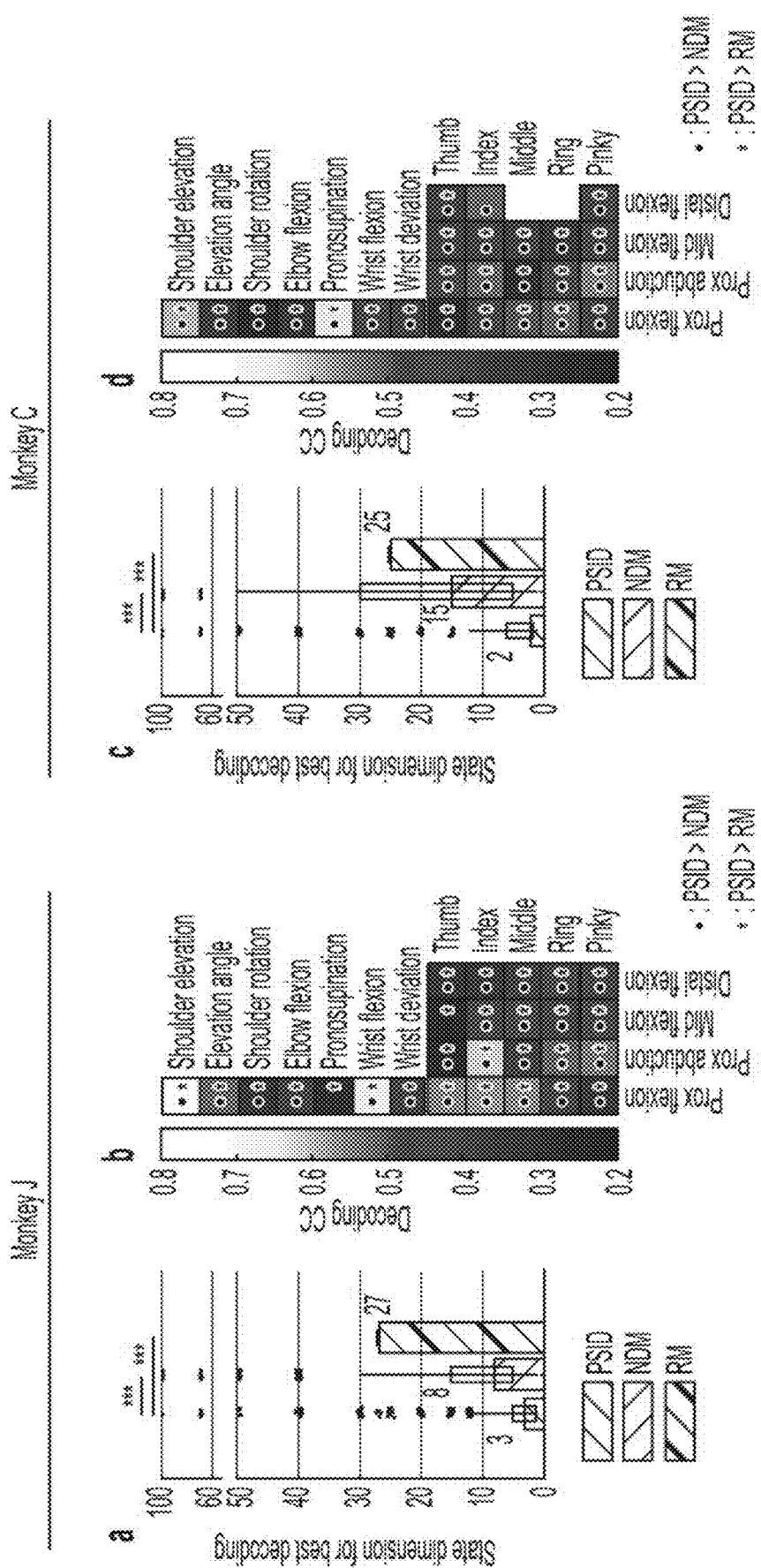
FIG. 21 illustrates that the PSID-extracted latent states with markedly lower dimension achieve significantly better decoding of almost all arm and finger joints according to an embodiment of the present invention.
Figure 22:
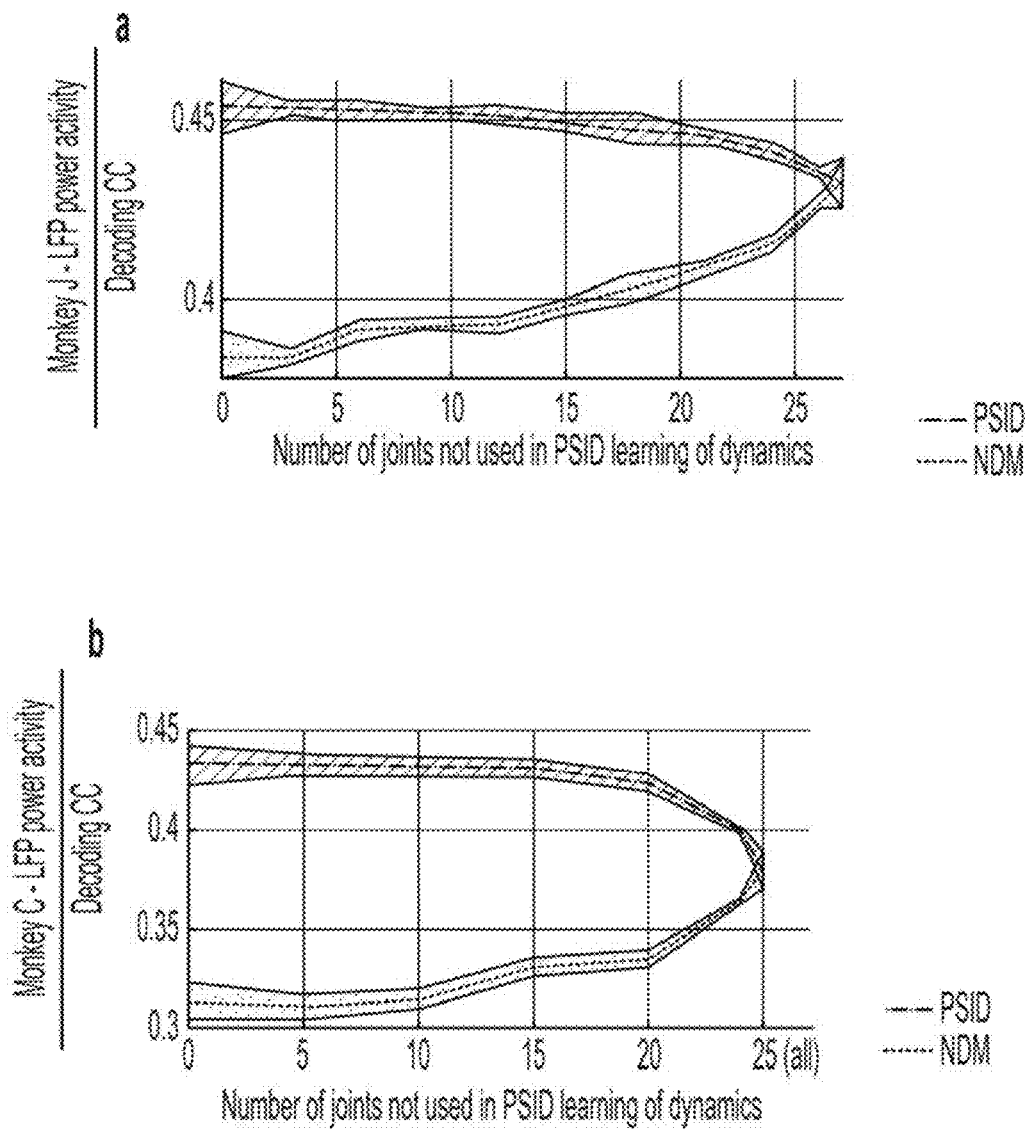
FIG. 22 illustrates that the dynamic model learned by PSID using a subset of joints in the training set was more predictive of the remaining joints in the test set compared with the dynamic model learned by NDM according to an embodiment of the present invention.

Similar results held for each individual joint, with PSID achieving better decoding than NDM and RM for almost all joints in both monkeys using significantly lower-dimensional states (FIG. 21). Also, even when a subset of joints was provided to PSID during learning, its extracted latent states in the test set were still more predictive of the remaining joints that were unseen by PSID compared with NDM latent states (FIG. 22). This result suggests that the learned behaviorally relevant dynamics may generalize across different behavioral measurements related to the same task.

The inventors next found that the dimensionality of the behaviorally relevant neural dynamics was much lower than that of neural dynamics or joint angle dynamics, suggesting that the low-dimensionality PSID finds is not simply because either neural or behavior dynamics are just as low-dimensional. The inventors found the latent state dimension required to achieve the best self-prediction of neural or behavioral signals using their own past, and defined it as the total neural or behavior dynamics dimension, respectively. The inventors confirmed in numerical simulations that this procedure correctly estimates the total latent state dimension in each signal (FIG. 17, c, d, e). In both monkeys the median latent state dimension required for best self-prediction was at least 100 for neural activity (FIG. 6, e, l) and was 40 for behavior joint angles (FIG. 6, f, m), which are both significantly larger than the behaviorally relevant neural dynamics dimension of 4 revealed by PSID (FIG. 6, g, n; $P<10^{-18}$ and $P<0.004$, for neural and behavior dimensions, respectively; one-sided rank-sum). Moreover, the self-prediction of behavior from its own past was much better than decoding it from neural activity (FIG. 6, a, f, h, m) and reached an almost perfect CC of 0.98 for both monkeys (FIG. 6, f, m), indicating that there are predictable dynamics in behavior that are not present in the recorded neural activity (corresponding to $\in_k$ in FIG. 4). These results are consistent with findings in prior studies that motor cortical activity can exhibit dynamics that are not related to behavior and that parts of behavior dynamics cannot be predicted from the recorded neural activity. Taken together, these results suggest that beyond the low-dimensional behaviorally relevant neural dynamics extracted via PSID, both recorded neural activity and behavior have significant additional dynamics that are predictable from their own past but are unrelated to the other signal. PSID uniquely enables the dissociation of shared dynamics from the dynamics that are present in one signal but not the other, and reveals that the shared dimension is much lower than implied by standard methods (FIG. 6).

Figure 23:
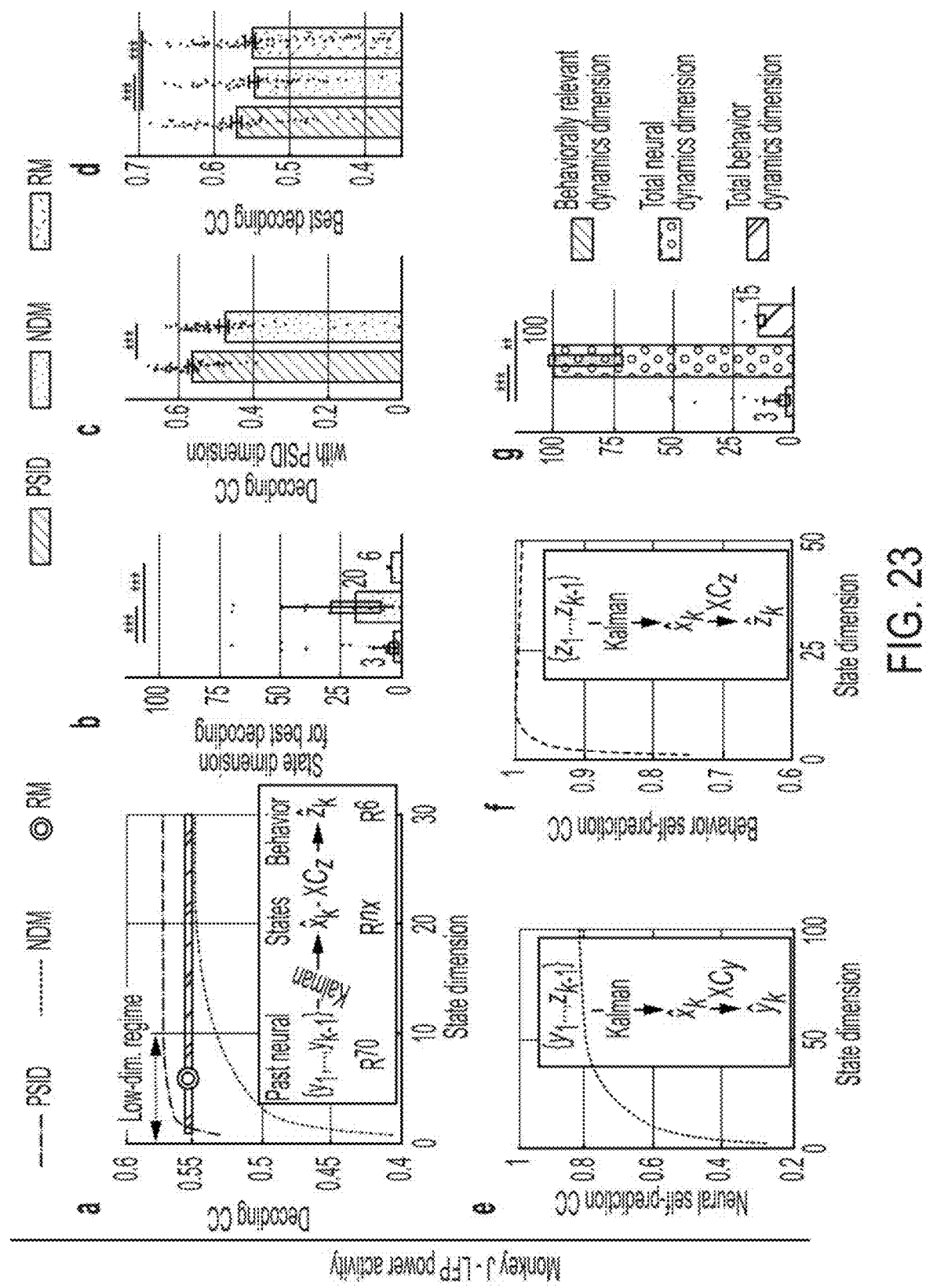
FIG. 23 illustrates that PSID again reveals a markedly lower dimension for behaviorally relevant neural dynamics in the motor cortex LFP activity when behavior is taken as the 3D end-point position (of hand and elbow) instead of the joint angles according to an embodiment of the present invention.
Figure 23:
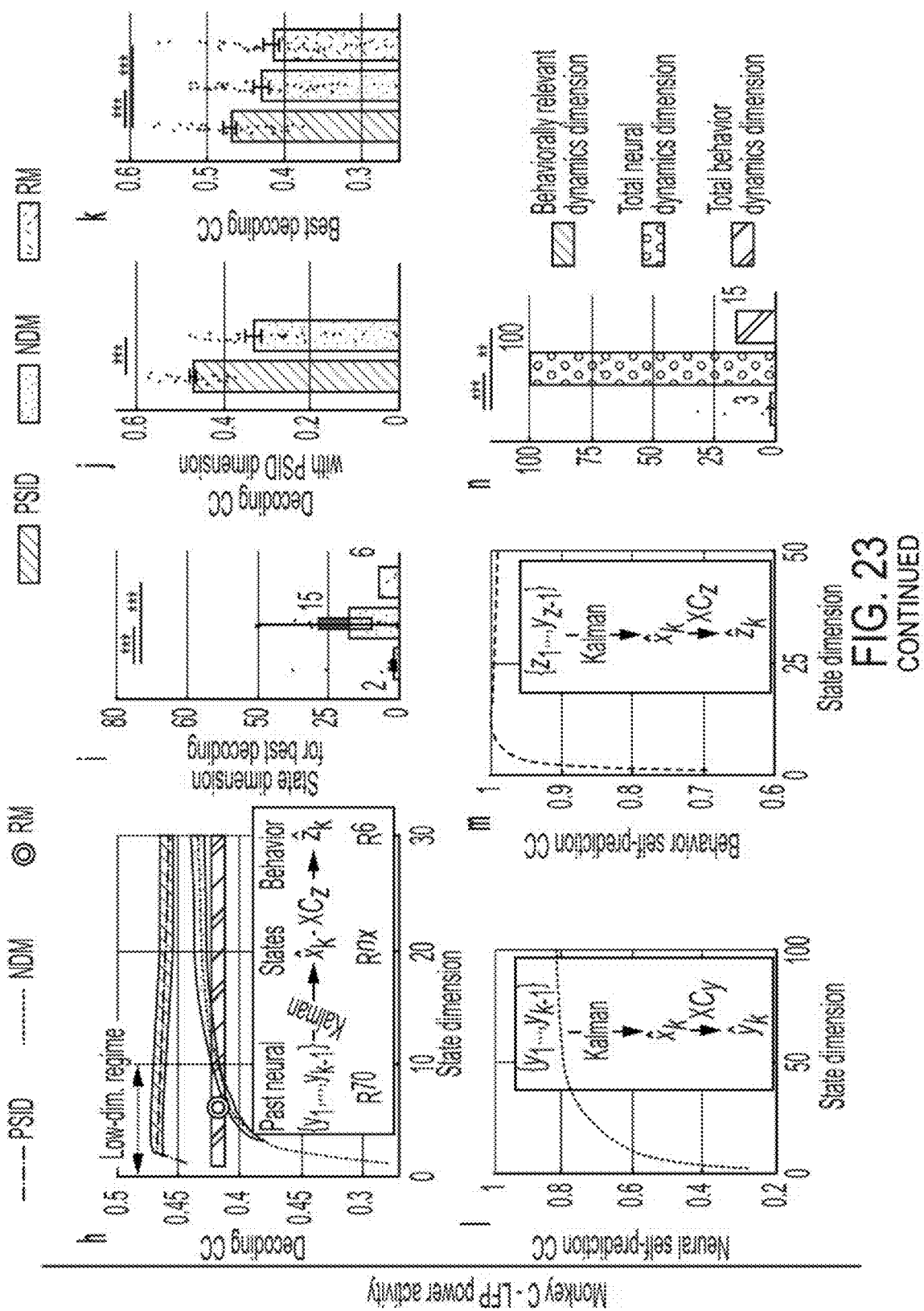
Figure 24:
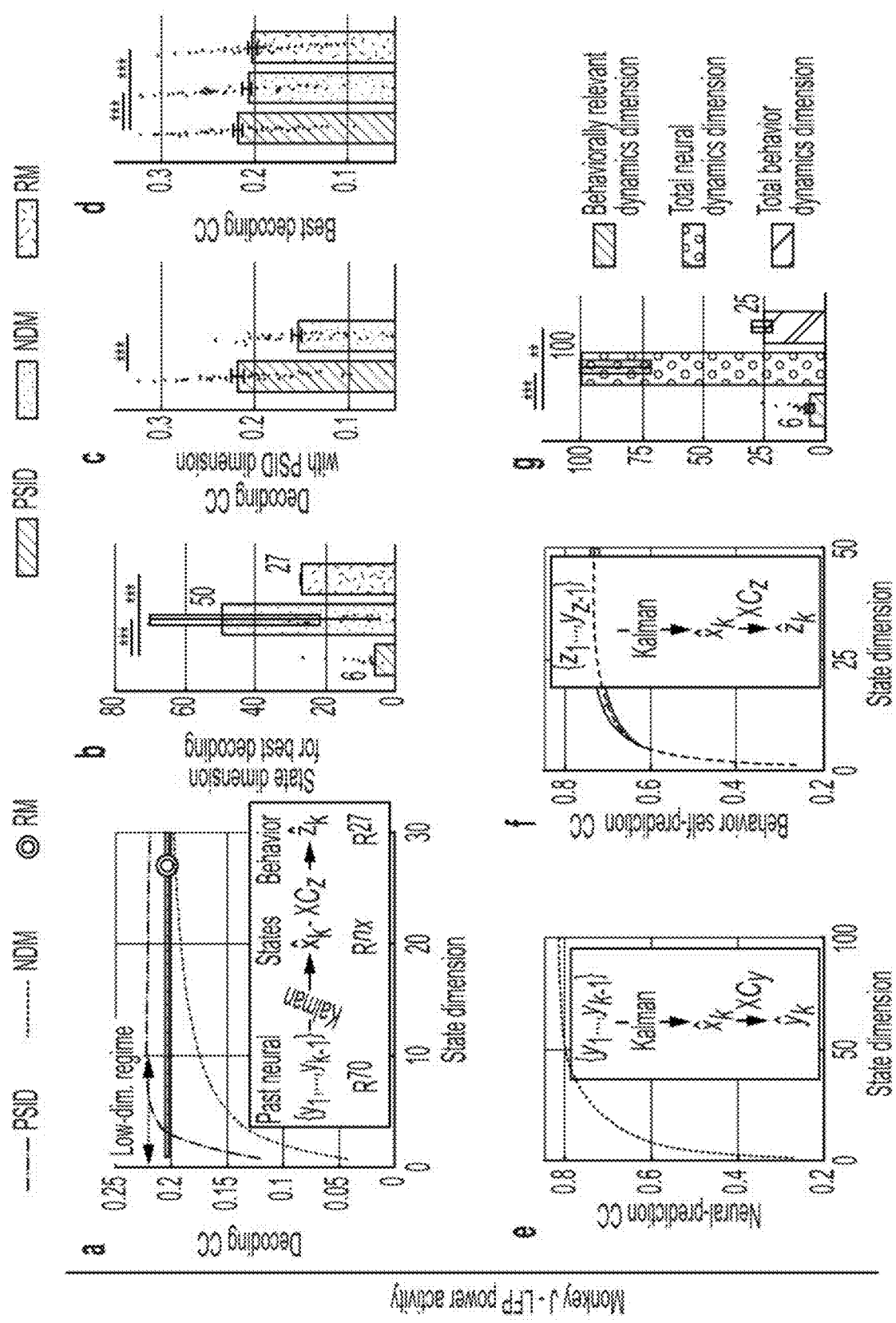
FIG. 24 illustrates that PSID again reveals a markedly lower dimension for behaviorally relevant neural dynamics in the motor cortex LFP activity when behavior is taken as the angular velocity of joint angles instead of the joint angles according to an embodiment of the present invention.
Figure 24:
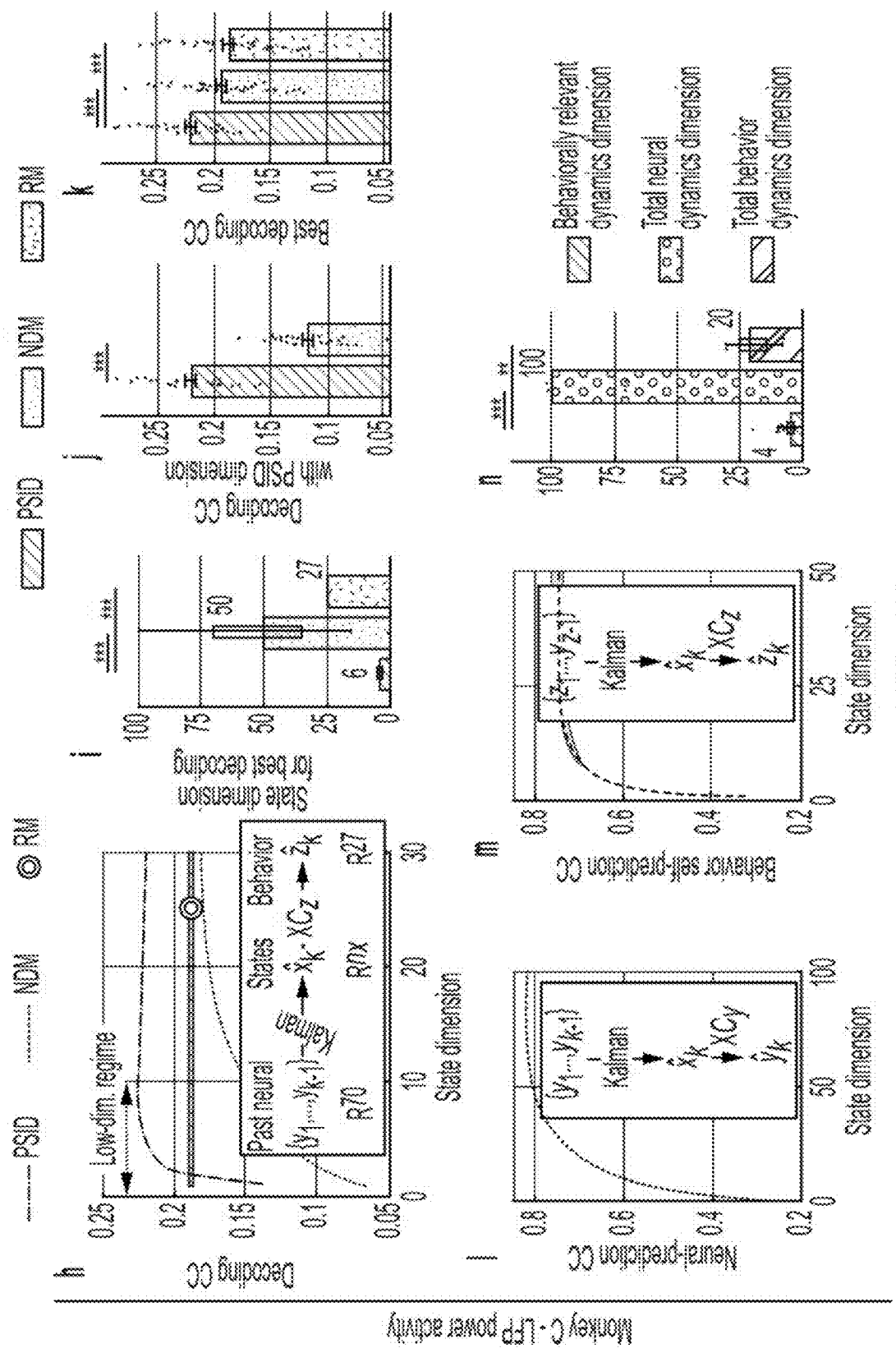
Figure 25:
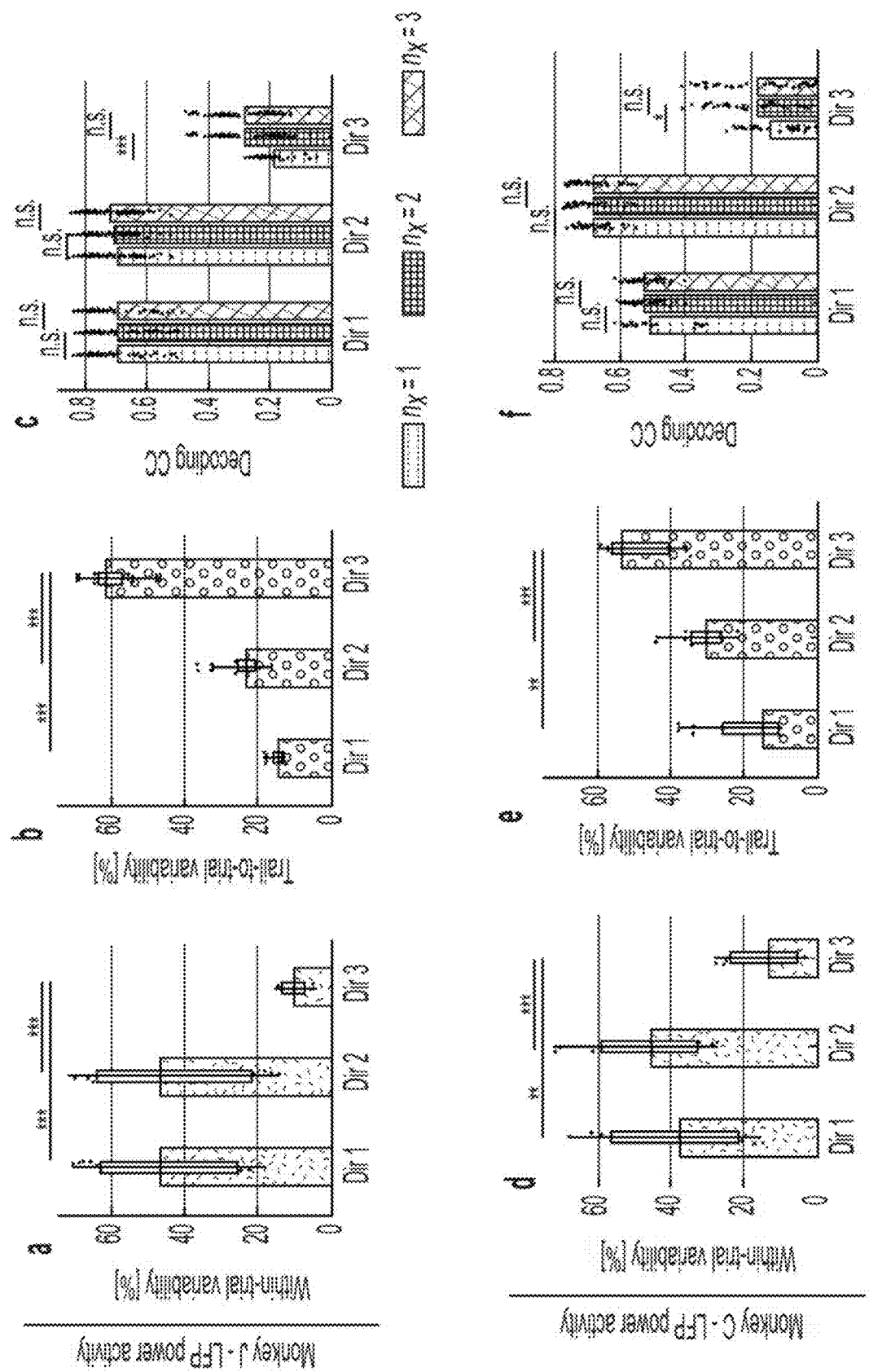
FIG. 25 illustrates PSID-extracted latent states capture both within-trial and trial-to-trial variability in behavior according to an embodiment of the present invention.

Finally, the above conclusions regarding the dimensionality of behaviorally relevant dynamics and decoding accuracy held irrespective of the exact behavioral signal and were replicated both when the angular velocity of joints or the 3D position of hand and elbow were taken as the behavioral signal (FIGS. 23 and 24). Lastly, while PSID does not have an explicit objective to separate within-trial vs. trial-to-trial variability, the latent states learned by PSID captured both within-trial and trial-to-trial variability (FIG. 25).

FIG. 6 illustrates that PSID reveals a markedly lower dimension for behaviorally relevant neural dynamics and extracts them more accurately in motor cortex LFP activity during 3D reach, grasp, and return movements. FIG. 6, a shows average joint angle decoding accuracy, i.e. cross-validated correlation coefficient (CC), as a function of the state dimension using PSID, NDM, and RM. Decoding CC is averaged across the datasets and the shaded area indicates the s.e.m. Dimensionality of neural activity (i.e. 70) and behavior (i.e. 27) are shown in a box along with the decoder structure. The shaded area indicates the relatively low-dimensional regime, which is often the operating regime of interest in dynamic modeling and dimensionality reduction. FIG. 6, b illustrates that the state dimension that achieves the best decoding in each dataset. Bars show the median (also written next to the bar), box edges show the $25^{th}$ and $75^{th}$ percentiles, and whiskers represent the minimum and maximum values (other than outliers). Outliers are the points that are more than 1.5 times the interquartile distance, i.e. the box height, away from the top and bottom of the box. All data points are shown. Asterisks indicate significance of statistical tests with *: P<0.05, : P<0.005, *: P<0.0005, and n.s.: P>0.05. FIG. 6, c shows decoding for each method, when using the same state dimension as PSID (not available for RM since it has a fixed state dimension equal to the behavior dimension). FIG. 6, d shows best decoding CC in each dataset (state dimensions from FIG. 6, b). For decoding, bars show the mean and whiskers show the s.e.m. FIG. 6, e shows one-step-ahead self-prediction of neural activity (cross-validated CC), averaged across datasets. FIG. 6, f shows the same as FIG. 6, e for behavior. FIG. 6, g shows the behaviorally relevant neural dynamics dimension (i.e. PSID result from FIG. 6, b), total neural dynamics dimension (i.e. state dimension from FIG. 6, e), and total behavior dynamics dimension (i.e. state dimension from FIG. 6, f) for all datasets. FIG. 6, h through FIG. 6, n show the same information as FIG. 6, a through FIG. 6, g, for monkey C.

Figure 7:
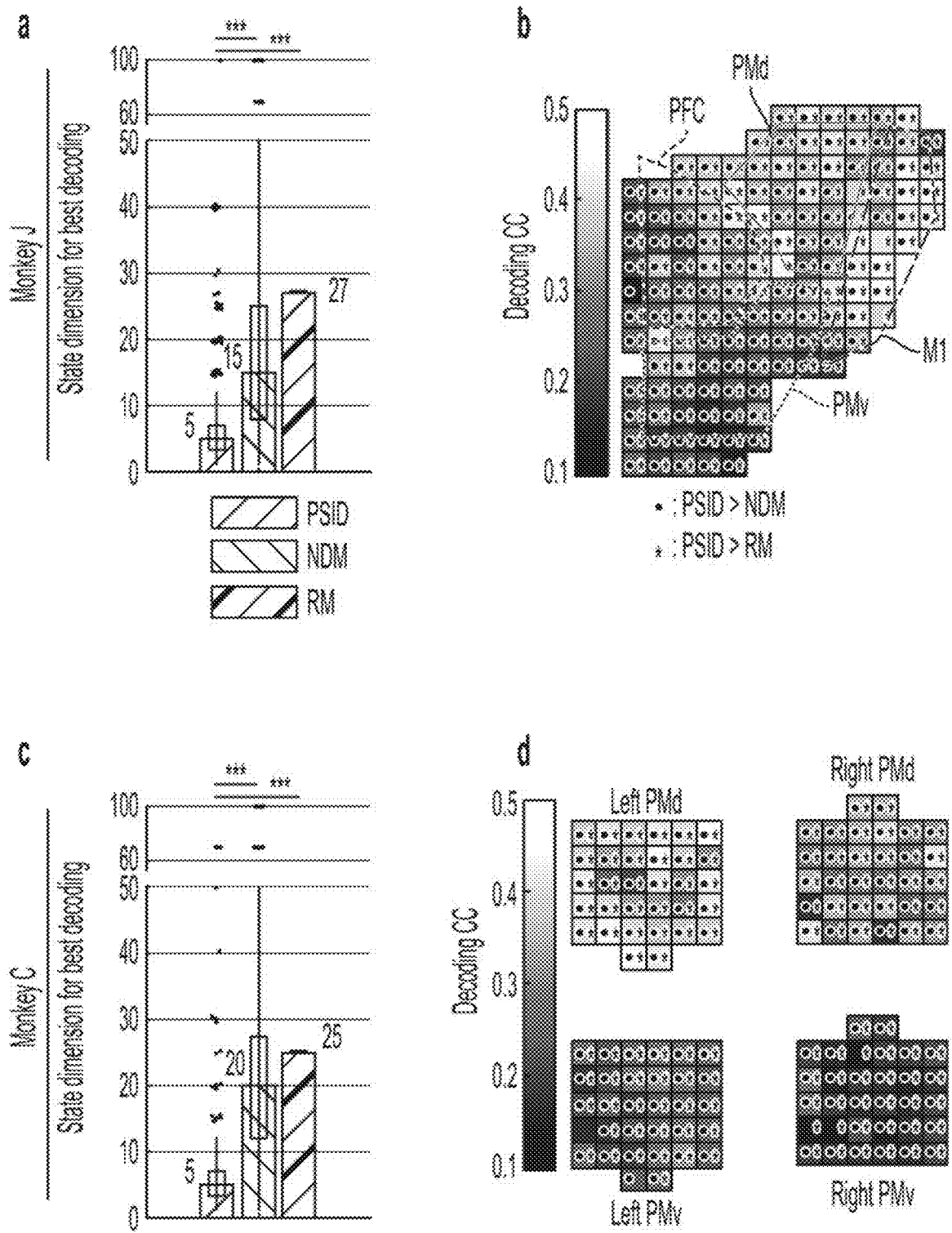
FIG. 7 illustrates that PSID extracts more behaviorally relevant information from each recording channel rather than performing an implicit channel selection by discarding some channels with no behaviorally relevant information according to an embodiment of the present invention.
Figure 26:
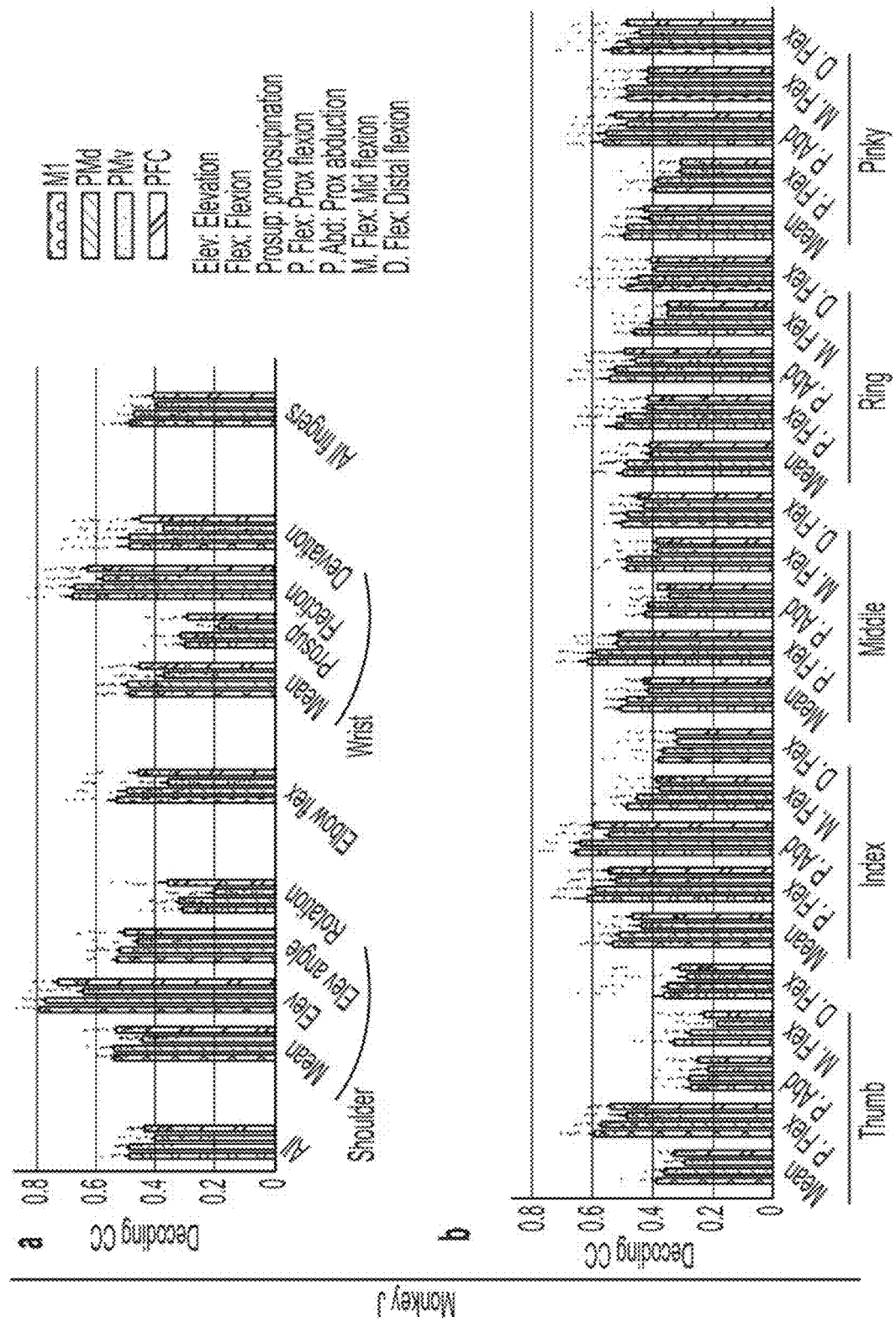
FIG. 26 illustrates that PSID extracts behaviorally relevant information across different brain regions in similar ways for different joints.
Figure 26:
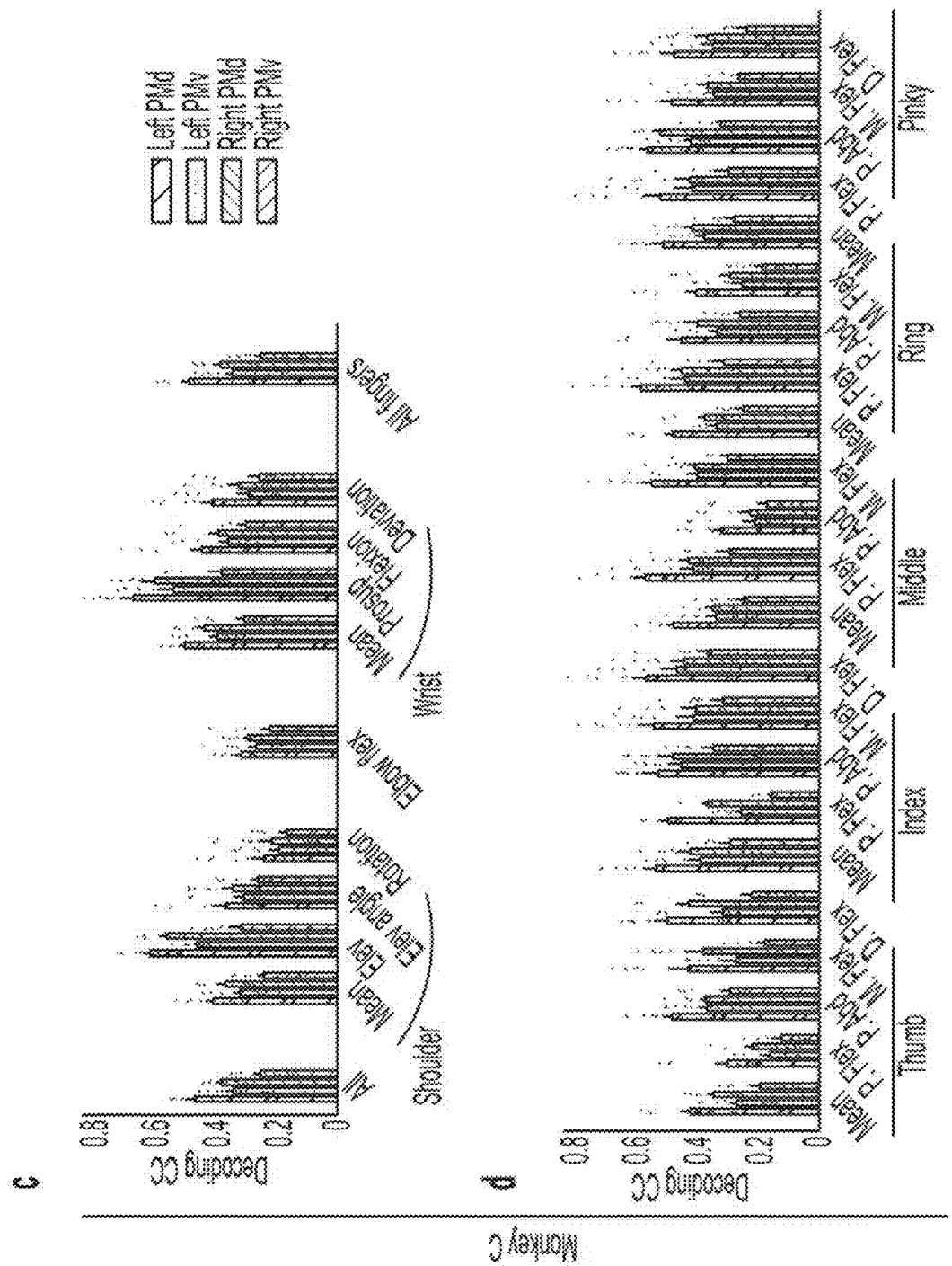

The inventors found that PSID was extracting more behaviorally relevant information from each recording channel rather than performing an implicit channel selection by discarding some channels with no behaviorally relevant information (FIG. 7). For both monkeys and when modeling channels separately, PSID achieved significantly better decoding of behavior in at least 96% and 98% of individual channels compared with NDM and RM, respectively (FIG. 7, b, d; P<0.05 for each channel; one-sided signed-rank; $N_s \geq 20$) while using significantly lower state dimensions than NDM and RM (FIG. 7, a, c; $P<10^{-68}$; one-sided signed-rank; $N_s \geq 512$). These results suggest that almost all channels contained behaviorally relevant dynamics and PSID could more accurately model these dynamics. Finally, the inventors modeled groups of channels within each anatomical region using PSID separately and quantified the decoding accuracy for each individual joint (FIG. 26). Across the joints, regions were predictive in the following order: M1>PMd>PFC>PMv (monkey J; $P<10^{-3}$; one-sided signed-rank; $N_s=27$) and L PMd>R PMd>L PMv>R PMv (monkey C; $P<10^{-4}$; one-sided signed-rank; $N_s=25$). Interestingly, the ipsilateral (i.e. right) areas in monkey C were predictive, with ipsilateral PMd being more predictive than the contralateral PMv.

FIG. 7, a shows the state dimension used by each method to achieve the best decoding using the neural features from each recoding channel separately. For PSID and NDM, for each channel, the latent state dimension is chosen to be the smallest value for which the decoding CC reaches within 1 s.e.m. of the best decoding CC using that channel among all latent state dimensions. Bars, boxes and asterisks are defined as in FIG. 6, b. FIG. 7, b shows cross-validated correlation coefficient (CC) between the decoded and true joint angles for PSID. Asterisks and circles mark channels for which PSID results in significantly (P<0.05) better decoding compared with NDM (circles) or RM (asterisks). The latent state dimension for each method is chosen as in FIG. 7, a. FIG. 7, c and FIG. 7, d show the same as FIG. 7, a and FIG. 7, b, for monkey C.

Reducing the dimension of neural population activity and finding its low-dimensional representation are essential for visualizing and characterizing the relationship of neural dynamics to behavior. The inventors hypothesized that PSID would be also particularly beneficial for doing this dimensionality reduction and visualization compared with standard NDM methods, because PSID can prioritize and directly dissociate the behaviorally relevant neural dynamics. To test this hypothesis, the inventors used PSID and NDM to extract a 2D representation of neural dynamics (FIG. 8), which is commonly done to visualize neural dynamics on planes and is a special case of what is shown in FIG. 6, a, h for any dynamics dimension. Using both PSID and NDM, the inventors fitted models with 2D latent states in the training set and then plotted the two extracted latent states from neural activity in the test set against each other during reach and return movement epochs (FIG. 8, a, b, d, e).

In both monkeys, both PSID and NDM extracted neural states from LFP power activity that exhibited rotational dynamics. However, surprisingly, a clear difference emerged in the properties of rotations uncovered by PSID compared with NDM. During the return epochs, the 2D neural dynamics extracted using PSID showed a rotation in the opposite direction of the rotation during the reach epochs (FIG. 8, a, d). In contrast, similar to neural rotations extracted in prior works using PCA or using NDM, neural dynamics extracted using NDM showed a rotation in the same direction during both reach and return epochs (FIG. 8, b, e). As the behavior involves opposite directions of movement during reach and return epochs, these results intuitively suggest that PSID finds a low-dimensional mapping of neural population activity that is more behaviorally relevant. Indeed, this suggestion was confirmed quantitatively since the 2D latent states extracted using PSID explained the behavior significantly better than those extracted using NDM and led to significantly better decoding (FIG. 8, c, f; $P<10^{-9}$; one-sided signed-rank; $N_s \geq 48$). Moreover, even when the inventors used support vector regression (SVR) to learn nonlinear mappings from the extracted latent states to behavior, PSID-extracted states still achieved significantly more accurate decoding than NDM-extracted states (FIG. 27; $P<10^{-9}$; one-sided signed-rank; $N_s \geq 48$). Thus, while both types of rotational dynamics depicted in FIG. 8 existed in the high-dimensional manifold traversed by the neural activity, PSID extracted a low-dimensional 2D mapping or dynamic projection (i.e. a projection that aggregates information over time) that preserved the more behaviorally relevant neural dynamics. These results suggest that PSID can reveal low-dimensional behaviorally relevant neural dynamics that may otherwise be missed when using standard NDM methods.

Figure 28:
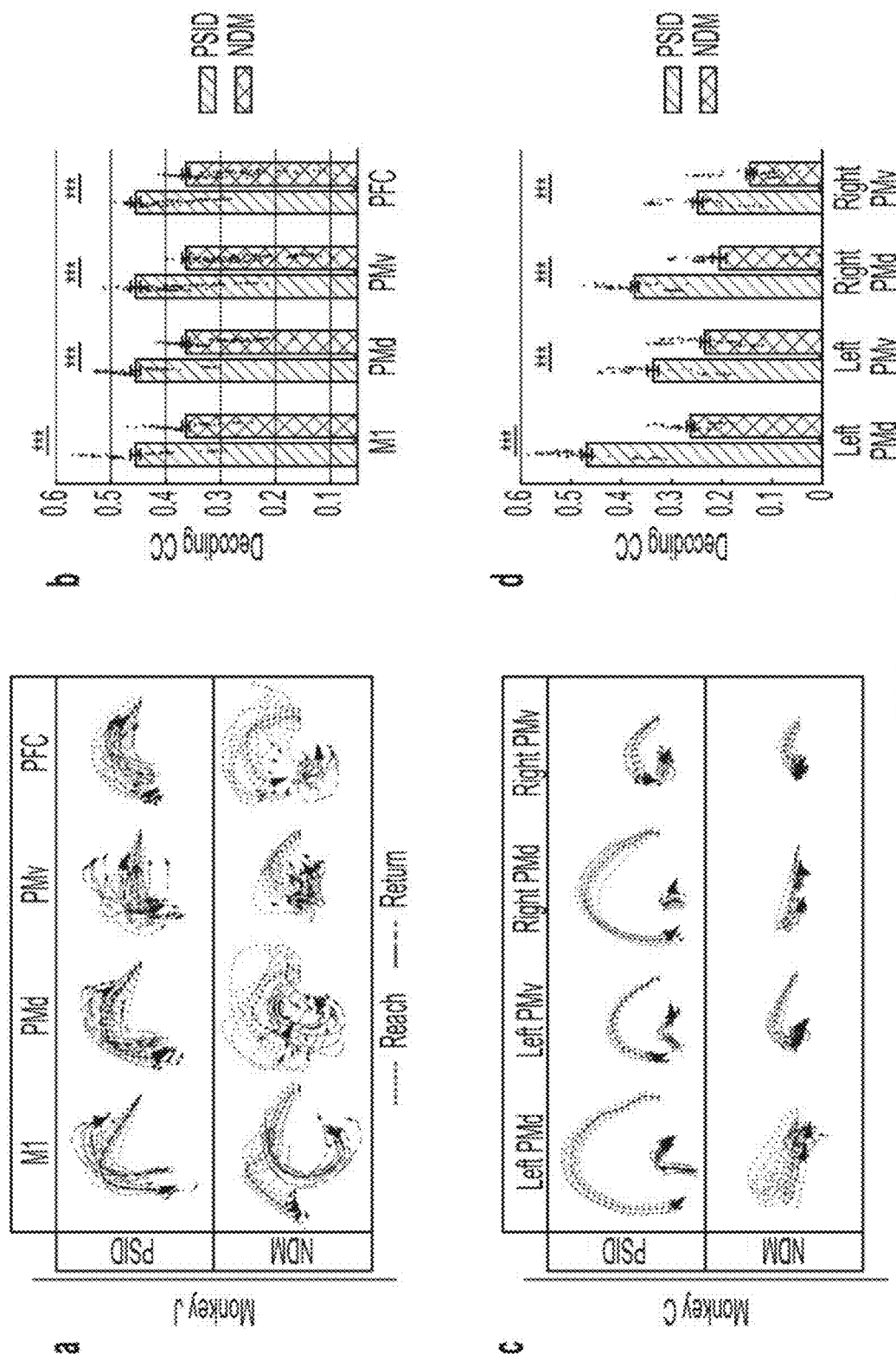
FIG. 28 illustrates that extraction of bidirectional rotational dynamics using PSID was robust to brain region and held also when modeling neural activity within different cortical regions separately according to an embodiment of the present invention.
Figure 29:
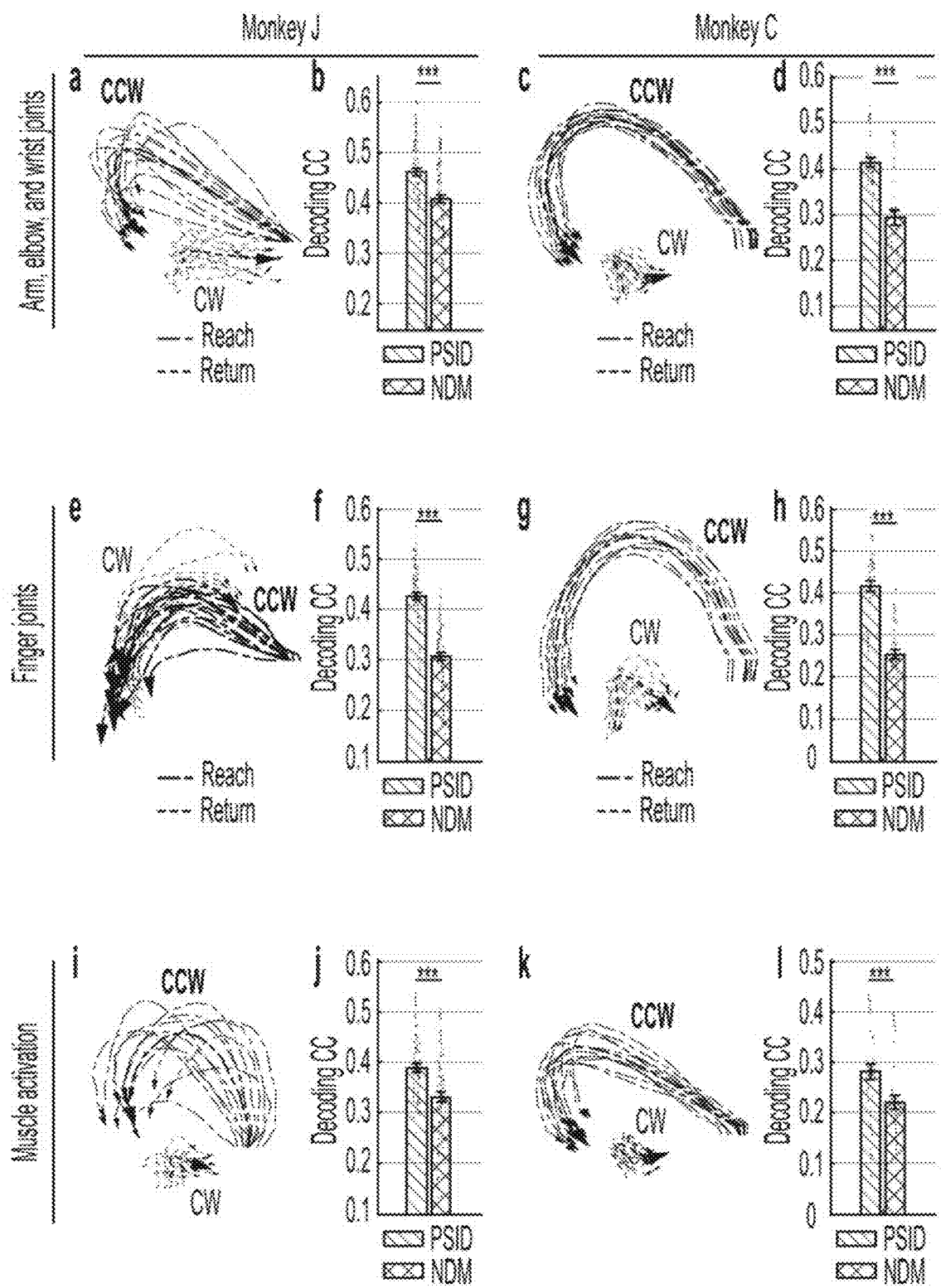
FIG. 29 illustrates that extraction of bidirectional rotational dynamics using PSID was robust to behavioral signals and held also when modeling different subsets of joints and simulated muscle activations according to an embodiment of the present invention.
Figure 30:
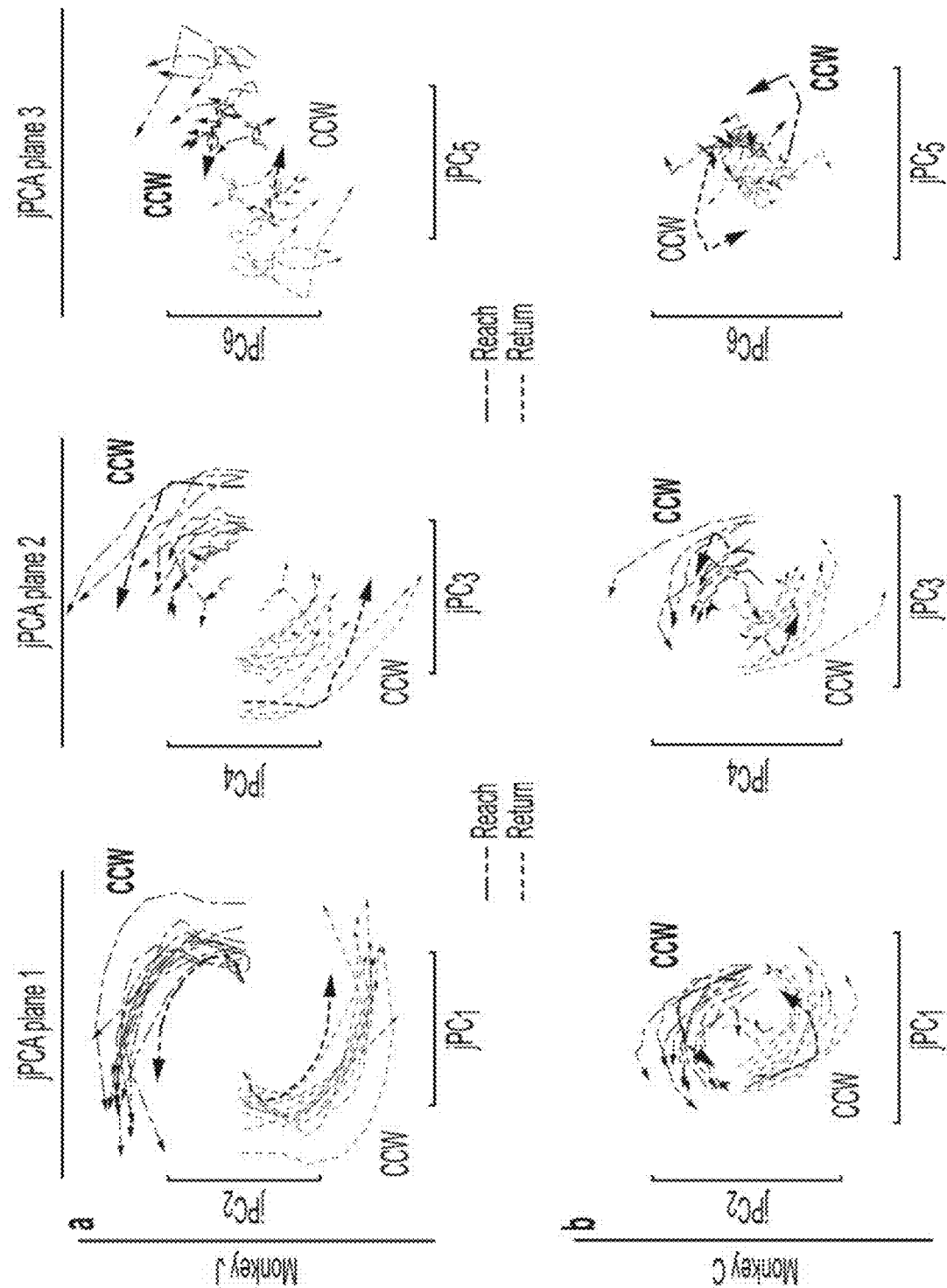
FIG. 30 illustrates that similar to NDM, jPCA extracts rotations that are in the same direction during reach and return epochs according to an embodiment of the present invention.

These distinct rotational patterns also appeared in different anatomical regions separately (FIG. 28) and when the behavior signal was taken to be different subsets of arm-hand joints or the inferred muscle activations in the arm (FIG. 29). This result again suggests that PSID more accurately explains the encoding of various relevant behavioral signals within the task. Finally, in two additional analyses, the inventors found that (i) NDM with EM instead of SID, and (ii) jPCA also extracted rotations similar to NDM that did not change direction during reach and return (FIG. 30). The inventors emphasize that beyond the above 2D results for visualization, the advantage of PSID over NDM when performing dimensionality reduction held across all dimensions (FIG. 6, a, h). Thus, PSID could be used as a general dynamic dimensionality reduction method that preferentially preserves the most behaviorally relevant dynamics unlike NDM.

Figure 8:
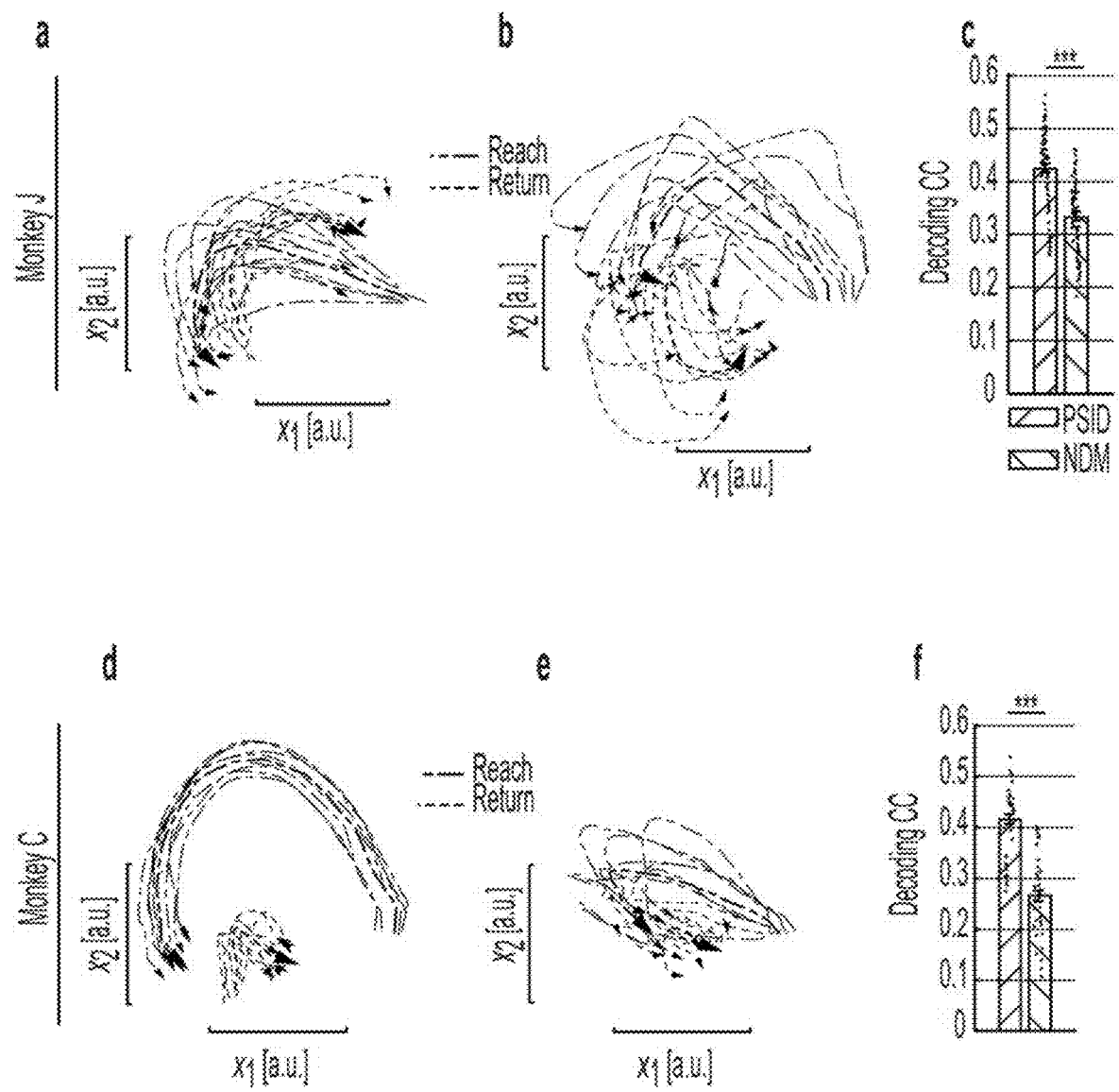
FIG. 8 illustrates that PSID reveals rotational neural dynamics with opposite direction during 3D reach and return movements, which is not found by conventional methods according to an embodiment of the present invention.

FIG. 8 shows that PSID reveals rotational neural dynamics with opposite direction during 3D reach and return movements, which is not found by conventional methods. FIG. 8, a shows the latent neural state dynamics during 3D reach and return movements found by PSID with 2D latent states ($n_x=n_1=2$). The disclosure plots the states starting at the beginning of a reach/return movement epoch; the arrows mark the end of the movement epoch. Light lines show the average trace over trials in each dataset and dark lines show the overall average trace across datasets. The direction of rotation is noted by CW for clockwise or CCW for counterclockwise. States have arbitrary units (a.u.). FIG. 8, b uses NDM with 2D latent states ($n_x=2$). FIG. 8, c shows cross-validated correlation coefficient (CC) between the decoded and true joint angles, decoded with the latent states extracted using PSID and NDM. Bars, whiskers and asterisks are defined as in FIG. 6, c. FIG. 8, d through FIG. 8, f show the same as FIG. 8, a through FIG. 8, c for monkey C. Decoding accuracy using the PSID-extracted 2D states was only 7% (Monkey J) or 4% (Monkey C) worse than the best PSID decoding whereas decoding accuracy using NDM-extracted 2D states was 23% (Monkey J) or 30% (Monkey C) worse than the best NDM decoding (FIG. 6, a, h).

Figure 9:
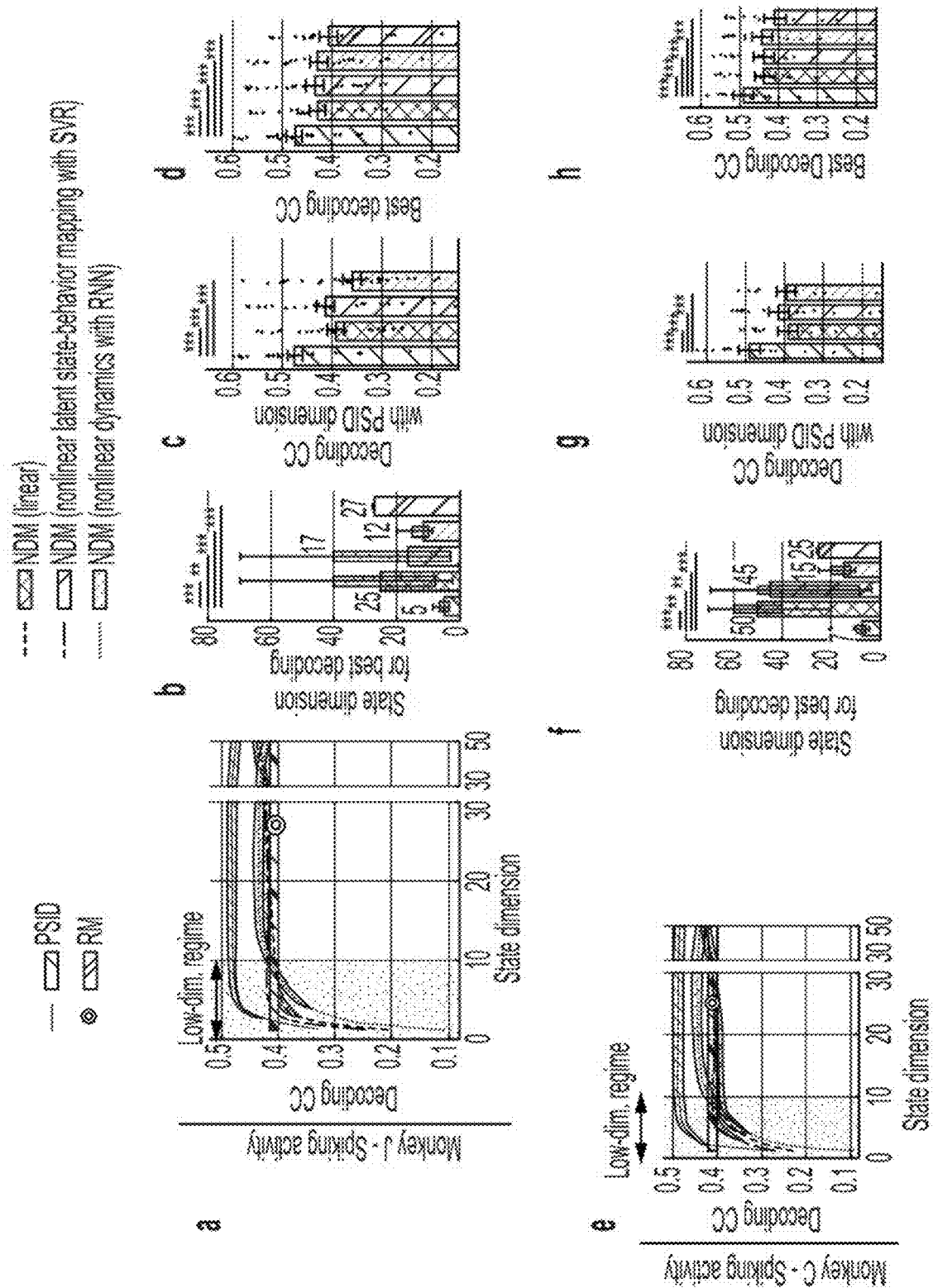
FIG. 9 illustrates that PSID reveals a markedly lower dimension for behaviorally relevant neural dynamics and extracts them more accurately in motor cortex population spiking activity according to an embodiment of the present invention.
Figure 31:
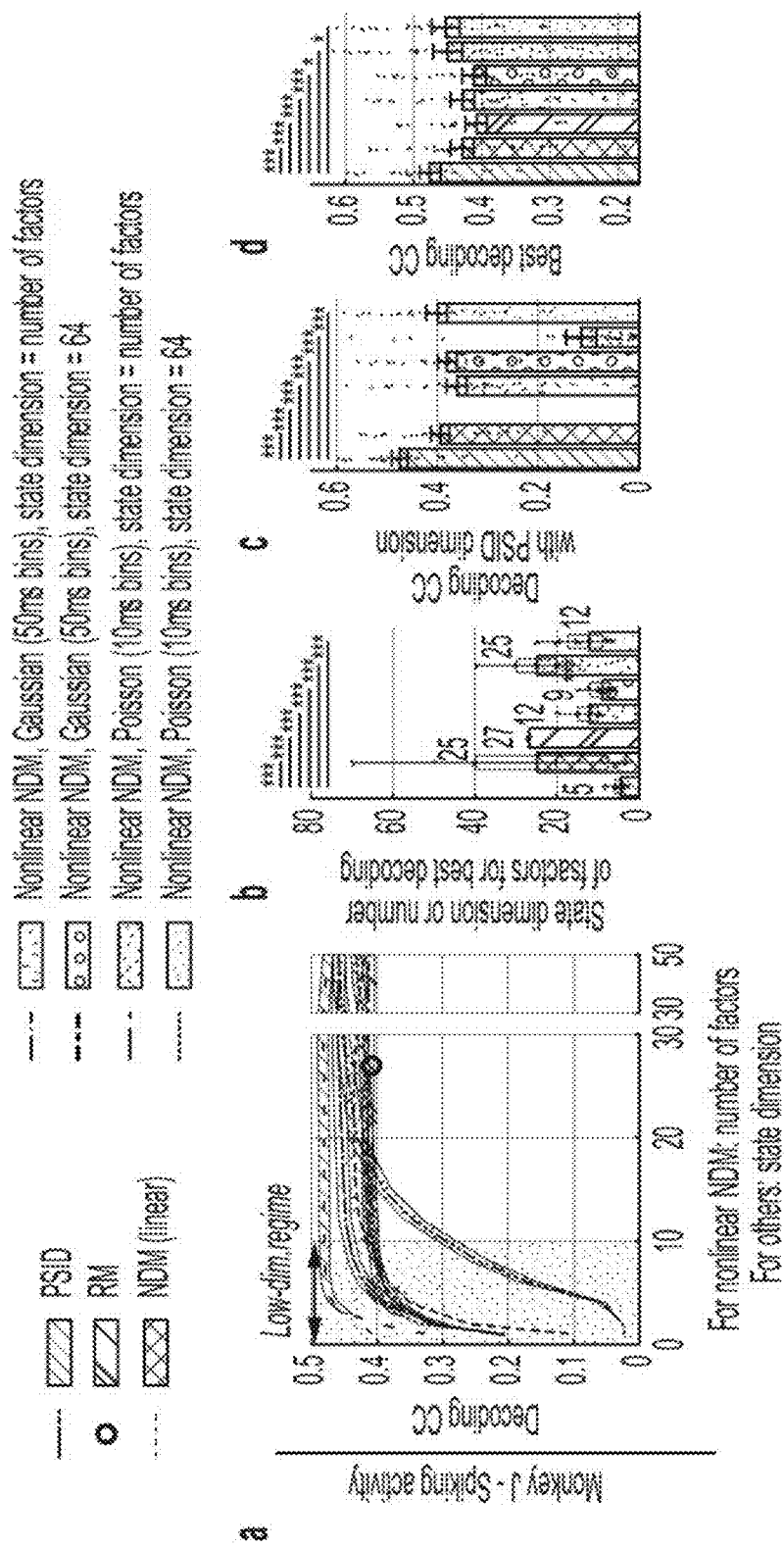
FIG. 31 illustrates that PSID again achieved better decoding using lower-dimensional latent states when RNN-based nonlinear NDM always used a dynamical latent state with much higher dimension of 64 and/or when RNN-based nonlinear NDM used a Poisson observation model with a faster time step according to an embodiment of the present invention.
Figure 31:
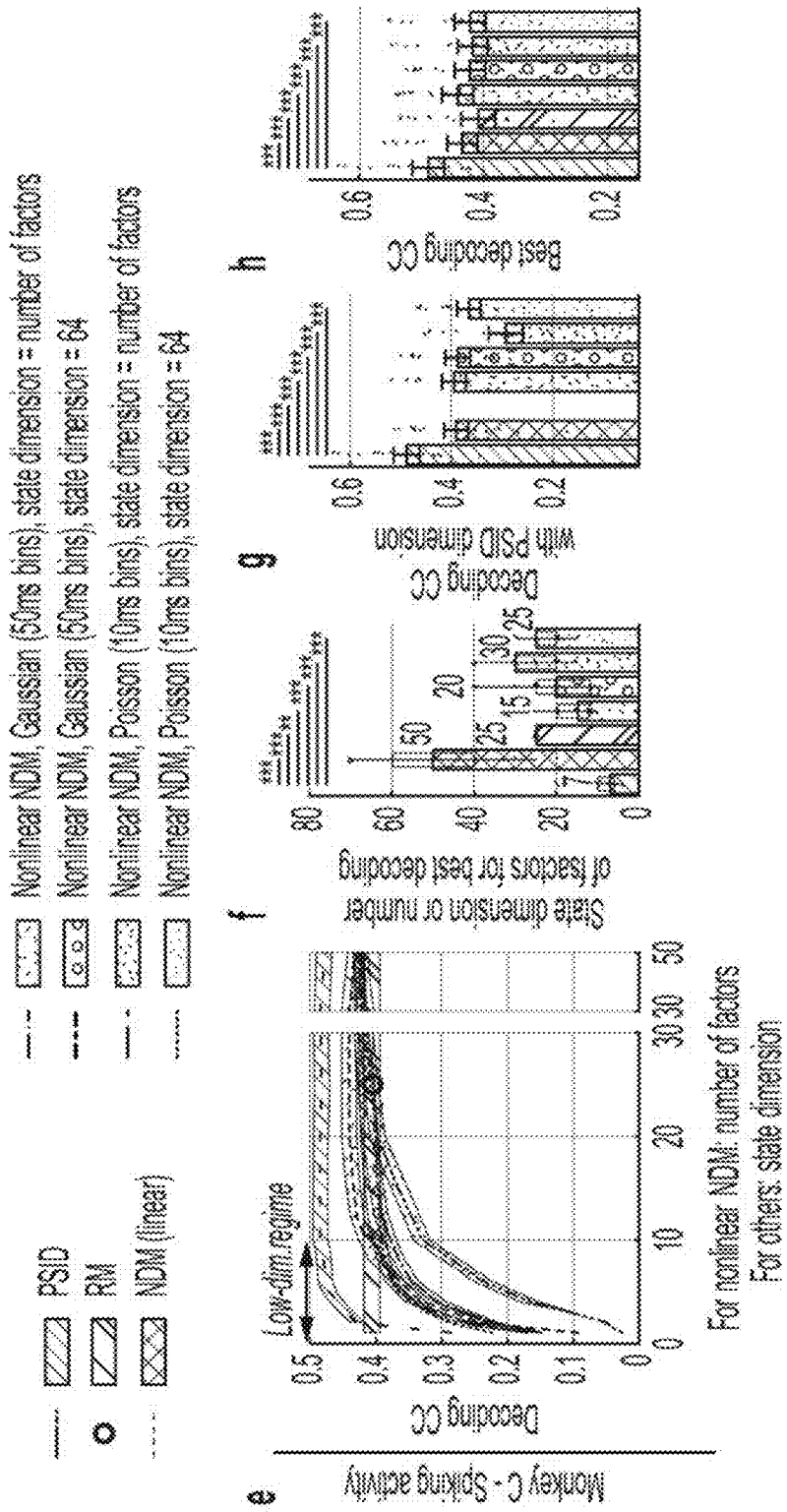

The inventors also applied PSID to existing datasets consisting of multi-unit spiking activity recorded during the same 3D reach, grasp and return task by taking neural activity $y_k$ from Equation 1 to represent the spike counts in consecutive time bins (FIG. 16, b). The results reported earlier for LFP activity generalized to spiking activity (FIG. 9). To demonstrate that PSID benefits in modeling behaviorally relevant dynamics stem from its consideration of behavior during learning and its novel two-stage learning approach irrespective of model structure, the inventors also compared the results with example nonlinear NDM methods. These nonlinear NDMs, similar to linear NDM, model neural dynamics regardless of their relevance to behavior. As the first example nonlinear NDM, the inventors used the model from linear NDM, and used SVR to learn nonlinear mappings from the latent states to behavior. As the second example nonlinear NDM, the inventors used a method based on RNNs termed latent factor analysis via dynamical systems (LFADS), which was recently applied successfully to spiking activity. In both monkeys, PSID revealed the behaviorally relevant dynamics in spiking activity to be markedly lower-dimensional than what was implied by RM and NDM, whether linear or nonlinear (FIG. 9, b, f; P<0.004; one-sided signed-rank; $N_s \geq 16$). Moreover, PSID learned these behaviorally relevant dynamics more accurately both compared to linear or nonlinear NDM with the same dimension (FIG. 9, a, c, e, g; P<0.0003; one-sided signed-rank; $N_s \geq 16$), and even compared with linear or nonlinear NDM and RM with much higher-dimensional states than PSID (FIG. 9, d, h; P<0.0005; one-sided signed-rank; $N_s \geq 16$). These results also held if instead of CC, explained variance was used (P<0.006; one-sided signed-rank; $N_s \geq 16$). Similar results held when the inventors allowed the RNN-based nonlinear NDM to use a Poisson process observation model with faster time steps compared with PSID and/or to always use much higher-dimensional latent states (FIG. 31).

FIG. 9 shows that PSID reveals a markedly lower dimension for behaviorally relevant neural dynamics and extracts them more accurately in existing datasets consisting of motor cortex population spiking activity. The convention for FIG. 9 is the same as for FIG. 6, a through FIG. 6, d. To show that the PSID advantage stems from its novel two-stage learning algorithm that considers behavior and thus holds regardless of NDM model structure, results are also shown for comparison with two example nonlinear NDM methods: 1) linear NDM with nonlinear SVR mapping from latent state to behavior, 2) RNN-based NDM with nonlinear dynamics using a method termed LFADS. Similar results held for several additional configurations of the RNN-based nonlinear NDM method as provided in FIG. 31.

Figure 32:
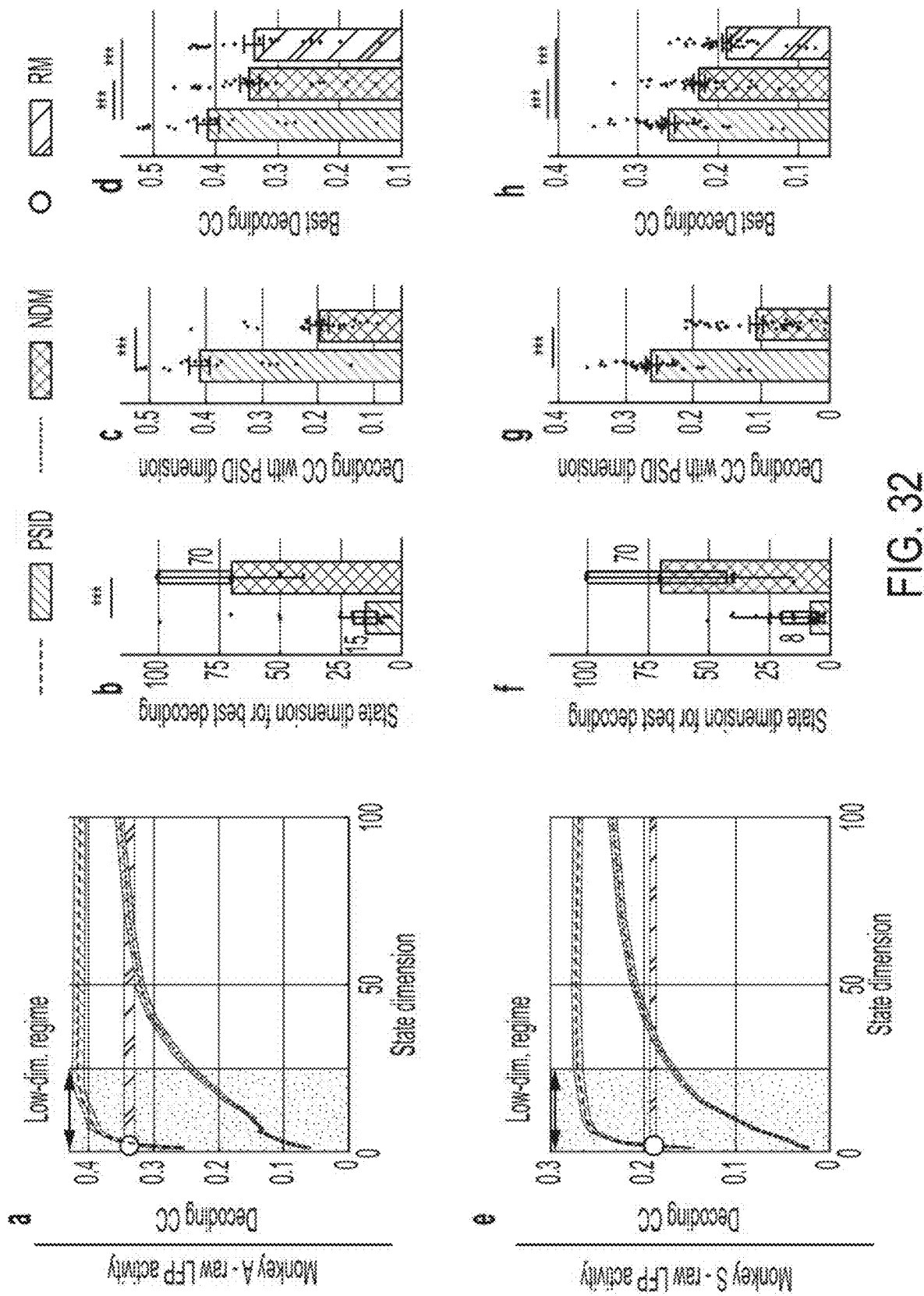
FIG. 32 illustrates that PSID reveals low-dimensional behaviorally relevant dynamics in existing data consisting of prefrontal raw LFP activity during a task with saccadic eye movements according to an embodiment of the present invention.

The inventors found that PSID had general utility for different behavioral tasks, neural signal types, and brain regions. The inventors applied PSID to another existing dataset consisting of PFC neural activity recorded in a second experiment in which two monkeys performed saccadic eye movements (FIG. 32). Here, the inventors modeled the raw LFP and took the 2D eye position as the behavioral signal. Compared with standard NDM, PSID revealed a markedly lower-dimensional latent representation (8-15 vs. 70) for behaviorally relevant dynamics (FIG. 32, b, f; $P<10^{-5}$; one-sided signed-rank; $N_s \geq 27$) and more accurately learned these dynamics both at the same dimension (FIG. 32, c, g; $P<10^{-5}$; one-sided signed-rank; $N_s \geq 27$) and even when NDM used much higher-dimensional latent states (FIG. 32, d, h; $P<10^{-5}$; one-sided signed-rank; $N_s \geq 27$). Finally, because the RM dimension is equal to the behavior dimension, here RM extracted a 2D state that resulted in significantly worse decoding of behavior (FIG. 32, d, h; $P<10^{-5}$; one-sided signed-rank; $N_s \geq 27$).

Figure 10:
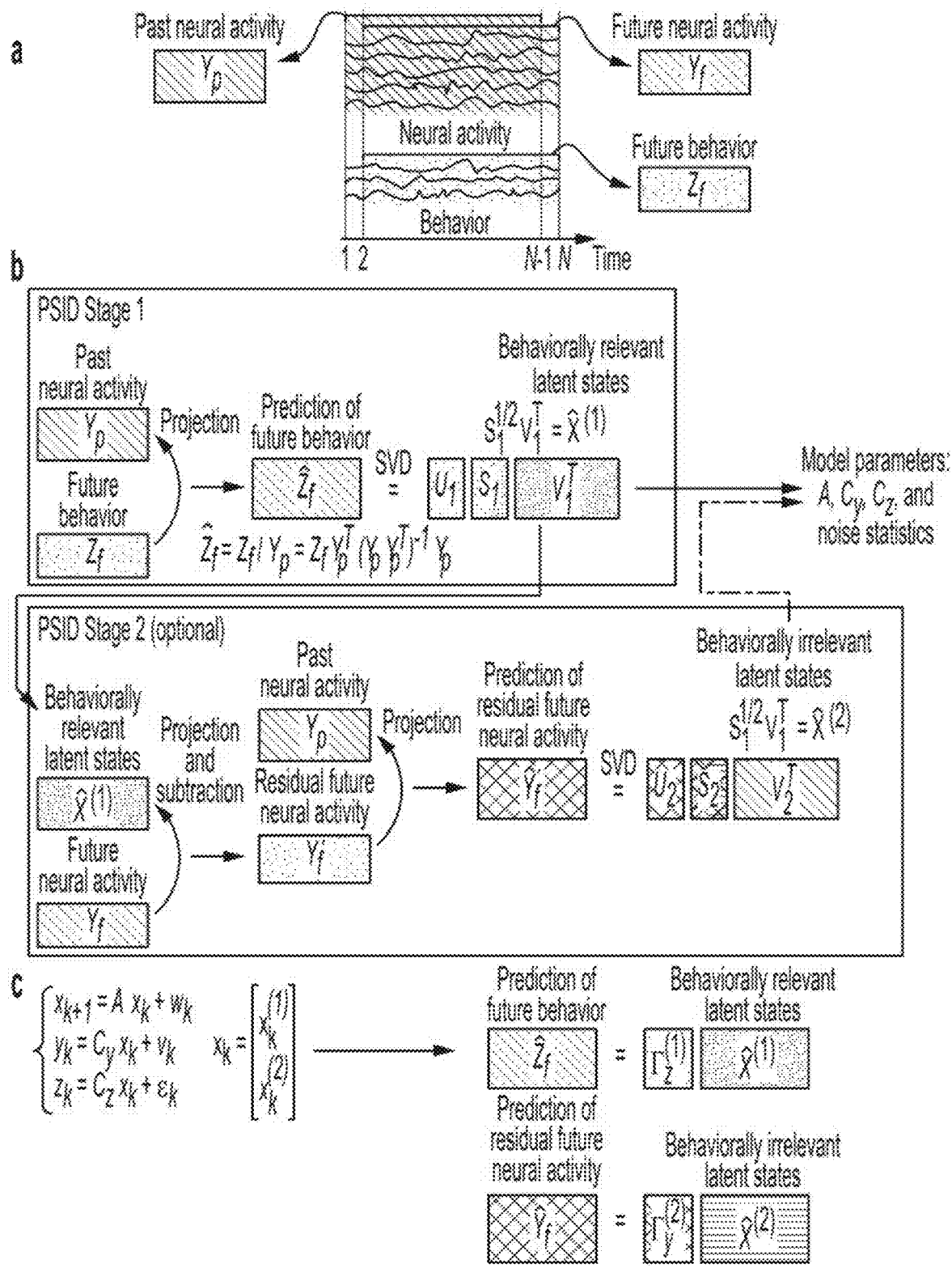
FIG. 10 illustrates another visualization of the PSID algorithm according to an embodiment of the present invention.

This disclosure outlines PSID, a novel algorithm for dissociating and modeling shared dynamics between different signal sources such as neural activity and behavior in which case it dissociates and models behaviorally relevant neural dynamics. A key idea is to ensure behaviorally relevant dynamics are not missed or confounded by considering both behavior and neural activity during learning using a novel two-stage algorithm: the first stage exclusively learns behaviorally relevant dynamics and the optional second stage learns any remaining dynamics (FIG. 10). Prior NDM methods with linear dynamics, generalized linear dynamic systems (GLDS), or nonlinear dynamics, are all agnostic to behavior in learning the dynamics. Thus, PSID can uniquely uncover behaviorally relevant dynamics that may otherwise be discarded, as evidenced both by its better decoding at any state dimension (FIGS. 6 and 9) and its discovery of distinct reversed rotational dynamics during return epochs in our motor task (FIG. 8).

Prior work has reported low-dimensional rotational neural dynamics during different motor tasks, often involving 2D control of a cursor. Interestingly, in the 3D task discussed herein, NDM and jPCA extracted rotations but in the same direction during reach and return epochs similar to prior work with a center-out 2D cursor control task; in contrast, PSID extracted rotations in opposite directions. Critically, the PSID rotations were significantly more predictive of behavior, demonstrating that while both types of rotational dynamics existed in high-dimensional neural activity, PSID uniquely revealed those that were more behaviorally relevant. Future application of PSID to other tasks and brain regions may similarly reveal behaviorally relevant features of neural dynamics that may otherwise go unnoticed.

Motor cortical activity strongly encodes movement, thus enabling motor brain machine interfaces (BMIs). Given this strong encoding, both RM, which models behavior dynamics agnostic to neural activity, and NDM, which models neural dynamics agnostic to behavior, have been successful in decoding movement. Nevertheless, PSID still significantly outperformed these methods in motor decoding and did so using markedly smaller latent state dimensions (FIGS. 6 and 9). Many brain functions such as memory and mood or brain dysfunctions such as epileptic seizures could have a more distributed or less targetable representation in neural activity. Using PSID in such applications may prove even more beneficial since the activity likely contains more behaviorally irrelevant dynamics.

PSID is also a dimensionally reduction method that is dynamic, i.e. models the temporal structure in neural activity (Equation 1), and thus can aggregate information over time to optimally extract low-dimensional representations of neural activity that preserve behaviorally relevant dynamics. PSID can do this because+unlike prior dynamic dimensionality reduction methods such as Gaussian process factor analysis (GPFA), LFADS, and SSM—PSID takes behavior into account during learning to ensure behaviorally relevant neural dynamics are not lost. As such, PSID can benefit studies that investigate neural mechanisms underlying a behavior of interest. For example, prior works have reported that variables with 10-30 dimensions can sufficiently explain motor cortical activity using various dimensionality reduction methods including PCA, GPFA, LFADS, and SSM. However, unlike PSID, these methods did not aim to explicitly dissociate the behaviorally relevant parts of neural dynamics. Here, PSID revealed a dimension of around 4-7 for behaviorally relevant neural dynamics, which was significantly lower than the dimension of 12-50 implied here by other linear, nonlinear, dynamic and non-dynamic dimension reduction methods while also being more predictive of behavior (FIGS. 6, 9, and 19). These results demonstrate the utility of PSID for accurately estimating the dimensionality of behaviorally relevant neural dynamics, which is a fundamental sought-after question across neuroscience.

For datasets with discrete classes of behavioral conditions, several non-dynamic dimensionality reduction methods such as linear discriminant analysis (LDA) and demixed principal component analysis (dPCA) can find low dimensional projections of neural activity that are suitable for dissociating those classes. However, unlike PSID, these methods are not applicable to continuous behavioral measurements such as movements and are not dynamic. For continuous behavioral variables, several non-dynamic methods such as reduced rank regression, partial least squares regression, targeted dimensionality reduction and canonical correlation analysis can build linear projections of one signal to another, for example to find the linear subspace of largest covariations between neural activity in two cortical areas, termed communication subspace. However, being non-dynamic, these methods do not model the temporal patterns of neural activity or aggregate information over time in recovering the dynamics or in decoding, which are important especially in studying temporally structured behaviors such as movements or speech. Thus, PSID uniquely enables extraction of behaviorally relevant low-dimensional representations for neural activity by being dynamic and applicable to continuous behaviors.

PSID may also enhance future neurotechnologies such as BMIs and closed-loop deep brain stimulation systems in decoding and modulating behaviorally relevant brain states —especially those encoded across distributed brain networks that are likely involved in various functions and thus exhibit more behaviorally irrelevant dynamics. Further, PSID achieved maximal decoding accuracy using markedly lower-dimensional states. As controllers designed for models with lower-dimensional states are generally more robust, PSID can significantly benefit developing model-based controllers to modulate various brain functions with electrical or optogenetic stimulation. Moreover, PSID not only is computationally efficient in learning the model, but also has a decoder based on a Kalman filter and can process neural activity causally and efficiently. These capabilities are essential for real-time closed-loop applications. Finally, developing adaptive learning methods that track changes in behaviorally relevant dynamics, for example due to learning or stimulation-induced plasticity, and can appropriately select the adaptation learning rate are important future directions.

In short, the novel PSID modeling algorithm introduced herein can advance understanding of how behaviorally observable brain functions are encoded in neural activity across broad tasks and brain regions. Also, PSID may prove to be particularly beneficial for studying distributed brain functions such as those involved in emotion, memory, and social behaviors.

Discussion will now turn to specific methods for implementing PSID. The first part of the present disclosure utilizes a linear state space dynamic model to describe the temporal evolution of neural activity and behavior as follows in Equation 2:

$$\begin{cases} x^s_{k+1} = A x^s_k + w_k \\ y_k = C_y x^s_k + v_k \\ z_k = C_z x^s_k + \epsilon_k \end{cases} \quad \text{Equation 2}$$

In Equation 2, k specifies the time index, $y_k \in \mathbb{R}^{n_y}$ is the recorded neural activity, $z_k \in \mathbb{R}^{n_z}$ is the behavior (e.g., movement kinematics), and $x^s_k \in \mathbb{R}^{n_x}$ is the latent dynamic state variable that drives the recorded neural activity $y_k$ and can also drive the behavior $z_k$. As shown herein, with a change of basis, Equation 2 can be written in an equivalent form that separates the behaviorally relevant and irrelevant components of $x^s_k$, as written in Equation 1 and more explicitly below in Equation 4. $\epsilon_k \in \mathbb{R}^{n_z}$ is a random process representing the dynamics in behavior that are not present in the recorded neural activity, and $w_k \in \mathbb{R}^{n_x}$, $v_k \in \mathbb{R}^{n_y}$ are zero-mean white noises that are independent of $x^s_k$, i.e. $E\{x^s_k w_k^T\}=0$ and $E\{x^s_k v_k^T\}=0$ with the following cross-correlations shown in Equation. 3:

$$E\left\{\begin{bmatrix} w_k \\ v_k \end{bmatrix}\begin{bmatrix} w_k^T & v_k^T \end{bmatrix}\right\} \triangleq \begin{bmatrix} Q & S \\ S^T & R \end{bmatrix} \quad \text{Equation 3}$$

In Equation 3, $\epsilon_k$ is a general random process denoting the variations of $z_k$ that are not generated by $x^s_k$ and thus are not present in the recorded neural activity. Thus, the only assumption is that $\epsilon_k$ is zero-mean and independent of $x^s_k$, i.e. $E\{x^s_k \epsilon_k^T\}=0$ and the other noises, i.e. $E\{w_k \epsilon_k^T\}=0$ and $E\{v_k \epsilon_k^T\}=0$ for any k', but no assumptions are made about the dynamics of $\epsilon_k$. In fact, $\epsilon_k$ does not need to be white and can be any general non-white (colored) random process. Note that $\epsilon_k$ is also independent of $y_k$ (since it is independent of $x^s_k$ and $v_k$), thus observing $y_k$ does not provide any information about $\epsilon_k$. Due to the zero-mean assumption for noise statistics, it is easy to show that $x^s_k$, $y_k$, and $z_k$ are also zero-mean, implying that in preprocessing, the mean of $y_k$ and $z_k$ should be subtracted from them and later added back to any model predictions if needed. The parameters (A, $C_y$, $C_z$, Q, R, S) fully specify the model in Equation 2 (if statistical properties of $\epsilon_k$ are also of interest, another set of latent state-space parameters can be used to model it). There are other sets of parameters that can also equivalently and fully specify the model; specifically, the set of parameters (A, $C_y$, $C_z$, $G_y$, $\Sigma_y$, $\Sigma_x$) with $G_y \triangleq E\{x^s_{k+1} y_k^T\}$, $\Sigma_y \triangleq E\{y_k y_k^T\}$, and $\Sigma_x \triangleq E\{x^s_k x^{s^T}_k\}$ can also fully characterize the model and is more suitable for evaluating learning algorithms.

Behaviorally relevant and behaviorally irrelevant latent states will now be explained in more detail. $x^s_k$ is a latent state that represents all dynamics in the neural activity $y_k$, which could be due to various internal brain processes including those related to the behavior of interest, other behaviors and brain functions, or internal states. Without loss of generality, it can be shown that Equation 2 can be equivalently written in a different basis as follows in Equation 4:

$$\begin{cases} \begin{bmatrix} x_k^{(1)} \\ x_k^{(2)} \end{bmatrix} = \begin{bmatrix} A_{11} & 0 \\ A_{21} & A_{22} \end{bmatrix} \begin{bmatrix} x_k^{(1)} \\ x_k^{(2)} \end{bmatrix} + \begin{bmatrix} w_k^{(1)} \\ w_k^{(2)} \end{bmatrix} \\ y_k = \begin{bmatrix} C_{y_1} & C_{y_2} \end{bmatrix} \begin{bmatrix} x_k^{(1)} \\ x_k^{(2)} \end{bmatrix} + v_k \quad , x_k = \begin{bmatrix} x_k^{(1)} \\ x_k^{(2)} \end{bmatrix} \\ z_k = \begin{bmatrix} C_{z_1} & 0 \end{bmatrix} \begin{bmatrix} x_k^{(1)} \\ x_k^{(2)} \end{bmatrix} + \epsilon_k \end{cases}$$

Equation 4

In Equation 4, $x_k^{(1)} \in \mathbb{R}^{n_1}$ is the minimal set of states that affect the specific behavior of interest and whose dimension $n_1$ is the rank of the behavior observability matrix (Equation 42). Thus, $x_k^{(1)}$ is referred to as the behaviorally relevant latent states and $x_k^{(2)} \in \mathbb{R}^{n_2}$ with $n_2 = n_x - n_1$ is referred to as the behaviorally irrelevant latent states. The disclosure interchangeably refer to the dimension of the latent states as the number of latent states (e.g. $n_x$ is the total number of latent states or the total latent state dimension).

Equation 4 presents a general formulation of which special cases also include the models used in neural dynamics modeling (NDM) and representational modeling (RM). If it is assumed that all latent states can contribute to behavior ($n_1 = n_x$ and $n_2 = 0$), Equation 4 reduces to the linear SSM typically used to model the dynamics of neural activity in NDM. If $C_z$ is taken to be the identity matrix and $\epsilon_k = 0$, the state will be set to the behavior $z_k$ and Equation 4 reduces to the linear SSMs used in RM. Thus, if the assumptions of standard NDM (i.e. all latent states can drive both neural activity and behavior) or RM (i.e. behavior drives neural activity) hold better for a given dataset, PSID would still identify these standard models because the solution would still fall within the model in Equation 4 used by PSID.

In the general learning problem, given training time series $\{y_k: 0 \leq k < N\}$ and $\{z_k: 0 \leq k < N\}$, the aim is to find the dimension of the latent state $n_x$ and all model parameters (A, $C_y$, $C_z$, $G_y$, $\Sigma_y$, $\Sigma_x$) that generate the data according to Equation 2 or equivalently Equation 4. Unlike prior work, the present disclosure critically requires an identification algorithm that can dissociate the behaviorally relevant and irrelevant latent states, and can prioritize identification of the behaviorally relevant latent states (i.e. $x_k^{(1)}$ from Equation 4). As shown later in the disclosure (also FIG. 10), the inventors achieve this prioritization by developing a novel two-stage analytical learning algorithm that can extract the behaviorally relevant latent states in its first stage without the need to extract or model the behaviorally irrelevant states; this ability leads to extraction of latent states that are both lower dimensional and at the same time more accurate in describing behavior. If desired, the behaviorally irrelevant latent states can then be extracted in the optional second stage. Prioritizing behaviorally relevant latent states in the first stage has two consequences. First, prioritizing means that the algorithm would include the behaviorally relevant latent states in the model even when performing dimensionality reduction and thus identifying a model with fewer states than the true $n_x$. If the algorithm does not prioritize these states, then there is no guarantee that the first few identified states will be behaviorally relevant and thus behavior information could be lost during dimensionality reduction (as shown herein). Second, and consequently, an algorithm that does not prioritize would need to identify a model with higher latent state dimension in order to ensure that behaviorally relevant latent states are included within them. Identifying a model with a high-dimensional latent state requires more training data, and thus, given the same finite training data is less accurate compared with identifying a model with a lower-dimensional latent state. So even a high-dimensional model that does not prioritize would recover the behaviorally relevant states less accurately than a low-dimensional model that allows for prioritization (as shown herein). Moreover, without prioritization, any identified behaviorally irrelevant latent states will need to be first detected and later discarded in a second regression step, which is wasteful of the training data and can lead to less accuracy in extracting behaviorally relevant dynamics (as shown herein).

The model parameters are learned in a training set using both neural activity and behavior measurements. However, once the model is learned, the extraction of behaviorally relevant dynamics/states in a test set or in new data is based purely on neural activity (i.e. without looking at behavior measurements) and is done with a Kalman filter operating on neural activity as described next.

Given the model parameters, the prediction (or decoding) problem is to provide the best estimate of behavior $z_{k+1}$ given the past neural activity $\{y_n: 0 \leq n \leq k\}$. Given the linear state-space formulation of Equation 2 and to achieve the minimum mean-square error, the best prediction of neural activity $y_{k+1}$ using $y_1$ to $y_k$ and similarly the best prediction of behavior $z_{k+1}$ using $y_1$ to $y_k$—which is denoted as $\hat{y}_{k+1|k}$ and $\hat{z}_{k+1|k}$, respectively—are obtained with the well-known recursive Kalman filter. Indeed, in the test set, the latent states are extracted by this Kalman filter from neural activity alone and used for decoding. By reformulating Equation 2 to describe neural activity and behavior in terms of the latent states extracted by the Kalman filter, it can be shown that the best prediction of future behavior using past neural activity is both a linear function of the past neural activity (that is readily measurable) and a linear function of the latent state (that is not measurable). In learning the model in the training set, this key insight enables one to first directly extract the behaviorally relevant latent states via a projection of future behavior onto past neural activity (without having the model parameters), and then use these extracted states to identify the model parameters.

The inventors developed a novel two-stage learning algorithm, named preferential system identification (PSID), to identify the parameters of the general dynamic model in Equation 4 using training time series $\{y_k: 0 \leq k < N\}$ and $\{z_k: 0 \leq k < N\}$ while prioritizing the learning of behaviorally relevant latent states $x_k^{(1)}$ and their dynamics—or equivalently the dynamics of $z_k$ that are predictable from $y_k$—, i.e., learn them first. A high-level summary of the algorithm is provided in Table 1 and FIG. 10 and the details are provided in Table 2 below. The detailed derivation is also provided below. This section provides an overview of the derivation.

PSID first extracts the latent states directly using the neural activity and behavior data, and then identifies the model parameters using the extracted latent states. The latent states are extracted in two stages. The first stage extracts behaviorally relevant latent states. Only if desired, the second stage, which is optional, extracts the remaining behaviorally irrelevant latent states. The first stage of PSID projects the future behavior ($Z_f$) onto the past neural activity ($Y_p$) (denoted as $Z_f/Y_p$ in FIG. 4, Equation 10, and Table 2), which can be shown to extract the behaviorally relevant latent states (the row space of this projection provides the states and can be found with a singular value decomposition). Once these behaviorally relevant latent states are extracted, the dynamic model parameters in Equation 4 can be learned for a model that only includes behaviorally relevant latent states $x_k^{(1)}$. Alternatively, and if desired, the second stage of PSID can be used to also extract the behaviorally irrelevant latent states $x_k^{(2)}$ and then learn the model parameters for a model that also includes these behaviorally irrelevant latent states as in Equation 4. The second stage first finds the part of the future neural activity that is not explained by the extracted behaviorally relevant latent states, i.e., does not lie in the subspace spanned by these states. This is found by subtracting the orthogonal projection of future neural activity onto the extracted behaviorally relevant latent states (Equation 21 in Table 2). This second stage then projects this unexplained future neural activity onto the past neural activity to extract the behaviorally irrelevant latent states (Equation 22 in Table 2). After all latent states—that is, depending on user's choice, either only behaviorally relevant states from the first stage or both behaviorally relevant and irrelevant states from both stages—are extracted, PSID then learns all model parameters from these states. Overall, PSID provides a computationally efficient solution for identifying the parameters of the model in Equation 4 that only involves a small number of matrix algebra and singular value decomposition (SVD) operations unlike iterative methods used for EM or for training RNNs for example.

Table 1 below shows a summary of the PSID algorithm. For visualization see FIG. 10, and for details see Table 2.

different values of $n_x$ and for each model, they computed the cross-validated accuracy of one-step-ahead prediction of neural activity $y_k$ using its past (Equation 45). This is referred to as neural self-prediction to emphasize that the input is the past neural activity itself, which is used to predict the value of neural activity at the current time step. The inventors used Pearson's correlation coefficient (CC) to quantify the self-prediction (averaged across dimensions of neural activity). The inventors then identified the total neural latent state dimension $n_x$ as the value that reaches within 1 s.e.m. of the best possible neural self-prediction accuracy among all considered latent state dimensions. As shown with numerical simulations, using this approach with PSID or standard SID for NDM accurately identifies the total number of latent states (FIG. 14, a-c and FIG. 17, c, e). The inventors thus used this procedure to quantify the total neural dynamics dimension in existing experimental NHP data (FIG. 6, e, l). The inventors also used the exact same procedure on the behavioral data using the behavior self-prediction to quantify the total behavior dynamics dimension in NHP data (FIG. 6, f, m).

To learn a model with PSID with a given latent state dimension $n_x$, it may be necessary to specify another model structure parameter $n_1$, i.e. the dimension of $x_k^{(1)}$ in Equation 4. To determine a suitable value for $n_1$, the inventors performed an inner cross-validation within the training data and fit models with the given $n_x$ and with different candidate values for $n_1$. Among considered values for $n_1$, the inventors

---

Given the training time series $\{y_k : 0 \leq k < N\}$ and $\{z_k : 0 \leq k < N\}$, state dimension $n_x$ and parameters $n_1 \leq n_x$ (number of states extracted in the first stage), this algorithm identifies parameters of a general dynamic linear state-space model as in Equation 4 while prioritizing behaviorally relevant dynamics.

Stage 1: extract $n_1$ latent states directly via a projection of future behavior onto past neural activity
1. Form examples of future behavior ($Z_f$) and the associated past neural activity ($Y_p$) and then project the former onto the latter: $\hat{Z}_f = Z_f Y_p^T (Y_p Y_p^T)^{-1} Y_p$
2. Compute the singular value decomposition (SVD) of $\hat{Z}_f$ and keep the top $n_1$ singular values:
$\hat{Z}_f = USV^T \cong U_1 S_1 V_1^T$
3. Compute the behaviorally relevant latent state $\hat{X}_i^{(1)}$ as: $\hat{X}_i^{(1)} = S_1^{\frac{1}{2}} V_1^T$ Stage 2 (optional): extract $n_x - n_1$ additional latent states via a projection of residual future neural activity onto past neural activity
1. Find the prediction of $Y_f$ using $\hat{X}_i^{(1)}$, and subtract this prediction from $Y_f$ and name the result $Y_f'$ (i.e. residual future neural activity).
2. Project the residual future neural activity ($Y_f'$) onto past neural activity ($Y_p$): $\hat{Y}_f' = Y_f' Y_p^T (Y_p Y_p^T)^{-1} Y_p$
3. Compute the SVD $\hat{Y}_f'$ of and keep the top $n_2 = n_x - n_1$ singular values:
$\hat{Y}_f' = US'V'^T \cong U_2 S_2 V_2^T$
4. Compute the remaining latent state $\hat{X}_i^{(2)}$ as: $\hat{X}_i^{(2)} = S_2^{\frac{1}{2}} V_2^T$ Final step: given the extracted latent states, based on Equation 4 identify model parameters via least squares
1. If stage 2 is used, concatenate $\hat{X}_i^{(2)}$ to $\hat{X}_i^{(1)}$ to get the full latent state $\hat{X}_i$, otherwise take $\hat{X}_i = \hat{X}_i^{(1)}$
2. Repeat all steps with a shift of one time step in time to extract the states at the next time step ($\hat{X}_{i+1}$)
3. Compute the least squares solution for the model parameters as ($.^\dagger$ denotes pseudoinverse):
$A = \hat{X}_{i+1} \hat{X}_i^\dagger$, $C_y = Y_i \hat{X}_i^\dagger$, $C_z = Z_i \hat{X}_i^\dagger$
4. Compute the covariance of the residuals in the above least square solutions to get the statistics of the noises in Equation 4.

---

For both PSID and NDM, the total number of latent states $n_x$ is a parameter of the model structure. When learning of all dynamics in the neural activity (regardless of their relevance to behavior) is of interest, the inventors identified the appropriate value for this parameter using the following cross-validation procedure. The inventors fit models with selected the final value $n_1^*$ as the value of $n_1$ that within the inner cross-validation in the training data, maximizes the accuracy for decoding behavior using neural activity in training data (Equation 45). The inventors quantified the decoding accuracy using CC (averaged across dimensions of behavior). As shown with numerical simulations, this approach accurately identifies $n_1$ (FIG. 14, d, e). Thus, when fitting a model with any given latent state dimension $n_x$ using PSID, unless otherwise noted, the inventors determined $n_1$ using an inner cross-validation as detailed above (e.g. FIG. 6, FIG. 9, FIG. 14, FIG. 17).

To validate the identification algorithms with numerical simulations, the inventors generated random models with the following procedure. Dimension of $y_k$ and $z_k$ are selected randomly with uniform probability from the following ranges: $5 \leq n_y$, $n_z \leq 10$. The full latent state dimension is selected with uniform probability from $1 \leq n_x \leq 10$ and then the number of states driving behavior ($n_1$) is selected with uniform probability from $1 \leq n_1 \leq n_x$. The inventors then randomly generated matrices with consistent dimensions to be used as the model parameters A, $C_y$, $C_z$, Q, R, S. Specifically, the eigenvalues of A are selected randomly from the unit circle and $n_1$ of them are then randomly selected to be used in the behaviorally relevant part of A (i.e. $A_{11}$ in Equation 4). Furthermore, noise statistics are randomly generated and then scaled with random values to provide a wide range of relative state and observation noise values. Finally, the inventors generated a separate randomly generated SSM with a random number of latent states as the model for the independent residual behavior dynamics $\epsilon_k$.

To generate a time-series realization with N data points from a given model, the inventors first randomly generated an N data point white gaussian noise with the covariance given as Equation 64 and assigned these random numbers to $w_k$ and $v_k$. The inventors then computed $x_k$ and $y_k$ by iterating through Equation 2 with the initial value $x_{-1}=0$. Finally, the inventors generated a completely independent N-point time-series realization from the behavior residual dynamics model (see the previous paragraph) and added its generated behavior time series (i.e. $\epsilon_k$) to $C_z x_k$ to get the total $z_k$ (Equation 2).

A similarity transform is a revertible transformation of the basis in which states of the model are described and can be achieved by multiplying the states with any invertible matrix. For example, any permutation of the states is a similarity transform. Since any similarity transform on the model gives an equivalent model for the same neural activity and behavior (just changes the latent state basis in which the model was described), the parameters of the identified model cannot be directly compared with the true model and all similarity transforms of the identified model need to be considered as well. Thus, to evaluate the identification of model parameters, the inventors first found a similarity transform that makes the basis of the latent states for the identified model as close as possible to the basis of the latent states for the true model. The inventors then evaluated the difference between the identified and true values of each model parameter. Purely to find such a similarity transform, from the true model the inventors generated a new realization with $q=1000n_x$ samples, which is taken to be sufficiently long for the model dynamics to be reflected in the states. The inventors then used both the true and the identified models to extract the latent state using the steady-state Kalman filter (Equation 45) associated with each model, namely $\hat{x}_{k+1|k}^{(true)}$ and $\hat{x}_{k+1|k}^{(id)}$. The inventors then found the similarity transform that minimizes the mean-squared error between the two sets of Kalman extracted states as shown in Equation 5 below:

$$\hat{T} = \underset{T}{\mathrm{argmin}}\left(\sum_{k=1}^{q}|T\hat{x}_{k+1|k}^{(id)} - \hat{x}_{k+1|k}^{(true)}|^2\right) = \hat{X}^{(true)}\hat{X}^{(id)\dagger} \quad \text{Equation 5}$$

In Equation 5, $\hat{X}^{(true)}$ and $\hat{X}^{(id)}$ are matrices whose kth column is composed of $\hat{x}_{k+1|k}^{(true)}$ and $\bar{x}_{k+1|k}^{(id)}$, respectively. The inventors then applied the similarity transform $\hat{T}$ to the parameters of the identified model to get an equivalent model in the same basis as the true model. The inventors emphasize again that the identified model and the model obtained from it using the above similarity transform are equivalent.

Given the true model and the transformed identified model, the inventors quantified the identification error for each model parameter $\Psi$ (e.g. $C_y$) using the normalized matrix norm as:

$$e_\Psi = \frac{|\Psi^{(id)} - \Psi^{(true)}|_F}{|\Psi^{(true)}|_F} \quad \text{Equation 6}$$

In Equation 6, $|\cdot|_F$ denotes the Frobenius norm of a matrix, which for any matrix $\Psi=[\Psi_{ij}]n\times m$ is defined as:

$$|\Psi|_F = \sqrt{\sum_{i=1}^{n}\sum_{j=1}^{m}|\psi_{ij}|^2} \quad \text{Equation 7}$$

Both for numerical simulations and for existing experimental NHP data, the inventors used the cross-validated accuracy of decoding behavior using neural activity as a measure of how accurately the behaviorally relevant neural dynamics are learned. In numerical simulations, the inventors also evaluated a more direct metric based on the eigenvalues of the state transition matrix A; this is because for a linear SSM, these eigenvalues specify the frequency and decay rate of the response of the latent states to excitations (i.e. $w_k$) and thus determine their dynamical characteristics. Specifically, the inventors evaluated the identification accuracy for the eigenvalues associated with the behaviorally relevant latent states (i.e. eigenvalues of $A_{11}$ in Equation 4). PSID identifies the model in the form of Equation 4 and thus the first block of A (i.e. $A_{11}$ in Equation 31) is associated with the behaviorally relevant states ($x_k^{(1)}$ in Equation 4). Thus, for PSID, the inventors simply computed the eigenvalues of $A_{11}$ and evaluate their identification accuracy. NDM identification methods do not specify which states are behaviorally relevant. So, to find these states, the inventors first applied a similarity transform to make the NDM identified A matrix block-diagonal with each complex conjugate pair of eigenvalues in a separate block (using MATLAB's bdschur command followed by the cdf2rdf command). The inventors then fit a linear regression from the states associated with each block to the behavior (using the training data) and sorted the blocks by their prediction accuracy of behavior $z_k$. The behaviorally relevant eigenvalues are then taken to be the top $n_1$ eigenvalues that result in the most accurate prediction of $z_k$. To evaluate decoding accuracy for a model that only keeps the top $n_1$ eigenvalues from an NDM model, the inventors reduced the learned model—that has a high-dimensional latent state—by only keeping the segments of model parameters that are associated with the top $n_1$ eigenvalues (FIG. 15).

Finally, given the true behaviorally relevant eigenvalues and the identified behaviorally relevant eigenvalues, the inventors found the closest pairing of the two sets (by comparing all possible pairings), placed the true and the associated closest identified eigenvalues in two vectors, and computed the normalized eigenvalue detection error using Equation 6.

When evaluating the identified eigenvalues for models with a latent state dimension that is smaller than the true $n_1$ (for example in FIG. 5 for $n_x<4$), the inventors added zeros in place of the missing eigenvalues since a model with a low latent state dimension of a is equivalent to a model with a higher latent state dimension of b with b-a states that are always equal to zero and have eigenvalues of zero associated with them.

To estimate the dimensionality of the behaviorally relevant neural dynamics, the inventors sought to find the minimal number (i.e., dimension) of latent states that is sufficient to best describe behavior using neural activity. To do this, for each method, the inventors fit models with different values of state dimension $n_x$, and computed the cross-validated accuracy of decoding behavior using neural activity (Equation 45). The inventors used Pearson's correlation coefficient (CC), averaged across behavior dimensions, to quantify the decoding accuracy. The inventors then estimated the dimension of the behaviorally relevant neural dynamics as the smallest latent state dimension that reaches within 1 s.e.m. of the best possible cross-validated decoding accuracy among all considered latent state dimensions (FIG. 6, a-d, g, h-k, n, FIG. 9).

The inventors studied the neural activity and behavior in two different existing datasets with different behavioral tasks, recording coverage, neural signal types, and subjects. The first existing dataset consisted of neural activity recorded from the motor cortical areas in two adult Rhesus macaques (monkeys J and C) while the subjects were performing 3D reach, grasp, and return movements to diverse locations. A cube (2.5 cm×2.5 cm×2.5 cm) or cylinder (6 mm radius, 1.5 cm length) was used as the target object, which was fixed during each recording session. The target object was manually moved by the experimenter to diverse random locations spanning a wide 3D area within the reach of the monkey and without any timing cues, the monkey was required to reach for the object, grasp it, release it, and return the hand to the resting position. The object and its movements remained visible in between reaches. The second existing dataset consisted of neural activity recorded from PFC while from two monkey (monkeys A and S) while they performed saccadic eye movements from a central fixation point toward one of 8 targets on a display.

In the existing dataset from Monkey J, neural activity was recorded from 137 electrodes on a micro-drive covering parts of primary motor cortex (M1), dorsal premotor cortex (PMd), ventral premotor cortex (PMv), and prefrontal cortex (PFC) on the left hemisphere and in the existing dataset from monkey C the activity was recorded from 128 electrodes on four thirty-two electrode microdrives covering PMd and PMv on both left and right hemispheres. Using 3D tracked retroreflective markers, the movement of various points on the torso, chest, right arm, hand and fingers were tracked within a 50 cm×50 cm×50 cm workspace. These markers were used to extract the angular position of the 27 (monkey J) or 25 (monkey C) joints of the upper-extremity, consisting of 7 joints in the shoulder, elbow, wrist, and 20 (monkey J) or 18 (monkey C) joints in fingers (4 in each, except 2 missing finger joints in monkey C). The inventors analyzed the neural activity during 7 (monkey J) or 4 (monkey C) recording sessions. For most of the analyses (unless otherwise specified), to further increase the sample size, the inventors randomly divided the electrodes into non-overlapping groups of 10 or 30 electrodes, for LFP and spiking analyses respectively, and performed modeling in each group separately. The specification refers to each random electrode group in each recording session as one dataset.

To model the existing data consisting of recorded LFP, the inventors performed common average referencing (CAR) and then as the neural features, extracted signal log-powers (i.e. in dB units) from 7 frequency bands (theta: 4-8 Hertz (Hz), alpha: 8-12 Hz, low beta: 12-24 Hz, high beta: 24-34 Hz, low gamma: 34-55 Hz, high-gamma 1: 65-95 Hz, and high gamma 2: 130-170 Hz) within sliding 300 ms windows at a time step of 50 ms using Welch's method (using 8 sub windows with 50% overlap). To model the existing data consisting of recorded multi-unit spiking activity, the inventors counted the spikes in 10 ms non-overlapping bins, applied a Gaussian kernel smoother (with s.d. 50 ms), and unless otherwise noted, down-sampled to a time step of 50 ms as in LFP. The extracted features were taken as the neural activity time series $y_k$ ($y_k \in \mathbb{R}^{70}$ in each LFP dataset and $y_k \in \mathbb{R}^{30}$ in each spike dataset). Unless otherwise noted, the behavior time series $z_k$ was taken as the joint angles at the end of each 50 ms time step of neural activity ($z_k \in \mathbb{R}^{27}$ in monkey J and $z_k \in \mathbb{R}^{25}$ in monkey C).

In the second existing dataset with saccadic eye movements, neural activity was recorded from a thirty-two electrode microdrive covering PFC. Eye position was measured with an infrared optical eye tracking system and was taken as the behavior to be modeled. In each trial, monkeys performed delayed saccadic eye movement to one of eight targets for liquid reward. The inventors analyzed the existing data consisting of neural activity during more than 4000 (monkey A) or 22000 (monkey S) trials collected over 27 (monkey A) or 43 (monkey S) days. To model the recorded LFP, the inventors performed common average referencing (CAR), applied a causal lowpass anti-aliasing filter with a cut-off of 8 Hz (order 4 IIR Butterworth filter) and then downsampled the LFP signals to 20 Hz sampling rate (i.e. 50 ms sampling time step). The inventors took the down-sampled raw LFP activity as the neural activity time series $y_k$ ($y_k \in \mathbb{R}^{32}$). The inventors took the eye position, similarly downsampled to a 20 Hz sampling rate, as the behavior time series $z_k$ ($z_k \in \mathbb{R}^2$).

For each method, the inventors performed the model identification and decoding within a 5-fold cross-validation and as the performance metric for predicting behavior, the inventors computed the cross-validated correlation coefficient between the true and predicted joint angles. For all methods, in each cross-validation fold, the inventors first z-scored each dimension of neural activity and behavior based on the training data to ensure that learning methods do not discount any behavior or neural dimensions due to a potentially smaller natural variance. In fitting the models with PSID, for each latent dimension $n_x$, unless specified otherwise, $n_1$ was selected using a 4-fold inner cross-validation within the training data. For PSID and standard SID, a horizon parameter of i=5 was used in all analyses, except for per channel analyses (FIG. 7), spiking activity analyses (FIG. 9) and raw LFP activity analyses (FIG. 32) where a horizon of i=20 was used due to the smaller neural feature dimension. For the control analyses with NDM, the inventors used the EM algorithm. Once models were learned in the train set, each method applied a Kalman filter—corresponding to the learned model—on neural activity in the test set to extract the latent states and to predict the behavior or self-predict the neural activity from these extracted states.

The inventors used the Wilcoxon signed-rank or rank-sum for all paired and non-paired statistical tests, respectively. To correct for multiple-comparisons when comparing the performance of methods for different joints or channels, the inventors corrected the P-values within the test data using the False Discovery Rate (FDR) control.

The new functionality offered by PSID is the ability to dissociate and model behaviorally relevant neural dynamics by considering both neural activity and behavior when learning the dynamic model in contrast with NDM (whether linear or nonlinear) that only considers neural activity in learning the dynamic model. To show that the advantage of PSID is due to its learning approach and thus holds regardless of NDM model structure, the inventors also compared with example nonlinear NDM methods. As the first example for nonlinear NDM, the inventors learned a model using linear NDM and then used nonlinear support vector regression (SVR) to regress the latent state to behavior. The inventors used the LIB SVM library to learn the SVR with a radial basis function kernel and an epsilon-SVR loss with default parameters. As the second example of a nonlinear NDM, the inventors used an RNN-based method termed LFADS, which has been successfully applied to neural spiking activity recently. LFADS fits an RNN autoencoder that can take fixed-length segments of data as input and encode the dynamics in each segment into an initial condition. Given this initial condition, an RNN termed the generator then generates a factor time-series that can linearly reconstruct a smoothed copy of the input data segment. Thus, one can apply LFADS on neural data by cutting the neural feature time series in fixed-length non-overlapping 1s segments, applying LFADS smoothing to each segment to denoise the neural activity during that segment, and getting a corresponding factor time-series. To decode behavior, a linear regression can be fitted from the factor time-series to the behavior. The inventors ran the LFADS model fitting and subsequently learned the linear regression from factors to the behavior using the training data and test the decoding accuracy in the test data. For the LFADS model, unless otherwise noted, the inventors always set the dimension of the initial condition to 64. In the LFADS formulation, the number of units in the LFADS generator indicates the dimension of dynamics or the state dimension—i.e. how many numbers are needed to generate the dynamics in the next time step from the current time step, similar to the dimension of $x_k$ in Equation 1. Nevertheless, for completeness, the inventors compared to two configurations of LFADS. First, to provide directly comparable results with other methods, as the inventors swept over different number of factors, the inventors always set the number of generator units (i.e. the dimension of dynamics) to be equal to the number of factors. Hence, in this configuration, the number of factors in LFADS also indicates the dimension of its dynamics and is thus comparable with the state dimension with other methods (FIG. 9). Second, in a control analysis, the inventors always set the number of units in the LFADS generator to 64 and then only swept the number of factors, but results were similar (FIG. 31). When applying LFADS to the same Gaussian smoothed spiking activity features that were used by PSID (FIG. 9), the inventors used a Gaussian observation model for LFADS. In another control analysis, the inventors additionally applied LFADS to non-smoothed spike counts in 10 ms non-overlapping bins (FIG. 31) in which case the inventors used a Poisson observation model for LFADS. Again, all conclusions were similar. It is worth noting that given its analytical form, PSID was computationally more efficient both in fitting the models in the training data (per dataset: 3.2 minutes for PSID vs. 120 hours for LFADS, i.e. 2250 times more efficient) and in estimating the latent representation from neural activity in the test data (per dataset: 0.53 seconds for PSID vs. 35 minutes for LFADS, i.e. 4000 times more efficient).

Referring to FIG. 10, another visualization of the PSID algorithm is shown. In particular, FIG. 10, a illustrates the extraction of future and past neural activity and future behavior from data is shown (see Table 2 for the general definition). Matrices are depicted as rectangles. Past and future neural activity matrices $Y_p$ and $Y_f$ are of the same size and only differ in terms of which time steps are included in them ($Y_f$ includes neural data for one step into the future relative to $Y_p$). Future behavior matrix $Z_f$ includes the time-series of behavior at the same time steps as $Y_f$.

FIG. 10, b shows the PSID learning algorithm. In stage one of PSID, performing SVD on the projection of future behavior $Z_f$ onto past neural activity $Y_p$ gives the behaviorally relevant latent states $\hat{X}^{(1)}$. These states can be used on their own to learn the parameters for a model that only includes behaviorally relevant latent states. Optionally, stage two of PSID can be used to also extract behaviorally irrelevant latent states $\hat{X}^{(2)}$. In stage two, residual future neural activity $Y'_f$ is obtained by subtracting from $Y_f$ its projection onto $\hat{X}^{(1)}$. Performing SVD on the projection of residual future neural activity $Y'_f$ onto past neural activity $Y_p$ gives the behaviorally irrelevant latent states $\hat{X}^{(2)}$. These states can then be used together with the behaviorally relevant latent states $\hat{X}^{(1)}$ to learn the parameters for a model that includes both sets of states. Once model parameters (Equation 1) are learned using only the neural and behavior data from the training set, the extraction of latent states and the decoding of behavior in the test set are done purely from neural activity and using a Kalman filter and linear regression as shown in FIG. 4, c (the Kalman filter and linear regression are specified by the learned model parameters).

FIG. 10, c illustrates a brief sketch of the main derivation step to obtain the PSID algorithm in FIG. 10, b. In the derivation of PSID, the disclosure shows that, theoretically, for the model in Equation 1, the prediction of future behavior $Z_f$ using past neural activity $Y_p$ (i.e. $\hat{Z}_f$) has the same row space as the behaviorally relevant latent states $\hat{X}^{(1)}$. Thus, empirically and from data, one can first compute the former prediction $\hat{Z}_f$ as in FIG. 10, b via a projection, and then find its row space using SVD to compute the behaviorally relevant latent states $\hat{X}^{(1)}$ from data. Similarly, the disclosure shows that, theoretically, the prediction of the residual future neural activity $Y'_f$ using past neural activity $Y_p$ (i.e. $\hat{Y}'_f$) has the same row space as the behaviorally irrelevant latent states $\hat{X}^{(2)}$. Thus, empirically and from data, one can first compute the former prediction $\hat{Y}'_f$ as in (b) via a projection, and then find its row space using SVD to compute the behaviorally irrelevant latent states $\hat{X}^{(2)}$ from data.

Referring to FIG. 11, an example numerical simulation illustrates how brain states may be related to behavior, neural activity or both and which states are identified by PSID, NDM, and RM. In particular, FIG. 11, a shows the eigenvalues of a simulated brain model that are color coded to show whether they are behaviorally relevant, behaviorally irrelevant, or not encoded in neural activity. FIG. 11, b shows sample data for each of the latent states and the generated neural activity and behavior. Two latent states ($x_k^{(2)}$) only drive the recorded neural activity ($y_k$), 2 latent states ($\in_k$) only drive the behavior ($z_k$) and 2 latent states ($x_k^{(1)}$) drive both. In other words, neural activity ($y_k$) is a linear combination of behaviorally relevant ($x_k^{(1)}$) and behaviorally irrelevant ($x_k^{(2)}$) states, and behavior is a linear combination of behaviorally relevant states ($x_k^{(1)}$) and states not encoded in neural activity ($\in_k$). FIG. 11, c shows eigenvalues identified using PSID, NDM and RM when a model with a latent state of dimension 2 is fitted to the simulated neural activity and behavior data from FIG. 11, b.

To identify the eigenvalues, NDM only considers neural activity, RM only considers behavior, and PSID considers both. FIG. 11, d shows the decoding of behavior with models learned using PSID, NDM, and RM, as well as the best possible decoding when the true model is used for decoding.

Referring now to FIG. 12, it is shown that PSID correctly learns model parameters at a rate of convergence similar to that of SID while also being able to prioritize behaviorally relevant dynamics. In particular, FIG. 12, a shows normalized error for identification of each model parameter using PSID (with $10^6$ training samples) across 100 random simulated models. Each model had randomly selected state, neural activity, and behavior dimensions as well as randomly generated parameters. The parameters A, $C_y$, $C_z$ from Equation 2 together with the covariance of the neural activity $\Sigma_y \triangleq E\{y_k y_k^T\}$ and the cross-covariance of the neural activity with the latent state $G_y \triangleq E\{x_{k+1} y_k^T\}$ fully characterize the model. Here, the same model structure parameters $n_x$ (total latent state dimension) and $n_1$ (dimension of the latent states extracted during the first stage of PSID) as the true model were used when applying PSID to data for each model (see FIG. 14 on how these model structure parameters are also accurately identified from data). The horizontal dark line on the box shows the median, box edges show the $25^{th}$ and $75^{th}$ percentiles, whiskers represent the minimum and maximum values (other than outliers) and the dots show the outlier values. Outliers are defined as in FIG. 6. Using $10^6$ samples, all parameters are identified with a median error smaller than 1%. FIG. 12, b shows normalized error for all parameters as a function of the number of training samples for PSID. The normalized error consistently decreases as more samples are used for identification. Solid line shows the average login of the normalized error and the shaded area shows the s.e.m. FIG. 12, c, d show the same as FIG. 12, a, b, shown for the standard SID algorithm. The rate of convergence for both PSID and SID, and for all parameters is around 10 times smaller error for 100 times more training samples (i.e. slope of –0.5 on (b), (d)).

Turning now to FIG. 13, it is shown that identification error is greater for models that are closer to unobservability and thus inherently more difficult to identify. FIG. 13, a shows normalized error for each parameter (identified with PSID using $10^6$ training samples) for the 100 random simulated models in FIG. 12 is shown as a function of the condition number of the neural observability matrix $\Gamma_y$ for the model, which is defined as the ratio of its largest to its smallest singular values. The P-value for Pearson's correlation coefficient between $\log_{10} \text{cond}(\Gamma_y)$ and $\log_{10}$ of normalized error is shown on each plot (number of data points is 100). The line shows the least squares solution to fitting a line to the data points and the shaded area shows the associated 95% confidence interval. The condition number of the neural observability matrix for each model is significantly correlated with the identification error for the three model parameters (i.e. A, $C_y$, and $C_z$) that have the widest range of identification errors (as seen from FIG. 12, a). As a model gets closer to being unobservable and more difficult to identify, the condition number for the observability matrix increases. Thus, this result indicates that the models for which these three parameters were less accurately identified were closer to being unobservable and thus were inherently more difficult to identify given the same number of training samples. FIG. 13, b shows the same as FIG. 13, a for SID, which similarly shows relatively larger error for models that are inherently less observable.

Turning to FIG. 14, it is shown that model structure parameters can be accurately identified using cross-validation. FIG. 14, a shows detection of the total latent state dimension ($n_x$) using cross-validation for numerical simulations. The inventors identified $n_x$ by considering candidate values of $n_x$ and selected the value whose associated model reaches (within 1 s.e.m. of) the best neural self-prediction (predicting $y_k$ using its past values) among all candidate values. The Pearson's correlation P-value between the true and identified values is shown on the plot. The line and shaded area are defined as in FIG. 13. $n_x$, which ranged from 1 to 10 across random models, was identified with no error in 98% of the models and with an average error of 0.040±0.028 (mean±s.e.m.).

FIG. 14, b shows the same as FIG. 14, a, for detection of $n_x$ using cross-validation in standard SID. Using SID, $n_x$ was identified with an average error of 0.08±0.039.

FIG. 14, c shows the distribution of true and identified values of $n_x$ from FIG. 14, a, b is shown as a box plot. Bars and boxes are defined as in FIG. 6, b. All data points are shown.

FIG. 14, d shows the same as FIG. 14, a, for detection of the PSID parameter $n_1$. $n_1$, which ranged from 1 to 10 across random models, was identified with no error in 94% of the models and with an average error of 0.050±0.021.

FIG. 14, e shows the distribution of true and identified values of $n_1$ from FIG. 14, d shown as a box plot. The true and identified $n_x$ and $n_1$ are always integer values, so for better visualization and to avoid having multiple points at the exact same location on the plots a random small displacement has been added to each point.

Referring to FIG. 15, it is shown that PSID requires orders of magnitude fewer training samples to achieve the same performance as an NDM with a larger latent state dimension, and NDM with the same latent state dimension as PSID or RM do not achieve a comparable performance to PSID even with orders of magnitude more samples. In particular, FIG. 15, a shows normalized eigenvalue error for 1000 random simulated models when using RM, PSID, or NDM with similar or larger latent state dimension. Solid lines show the average across the 1000 models, and the shaded areas show the s.e.m. For NDM, to learn the behaviorally relevant dynamics using a model with a high-dimensional latent state ($n_x$=16), the inventors first identified this model, then sorted the dimensions of the extracted latent state in order of their decoding accuracy, and then reduce the model to keep the 4 most behavior predictive latent state dimensions. These operations provide the estimate of the 4 behaviorally relevant eigenvalues. For RM, the state dimension is the behavior dimension (here $n_z$=5).

FIG. 15, b shows cross-validated behavior decoding CC for the models in FIG. 15, a. Note that unlike in FIG. 15, a, here the disclosure provides decoding results using the NDM with a 16-dimensional latent state both with and without any model reduction, as the two versions result in different decoding while they don't differ in their most behavior predictive dimensions and thus have the same eigenvalue error in FIG. 15, a. Optimal decoding using the true model is shown as black. For NDM with a 4-dimensional latent state (i.e. in the dimension reduction regime) and RM, eigenvalue identification in FIG. 15, a and decoding accuracies in FIG. 15, b almost plateaued at some final value below that of the true model, indicating that the asymptotic performance of having unlimited training samples has almost been reached. In both FIG. 15, a, b, even for an NDM with a latent state dimension as large as the true model (i.e. not performing any dimension reduction and using $n_x$=16), (i) NDM was inferior in performance compared with PSID with a latent state dimension of only 4 when using the same number of training samples, and (ii) NDM required orders of magnitude more training samples to reach the performance of PSID with the smaller latent state dimension as shown by the arrow. Parameters are randomized as disclosed herein except the state noise ($w_t$), which is about 30 times smaller (i.e. $-2.5 \leq \alpha_1 \leq -0.5$), and the behavior signal-to-noise ratio, which is 2 times smaller (i.e. $-0.3 \leq \alpha_3 \leq +1.7$), both adjusted to make the decoding performances more similar to the NHP results (FIG. 6).

Referring now to FIG. 16, it is shown that PSID can be used to model neural activity for different neural signal types including LFP power activity and population spiking activity. In particular, modeling neural activity using PSID is demonstrated with example signals, extracted latent states, and decoded behavior for FIG. 16, a LFP power activity (i.e. signal power in different frequency bands, which are shown with different colors,) and FIG. 16, b population spiking activity. In both cases, regardless of neural signal type, after extracting the neural feature time-series, decoding consists of two steps: 1) applying Kalman filter to extract the latent states given the neural feature time series, 2) computing a linear combination of the states to get the decoding of behavior. By learning the dynamical model parameters, PSID specifies the Kalman filter parameters as well as the linear combination.

FIG. 17 shows that PSID can accurately estimate the behaviorally relevant dynamics dimension, as well as the total neural dynamics dimension and the total behavior dynamics dimension in simulations. FIG. 17, a shows cross-validated behavior decoding correlation coefficient (CC) as a function of latent state dimension using PSID and NDM within numerical simulations. Decoding CC is averaged across 100 random simulated models and the shaded area indicates the s.e.m. In each model, a random number of neural states were behaviorally irrelevant. FIG. 17, b shows the behaviorally relevant neural dynamics dimension identified using PSID and NDM. This number is identified for each model as the smallest state dimension for which the CC reaches the best decoding performance. Bars, boxes and asterisks are defined as in FIG. 6, b. While PSID accurately identifies the behaviorally relevant dynamics dimension, NDM overestimates it. FIG. 17, c shows one-step-ahead self-prediction of neural activity (cross-validated CC) as a function of latent state dimension. To compute the self-prediction, SID (i.e., PSID with $n_1=0$) is always used for modeling since dissociation of behaviorally relevant states is not needed. FIG. 17, d shows the same as FIG. 17, c for one-step-ahead self-prediction of behavior. FIG. 17, d shows true and identified values for behaviorally relevant neural dynamics dimension (PSID results from FIG. 17, b), the total neural dynamics dimension (identified as the state dimension for best neural self-prediction from FIG. 17, c) and the total behavior dynamics dimension (identified as the state dimension for best behavior self-prediction from FIG. 17, d). These results confirm with numerical simulations that the inventors' approach for identifying the total neural and behavior dynamics dimensions correctly estimates these numbers, and that PSID accurately identifies the behaviorally relevant dynamics dimension from data. Consequently, the same cross-validation approach is used in FIGS. 6, 9, 18-24, 31, and 32 for the real NHP data to compute the dimensions.

FIG. 18 shows that PSID is more predictive of behavior than NDM for multiple-step-ahead prediction of behavior from neural activity. FIG. 18, a shows that decoding CC is shown for PSID and NDM when predicting the behavior multiple steps into the future from neural activity. Here n-step-ahead prediction of the latent state at time step k is obtained via a Kalman filter but with neural activity provided only up to time step k−n. In running the Kalman filter, for time steps after k−n that have no neural observation, the Kalman gain is equal to zero and the estimation of the latent state continues purely based on the previous latent state and the state transition matrix A in the model. Behavior at time step k is decoded via a regression from the predicted latent state at time step k with the parameter $C_z$. NDM used the same latent state dimension as PSID (as in FIG. 6, c). Solid lines show the mean and the shaded areas show the s.e.m. FIG. 18, b shows the same as FIG. 18, a, for neural self-prediction. Neural activity at time step k is predicted via a regression from the predicted latent state at time step k with the parameter $C_y$. As expected, at the same latent state dimension, PSID does better in behavior decoding and NDM does better in neural self-prediction, since NDM's only objective is to explain variance in neural activity regardless of relevance to behavior. However, the second stage of PSID allows it to also explain additional neural variance in higher latent state dimensions if desired (see FIG. 20). FIG. 18, c, d shows the same as FIG. 18, a, b, for monkey C.

FIG. 19 shows that PSID also reveals a markedly lower behaviorally relevant neural dimension and does better decoding compared with non-dynamic dimension reduction using principal component analysis (PCA), factor analysis (FA) and direct regression (DR) (i.e. PSID extracts the behaviorally relevant dynamics more accurately). FIG. 19 has the same figure convention as FIG. 6 with non-dynamic PCA and FA dimension reduction, as well as DR without any dimension reduction added to the comparison. In PSID, NDM, and RM, temporal dynamics are modeled (Equation 1) and the decoder consists of a Kalman filter aggregating information from past neural activity to extract the state (allowing for denoising in time). In contrast, PCA, FA, and DR are non-dynamic methods that do not model temporal dynamics, thus their extraction of the state (i.e. principal components for PCA or factors for FA) involves a linear projection from neural activity only at the current time step. Note in DR neural activity is used as the state itself, without dimensionality reduction. In all methods, the next step for decoding behavior after the extraction of states may be the same and involves a linear combination of the extracted states to get the decoding of behavior. Compared with other methods, PSID revealed a significantly lower dimension for behaviorally relevant dynamics (panels b, f; $P<10^{-5}$; one-sided signed-rank; $N_s \geq 48$) and achieved significantly better decoding both at that dimension (panels c, g; $P<10^{-8}$; one-sided signed-rank; $N_s \geq 48$) and when other methods used much higher dimensions (panels d, h; $P<10^{-8}$; one-sided signed-rank; $N_s \geq 48$).

FIG. 20 shows that as the dimension of the latent state extracted by PSID increases, it first covers the subspace of neural dynamics that are behaviorally relevant and then covers the subspace of residual neural dynamics. FIG. 20, a shows that for different state dimensions (or different number of principal components (PCs) in the case of PCA), the cross-validated behavior decoding CC is shown versus the cross-validated accuracy of reconstructing neural activity using the same states/PCs quantified by CC. For PSID, NDM, and RM, reconstruction of neural activity is done using a Kalman filter for one time step into the future (i.e. one-step-ahead self-prediction, Methods). For PCA, reconstruction is done for the same time step by multiplying the extracted PCs by the transpose (i.e. inverse) of the PCA decomposition matrix. Solid lines show the average decoding CC and shaded areas show the s.e.m. Multiple points on the curves associated with equal number of states/PCs are marked with the same symbol (plus/cross/asterisks). FIG. 20, b shows the same as FIG. 20, 1 for monkey C.

FIG. 21 shows that the PSID-extracted latent states with markedly lower dimension achieve significantly better decoding of almost all arm and finger joints. FIG. 21, a shows that the state dimension used by each method to achieve the best decoding for individual joints. For all methods, models are fitted to all joints as in FIG. 6. For PSID and NDM, models are fitted using various state dimensions; then for each joint, the latent state dimension is chosen to be the smallest value for which the decoding CC reaches within 1 s.e.m. of the best decoding CC possible for that joint among all latent state dimensions. Bars, boxes and asterisks are defined as in FIG. 6, b. For better visualization of outliers, the vertical axis is broken. FIG. 21, b shows cross-validated correlation coefficient (CC) between the decoded and true joint angles for PSID. Asterisks mark joints for which PSID results in significantly ($P<0.05$) better decoding compared with NDM (red asterisk) or RM (dark blue asterisk). The latent state for each method is chosen as in FIG. 21, a. FIG. 21, c, d show the same as FIG. 21, a, b, for monkey C. In both monkeys, compared with NDM, PSID achieved better decoding for all individual joints with the difference being statistically significant in almost all joints (panels b, d; $P<10^{-4}$ for all joints in monkey C and $P<10^{-12}$ for 25 of 27 joints in monkey J; one-sided signed-rank test; $N_s=240$ and $N_s=455$ for monkeys C and J, respectively). Compared with RM, PSID achieved significantly better decoding for all 27 joints in monkey J (panel b; $P<0.04$ for each joint; one-sided signed-rank; $N_s=455$) and for 24 of the 25 joints in monkey C (panel d; $P<0.004$ for each joint; one-sided signed-rank; $N_s=240$), and similar decoding for 1 joint in monkey C ($P=0.27$; two-sided signed-rank; $N_s=240$). The significantly better decoding in PSID was achieved using significantly lower-dimensional states compared with NDM and RM (panels a, c; $P<10^{-90}$; one-sided signed-rank; $N_s\geq1200$). In degree units, the average root mean-squared error in decoding joint angles was 9.8 and 7.2 for monkeys J and C, respectively. Joints with larger activity ratio (quantified as std of motion divided by its range) during a given experiment session had better decoding ($P<10^{-6}$; Spearman's rank correlation; $N_s\geq100$) with those with at least 0.25 activity ratio (covering 12 and 11 joints in monkeys J and C, respectively) reaching an average CC of 0.63 and 0.56 and an explained variance of 0.41 and 0.32 for monkeys J and C, respectively.

FIG. 22 shows that the dynamic model learned by PSID using a subset of joints in the training set was more predictive of the remaining joints in the test set compared with the dynamic model learned by NDM. The inventors selected a subset of joints and excluded them from the PSID modeling. After learning the dynamic model and extracting the latent states in the training set, the inventors fitted a linear regression from these latent states to predict the remaining joints that were unseen by PSID (i.e. the regression solution constituting the parameter $C_z$ in the model). Similarly, NDM learned its dynamic model and extracted the latent states in the training set, and then fitted a linear regression from these latent states to predict the joints. The inventors then evaluated the final learned models in the test set. The inventors repeated this procedure for multiple random joint subsets while ensuring that overall, all joints are a member of the unseen subsets equal number of times. FIG. 22, a shows the peak cross-validated decoding accuracy (CC) for PSID as a function of the number of joints that were unseen when learning the dynamic model. In each dataset, the same latent state dimension as PSID is used for NDM. In NDM, joints are never used in learning the dynamic model, equivalent to having all joints in the unseen subset. Indeed, PSID reduces to NDM in the extreme case when no joint is provided to PSID in learning the dynamic model as evident from the green and red curves converging at the end (in this case only stage 2 of PSID is performed). Solid lines show the average decoding CC and shaded areas show the s.e.m. FIG. 22, b shows the same as FIG. 22, a, for monkey C. For both subjects and in all cases (other than PSID not seeing any joint for which it reduces to NDM), PSID decoding was significantly better than NDM decoding ($P<10^{-6}$; one-sided signed-rank; $N_s\geq48$).

FIG. 23 shows that PSID again reveals a markedly lower dimension for behaviorally relevant neural dynamics in the motor cortex LFP activity when behavior is taken as the 3D end-point position (of hand and elbow) instead of the joint angles. The convention for FIG. 23 is the same as FIG. 6, but this time for behavior taken as the 3D position of hand and elbow ($n_z=6$). Similar to the results for joint angles (FIG. 6), here, PSID again revealed a significantly lower dimension for behaviorally relevant neural dynamics compared with NDM for both monkeys (panels b, i; $P<10^{-6}$; one-sided signed-rank; $N_s\geq48$) and achieved a significantly better decoding compared with NDM and RM even when they used much higher-dimensional states (panels c, d, j, k; $P<10^{-8}$; one-sided signed-rank; $N_s\geq48$). Moreover, in both monkeys, the dimension of behaviorally relevant neural dynamics revealed by PSID was again significantly smaller than the dimension of dynamics in the recorded neural activity ($P<10^{-18}$; one-sided rank-sum) and in behavior ($P<0.004$; one-sided rank-sum) as estimated based on their self-prediction (panels g, n).

FIG. 24 shows that PSID again reveals a markedly lower dimension for behaviorally relevant neural dynamics in the motor cortex LFP activity when behavior is taken as the angular velocity of joint angles instead of the joint angles. The convention for FIG. 24 is the same as FIG. 6, but this time for behavior taken as the first order derivative of joint angles (i.e., joint velocity). Statistics and conclusions are as in FIG. 23.

FIG. 25 shows PSID-extracted latent states capture both within-trial and trial-to-trial variability in behavior. FIG. 25, a shows within-trial variability, quantified as the variance of behavior trajectory averaged separately across all reach and return epochs (square root of average variance in each movement direction (Dir)). Dir 1, 2 and 3 were depth, height and breadth from the perspective of the subject, respectively. Behavior is taken as the 3D end-point position of hand and elbow as in FIG. 23. Bars and asterisks are defined in as in FIG. 6, c. % indicates what percentage of total within-trial variability is due to a given direction. FIG. 25, b shows trial-to-trial variability, quantified as the s.d. of target position in each direction in the 3D physical space. % indicates what percentage of total trial-to-trial variability is due to a given direction. FIG. 25, c shows the PSID behavior decoding accuracy is shown averaged in each of the 3 movement directions for different neural latent state dimensions of $n_x=1, 2, 3$. FIG. 25, d-f shows the same as FIG. 25, a-c, for monkey C. In both monkeys, out of the 3 directions in 3D movement space, in some directions the behavior showed relatively more within-trial variability and relatively less trial-to-trial variability (i.e. Dir 1 and 2, panels a, b, d, e; $P<0.004$; one-sided signed-rank; $N_s\geq16$). The two movement directions that had relatively larger within-trial variability in behavior (i.e. Dir 1 and Dir 2) reached almost peak decoding accuracy with only a 1D latent state (panels c, f). Learning a model with a 2D latent state only significantly improved the decoding for the third movement direction that had relatively larger trial-to-trial variability in behavior (i.e. Dir 3, panels c, f; P<0.05; one-sided rank-sum; $N_s \geq 48$). This suggests that compared with a 1D latent state, a 2D latent state encoded additional dynamics that were largely related to the trial-to-trial variability in behavior.

FIG. 26 illustrates that PSID reveals that behaviorally relevant information varies across different brain regions in similar ways for different joints, with M1 and PMd consistently containing more information than PMv or PFC. FIG. 26, a shows decoding accuracy using PSID when channels within different anatomical regions are used for decoding. Decoding for each arm, elbow and wrist joint is shown, as well as average decoding over different joint groups. FIG. 26, b shows the same as FIG. 26, a for all finger joints separately and averaged within joints of each finger. FIG. 26, c, d show the same as FIG. 26, a, b for monkey C. The ipsilateral (right) hemisphere in monkey C was also predictive of behavior, which is consistent with prior work.

Figure 27:
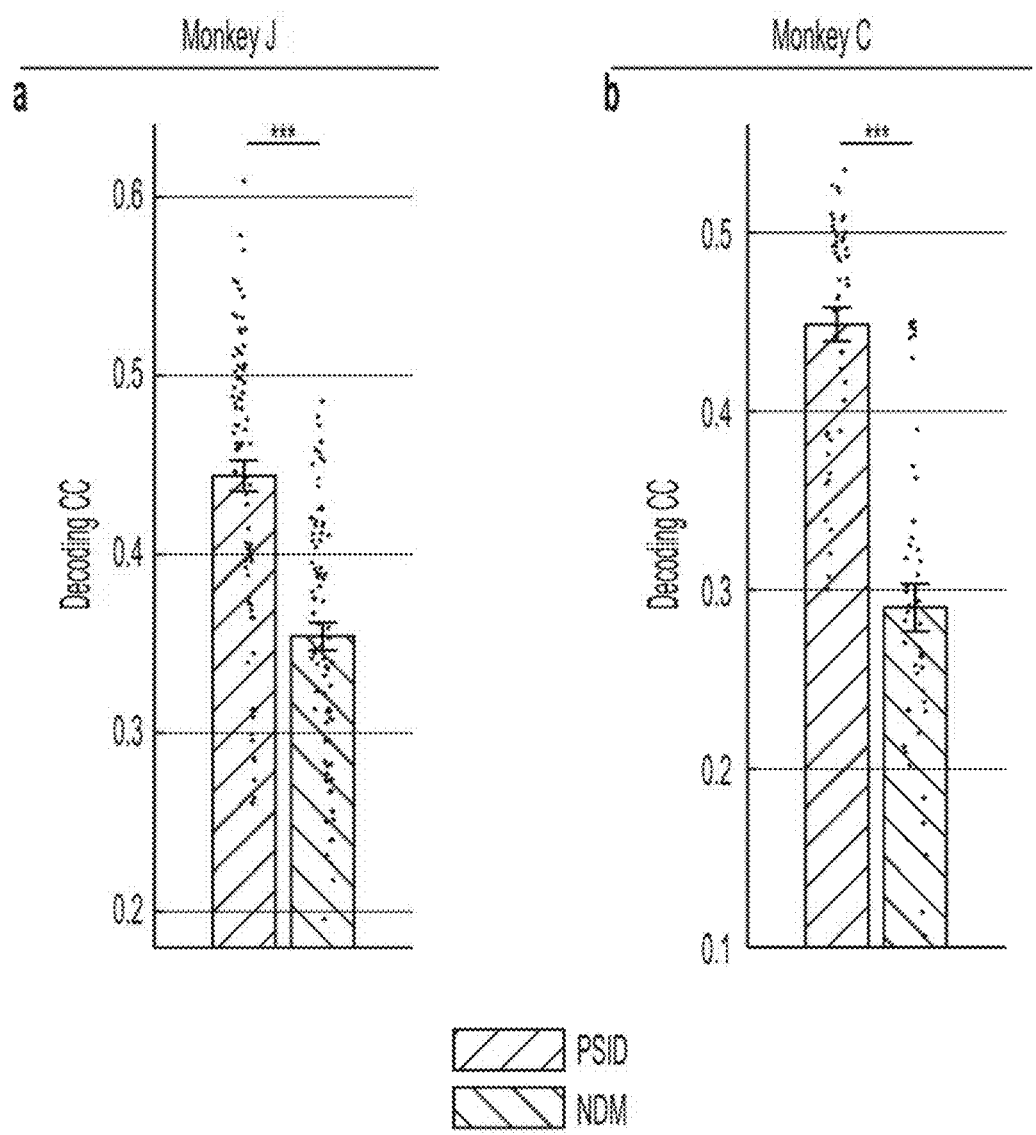
FIG. 27 illustrates that even when nonlinear Support Vector Regression (SVR) is used to map the latent state to behavior, the rotational states extracted by PSID are more predictive of behavior than those extracted by standard NDM according to an embodiment of the present invention.

FIG. 27 shows that even when nonlinear Support Vector Regression (SVR) is used to map the latent state to behavior, the rotational states extracted by PSID are more predictive of behavior than those extracted by standard NDM. FIG. 27, a shows nonlinear SVR decoding for exactly the same rotational latent states shown in FIG. 8, a, b. The figure convention is the same as in FIG. 8, c. FIG. 27, b shows the same as FIG. 27, a for monkey C.

FIG. 28 shows that extraction of bidirectional rotational dynamics using PSID was robust to brain region and held also when modeling neural activity within different cortical regions separately. FIG. 28, a shows average trajectory of 2D states identified by PSID during reach and return epochs, when neural activity within different cortical areas is modeled separately. The figure convention is the same as in FIG. 8, a. FIG. 28, b shows decoding accuracy of using the 2D PSID states or the 2D NDM states (from FIG. 28, a) to decode behavior. The figure convention is the same as in FIG. 8, c. FIG. 28, c, d show the same as FIG. 28, a, b for monkey C. In both monkeys, similar to the results in FIG. 8, PSID again extracted latent states that, unlike the latent states extracted using NDM, rotated in opposite directions during reach and return (panels a, c) and resulted in more accurate decoding of behavior (panels b, d; $P<10^{-11}$; one-sided signed-rank; $N_s \geq 60$).

FIG. 29 shows that extraction of bidirectional rotational dynamics using PSID was robust to behavioral signals and held also when modeling different subsets of joints and simulated muscle activations. FIG. 29, a shows average trajectory of 2D states identified by PSID during reach and return epochs, when only arm, elbow, and wrist joints are taken as the behavior. The figure convention is the same as in FIG. 8, a. For standard NDM, extracted 2D states do not depend on the behavior being modeled and are always the same as those shown in FIG. 8, b, e, regardless of the behavior that is being modeled. FIG. 29, b shows decoding accuracy of using PSID 2D states (from FIG. 29, a) or NDM 2D states (from FIG. 8, b) to decode behavior. The figure convention is the same as in FIG. 8, c. FIG. 29, c, d show the same as FIG. 29, a, b for monkey C. FIG. 29, e-h shows the same as FIG. 29, a-d for when only finger joints are taken as the behavior. FIG. 29, i-1 shows the same as FIG. 29, a-d for when inferred muscle activations for upper and lower arm muscles (inferred from joint angles using OpenSim) are taken as the behavior. For all behavioral signals, similar to the results in FIG. 8, PSID again extracted latent states that, unlike the latent states extracted using NDM, rotated in opposite directions during reach and return (panels a, c, e, g, i, k) and resulted in more accurate decoding of behavior (panels b, d, f, h, j, 1; $P<10^{-6}$; one-sided signed-rank; $N_s \geq 48$).

FIG. 30 shows that similar to NDM, jPCA extracts rotations that are in the same direction during reach and return epochs. FIG. 30, a uses the same convention as FIG. 8 for projections to 2D spaces extracted using jPCA. FIG. 30, b shows the same as FIG. 30, a for monkey C.

FIG. 31 shows that PSID again achieved better decoding using lower-dimensional latent states when RNN-based nonlinear NDM always used a dynamical latent state with much higher dimension of 64 and/or when RNN-based nonlinear NDM used a Poisson observation model with a faster time step. The figure convention is the same as in FIG. 9, with additional configurations for the RNN-based nonlinear NDM method (i.e. LFADS) added to the comparison (Methods). As in FIG. 9, the dimension of the initial condition for LFADS is always 64. The alterations from FIG. 9 are as follows. First, in FIG. 9, the state dimension for LFADS—which is equal to the number of LFADS generator units in its formulation and determines how many variables are needed to generate the dynamics in the next time step from the dynamics in the current time step—was set to the number of factors to provide a directly comparable result with other methods (with this choice number of LFADS factors is equal to its state dimension and is thus comparable with the state dimension in other methods). Here, instead, the inventors also considered always setting the LFADS state dimension (i.e. number of generator units) to 64 regardless of the number of factors. Thus, for this configuration of LFADS, the horizontal axis in panels (a) and (e) and the vertical axis in panels (b) and (f) only refer to number of factors, which is always smaller than the LFADS state dimension of 64. Even in this case where nonlinear NDM always uses 64 dimensional states to describe the dynamics, PSID reveals a markedly lower dimension than the number of factors in nonlinear NDM, and achieves better decoding than nonlinear NDM. Second, in FIG. 9, to provide a directly comparable result with PSID, the same Gaussian smoothed spike counts with 50 ms bins were used for both PSID and LFADS as inputs. Here, instead, the inventors also allow LFADS to use non-smoothed spike counts with 10 ms bins and a Poisson observation model. Interestingly, for nonlinear NDM, switching the observation model from Gaussian to Poisson improved the peak decoding in monkey J ($P<10^{-3}$; one-sided signed-rank; $N_s=26$), while both observation models achieved similar decoding in monkey C ($P>0.07$; two-sided signed-rank; $N_s=16$). Nevertheless, comparisons with PSID remained as before for all these nonlinear NDM configurations (regardless of it using Poisson or Gaussian observations): PSID revealed a markedly lower dimension than the number of factors in nonlinear NDM (panels b, f; $P<0.004$; one-sided signed-rank; $N_s \geq 16$) and achieved better decoding than even a nonlinear NDM with a larger number of factors than the PSID state dimension (panels a, c, d, e, g, h; $P<0.03$; one-sided signed-rank; $N_s \geq 16$). This is because nonlinear NDM, similar to linear NDM and unlike PSID, only considers neural activity when learning the dynamic model. This shows that the PSID advantage is in its novel formulation and two-stage approach for learning the dynamic model by considering both neural activity and behavior.

FIG. 32 shows that PSID reveals low-dimensional behaviorally relevant dynamics in an existing data consisting of prefrontal raw LFP activity during a task with saccadic eye movements. The figure convention is the same as FIG. 6, a-d, except for a completely different behavioral task, brain region, and neural signal type. Here monkeys perform saccadic eye movements while PFC activity is being recorded. Raw LFP activity is modeled and the behavior consists of the 2D position of the eye. Similar results hold with PSID more accurately identifying the behaviorally relevant dynamics than both NDM and RM. PSID again reveals a markedly lower dimension for behaviorally relevant dynamics than NDM. Also, note that RM provides no control over the dimension of dynamics and is forced to use a state dimension equal to the behavior dimension ($n_z=2$), which in this case is an underestimation of dimension of behaviorally relevant dynamics in neural activity as evident by RM's much worse decoding accuracy compared with PSID.

Table 2 below shows an exemplary preferential system identification (PSID) algorithm. A visualization is shown in FIG. 10.

---

Given the training time series $\{y_k: 0 \leq k < N, y_k \in \mathbb{R}^{n_y}\}$ and $\{z_k: 0 \leq k < N, z_k \in \mathbb{R}^{n_z}\}$, state dimension $n_x$ and parameters $n_1 \leq n_x$ (number of states extracted in the first stage) and $i \geq 2$ (projection horizon), this algorithm identifies parameters of a general dynamic linear state-space model as in Equation 4.

1. Form the following matrices (visualized in FIG. 10, a for the simplified case of $i = 1$):

$$\begin{bmatrix} Y_p \\ Y_f \end{bmatrix} \triangleq \begin{bmatrix} y_0 & y_1 & \cdots & y_{j-1} \\ y_1 & y_2 & \cdots & y_j \\ \vdots & \vdots & \ddots & \vdots \\ y_{i-1} & y_i & \cdots & y_{j+i-1} \\ \hline y_i & y_{i+1} & \cdots & y_{j+1} \\ y_{i+1} & y_{i+2} & \cdots & y_{j+i+1} \\ \vdots & \vdots & \ddots & \vdots \\ y_{2i-1} & y_{2i} & \cdots & y_{j+2i-1} \end{bmatrix} = \begin{bmatrix} y_0 & y_1 & \cdots & y_{j-1} \\ y_1 & y_2 & \cdots & y_j \\ \vdots & \vdots & \ddots & \vdots \\ y_{i-1} & y_i & \cdots & y_{j+i-1} \\ y_i & y_{i+1} & \cdots & y_{j+1} \\ \hline y_{i+1} & y_{i+2} & \cdots & y_{j+i+1} \\ \vdots & \vdots & \ddots & \vdots \\ y_{2i-1} & y_{2i} & \cdots & y_{j+2i-1} \end{bmatrix} \triangleq \begin{bmatrix} Y_p^+ \\ Y_f^- \end{bmatrix} \triangleq \begin{bmatrix} Y_p \\ Y_i \\ Y_f \end{bmatrix} \quad (1)$$

$$\begin{bmatrix} Z_p \\ Z_f \end{bmatrix} \triangleq \begin{bmatrix} z_0 & z_1 & \cdots & z_{j-1} \\ z_1 & z_2 & \cdots & z_j \\ \vdots & \vdots & \ddots & \vdots \\ z_{i-1} & z_i & \cdots & z_{j+i-1} \\ \hline z_i & z_{i+1} & \cdots & z_{j+1} \\ z_{i+1} & z_{i+2} & \cdots & z_{j+i+1} \\ \vdots & \vdots & \ddots & \vdots \\ z_{2i-1} & z_{2i} & \cdots & z_{j+2i-1} \end{bmatrix} = \begin{bmatrix} z_0 & z_1 & \cdots & z_{j-1} \\ z_1 & z_2 & \cdots & z_j \\ \vdots & \vdots & \ddots & \vdots \\ z_{i-1} & z_i & \cdots & z_{j+i-1} \\ z_i & z_{i+1} & \cdots & z_{j+1} \\ \hline z_{i+1} & z_{i+2} & \cdots & z_{j+i+1} \\ \vdots & \vdots & \ddots & \vdots \\ z_{2i-1} & z_{2i} & \cdots & z_{j+2i-1} \end{bmatrix} \triangleq \begin{bmatrix} Z_p^+ \\ Z_f^- \end{bmatrix} \triangleq \begin{bmatrix} Z_p \\ Z_i \\ Z_f \end{bmatrix} \quad (2)$$

Number of rows in the matrices defined above are as follows:

$Y_p$ and $Y_f$ have $i \times n_y$ rows. $Y_p^+$ has $(i + 1) \times n_y$ rows. $Y_f^-$ has $(i - 1) \times n_y$ rows. $Y_i$ has $n_y$ rows.

$Z_p$ and $Z_f$ have $i \times n_z$ rows. $Z_p^+$ has $(i + 1) \times n_z$ rows. $Z_f^-$ has $(i - 1) \times n_z$ rows. $Z_i$ has $n_z$ rows.

Number of columns in all these matrices is $j = N - 2i + 1$.

2. If $n_1 = 0$ (no behaviorally relevant latent states), skip to step 9
3. [Begins stage 1 of PSID]: Compute the least squares prediction of $Z_f$ from $Y_p$, and $Z_f^-$ from $Y_p^+$ as:

$$\hat{Z}_f = Z_f Y_p^T (Y_p Y_p^T)^{-1} Y_p \quad (3)$$
$$\hat{Z}_f^- = Z_f^- Y_p^{+T} (Y_p^+ Y_p^{+T})^{-1} Y_p^+ \quad (4)$$

4. Compute the singular value decomposition (SVD) of $\hat{Z}_f$ and keep the top $n_1$ singular values:

$$\hat{Z}_f = USV^T \cong U_1 S_1 V_1^T \quad (5)$$

5. Compute the behavior observability matrix $\Gamma_{z_i}^{(1)}$ and the behaviorally relevant latent state $\hat{X}_i^{(1)}$ as ($\dagger$ denotes pseudoinverse):

$$\Gamma_{z_i}^{(1)} = U_1 S_1^{1/2} \quad (6)$$
$$\hat{X}_i^{(1)} = \Gamma_{z_i}^{(1)\dagger} \hat{Z}_f \quad (7)$$

6. Remove the last $n_z$ rows of $\Gamma_{z_i}^{(1)}$ to get $\Gamma_{z_{i-1}}^{(1)}$ and then compute the behaviorally relevant latent state at the next time step $(\hat{X}_{i+1}^{(1)})$ as:

$$\Gamma_{z_{i-1}}^{(1)} = \Gamma_{z_i}^{(1)}{}_{(1:(i-1)\times n_z, :)} \quad (8)$$

$$\hat{X}_{i+1}^{(1)} = \Gamma_{z_{i-1}}^{(1)\dagger} \hat{Z}_f^- \quad (9)$$

7. Compute the least squares solution for $A_{11}$ using the latent states as:

$$A_{11} = \hat{X}_{i+1}^{(1)} \hat{X}_i^{(1)\dagger} \quad (10)$$

8. If $n_x = n_1$ (no additional states), set $A = A_{11}$, $\hat{X}_i = \hat{X}_i^{(1)}$ and $\hat{X}_{i+1} = \hat{X}_{i+1}^{(1)}$ and skip to step 17
9. [Begins stage 2 of PSID]: If $n_1 > 0$, find the neural observability matrix $\Gamma_{y_i}^{(1)}$ for $\hat{X}_i^{(1)}$ as the least squares solution of predicting $Y_f$ using $\hat{X}_i^{(1)}$, and subtract this prediction from $Y_f$ (otherwise set $Y_f' = Y_f$).

$$\Gamma_{y_i}^{(1)} = Y_f \hat{X}_i^{(1)T} (\hat{X}_i^{(1)} \hat{X}_i^{(1)T})^{-1} \quad (11)$$
$$Y_f' = Y_f - \Gamma_{y_i}^{(1)} \hat{X}_i^{(1)} \quad (12)$$

10. If $n_1 > 0$, remove the last $n_y$ rows of $\Gamma_{y_i}^{(1)}$ to find the neural observability matrix for $\hat{X}_{i+1}^{(1)}$ and subtract the corresponding prediction from $Y_f^-$ (otherwise if $n_1 = 0$, set $Y_f^{-'} = Y_f^-$).

$$\Gamma_{y_{i-1}}^{(1)} = \Gamma_{y_i}^{(1)}{}_{(1:(i-1)\times n_y, :)} \quad (13)$$

-continued $$Y_f^{-\prime} = Y_f^- - \Gamma_{y_{i-1}}^{(1)}\hat{X}_{i+1}^{(1)}$$ (14)

11. Compute the least squares prediction of $Y_f'$ from $Y_p$, and $Y_f^{-\prime}$ from $Y_p^+$ as:

$$\hat{Y}_f' = Y_f' Y_p^T (Y_p Y_p^T)^{-1} Y_p$$ (15)

$$\hat{Y}_f^{-\prime} = Y_f^{-\prime} Y_p^{+T} (Y_p^+ Y_p^{+T})^{-1} Y_p^+$$ (16)

12. Compute the SVD of $\hat{Y}_f'$ and keep the top $n_2 = n_x - n_1$ singular values:

$$\hat{Y}_f' = U'S'V'^T \cong U_2 S_2 V_2^T$$ (17)

13. Compute the remaining neural observability matrix $\Gamma_{y_i}^{(2)}$ and the corresponding latent state $\hat{X}_i^{(2)}$ as:

$$\Gamma_{y_i}^{(2)} = U_2 S_2^{1/2}$$ (18)

$$\hat{X}_i^{(2)} = \Gamma_{y_i}^{\dagger} \hat{Y}_f'$$ (19)

14. Remove the last $n_y$ rows of $\Gamma_{y_i}^{(2)}$ to get $\Gamma_{y_{i-1}}^{(2)}$ and then compute the remaining latent states at the next time step ($\hat{X}_{i+1}^{(2)}$) as:

$$\Gamma_{y_{i-1}}^{(2)} = \Gamma_{y_i}^{(2)}{}_{(1:(i-1)\times n_y,:)}$$ (20)

$$\hat{X}_{i+1}^{(2)} = \Gamma_{y_{i-1}}^{(2)\dagger} \hat{Y}_f^{-\prime}$$ (21)

15. If $n_1 > 0$, concatenate $\hat{X}_i^{(2)}$ to $\hat{X}_i^{(1)}$ and $\hat{X}_{i+1}^{(2)}$ to $\hat{X}_{i+1}^{(1)}$ to get the full latent state (otherwise set $\hat{X}_i = \hat{X}_i^{(2)}$ and $\hat{X}_{i+1} = \hat{X}_{i+1}^{(2)}$):

$$\hat{X}_i = \begin{bmatrix} \hat{X}_i^{(1)} \\ \hat{X}_i^{(2)} \end{bmatrix}, \hat{X}_{i+1} = \begin{bmatrix} \hat{X}_{i+1}^{(1)} \\ \hat{X}_{i+1}^{(2)} \end{bmatrix}$$ (22)

16. Compute the least squares solution for $A_{21}$ and $A_{22}$ using the latent states and form the full A as:

$$[A_{21}\ A_{22}] = \hat{X}_{i+1}^{(2)} \hat{X}_i^{\dagger}$$ (23)

$$A = \begin{bmatrix} A_{11} & 0 \\ A_{21} & A_{22} \end{bmatrix}$$ (24)

17. Compute the least squares solution for $C_y$ and $C_z$ using the latent states and the observations as:

$$C_y = Y_i \hat{X}_i^{\dagger}$$ (25)

$$C_z = Z_i \hat{X}_i^{\dagger}$$ (26)

18. Compute the residuals as:

$$\begin{bmatrix} W_i \\ V_i \end{bmatrix} = \begin{bmatrix} \hat{X}_{i+1} \\ Y_i \end{bmatrix} - \begin{bmatrix} A \\ C_y \end{bmatrix} \hat{X}_i$$ (27)

19. Compute the noise statistics as the sample covariance of the residuals:

$$\begin{bmatrix} Q & S \\ S^T & R \end{bmatrix} = \frac{1}{j} \begin{bmatrix} W_i \\ V_i \end{bmatrix} \begin{bmatrix} W_i \\ V_i \end{bmatrix}^T$$ (28)

20. Solve Equation 47 to find the steady-state solution $\bar{P}$, and substitute $\bar{P}$ in Equation 46 to get the steady-state Kalman gain K.
21. If parameters $L_y$ and $G_y$ are of interest, solve the Lyapunov Equation 37 to get $\Sigma_x$, and then use Equations 38, 39 to compute $\Sigma_y$ and $G_y$, respectively. These parameters are not needed for Kalman filtering or for decoding behavior from neural activity (Equation 45).

Discussion will now turn to the distinction between primary and secondary signals. To clarify the difference between the signals $y_k$ and $z_k$ in Equation 2, it is worth noting that in the formulation of Equation 2, $y_k$ is taken as the primary signal in the sense that the latent state $x_k$ describes the complete dynamics of $y_k$ that also includes its shared dynamics with the secondary signal $z_k$. The designation of the primary and secondary signals (e.g. taking $y_k$ to be the neural activity and $z_k$ to be the behavior or vice versa) is interchangeable as far as the shared dynamics of the two signals are of interest and the choice of the primary signal only determines which signal's dynamics are fully described beyond the shared dynamics. In this work the inventors took the primary signal $y_k$ to be the neural activity and the secondary signal $z_k$ to be the behavior. This is motivated by the typical scenario in neuroscience and neuroengineering where the neural activity is often considered the primary signal and the goal is to learn how behavior is encoded in it or to decode behavior from it.

The term $C_z x_k^s$ in Equation 2 may be referred to as:

$$z_{1_k} = C_z x_k^s,$$ Equation 36:

This equation represents the part of the secondary signal $z_k$ that is contributed by $x_k^s$ and thus shared with the primary signal. Any additional dynamics of the secondary signal that are not shared with the primary signal are modeled as the general independent signal $\epsilon_k$. If modeling these dynamics of the secondary signal is also of interest, after learning the parameters of Equation 2, one could use the model to estimate $z_{1_k}$ and thus $\epsilon_k$ (as $\epsilon_k = z_k - z_{1_k}$) in the training data and then use standard dynamic modeling techniques (e.g. SID) to characterize the dynamics of $\epsilon_k$ in terms of another latent state-space model. But since these dynamics are independent of $y_k$, such characterization would not be helpful in describing the encoding of $z_k$ in $y_k$ or in decoding of $z_k$ from $y_k$ and thus the disclosure will not discuss their identification, and only discusses their generation in the numerical simulations.

Equivalent sets of parameters can be used to fully describe the model. The specification defines $G_y \triangleq$ $E\{x_{k+1}{}^s y_k{}^T\}$ specifying the cross-covariance of $y_k$ with the state at the next time step, $\Sigma_x \triangleq E\{x_k{}^s x_k{}^{s^T}\}$ specifying the covariance of $x_k{}^s$ and $\Sigma_y \triangleq E\{y_k y_k{}^T\}$ specifying the covariance of $y_k$. From Equation 2, it is straight forward to show that these covariances are related to the model noise statistics (Equation 3) via the following equations:

$$\Sigma_x = A\Sigma_x A^T + Q \qquad \text{Equation 37:}$$

$$\Sigma_y = C_y \Sigma_x C_y{}^T + R \qquad \text{Equation 38:}$$

$$G_y = A\Sigma_x C_y{}^T + S \qquad \text{Equation 39:}$$

Equation 37 is also known as the Lyapunov equation. The Lyapunov Equation 37 has a unique solution for $\Sigma_x$ if A is stable (i.e. the absolute value of all its eigenvalues are less than 1). For stable systems (models with a stable A), it is clear from Equations 37-39 that there is a one to one relation between the set of parameters $(A, C_y, C_z, G_y, \Sigma_y, \Sigma_x)$ and the set $(A, C_y, C_z, Q, R, S)$, and thus both sets can be used to describe the model in Equation 2.

Equation 2 is known as the forward stochastic formulation for a linear state-space model. Given that only $y_k$ and $z_k$ are measurable real quantities and that the stochastic latent state $x_k{}^s$ is not directly accessible, Equation 2 is called an internal description for the signals $y_k$ and $z_k$. This internal description is not unique and a family of infinitely many models with different $x_k{}^s$ can describe the same $y_k$ and $z_k$. For example, any non-singular matrix T' can transform Equation 2 to an equivalent model with $x_{k_{new}}{}^s = T' x_k{}^s$, a process known as a similarity transform (or a change of basis). Moreover, Faurre's stochastic realization problem shows that even beyond similarity transforms, there are non-unique sets of noise statistics (Q, R, and S) that give the exact same second order statistics for $y_k$. The unique and complete external description for $y_k$ and $z_k$ consists of their second order statistics. Thus, in the model learning problem, all models that give the correct external description are equally valid solutions. The set of parameters $(A, C_y, C_z, G_y, \Sigma_y, \Sigma_x)$ are thus more suitable (compared with the equivalent set of parameters $(A, C_y, C_z, Q, R, S)$) for evaluating model learning because among this set, all parameters other than $\Sigma_x$ are uniquely determined from second order statistics of $y_k$ and $z_k$, up to within a similarity transform.

The discussion will now turn to an equivalent model formulation with behaviorally relevant states separated from other states giving rise to Equation 4. Given the second order statistics of $y_k$ (its auto-covariances at all possible time differences, see Equation 52), any set of parameters for that would describe how the same second order statistics could be generated from a latent state $x_k{}^s$ is known as a realization for $y_k$. Equation 2 can be rewritten in an equivalent realization in which the behaviorally relevant states are clearly separated from the others. To do this, without loss of generality, it is first assumed that Equation 2 is written as a minimal realization of $y_k$, defined as a realization with the smallest possible state dimension $n_x$. For such a minimal realization, it can be shown that the pair $(A, C_y)$ is observable and the pair $(A, G_y)$ is reachable. Equivalently, both the neural observability matrix of Equation 40 and the neural reachability matrix of Equation 41 are full rank with rank of $n_x$.

$$\Gamma_y = \begin{bmatrix} C_y \\ C_y A \\ \vdots \\ C_y A^{n_x-1} \end{bmatrix} \qquad \text{Equation 40}$$

$$\Delta_y = [G_y A G_y \ldots A^{n_x-1} G_y] \qquad \text{Equation 41:}$$

Since not all latent states that contribute to the neural activity are expected to also contribute to a specific behavior of interest (Equations 2 and 36), the pair $(A, C_z)$ is not necessarily observable (i.e. it may not be possible to uniquely infer the full latent state $x_k{}^s$ only from behavioral observations $z_k$). In other words, the behavior observability matrix of Equation 42:

$$\Gamma_z = \begin{bmatrix} C_z \\ C_z A \\ \vdots \\ C_z A^{n_x-1} \end{bmatrix} \qquad \text{Equation 42}$$

may not be full rank. $n_1 = \text{rank}(\Gamma_z)$ is defined as the number of latent states that drive behavior because as shown next, the latent state $x_k{}^s$ can be separated into two parts in a way that only $n_1$ dimensions contribute to the behavior $z_k$. It can be shown that if $n_1 < n_x$, there exists a nonsingular matrix T' that via the similarity transform of Equation 43:

$$\begin{bmatrix} x_k^{(1)} \\ x_k^{(2)} \end{bmatrix} = x_k = T' x_k^s \qquad \text{Equation 43}$$

gives Equation 4 as an equivalent formulation for Equation 2. Finally, replacing the A and $C_z$ matrices in Equation 42 with their values in Equation 4 gives:

$$\Gamma_z = \begin{bmatrix} C_{z_1} & 0 \\ C_{z_1} A_{11} & 0 \\ \vdots & 0 \\ C_{z_1} A_{11}^{n_x-1} & 0 \end{bmatrix} = [\Gamma_z^{(1)} \ 0] \qquad \text{Equation 44}$$

showing that in the formulation of Equation 4, the behavior observability matrix has exactly $n_1$ non-zero columns (i.e. its first $n_1$ columns, denoted by $\Gamma_z^{(1)}$ in Equation 44), which is consistent with its rank being $n_1$.

Discussion now turns to Kalman filtering and the equivalent forward innovation formulation. Given the linear state-space formulation of Equation 2, it can be shown that the best prediction of $y_{k+1}$ using $y_1$ to $y_k$ (denoted as $\hat{y}_{k+1|k}$) in the sense of having the minimum mean-square error, and similarly the best prediction of $z_{k+1}$ using $y_1$ to $y_k$ (denoted as $\hat{z}_{k+1|k}$) are obtained with the well-known recursive Kalman filter, which can be written as:

$$\begin{cases} \hat{x}_{k+1|k} = A\hat{x}_{k|k-1} + K_k(y_k - C\hat{x}_{k|k-1}) \\ \hat{y}_{k+1|k} = C_y \hat{x}_{k+1|k} \\ \hat{z}_{k+1|k} = C_z \hat{x}_{k+1|k} \end{cases} \qquad \text{Equation 45}$$

where the recursion is initialized with $\hat{x}_{0|-1} = 0$ and $K_k$ is the Kalman gain equal to $$K_k = (A\tilde{P}_{k|k-1} C_y{}^T + S)(C_y \tilde{P}_{k|k-1} C_y{}^T + R)^{-1} \qquad \text{Equation 46:}$$

Here $\tilde{P}_{k|k-1}$ is the covariance of the error for one-step-ahead prediction of the state (i.e. covariance of $\tilde{x}_{k|k-1} = \hat{x}_{k|k-1} - x_k$) and can be computed via the recursive Riccati equation:

$$\tilde{P}_{k+1|k} = A\tilde{P}_{k|k-1} A^T + Q - (A\tilde{P}_{k|k-1} C_y{}^T + S)(C_y \tilde{P}_{k|k-1} C_y{}^T + R)^{-1}(A\tilde{P}_{k|k-1} C_y{}^T + S)^T \qquad \text{Equation 47:}$$

with the recursion initialized with $P_{0|-1}=R_y$. The steady-state solution of Riccati equation can be obtained by replacing $\tilde{P}_{k+1|k}$ with $\tilde{P}_{k|k-1}$ in the equation and solving for $\tilde{P}_{k|k-1}$. The specification drops the subscript and denotes the steady-state solution of Equation 47 as $\tilde{P}$ and the associated steady-state Kalman gain as K, which is obtained by substituting $\tilde{P}$ in Equation 46.

Writing the outputs in terms of the Kalman filter states gives an alternative formulation for Equation 2, which is known as the forward innovation formulation and is more convenient for deriving PSID (see Equation 48 below). In particular, first, this formulation shows that the optimal estimate of the latent state is a linear function of the past neural activity (see Equation 49 below). Second, this formulation shows that the best prediction of future behavior and neural activity using past neural activity is a linear function of the latent state (Equation 45 or Equation 48 below). Together, with these two facts, it can be shown that linear projections of future behavior and neural activity onto the past neural activity can be used to directly extract the latent states from the data (as the latent state is a linear function of past neural activity and thus involves a projection onto the past neural activity), without knowing model parameters. This extracted latent state can then be used to learn the model parameters. The forward innovation formulation is given by:

$$\begin{cases} x_{k+1} = A x_k + K e_k \\ y_k = C_y x_k + e_k \\ z_k = C_z x_k + \varepsilon_k \end{cases} \qquad \text{Equation 48}$$

In Equation 48, $x_k \triangleq \hat{x}_{k|k-1}$, K is the steady-state Kalman gain and $e_k$ is the innovation process, which is the part of $y_k$ that is not predictable from its past values. Equations 2 and 48 have different state and noise time-series but are equivalent alternative internal descriptions for the same $y_k$ and $z_k$. The forward innovation formulation in Equation 48 is more convenient (compared with the forward stochastic formulation in Equation 2) for the derivation of PSID. Specifically, by recursively substituting the previous iteration of Equation 48 into its current iteration, it can be shown that:

$$\hat{x}_{k|k-1} = \Delta_{y_k}^c \Lambda_{y_k}^{-1} \begin{bmatrix} y_0 \\ \vdots \\ y_{k-1} \end{bmatrix} \qquad \text{Equation 49}$$

Where:

$$\Delta_{y_k}^c = [A^{k-1} G_y \; A^{k-2} G_y \; \ldots \; A G_y \; G_y] \qquad \text{Equation 50}$$

And:

$$\Lambda_{y_k} \triangleq \begin{bmatrix} \Sigma_{y_0} & \Sigma_{y_{-1}} & \cdots & \Sigma_{y_{1-k}} \\ \Sigma_{y_1} & \Sigma_{y_0} & \cdots & \Sigma_{y_{2-k}} \\ \vdots & \vdots & \ddots & \vdots \\ \Sigma_{y_{k-1}} & \Sigma_{y_{k-2}} & \cdots & \Sigma_{y_0} \end{bmatrix} \qquad \text{Equation 51}$$

with the notation $\Sigma_{y_d} \triangleq E\{y_{k+d} y_k^T\}$. This formulation reveals a key observation that enables identification of model parameters via a direct extraction of the latent state: the latent state in Equation 48 (which is an equivalent formulation for Equation 2), is a linear function of the past neural activity $y_k$. Moreover, from Equation 2, it can be shown that for $d \geq 1$:

$$\Sigma_{y_d} \triangleq E\{y_{k+d} y_k^T\} = C_y A^{d-1} G_y, \Sigma_{y_{-d}} = (C_y A^{d-1} G_y)^T \qquad \text{Equation 52}$$

indicating that $\Lambda_{y_k}$ in Equation 51 and thus the linear prediction function $\Delta_{y_k}^c \Lambda_{y_k}^{-1}$ in Equation 49 only depend on $\Sigma_y$, A, $C_y$ and $G_y$. Thus, from Equations 45 and 49 it is clear that the only parameters that are needed for optimal prediction of $y_k$ and $z_k$ using past $y_k$ are A, $C_y$, $C_z$, $G_y$ and $\Sigma_y$, which are all parameters that are uniquely identifiable within a similarity transform. As confirmed with numerical simulations, all these parameters can be accurately identified using PSID (FIG. 12).

Discussion now turns to PSID stage 1; extracting behaviorally relevant latent states. The central idea in PSID is that the part of $z_k$ that is predictable from past $y_k$ not only is a linear function of the latent state (Equation 45), but also is a linear combination of the past $y_k$ (Equations 45 and 49) and thus must lie in a subspace of the space spanned by the past $y_k$. An orthogonal projection can thus be used from future $z_k$ onto past $y_k$ to extract the part of $z_k$ that is predictable from past $y_k$, which leads to the direct extraction of the behaviorally relevant latent states from the neural and behavior data $y_k$ and $z_k$, even before the model parameters are known. Given the extracted latent states, the model parameters can then be identified using least squares based on Equation 4 as described below.

In the first stage of PSID, the part of $z_k$ that is predictable from past $y_k$ is extracted from the training data by projecting the future $z_k$ values onto their corresponding past $y_k$ values. To find the projection, for each time k, the inventors considered the corresponding 'past' and 'future' to be the previous i samples and the next i−1 samples respectively, with i being a user specified parameter termed the projection horizon. For each sample $y_k$ with $i \leq k \leq N-i$, the previous (past) i samples (from $y_{k-i}$ to $y_{k-1}$) are all stacked together as the (k−i+1)th column of one large matrix $Y_p \in \mathbb{R}^{in_y \times j}$ (with j=N−2i+1); correspondingly, for each sample $y_k$ with $i \leq k \leq N-i$, that sample together with the next (future) i−1 samples (from $y_k$ to $y_{k+i-1}$) are all stacked together as the (k−i+1)th column of one large matrix $Y_f \in \mathbb{R}^{in_y \times j}$ (Equation 8). Analogously, matrices $Z_p \in \mathbb{R}^{in_z \times j}$ and $Z_f \in \mathbb{R}^{in_z \times j}$ are formed from $z_k$ (Equation 9). Thus, $Z_f$ and $Y_p$ have the same number of columns with each column of $Z_f$ containing some consecutive samples of behavior while the corresponding column in $Y_p$ contains the previous i samples from neural activity. The goal is to find the part of $Z_f$ that is linearly predictable from corresponding columns of $Y_p$ (i.e. the behavior in each column of $Z_f$ from its past neural activity). The linear least squares solution for this prediction problem has the closed form solution given in Equation 10, which is in the form of a projection from future behavior onto past neural activity. It is shown below that this projection can be decomposed into the multiplication of an observability matrix for behavior and a running estimate of the Kalman estimated latent states, which will thus enable these states to be directly extracted first and then the model parameters to be identified using the extracted latent states.

First, note that the least squares solution of Equation 10 can also be written as shown in Equation 53 below:

$$\Sigma_{z_y d} \triangleq E\{z_{k+d} y_k^T\} = C_z A^{d-1} G_y, \Sigma_{z_{y_{-d}}} = (C_z A^{d-1} G_y)^T \qquad \text{Equation 53}$$

where $$\sum\nolimits_{z_f y_p} \triangleq \frac{1}{j} Z_f Y_p^T \text{ and } \sum\nolimits_{y_p y_p} \triangleq \frac{1}{j} Y_p Y_p^T$$

are sample covariance matrices for the covariance of past neural activity with future behavior and past neural activity, respectively, computed using their observed time-samples from Equations 8 and 9. Sample covariance estimates are asymptotically unbiased and thus for $j \to \infty$ they would converge to their true value in the model. Consequently, for the model in Equation 2, it can be shown (by replacing samples covariances with exact covariances from the model) that for $j \to \infty$, $\Sigma_{y_p y_p}$ converges to $\Lambda_{y_i}$ defined per Equation 51 and $\Sigma_{z_p y_p}$ converges to that shown in Equation 54:

$$\Lambda_{z y_i} \triangleq \begin{bmatrix} \sum_{z y_i} & \sum_{z y_{i-1}} & \cdots & \sum_{z y_1} \\ \sum_{z y_{i+1}} & \sum_{z y_i} & \cdots & \sum_{z y_2} \\ \vdots & \vdots & \ddots & \vdots \\ \sum_{z y_{1i-1}} & \sum_{z y_{2i-2}} & \cdots & \sum_{z y_i} \end{bmatrix} \quad \text{Equation 54}$$

where the specification uses the notation $\Sigma_{z y_d} \triangleq E\{z_{k+d} y_k^T\}$. From Equation 2 it can be shown that:

$$\Sigma_{z y_d} \triangleq E\{z_{k+d} y_k^T\} = C_z A^{d-1} G_y, \Sigma_{z y_{-d}} = (C_z A^{d-1} G_y)^T \quad \text{Equation 55}$$

which has a form similar to Equation 52. Substituting into the definition of $\Lambda_{z y_i}$ from Equation 54 gives:

$$\Lambda_{z y_i} \triangleq \begin{bmatrix} \sum_{z y_i} & \sum_{z y_{i-1}} & \cdots & \sum_{z y_1} \\ \sum_{z y_{i+1}} & \sum_{z y_i} & \cdots & \sum_{z y_2} \\ \vdots & \vdots & \ddots & \vdots \\ \sum_{z y_{2i-1}} & \sum_{z y_{2i-2}} & \cdots & \sum_{z y_i} \end{bmatrix} \begin{bmatrix} C_z \\ C_z A \\ \vdots \\ C_z A^{i-1} \end{bmatrix} = \quad \text{Equation 56}$$

$$[A^{i-1} G_y \quad A^{i-2} G_y \quad \cdots \quad A G_y \quad G_y] \triangleq \Gamma_{z_i} \Delta_{y_i}^c$$

where $\Gamma_{z_i}$ is termed the extended observability matrix for the pair $(A, C_z)$ and $\Delta_{y_i}^c$ is termed the reversed extended controllability matrix for the pair $(A, G_y)$. Moreover, based on Equation 49, the Kalman filter prediction at time $k$ using only the last $i$ observations ($y_{k-i}$ to $y_{k-1}$) can be written in terms of $\Delta_{y_i}^c$ (Equation 56) as:

$$\hat{x}_{k|k-1} = \Delta_{y_i}^c \Lambda_{y_i}^{-1} \begin{bmatrix} y_{k-i} \\ \vdots \\ y_{k-1} \end{bmatrix} \quad \text{Equation 57}$$

Thus, for $j \to \infty$, Equation 53 can be written as:

$$\hat{Z}_f = Z_f Y_p^T (Y_p Y_p^T)^{-1} Y_p = \Sigma_{z_p y_p} \Sigma_{y_p y_p}^{-1} Y_p = \Lambda_{z y_i} \Lambda_{y_i}^{-1} Y_p = \Gamma_{z_i} \Delta_{y_i}^c \Lambda_{y_i}^{-1} Y_p = \Gamma_{z_i} \hat{X}_i \quad \text{Equation 58}$$

where the last equality follows from Equation 57 by setting columns of $\hat{X}_i$ to be the Kalman estimates obtained using the past $i$ observations of $y_k$ per Equation 57. Note that Equations 56 and 57 hold for any similarity transform of the model, including the formulation in Equation 4. Rewriting Equation 58 for this formulation and replacing $\Gamma_{z_i}$ with its value for this formulation (defined in Equation 44) gives:

$$\hat{Z}_f = Z_f Y_p^T (Y_p Y_p^T)^{-1} Y_p = \quad \text{Equation 59}$$

$$\Gamma_{z_i} \hat{X}_i = [\Gamma_{z_i}^{(1)} \quad 0] \hat{X}_i = [\Gamma_{z_i}^{(1)} \quad 0] \begin{bmatrix} \hat{X}_i^{(1)} \\ \hat{X}_i^{(2)} \end{bmatrix} = \Gamma_{z_i}^{(1)} \hat{X}_i^{(1)}$$

where $\hat{X}_i^{(1)}$ is defined as the first $n_1$ rows of $\hat{X}_i$ and is thus the Kalman estimate for the behaviorally relevant states $x_k^{(1)}$ from Equation 4 and $\hat{X}_i^{(2)}$ is defined as the remaining rows of $\hat{X}_i$ and is the Kalman estimate for the behaviorally irrelevant states $x_k^{(2)}$ from Equation 4. Given that $\Gamma_{z_i}^{(1)}$ and $\hat{X}_i^{(1)}$ are both full rank of rank $n_1$, Equation 59 shows that the row space of $\hat{Z}_f$ (i.e. the space spanned by the rows of $\hat{Z}_f$) is equal to the row space of the behaviorally relevant states $\hat{X}_i^{(1)}$. This is the key insight that, as the discussion shows next, allows the first stage of PSID to use SVD to recover this row space and thus extract behaviorally relevant latent states directly from data (without knowing the model parameters), without the need to extract the behaviorally irrelevant latent states (i.e. prioritize the behaviorally relevant latent states).

Before using Equation 59 to conclude the derivation of the first stage of PSID, it is useful for the derivation of the second stage to note that if the above steps are repeated for the projection of $Y_f$ onto $Y_p$, the result will be:

$$\hat{Y}_f = Y_f Y_p^T (Y_p Y_p^T)^{-1} Y_p = \sum\nolimits_{y_f y_p} \sum\nolimits_{y_p y_p}^{-1} Y_p = \quad \text{Equation 60}$$

$$\Gamma_{y_i} \Delta_{y_i}^c \Lambda_{y_i}^{-1} Y_p = \Gamma_{y_i} \hat{X}_i = [\Gamma_{y_i}^{(1)} \quad \Gamma_{y_i}^{(2)}] \begin{bmatrix} \hat{X}_i^{(1)} \\ \hat{X}_i^{(2)} \end{bmatrix}$$

where $\Gamma_{y_i}$ is the extended observability matrix for the pair $(A, C_y)$, $\Gamma_{y_i}^{(1)}$ denotes the first $n_1$ columns of $\Gamma_{y_i}$, $\Gamma_{y_i}^{(2)}$ denotes the remaining columns of $\Gamma_{y_i}$, and $\hat{X}_i$, $\hat{X}_i^{(1)}$ and $\hat{X}_i^{(2)}$ are the same Kalman states as in Equation 59. Equation 60 shows that the row space of $\hat{Y}_f$ is the union of the row spaces of both behaviorally relevant and behaviorally irrelevant latent states. As shown later in the derivation of stage 2 of PSID, this insight allows the second stage of PSID to recover the subspace of behaviorally irrelevant latent states by first subtracting the subspace of behaviorally relevant latent states—that are already extracted in stage 1—, and then applying SVD to the residual to recover the row space of behaviorally irrelevant latent states $\hat{X}_i^{(2)}$.

Equation 59 shows how $\hat{Z}_f$, which is the projection of future behavior onto past neural activity and is directly computable from data, can be decomposed into the extended behavior observability matrix $\Gamma_{z_i}^{(1)}$ and the behaviorally relevant Kalman states $\hat{X}_i^{(1)}$. This decomposition allows for extraction of the behaviorally relevant latent states even before the model parameters are learned and paves the way for subsequent learning of the model parameters. The decomposition can be performed by taking singular value decomposition (SVD) from $Z_f$ in Equation 59 (shown in Equation 12), which gives:

$$\Gamma_{z_i}^{(1)} = U S^{1/2}, \hat{X}_i^{(1)} = S^{1/2} V^T \quad \text{Equation 61:}$$

Note that the above is only one of many valid decompositions since multiplying any non-singular matrix $T$ onto $\Gamma_{z_i}$ from the right and its inverse $T^{-1}$ onto $\hat{X}_i^{(1)}$ from the left amounts to a similarity transform and gives an equivalent model with a different basis. For $j \to \infty$, as shown earlier, Equation 59 holds exactly and thus the row rank of $\hat{Z}_f$ and the number of its non-zero singular values will be equal to the rank of $\hat{X}_i^{(1)}$ and $\Gamma_{z_i}^{(1)}$, which is $n_1$. For finite data ($j<\infty$), it is expected that an approximation of this relation will hold and thus one could find $n_1$ via inspection of the singular values of $\hat{Z}_f$. This disclosure proposed a more general method of using cross validation to find both $n_1$ and $n_x$, which doesn't require an ad-hoc determination of which singular values are notably larger than the others. Regardless of how $n_1$ is determined, keeping the top $n_1$ singular values from the SVD, the inventors can extract $\hat{X}_i^{(1)}$ as in Equation 16. Note that intuitively, keeping of the top singular values ensures that the states that describe the behavior best (i.e. best approximate $\hat{Z}_f$) are prioritized.

Having decomposed $\hat{Z}_f$ into $\Gamma_{z_i}^{(1)}$ and $\hat{X}_i^{(1)}$, determining the model parameters from these matrices is straight forward and there are multiple possible ways to accomplish this. This disclosure uses the state matrix $\hat{X}_i^{(1)}$ to identify the model parameters. This method has the advantage of guaranteeing that the identified noise statistics are positive semi-definite, which is necessary for the model to be physically meaningful. The disclosure first computes the subspace for the latent states at the next time step (having observed $Y_i$ as defined in Equation 8 in addition to $Y_p$, i.e. having observed the past i+1 samples) by projecting $Z_f^-$ onto $Y_p^+$ (Equation 11). Similar to Equation 59, this projection can be decomposed as:

$$\hat{Z}_f^- = Z_f^- Y_p^{+T}(Y_p^+ Y_p^{+T})^{-1} Y_p^+ = \Gamma_{z_{i-1}} \Delta_{y_{i+1}}{}^c \Lambda_{y_{i+1}}^{-1} Y_p^+ = \Gamma_{z_{i-1}} \hat{X}_{i+1} = \Gamma_{z_{i-1}}^{(1)} \hat{X}_{i+1}^{(1)}$$  Equation 62:

where $\Gamma_{z_{i-1}}$, $\Gamma_{z_{i-1}}^{(1)}$, $\Delta_{y_{i+1}}{}^c$ and $\Lambda_{y_{i+1}}$ are defined similar to Equations 56, 44, and 51 and columns of $\hat{X}_{i+1}$ are Kalman estimates obtained using the past i+1 observations of $y_k$ (from Equation 57), and $\hat{X}_{i+1}^{(1)}$ is defined as the first $n_1$ rows of $\hat{X}_{i+1}$. From the definition of observability matrix, it is clear that $\Gamma_{z_{i-1}}^{(1)}$, can be computed by removing the last block row of $\Gamma_{z_i}^{(1)}$ (Equation 15). $\hat{X}_{i+1}^{(1)}$ can then be computed (in the same basis as $\hat{X}_i^{(1)}$) by multiplying both sides of Equation 62 with $\Gamma_{z_{i-1}}^{(1)\dagger}$ from the left (Equation 16). This concludes the extraction of behaviorally relevant latent states. If one is not interested in behaviorally irrelevant latent states, then all model parameters for a model for the behaviorally relevant latent states can also be identified at this point by skipping the second stage of PSID and performing the parameter identification (steps 7 and 17-19 in Table 2). Alternatively, if behaviorally irrelevant latent states are also of interest, before parameter identification, in the second stage of PSID, the behaviorally irrelevant latent states may be extracted (optional) and added to the previously extracted behaviorally relevant latent states. Then parameter identification can be performed to learn all model parameters as described below.

Discussion now turns to stage 2; extracting behaviorally irrelevant latent states. So far, the specification has extracted the behaviorally relevant latent states as the key first step toward learning the model parameters. Optionally, to also find any remaining behaviorally irrelevant states, one may desire to find the variations in neural activity that are not explained by the behaviorally relevant latent states. The specification thus first removes any variations in $Y_f$ (and $Y_f^-$) that lies in the subspace spanned by the extracted behaviorally relevant states $\hat{X}_i^{(1)}$ (and $\hat{X}_{i+1}^{(1)}$) (i is horizon as defined previously), and then applies a procedure akin to the standard SID to the residual. The least squares solution for the best linear prediction of $Y_f$ using $\hat{X}_i^{(1)}$ is given by Equation 18, and is termed $\Gamma_{y_i}^{(1)}$. This solution can be thought of as the neural observability matrix associated with the behaviorally relevant states $\hat{X}_i^{(1)}$ (Equation 60). Thus, similar to Equation 62, the associated observability matrix for $\hat{X}_{i+1}^{(1)}$ can be computed by removing the last block row from the solution (Equation 20). The specification then subtracts the best prediction of $Y_f$ ($Y_f^-$) using $\hat{X}_i^{(1)}$ ($\hat{X}_{i+1}^{(1)}$) from it as shown in Equation 19 (Equation 21), and calls the result $Y_f'$ ($Y_f^{-'}$). In other words, $Y_f'$ ($Y_f^{-'}$) is the part of $Y_f$ ($Y_f^-$) that does not lie in the space spanned by $\hat{X}_i^{(1)}$ ($\hat{X}_{i+1}^{(1)}$). Given that $\hat{X}_i^{(1)}$ and thus $\Gamma_{y_i}^{(1)} \hat{X}_i^{(1)}$ (i.e. the linear prediction of $Y_f$ using $\hat{X}_i^{(1)}$) are of rank $n_1$ and that $\hat{Y}_f$ (i.e. the projection of $Y_f$ onto $Y_p$) is of rank $n_x$ (Equation 60), the projection of $Y_f' = Y_f - \Gamma_{y_i}^{(1)} \hat{X}_i^{(1)}$ (i.e. residual future neural activity) onto $Y_p$ will be of rank $n_2 = n_x - n_1$. A similar procedure to what was applied to $Z_f$ (and $Z_f^-$) to find $\hat{X}_i^{(1)}$ (and $\hat{X}_{i+1}^{(1)}$) can be applied to $Y_f'$ (and $Y_f^{-'}$) to extract the $n_2$ remaining states $\hat{X}_i^{(2)}$ (and $\hat{X}_{i+1}^{(2)}$) (steps 11-14 from Table 2). Of note is that in this stage, keeping the top singular values after SVD (Equation 24) ensures that the remaining states that describe the unexplained neural activity best (i.e. best approximate $\hat{Y}_f'$) are prioritized.

The above concludes the extraction of behaviorally irrelevant latent states. Concatenating the states extracted from both stages (i.e. $\hat{X}_i^{(1)}$ and $\hat{X}_i^{(2)}$ as well as $\hat{X}_{i+1}^{(1)}$ and $\hat{X}_{i+1}^{(2)}$) together as in Equation 29 concludes the extraction of all latent states, including behaviorally relevant and irrelevant ones.

Next, given the extracted latent states from stage 1 and optionally stage 2, one may identify the model parameters. First, one can identify blocks of the A matrix in the format of Equation 4. To identify $A_{11}$, which is the block associated with the behaviorally relevant latent states, one can take columns of $\hat{X}_{i+1}^{(1)}$ and $\hat{X}_i^{(1)}$ (extracted in stage 1) as samples of the current state and the corresponding next state (i.e. $x_{k+1}^{(1)}$ and $x_k^{(1)}$ from Equation 4), respectively; based on Equation 4, one can compute the least squares solution for $A_{11}$ as given in Equation 17. Second, if behaviorally irrelevant latent states are also desired to be included in the model, one can follow a similar approach as was taken for $A_{11}$ (Equation 17), to find the least squares solution for $A_{21}$ and $A_{22}$ (Equation 30). Then one can find the least squares solution for $C_y$ (Equation 32) and $C_z$ (Equation 33) using both the behaviorally relevant and the behaviorally irrelevant latent states extracted in stages 1 and 2 (or using just the behaviorally relevant latent states if behaviorally irrelevant dynamics are not of interest and thus the optional stage 2 is not performed). Finally, the residuals from the least squares solutions to Equations 17, 30, and 32 provide estimated values for $w_k$ and $v_k$ at each time step and thus one can compute the sample covariance of these residuals to identify the noise covariance parameters (Equation 35). This concludes the identification of all model parameters.

Finally, in addition to Equation 33, another viable alternative for finding the parameter $C_z$ is to learn it using linear regression, which is the procedure needed for the standard SID to relate its extracted latent state to behavior and used in this disclosure for both SID and PSID. Since $C_z$ is not involved in the Kalman filter recursions (first 2 rows of Equation 45), it does not have any effect on the extraction of latent states from $y_k$ and it only affects the later prediction of $z_k$ from those latent states. Consequently, one can use the other identified parameters to apply Kalman filter to the training $y_k$ and estimate the latent states $\hat{x}_{k+1|k}$ (Equation 45). One can then use linear regression to find the $C_z$ that minimizes the prediction of $z_k$ using $\hat{x}_{k+1|k}$ as:

$$C_z = Z_k \hat{X}_{k+1|k}^\dagger$$  Equation 63:

where columns of $Z_k$ contain $z_k$ for different time steps and columns of $\hat{X}_{k+1|k}$ contain the corresponding $\hat{x}_{k+1|k}$ estimates for those time steps. The advantage of using this alternative identification of $C_z$ is that $\hat{X}_{k+1|k}$ (used in Equation 63) are more accurate estimates of the latent states obtained using all past observations whereas $\hat{X}_i$ (used in Equation 33) are less accurate estimates obtained using only the past i observations.

Discussion now turns to standard SID as a special case of PSID and the asymptotic characteristics of PSID. For $n_1=0$, PSID (Table 2) reduces to the standard SID. This is because if $n_1=0$, no behaviorally relevant states ($\hat{X}_i^{(1)}$) will be extracted leaving all variation of $Y_f$ to be identified in stage 2 of PSID, which is similar to using standard SID. Thus, the extracted $\hat{X}_i^{(2)}$ in this case will be the same as the $\hat{X}_i$ that is obtained from applying SID on $y_k$. So, to compare PSID with SID, one can simply use PSID with $n_1=0$.

As a generalization of the abovementioned version of SID, PSID has similar asymptotic characteristics. In some other variations of SID, instead of applying SVD to $\hat{Y}_f$, SVD is applied to the empirical cross-covariance $\Sigma_{y_f y_p}$ to decompose it into $\Gamma_{y_i}$ and $\Delta_{y_i}^c$ (Equation 60), giving an estimation of these matrices, which for $j \to \infty$ is unbiased. From this decomposition, model parameters A, $C_y$, and $G_y$ can then be extracted—$C_y$ as the first block of $\Gamma_{y_i}$, $G_y$ as the last block of $\Delta_{y_i}^c$, and A with a least squares solution within blocks of $\Gamma_{y_i}$—leaving the final uniquely identifiable model parameter $\Sigma_y$ to be extracted as the first block of the auto-covariance $\Sigma_{y_p y_p}$ again in an asymptotically unbiased manner (for details see the SID variants mentioned in the previous sentence). However, this approach cannot guarantee that for finite data ($j<\infty$) the identified A, $C_y$, $G_y$, and $\Sigma_y$ will be associated with a positive real covariance sequence (i.e. Faurre's stochastic realization may have no solution). In the alternative approach taken by PSID, A and $C_y$ (and $C_z$) are computed as least squares solution of forming Equation 2 with g, taken as the value of the latent state and $G_y$ and $\Sigma_y$ are identified later based on the residuals of the least squares solution (from Equations 37-39 as detailed in Table 2). This approach cannot guarantee an asymptotically unbiased estimate of $G_y$ and $\Sigma_y$ (unless $i \to \infty$ in which case Kalman estimates in Equation 57 will be exact), but it guarantees that even for finite data ($j<\infty$) the identified parameters will be associated with a positive real covariance sequence, which is essential for the model to be physically meaningful.

Discussion now turns to generating random model parameters for simulations. For a model with given $n_x$ and $n_1$, A was generated by first randomly generating its eigenvalues and then generating a block diagonal real matrix with the randomly selected eigenvalues (using MATLAB's cdf2rdf command). The inventors drew the eigenvalues with uniform probability from across the complex unit circle and then randomly selected $n_1$ of the $n_x$ to be later used as behaviorally relevant eigenvalues. As a technical detail, in both the original random generation of eigenvalues and in selecting $n_1$ of them for behavior the inventors made sure eigenvalues are either real valued or are in complex-conjugate pairs (as needed for models with real observations). To do this, the inventors first drew $\lfloor n_x/2 \rfloor$ points with uniform probability from across the complex unit circle and then added the complex conjugate of each to the set of eigenvalues. If $n_x$ was odd, the inventors then drew an additional eigenvalue from the unit circle and set its angle to 0 or $\pi$, whichever was closer. Finally, to randomly select $n_1$ of the $n_x$ eigenvalues to be used as behaviorally relevant, the inventors repeatedly permuted the values until the first $n_1$ eigenvalues also formed a set of complex conjugate pairs or real values.

Next, the inventors generated $C_y \in \mathbb{R}^{n_y \times n_x}$ by drawing values from the standard normal distribution. The inventors generated $C_z \in \mathbb{R}^{n_z \times n_x}$ by drawing values from the standard normal distribution for the elements associated with the behaviorally relevant eigenvalues of A (or equivalently for the dimensions of $x_k$ that drive behavior) and setting the other elements to 0 (see Equation 4).

For noise statistics Q, R, and S, the inventors generated general random covariance matrices and applied random scaling factors to them to get a wide range of relative variances for the state noise $w_k$ and observation noise $v_k$. To do this, the inventors first generated a random square matrix $\Omega$ of the size $n_x+n_y$ by drawing elements from standard normal distribution and computed $L=\delta \delta^T$, which is guaranteed to be symmetric and positive semi-definite. The inventors next selected random scaling factors for the state noise $w_k$ and the observation noise $v_k$ by independently selecting two real numbers $a_1$, $a_2$ with uniform probability from the range $(-1, +1)$. The inventors then applied the following scaling to matrix L to get the noise statistics as:

$$\begin{bmatrix} Q & S \\ S^T & R \end{bmatrix} = \begin{bmatrix} 10^{a_1} I_{n_x} \\ 10^{a_2} I_{n_y} \end{bmatrix} L \begin{bmatrix} 10^{a_1} I_{n_x} & 10^{a_2} I_{n_y} \end{bmatrix} \qquad \text{Equation 64}$$

where $I_n$ denotes the identity matrix of the size n. This is equivalent to scaling $v_k$ by $10^{a_1}$ and independently scaling $w_k$ by $10^{a_2}$ and generates a wide range of state and observation noise statistics.

Finally, to build a model for generating the independent behavior residual dynamics $\epsilon_k$ (which can be a general colored signal and is not assumed to be white), one can generate another random dynamic linear SSM with independently selected latent state dimension of $1 \leq n'_x \leq 10$ and parameters generated as explained above for the main model. The specification will refer to this model as the behavior residual dynamics model. To diversify the ratio of behavior dynamics that are shared with neural activity (Equation 36) to the residual behavior dynamics (i.e. $\epsilon_k$), one can draw a random number $a_3$ in the range $(0, +2)$. One can then multiply the rows of the $C_z$ parameter in the behavior residual dynamics model with different scalar values such that for each behavior dimension m, the shared-to-residual ratio, defined as the ratio of the std of the term $z_{k_1}^{(m)}$ (Equation 36) to the std of the term $\epsilon_k^{(m)}$, is equal to $10^{a_3}$.

Modeling the effect of external inputs to the brain on the neural activity is important both in neurotechnology and in neuroscience applications. Examples of external inputs to the brain include electrical stimulation applied to the brain in brain-machine interfaces (BMI) for closed-loop brain simulation, as well as sensory instructions provided to the subjects during neuroscience experimental tasks. If these external inputs to the brain are not considered during modeling, their variations may be incorrectly interpreted as internal brain dynamics by the model. Moreover, both in BMI applications and in neuroscience research, a specific behaviorally measurable brain function (e.g. the subject's mood or movements) are of interest and thus it is desired that modeling method prioritizes the learning of those neural dynamics that are relevant to the behavior of interest. Previous discussion is related to a novel algorithm termed preferential system identification (PSID), that models neural dynamics while dissociating and prioritizing behaviorally relevant dynamics. Discussion now turns to a generalization to PSID that enables the same goals in presence of external inputs to the brain. The inventors demonstrate with extensive numerical simulations that this extension of PSID correctly (i) learns all model parameters correctly, and (ii) prioritizes the learning of behaviorally relevant neural dynamics, in presence of external inputs to the brain. This novel algorithm has important implications for neuroscience and neurotechnology applications.

The first portion of the disclosure discusses a novel algorithm termed preferential system identification (PSID), that models neural dynamics while dissociating and prioritizing behaviorally relevant dynamics. Here, the disclosure presents a generalization to PSID that enables the same goals in presence of external inputs to the brain. Modeling the effect of external inputs on neural dynamics is important both in neurotechnology and in neuroscience applications. First, in building closed-loop stimulation treatments for neuropsychiatric disorders, electrical stimulation applied to the brain is an external input that affects the state of the brain. A model of the neural activity that incorporates how the electrical stimulation effects the neural activity is needed to enable design of closed-loop controllers that can determine what stimulation needs to be applied at each point in time. Second, in neuroscientific studies of brain function, neural data is often collected while the subject performs a structured experimental task with sensory instructions. During such experiments, the task instructions presented to the subject are an external input applied to the brain, which if not accounted for, may lead to inaccurate models of neural activity. Finally, when studying a specific brain area, neural activity in other brain areas that precede the area of interest in signal processing may be considered as external inputs for the primary area. Here, the disclosure presents a generalization of the PSID algorithm that can incorporate the effect of external inputs and validate it with extensive numerical simulations.

To expand PSID for the case where an external known input is applied to the brain, the inventors use a general state-space model with added linear functions of the input signal $u_k \in \mathbb{R}^{n_u}$ to the right side of the state space equation as:

$$\begin{cases} x_{k+1} = A x_k + B u_k + w_k \\ y_k = C_y x_k + D_y u_k + v_k , \\ z_k = C_z x_k + D_z u_k + \epsilon_k \end{cases} \quad \text{Equation 65}$$

$$x_k = \begin{bmatrix} x_k^{(1)} \\ x_k^{(2)} \end{bmatrix}$$

where B, $D_y$ and $D_z$ are new parameters to be learned by PSID. B describes the effect of external input on the latent state $x_k$, which in turn captures the dynamic effect of input on future neural activity and behavior. $D_y$ and $D_z$ are known as feed-through terms and describe any immediate non-dynamic effect from the external input on the neural activity $y_k$ and behavior $z_k$, respectively. Finally, $x_k$ consists of two parts, $x_k^{(1)} \in \mathbb{R}^{n_1}$ and $x_k^{(2)} \in \mathbb{R}^{n_x-n_1}$, which respectively denote the behaviorally relevant and irrelevant dimensions of $x_k$.

Given the model parameters, the latent states can be estimated from the neural activity $y_k$ using a Kalman filter:

$$\hat{x}_{k+1|k} = A \hat{x}_{k|k-1} + B u_k + K (y_k - C_y \hat{x}_{k|k-1}) \quad \text{Equation 66:}$$

where K is the Kalman gain. Next, the decoding of behavior and if needed, the one-step-ahead self-prediction of neural activity can be obtained as:

$$\begin{cases} \hat{y}_{k|k-1} = C_y \hat{x}_{k|k-1} + D_y u_k \\ \hat{z}_{k|k-1} = C_z \hat{x}_{k|k-1} + D_z u_k \end{cases} \quad \text{Example 67}$$

Figure 33:
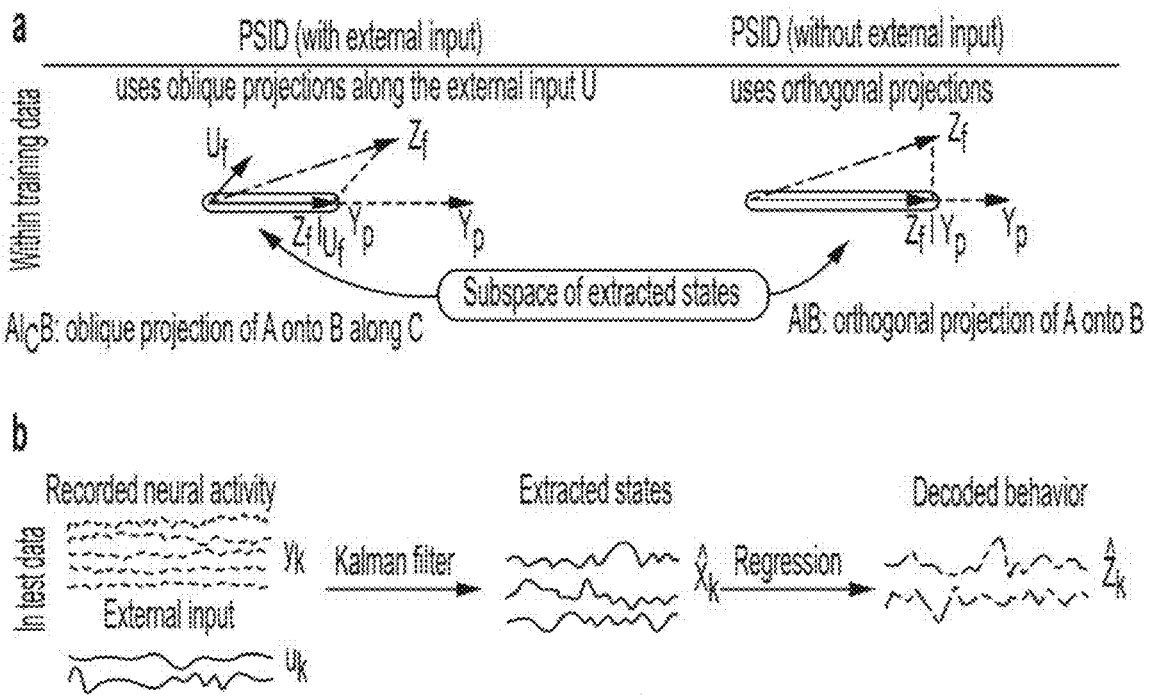
FIG. 33 illustrates a high-level view of PSID in the presence of external inputs according to an embodiment of the present invention.

The formulation for PSID in presence of external inputs is provided below. Here, the disclosure briefly explains the main distinction of having external inputs and the intuition behind how it affects the learning. Existence of the external input introduces a fundamental difference in how the projection steps in PSID need to be performed. In presence of external input, the projection of future behavior onto past neural activity would give a mixture of the subspaces spanned by the latent states and the input. Thus, to estimate the subspace associated with the latent state, the projection of future behavior onto past neural activity is done along the direction of the space spanned by the input instead of the orthogonal projection in the PSID without input (FIG. 33). This ensures that the result of the projection is orthogonal to the space spanned by the input, hence separating the effect of external input and giving an estimate of the latent states in their presence. The remainder of the algorithm follows similarly to PSID without input, by a secondary projection from future neural activity onto its own past (again along the space spanned by the input) and subsequently estimating the model parameters with least squares.

For the special case of extracting no states in the first stage (i.e. $n_1=0$), PSID reduces to standard SID with external input (discussed further below). Thus, the disclosure implements standard SID with external input simply by setting $n_1=0$ in PSID. Note that in standard SID, the behavior observation parameters $C_z$ and $D_z$ are not normally part of the model and thus are not learned. However, in the generalization of implementing SID as PSID with $n_1=0$, these parameters can also be learned. The intuition is that the behavior observation parameters $C_z$ and $D_z$ are not necessary to estimate the latent states via a Kalman filter (Equation 66). Thus, learning them can be postponed to after all other model parameters are learned with standard SID. After that, a Kalman filter can estimate the latent states and $C_z$ and $D_z$ can be learned with a regression from the extracted latent states and external inputs.

Referring to FIG. 33, a high-level view of PSID in the presence of external inputs is shown. FIG. 33, a shows that in the presence of external inputs, in the first stage of PSID, instead of an orthogonal projection of future behavior $Z_f$ onto past neural activity $Y_p$, an oblique projection along the subspace spanned by future behavior $U_f$ is used (described more fully below). FIG. 33, b shows that extraction of latent states and decoding behavior in the test data consist of a Kalman filter with input applied to neural activity followed by a linear combination of the extracted latent states.

To validate PSID in presence of external inputs, the inventors applied it to simulated data generated from models with random parameters. For each simulated model, similar to the validation of PSID, the inventors first randomly select its neural, behavior, and latent state dimensions, and an LS SM to model (i.e. behavior noise model) its behavior dynamics that are not encoded in neural activity (i.e. $\epsilon_k$). Here, the inventors also generate a random LSSM with $n_{x_u}$ latent state dimensions and $n_u$ outputs as the model for the external input (i.e. input model). Given the dimensions of the model, all the model parameters are then randomly generated. To generate data from the models, the inventors first generate a random realization $u_k$ from the input model, a random realization $\in_k$ from the behavior noise model and random noise time series $w_k$ and $v_k$ from their respective covariances based on the model parameters. The inventors then generate neural and behavioral time series by feeding $u_k$, $\in_k$, $w_k$ and $v_k$ in the iterative formulation of the model from Equation 65. This concludes the generation of random realizations of neural and behavioral signals $y_k$ and $z_k$ from random models, in presence of external input $u_k$. After model learning using PSID, accuracy in learning model parameters, and behaviorally relevant latent states are performed.

Figure 34:
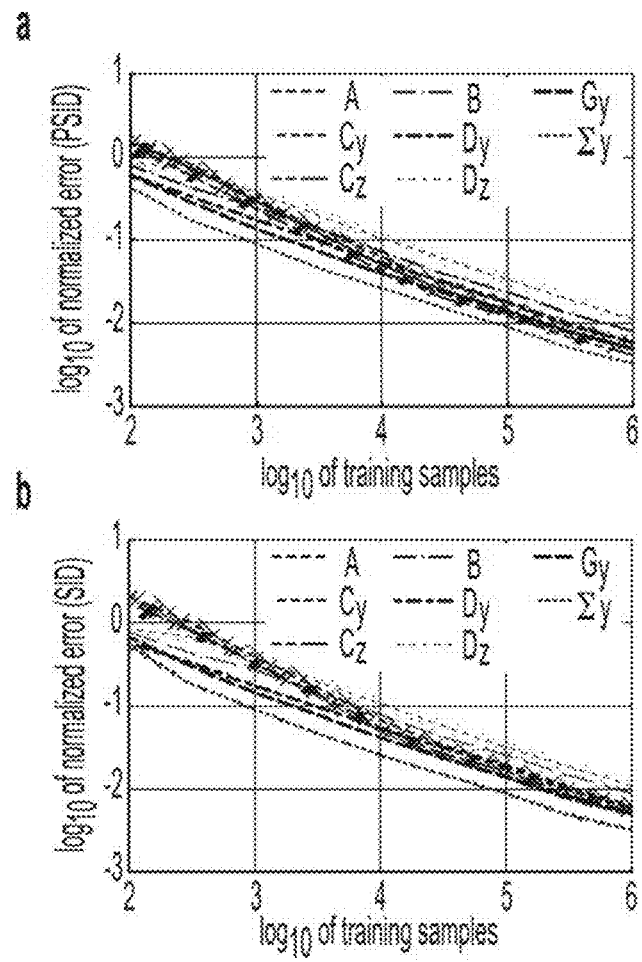
FIG. 34 illustrates that PSID correctly learns all model parameters in the presence of external inputs according to an embodiment of the present invention.

Experiments show that PSID correctly learns all model parameters in the presence of external inputs. During experiments, the inventors generated 100 models with random parameters and random dimensions for neural signals, behavioral signal, external input and the latent state. For each model, the inventors generated the external input as a random realization of a random LSSM, which are referred to as the input model. For each model, the inventors then generated random realizations of the neural and behavior time series, provided them to PSID, and compared the learned parameters with their true values (FIG. 34, a). The inventors found that PSID learned all model parameters, including those related to the external input, correctly with the error converging toward zero as the number of training samples increased (FIG. 34, a). Moreover, the errors and their rate of convergence were similar to that of standard SID with external input (FIG. 34, b). These results suggest that even when learning all dynamics including behaviorally irrelevant ones is of interest, PSID can learn the dynamics with similar accuracy to standard SID while also dissociating the behaviorally relevant and irrelevant dynamics.

In particular, FIG. 34 shows that PSID correctly learns all model parameters in the presence of external inputs. FIG. 34, a shows normalized identification error versus the number of training samples, across 100 random models. Solid lines show the mean and shaded areas show the s.e.m. FIG. 34, b shows the same as FIG. 34, a, for standard SID with external input. See above discussion on how $C_z$ and $D_z$ were learned using standard SID.

Figure 35:
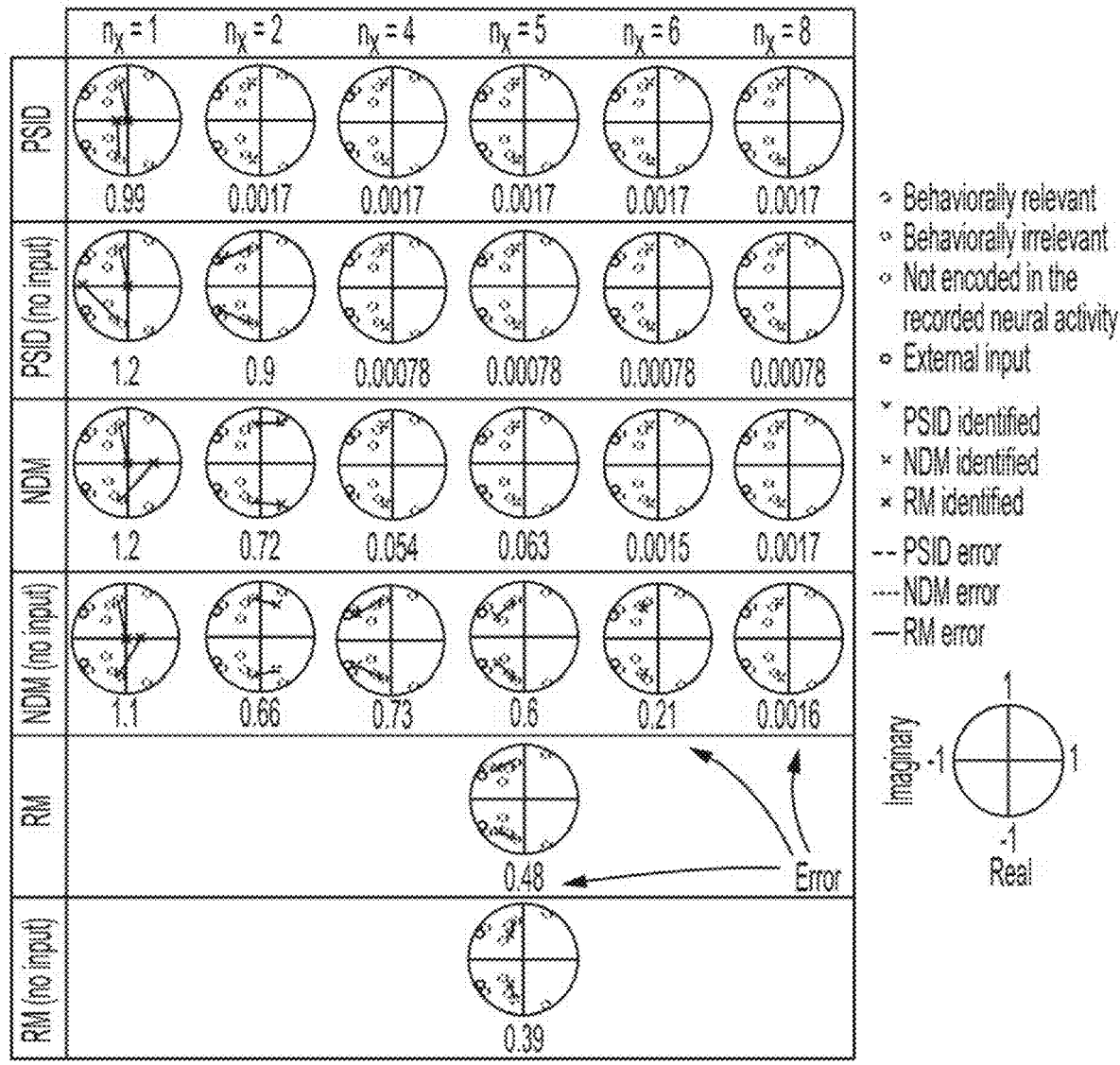
FIG. 35 illustrates an example simulated model showing that PSID prioritizes behaviorally relevant dynamics in the presence of external inputs according to an embodiment of the present invention.
Figure 36:
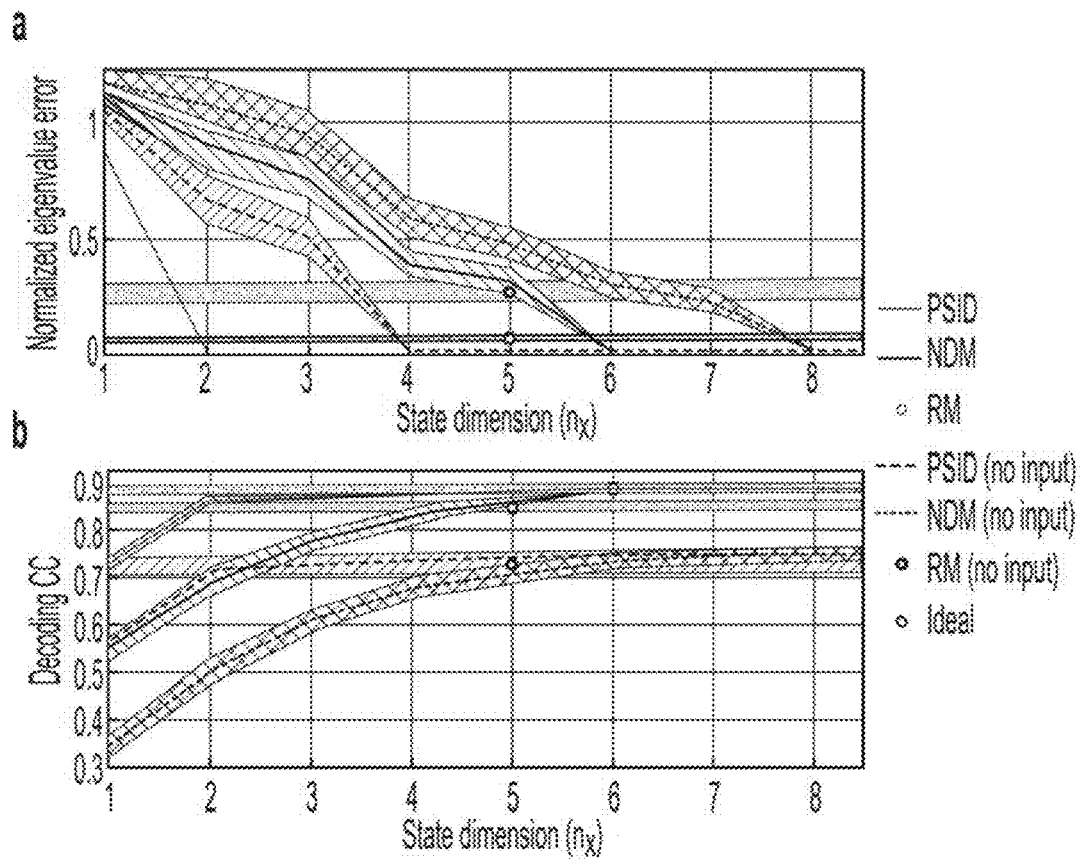
FIG. 36 illustrates that PSID prioritizes behaviorally relevant dynamics in the presence of external inputs according to an embodiment of the present invention.

Discussion now turns to how PSID correctly prioritizes behaviorally relevant internal neural dynamics in the presence of external inputs. To validate that PSID correctly prioritizes behaviorally relevant internal neural dynamics in presence of external inputs, the inventors generated 100 random models and compared the learned behaviorally relevant dynamics with that of the true model. As the first performance measure, the inventors found the identified behaviorally relevant eigenvalues as the closest eigenvalues in the identified A to the eigenvalues for the behaviorally relevant segment of the A in the true model. The true and identified eigenvalues using different methods are shown in FIG. 35 for an example random model. The error for learning the behaviorally relevant eigenvalues averaged over the 100 random models is provided in FIG. 36, a. Each random model had 6 latent state dimensions, out of which 2 were behaviorally relevant. The inventors found that PSID correctly learned the behaviorally relevant latent states with the minimal latent state dimension of 2 (FIGS. 35, 36, a). In contrast, standard SID even when considering the external input, learned behaviorally irrelevant latent states as well and thus required a higher latent state dimension of 6 to ensure all behaviorally relevant eigenvalues were also learned. The inventors also compared the results with using PSID or standard SID without external inputs. In this case, both methods may learn the dynamics of the external input, and thus both required higher dimensional latent states to ensure behaviorally relevant eigenvalues were also learned (FIGS. 35, 36, a). As a second performance measure, the inventors computed the cross-validated decoding accuracy of using the learned models to decode behavior using the observed neural activity and external input (FIG. 36, a). The inventors found that again PSID with external input could decode behavior as accurately as the true model, within minimal latent state dimensions while other methods could not achieve a similar performance. These results show that PSID correctly prioritizes the learning of behaviorally relevant neural dynamics in presence of external inputs.

FIG. 35 illustrates an example simulated model showing that PSID prioritizes behaviorally relevant dynamics in the presence of external inputs. In particular, FIG. 35 shows true and identified eigenvalues for an example model for identified models with different state dimensions using PSID, NDM, and RM, each both when provided with the external input and without the external input. Errors in identification of behaviorally relevant eigenvalues are shown with solid lines with the normalized error in each case denoted below the unit circle.

FIG. 36 illustrates that PSID prioritizes behaviorally relevant dynamics in the presence of external inputs. FIG. 36, a shows the error for identification of behaviorally relevant eigenvalues versus the latent state dimension, when using PSID, NDM, and RM, each both when provided with the external input and without the external input. Solid lines show the average error over 100 random models and the shaded areas show the s.e.m. Each random model had 6 latent state dimensions out of which 2 were behaviorally relevant. Solid lines show the average error and shaded areas show the s.e.m. FIG. 36, b shows the same as FIG. 36, a, showing the cross-validated decoding correlation coefficient (CC) for the same random models. Ideal decoding CC for when the true model parameters are used is also shown.

The inventors developed a generalization of PSID that supports modeling behaviorally relevant neural dynamics in presence of external inputs. Modeling in presence of external inputs is critical both for neuroscience and neuroengineering applications. One important application is in developing closed-loop stimulation systems to treat neuropsychiatric disorders such as depression with electrical stimulation. In prior work, the inventors have developed neural decoders for human mood variations using intracranial neural recordings. To use such decoders in a closed-loop stimulation system, unless the model can also describe how stimulation affects the brain signals, one would be limited to simple on-off control strategies. The effect of electrical stimulation can be incorporated into the mood decoding model as an external input. This will enable more sophisticated model-based control strategies such as linear quadratic Gaussian control. The addition of support for external inputs to PSID in this work could pave the way to making PSID beneficial for use in such applications.

Another potential application for PSID with external input is in investigating behaviorally relevant neural dynamics in behavioral tasks with external instructions. Behavioral tasks often involve sensory cues that guide the subject through the task, for example by specifying the next target that needs to be reached, or the time that movements or decisions need to start, etc. These sensory inputs are external inputs to the brain and as shown in simulations in this work, not considering the external inputs may lead to less accurate learning of behaviorally relevant neural dynamics. Thus, using PSID with external inputs could benefit neuroscience applications by learning more accurate models of how behavior is encoded in neural activity while also taking the effect of task instructions into account.

Discussion now turns to the PSID algorithm in the presence of external inputs. To simplify the description of PSID with external inputs, the specification defines some notations. First, the specification defines the notation:

$$Z/Y \triangleq ZY^T(YY^T)^\dagger Y \qquad \text{Equation 68}$$

to denote the orthogonal projection of the wide matrix $Z \in \mathbb{R}^{m \times j}$ onto another wide matrix $Y \in \mathbb{R}^{n \times j}$. An orthogonal projection can also be thought of as the linear minimum mean squared prediction of columns of Z using columns of Y since $ZY^T(YY^T)^\dagger$ is equal to cross-covariance of columns of Z and Y, multiplied by the inverse of the covariance of the columns of Y. Second, the specification defines the shorthand notation $$\Pi_U \triangleq I - U^T(UU^T)^\dagger U \qquad \text{Equation 69}$$

where $I \in \mathbb{R}^{j \times j}$ is the identity matrix, to denote the matrix $\Pi_U$ that when multiplied from the left by a matrix Z, would remove the orthogonal projection of Z onto U from Z. In other words, the result is $Z\Pi_U \triangleq Z - ZU^T(UU^T)^\dagger U = Z - Z/U$ for any matrix $Z \in \mathbb{R}^{m \times j}$. Third, the specification defines the notation $$Z/_U Y \triangleq (Z - Z/U)(Y - Y/U)^\dagger Y = (Z\Pi_U)(Y\Pi_U)^\dagger Y \qquad \text{Equation 70}$$

to denote the oblique (i.e. non-orthogonal) projection of matrix Z onto Y along matrix $U \in \mathbb{R}^{p \times j}$. Intuitively, the oblique projection in Equation 70 means that one would first find the part of Z that is not predictable from U (i.e. $Z - Z/U$), and then project that part onto the part of Y that is not predictable from U (i.e. $Y - Y/U$).

The disclosure also defines the following matrices form the training neural time series $\{y_k \in \mathbb{R}^{n_y}: 0 \leq k < N\}$ $$\begin{bmatrix} Y_p \\ - \\ Y_f \end{bmatrix} \triangleq \begin{bmatrix} y_0 & y_1 & \cdots & y_{j-1} \\ y_1 & y_2 & \cdots & y_j \\ \vdots & \vdots & \ddots & \vdots \\ y_{i-1} & y_i & \cdots & y_{j+i-1} \\ - & - & - & - \\ y_i & y_{i+1} & \cdots & y_{j+1} \\ y_{i+1} & y_{i+2} & \cdots & y_{j+i+1} \\ \vdots & \vdots & \ddots & \vdots \\ y_{2i-1} & y_{2i} & \cdots & y_{j+2i-1} \end{bmatrix} = \qquad \text{Equation 71}$$

$$\begin{bmatrix} y_0 & y_1 & \cdots & y_{j-1} \\ y_1 & y_2 & \cdots & y_j \\ \vdots & \vdots & \ddots & \vdots \\ y_{i-1} & y_i & \cdots & y_{j+i-1} \\ y_i & y_{i+1} & \cdots & y_{j+1} \\ - & - & - & - \\ y_{i+1} & y_{i+2} & \cdots & y_{j+i+1} \\ \vdots & \vdots & \ddots & \vdots \\ y_{2i-1} & y_{2i} & \cdots & y_{j+2i-1} \end{bmatrix} \triangleq \begin{bmatrix} Y_p^+ \\ - \\ Y_f^- \end{bmatrix} \triangleq \begin{bmatrix} Y_p \\ - \\ Y_i \\ - \\ Y_f^- \end{bmatrix}$$

and analogously define the following from the training behavior time series $\{z_k \in \mathbb{R}^{n_z}: 0 \leq k < N\}$ $$\begin{bmatrix} Z_p \\ - \\ Z_f \end{bmatrix} \triangleq \begin{bmatrix} z_0 & z_1 & \cdots & z_{j-1} \\ z_1 & z_2 & \cdots & z_j \\ \vdots & \vdots & \ddots & \vdots \\ z_{i-1} & z_i & \cdots & z_{j+i-1} \\ - & - & - & - \\ z_i & z_{i+1} & \cdots & z_{j+1} \\ z_{i+1} & z_{i+2} & \cdots & z_{j+i+1} \\ \vdots & \vdots & \ddots & \vdots \\ z_{2i-1} & z_{2i} & \cdots & z_{j+2i-1} \end{bmatrix} = \qquad \text{Equation 72}$$

$$\begin{bmatrix} z_0 & z_1 & \cdots & z_{j-1} \\ z_1 & z_2 & \cdots & z_j \\ \vdots & \vdots & \ddots & \vdots \\ z_{i-1} & z_i & \cdots & z_{j+i-1} \\ z_i & z_{i+1} & \cdots & z_{j+1} \\ - & - & - & - \\ z_{i+1} & z_{i+2} & \cdots & z_{j+i+1} \\ \vdots & \vdots & \ddots & \vdots \\ z_{2i-1} & z_{2i} & \cdots & z_{j+2i-1} \end{bmatrix} \triangleq \begin{bmatrix} Z_p^+ \\ - \\ Z_f^- \end{bmatrix} \triangleq \begin{bmatrix} Z_p \\ - \\ Z_i \\ - \\ Z_f^- \end{bmatrix}$$

and the following from the external input time series $\{u_k \in \mathbb{R}^{n_u}: 0 \leq k < N\}$ $$\begin{bmatrix} U_p \\ - \\ U_f \end{bmatrix} \triangleq \begin{bmatrix} u_0 & u_1 & \cdots & u_{j-1} \\ u_1 & u_2 & \cdots & u_j \\ \vdots & \vdots & \ddots & \vdots \\ u_{i-1} & u_i & \cdots & u_{j+i-1} \\ - & - & - & - \\ u_i & u_{i+1} & \cdots & u_{j+1} \\ u_{i+1} & u_{i+2} & \cdots & u_{j+i+1} \\ \vdots & \vdots & \ddots & \vdots \\ u_{2i-1} & u_{2i} & \cdots & u_{j+2i-1} \end{bmatrix} = \qquad \text{Equation 73}$$

$$\begin{bmatrix} u_0 & u_1 & \cdots & u_{j-1} \\ u_1 & u_2 & \cdots & u_j \\ \vdots & \vdots & \ddots & \vdots \\ u_{i-1} & u_i & \cdots & u_{j+i-1} \\ u_i & u_{i+1} & \cdots & u_{j+1} \\ - & - & - & - \\ u_{i+1} & u_{i+2} & \cdots & u_{j+i+1} \\ \vdots & \vdots & \ddots & \vdots \\ u_{2i-1} & u_{2i} & \cdots & u_{j+2i-1} \end{bmatrix} \triangleq \begin{bmatrix} U_p^+ \\ - \\ U_f^- \end{bmatrix} \triangleq \begin{bmatrix} U_p \\ - \\ U_i \\ - \\ U_f^- \end{bmatrix}$$

where i is a provided quantity termed the projection horizon.

Here, the specification briefly describes the PSID algorithm in presence of external inputs. Given the neural, behavioral, and input training time series $\{y_k \in \mathbb{R}^{n_y}: 0 \leq k < N\}$, $\{z_k \in \mathbb{R}^{n_z}: 0 \leq k < N\}$ and $\{u_k \in \mathbb{R}^{n_u}: 0 \leq k < N\}$, and given the state dimension $n_x$, parameter $n_1 \leq n_x$, and the projection horizon i, this algorithm learns the parameters of the model in Equation 65, while prioritizing the behaviorally relevant neural dynamics.

Stage 1: Extract $n_1$ latent states directly via oblique projection of future behavior onto past neural activity:
1. Form examples of future behavior $Z_f$ (Equation 72) and the associated past neural activity $Y_p$ (Equation 71). Also form corresponding samples of future and past external input $U_f$ and $U_p$ (Equation 73). Project $Z_f$ onto $Y_p$ and $U_p$ along $U_f$ and remove the part predictable from $U_f$ to get $$\hat{Z}_f^{(O)} = Z_f / U_f \begin{bmatrix} U_p \\ Y_p \end{bmatrix} \Pi_{U_f} \qquad \text{Equation 74}$$

where oblique projection is defined as in Equation 70 and $\Pi_{U_f}$ is defined as in Equation 69.

2. Compute the singular value decomposition (SVD) of $\hat{Z}_f^{(O)}$, and keep the top $n_1$ singular values:

$$\hat{Z}_f^{(O)} = USV^T \approx U_1 S_1 V_1^T \qquad \text{Equation 75:}$$

3. Compute the behaviorally relevant latent state as:

$$\hat{X}_i^{(1)} = \left(U_1 S_1^{\frac{1}{2}}\right)^\dagger Z_f / \begin{bmatrix} U_p \\ Y_p \\ U_f \end{bmatrix} \qquad \text{Equation 76}$$

Stage 2 (optional): extract $n_x - n_1$ additional latent states via an oblique projection of residual future neural activity onto past neural activity.

1. Find the prediction of $Y_f$ using $\hat{X}_i^{(1)}$ and subtract this prediction from $Y_f$ using an oblique projection to keep the part that is predictable from $U_f$ and $U_p$. Name the result $Y'_f$ (i.e. residual future neural activity):

$$Y'_f = Y_f - Y_f / \begin{bmatrix} U_p \\ U_f \end{bmatrix} \hat{X}_i^{(1)} \qquad \text{Equation 77}$$

2. Project the residual future neural activity ($Y'_f$) onto $Y_p$ and $U_p$ along $U_f$, and remove the part predictable from $U_f$ to get:

$$\hat{Y}_f^{\prime(o)} = Y'_f / U_f \begin{bmatrix} U_p \\ Y_p \end{bmatrix} \Pi_{U_f} \qquad \text{Equation 78}$$

3. Compute the SVD of $\hat{Y}_f^{\prime(O)}$, and keep the top $n_x - n_1$ singular values:

$$\hat{Y}_f^{\prime(O)} = U'S'V'^T \approx U_2 S_2 V_2^T \qquad \text{Equation 79:}$$

4. Compute the remaining latent states as:

$$\hat{X}_i^{(2)} = \left(U_2 S_2^{\frac{1}{2}}\right)^\dagger Y_f / \begin{bmatrix} U_p \\ Y_p \\ U_f \end{bmatrix} \qquad \text{Equation 80}$$

Final Step: Given the extracted latent states, identify model parameters.

1. If stage 2 is used, concatenate $\hat{X}_i^{(2)}$ to $\hat{X}_i^{(1)}$ to get the full latent state otherwise take $\hat{X}_i = \hat{X}_i^{(1)}$
2. Repeat all steps with a shift of one step in time to extract the states at the next time step ($\hat{X}_{i+1}$). To shift the time step, use $Z_f^-$ (equation (8)), $Y_p^+$ (equation (7)), $U_f^-$ (equation (9)), and $U_p^+$ (equation (9)) instead of $Z_f$, $Y_p$, $U_f$ and $U_p$, respectively.
3. Compute $A_{11}$, $A_{21}$, $A_{22}$, $C_y$ and $C_z$ as:

$$A_{11} = \hat{X}_{i+1}^{(1)} \begin{bmatrix} \hat{X}_i^{(1)} \\ U_f \end{bmatrix}^\dagger \bigg|_{\text{first } n_1 \text{columns}} \qquad \text{Equation 81}$$

-continued $$[A_{21}\, A_{22}] = \hat{X}_{i+1}^{(2)} \begin{bmatrix} \hat{X}_i \\ U_f \end{bmatrix}^\dagger \bigg|_{\text{first } n_x \text{columns}} \qquad \text{Equation 82}$$

$$C_y = Y_i \begin{bmatrix} \hat{X}_i \\ U_f \end{bmatrix}^\dagger \bigg|_{\text{first } n_x \text{columns}} \qquad \text{Equation 83}$$

$$C_z = Z_i \begin{bmatrix} \hat{X}_i \\ U_f \end{bmatrix}^\dagger \bigg|_{\text{first } n_x \text{columns}} \qquad \text{Equation 84}$$

where $Y_i$ and $Z_i$ are as defined in Equations 71 and 72, respectively.

4. Compute an estimate of the noise time series $w_k$ and $v_k$ from Equation 65 as:

$$\hat{W}^{(1)} = \hat{X}_{i+1}^{(1)} - \hat{X}_{i+1}^{(1)} / \begin{bmatrix} \hat{X}_i^{(1)} \\ U_f \end{bmatrix} \qquad \text{Equation 85}$$

$$\hat{W}^{(2)} = \hat{X}_{i+1}^{(2)} - \hat{X}_{i+1}^{(2)} / \begin{bmatrix} \hat{X}_i \\ U_f \end{bmatrix} \qquad \text{Equation 86}$$

$$\hat{V} = Y_i - Y_i / \begin{bmatrix} \hat{X}_i \\ U_f \end{bmatrix} \qquad \text{Equation 87}$$

5. Compute the covariances and cross-covariance of $w_k$ and $v_k$ as:

$$\begin{bmatrix} Q & S \\ S^T & R \end{bmatrix} = \frac{1}{j} \begin{bmatrix} \hat{W}^{(1)} \\ \hat{W}^{(2)} \\ \hat{V} \end{bmatrix} \begin{bmatrix} \hat{W}^{(1)} \\ \hat{W}^{(2)} \\ \hat{V} \end{bmatrix}^T \qquad \text{Equation 88}$$

6. Follow a procedure to find the least squares solution for the model parameters B and $D_y$.
7. This concludes the learning of all model parameters in the first two rows of Equation 65 and thus one can now run a Kalman filter to recursively estimate the latent states as:

$$\hat{x}_{k+1} = (A - KC_y)\hat{x}_k + Bu_k + Ky_k \qquad \text{Equation 89:}$$

where K is the steady state Kalman gain.

8. Finally, compute behavior projection parameter D, as:

$$D_z = \{z_k - C_z \hat{x}_k\}_{1:N} / \{u_k\}_{1:N} \qquad \text{Equation 90:}$$

where $\{a_k\}_{1:N}$ denotes constructing an N-column matrix with column n containing $a_n$.

The above concludes the learning of all model parameters using PSID in presence of external inputs. For the special case of $n_1 = 0$, only stage 2 will be performed and the algorithm will reduce to standard subspace identification with external input.

Discussion now turns to the use of recurrent neural networks to perform PSID. Neural activity contains complex dynamics that may simultaneously be related to various brain functions. This complexity poses a challenge for brain-machine interface applications and neuroscience research when studying a specific behaviorally measurable brain function is of interest, as the neural dynamics relevant to the study may be masked by other dynamics. The inventors have previously developed a novel algorithm termed preferential system identification (PSID), that models neural dynamics while dissociating and prioritizing behaviorally relevant dynamics. Here, the specification presents a variation of PSID that is based on numerical optimization of recurrent neural networks (RNN), termed RNN PSID, which adds support for multiple new applications. First, RNN PSID allows learning of nonlinear dynamics. Second, RNN PSID can learn behaviorally relevant dynamics even if neural or behavioral signals are intermittently sampled. Third, RNN PSID can more accurately model non-Gaussian neural activity such as Poisson distributed spike counts. Fourth, RNN PSID can model non-Gaussian behavioral signals, such as categorical behaviors. The inventors demonstrate these applications of RNN PSID using real neural activity in existing datasets. The inventors find that RNN PSID learns more accurate models of behaviorally relevant neural dynamics that enable more accurate decoding of behavior. This new method can help neuroscience research and brain-machine interface applications by learning more accurate models of behaviorally relevant neural dynamics.

Figure 37:
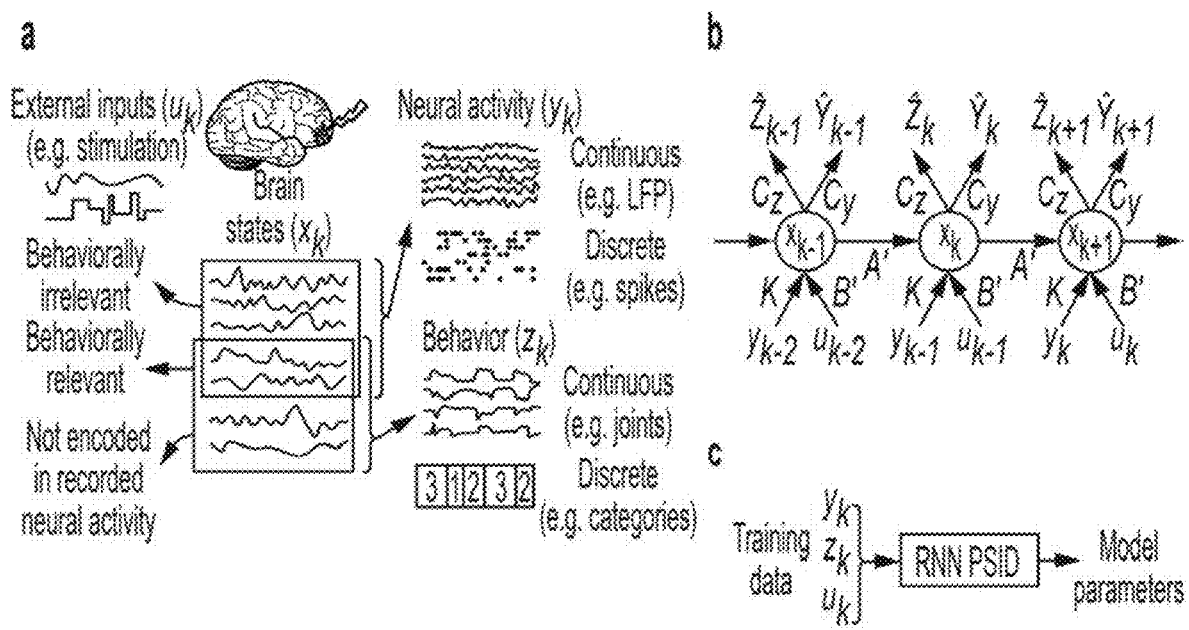
FIG. 37 illustrates a high-level view of RNN PSID according to an embodiment of the present invention.

The specification previously discussed an algorithm termed PSID for modeling behaviorally relevant neural dynamics. PSID performs a series of algebraic operations (e.g. linear projections) on the recorded neural and behavioral time series to learn the parameters of a linear state-space model that jointly describes the neural and behavioral signals. The inventors developed a variation of PSID by reformulating the model as a recurrent neural network (RNN) and learning its parameters via numerical optimizations with appropriate objective functions. This new method that is termed RNN PSID adds support for multiple new applications (FIG. 37, a). First, by using numerical optimization, RNN PSID can gracefully handle the learning even if the provided neural or behavioral signals are only intermittently sampled. This capability is important for applications such as modeling the neural encoding of human mood variations, where behavioral samples are self-reports of mood that are only intermittently available. It is also useful for modeling neural signals that are interrupted by artifactual or saturated segments and thus are again intermittently available. Second, by using numerical optimization, RNN PSID is flexible in terms of the model structure and can incorporate arbitrary nonlinear neural network models in place of every model parameter (FIG. 37, b, c). This allows RNN PSID to be applicable for modeling and studying nonlinear neural dynamics, for example dynamics with multiple fixed-points. Finally, by appropriately adjusting the objective functions for the numerical optimizations, RNN PSID can model neural and behavioral signals with non-Gaussian distributions. An important application for this capability is modeling categorical behavioral measurements such as the choice in a decision-making task. Another application is modeling neural spiking activity as a Poisson distributed count process, which is mathematically more appropriate for spiking activity and can also improve brain-machine interface performance. The specification will demonstrate these applications in real neural activity from non-human primates.

FIG. 37 presents a high-level view of RNN PSID. FIG. 37, a shows that RNN PSID supports modeling intermittently sampled and non-Gaussian neural and behavioral signals. Some important applications are modeling Poisson distributed spike counts and modeling categorical behavioral signals. FIG. 37, b shows that in RNN PSID, the inventors reformulated the PSID model (Equation 94) as a recurrent neural network with the depicted computation graph. For simplicity, the case with no feed-through is shown (i.e. $D_y \equiv D_z \equiv 0$). Model parameters to be learned are indicated with arrows. FIG. 37, c shows that RNN PSID learns the model parameters using numerical optimization. Due to flexibility in numerical optimization, each model parameter can be arbitrary nonlinear functions implemented as a multi-layer neural network.

Discussion now turns to reformulating PSID as fitting RNNs via numerical optimization. PSID models the neural activity $y_k \in \mathbb{R}^{n_y}$, behavior $z_k \in \mathbb{R}^{n_z}$, and the effect of any external input $u_k \in \mathbb{R}^{n_u}$ as the following state-space model:

$$\begin{cases} x_{k+1} = Ax_k + Bu_k + w_k \\ y_k = C_y x_k + D_u u_k + v_k \\ z_k = C_z x_k + D_z u_k + \epsilon_k \end{cases}, x_k = \begin{bmatrix} x_k^{(1)} \\ x_k^{(2)} \end{bmatrix} \quad \text{Equation 91}$$

where $x_k \in \mathbb{R}^{n_x}$ is a latent variable whose behaviorally relevant and irrelevant dimensions are separated as $x_k^{(1)} \in \mathbb{R}^{n_1}$ and $x_k^{(2)} \in \mathbb{R}^{n_x - n_1}$. $w_k$ and $v_k$ are Gaussian white noises and $\epsilon_k$ is a general random process that is independent of neural activity and represent any behavior dynamics that are not encoded in neural activity. Given the model parameters, the latent states can be estimated from the neural activity $y_k$ using a Kalman filter:

$$\hat{x}_{k+1|k} = A\hat{x}_{k|k-1} + Bu_k + K(y_k - C_y \hat{x}_{k|k-1}) \quad \text{Equation 92:}$$

where K is the Kalman gain. Equation 91 can be equivalently written with a similarity transform in terms of the Kalman estimation of the latent states as:

$$\begin{cases} x_{k+1} = A x_k + Bu_k + Ke_k \\ y_k = C_y x_k + D_y u_k + e_k \\ z_k = C_z x_k + D_z u_k + \epsilon_k \end{cases} \quad \text{Equation 93}$$

where $x_k \triangleq \hat{x}_{k|k-1}$ and $e_k$ and $\epsilon_k$ are respectively the parts of neural and behavior signals that cannot be predicted from the input (i.e. $\{u_{k'} \in \mathbb{R}^{n_u}: 0 \le k' < k\}$) and past neural activity (i.e. $\{y_{k'} \in \mathbb{R}^{n_y}: 0 \le k' < k\}$). Equivalently, by replacing $e_k$ from the first line with its value from the second line, one can also write Equation 93 as:

$$\begin{cases} x_{k+1} = A'x_k + B'u_k + Ky_k \\ y_k = C_y x_k + D_y u_k + e_k \\ z_k = C_z x_k + D_z u_k + \epsilon_k \end{cases} \quad \text{Equation 94}$$

where $A' \triangleq A - KC_y$ and $B' \triangleq B - KD^y$. Equations 91 and 94 can describe the same second order statistics for the observed times series $y_k$ and $z_k$ and thus are equivalent. Equation 91 is referred to as the stochastic form while Equation 94 is referred to as the predictor form.

In Equation 94, each multiplication between a model parameter and a vector (e.g. $A'x_k$) can be thought of as a linear function applied to an input vector (e.g. function $A'(\cdot)$, applied to $x_k$). Moreover, the parameters operating on the external input can be absorbed into other parameters, resulting in a more general form for Equation 94 as:

$$\begin{cases} x_{k+1} = A'(x_k) + K(y_k, u_k) \\ y_k = C_y(x_k, u_k) + e_k \\ z_k = C_z(x_k, u_k) + \epsilon_k \end{cases} \quad \text{Equation 95}$$

where each function (e.g. $A'(\cdot)$) is a parameter to be learned. In this formulation, functions $C_y$, $C_z$, and K operate on both the external input $u_k$ (if any) and either neural activity $y_k$ or latent states $x_k$ to also incorporate the operations related to B', $D_y$, and $D_z$ from Equation 94.

The inventors recognize that in the predictor form of Equation 95, the model corresponds to an RNN computation graph (FIG. 37, b) and thus its parameters can be learned using standard tools for numerical optimization. Neural activity $y_k$ and external input $u_k$ (if any) are both inputs of the RNN and predictions of neural and behavioral signals:

$$\begin{cases} \hat{y}_k = C_y(x_k, u_k) \\ \hat{z}_k = C_z(x_k, u_k) \end{cases} \qquad \text{Equation 96}$$

are the outputs of the RNN (FIG. 37, b). The inventors learned the model parameters by minimizing the mean squared error in the predictions of neural and behavioral signals, defined as:

$$L_y = \Sigma_k \|y_k - \hat{y}_k\|_2^2 \qquad \text{Equation 97:}$$

and $$L_z = \Sigma k \|z_k - \hat{z}_k\|_2^2 \qquad \text{Equation 98}$$

where the sum is over all available samples of $y_k$ and $z_k$, respectively. Importantly, since a key goal of RNN PSID is to prioritize learning of the behaviorally relevant neural dynamics, the inventors devised a two-stage approach for optimizing the above objective functions, which will be explained in the next section. Once the model parameters are learned, the extraction of latent states involves iteratively applying the first line from Equation 95, and predicting behavior or neural activity involves applying Equation 96.

A more general formulation for the loss in both stages of RNN PSID can be written as:

$$L = L_z + \lambda L_y = \Sigma_k \|z_k - \hat{z}_k\|_2^2 + \lambda \Sigma_k \|y_k - \hat{y}_k\|_2^2 \qquad \text{Equation 99:}$$

where $\lambda$ determines how much attention is paid to each of the two terms. Here, the inventors use the extreme cases of $\lambda = 0$ and $\lambda \to \infty$ for extraction of latent states in stages one and two, respectively. More generally, one could modify stage one to also incorporate some dynamics beyond the behaviorally relevant dynamics by using a non-zero $\lambda$.

The inventors note that assuming Gaussian distributions for $y_k$ and $z_k$, the losses $L_y$ and $L_z$ (Equations 97 and 98) can also be interpreted as the negative log likelihood of $y_k$ and $z_k$, respectively. Indeed, the log likelihood interpretation is how one extends RNN PSID to other distributions for neural activity $y_k$ and behavior $z_k$ in later sections.

Discussion now turns to a two-stage numerical optimization approach. A key idea in PSID that allows dissociation and prioritization of the behaviorally relevant neural dynamics is the novel two stage procedure for extracting the latent states. The inventors devised a similar procedure in RNN PSID. The inventors separate the latent states into behaviorally relevant and irrelevant parts (i.e. $x_k^{(1)}$ and $x_k^{(2)}$) that will be learned in the first and second stages of RNN PSID, respectively, with the second stage being optional. Given parameters $n_1$ and $n_x$, the inventors separate the latent states into two parts as:

$$\begin{cases} \begin{bmatrix} x_{k+1}^{(1)} \\ x_{k+1}^{(2)} \end{bmatrix} = \begin{bmatrix} A_1'(x_k^{(1)}) \\ A_2'(x_k^{(2)}) \end{bmatrix} + \begin{bmatrix} K^{(1)}(y_k, u_k) \\ K^{(2)}(y_k, u_k, x_{k+1}^{(1)}) \end{bmatrix} \\ y_k = C_y^{(1)}(x_k^{(1)}, u_k) + C_y^{(2)}(x_k^{(2)}) + +e_k \\ z_k = C_z^{(1)}(x_k^{(1)}, u_k) + \epsilon_k \end{cases} \qquad \text{Equation 100}$$

where $x_k^{(1)} \in \mathbb{R}^{n_1}$ denotes the latent states to be extracted in the first stage and $x_k^{(2)} \in \mathbb{R}^{n_2}$ with $n_2 = n_x - n_1$ denotes those to be extracted in the second stage. Note that the recursions for computing $x_k^{(1)}$ are not dependent on $x_k^{(2)}$, thus allowing the former to be computed without the latter. In contrast, $x_k^{(2)}$ can depend on $x_k^{(1)}$ and this dependence is modeled via $K^{(2)}$, which conceptually incorporates the role of the matrix $A_{21}$ in PSID.

In the first stage, the objective is to learn behaviorally relevant latent states $x_k^{(1)}$ and their associated parameters. This stage consists of two numerical optimizations. In the first optimization, the inventors learn the parameters $A_1'$, $C_z^{(1)}$, and $K^{(1)}$ of the following RNN:

$$\begin{cases} x_{k+1}^{(1)} = A_1'(x_k^{(1)}) + K^{(1)}(y_k, u_k) \\ z_k = C_z^{(1)}(x_k^{(1)}, u_k) + \epsilon_k \end{cases} \qquad \text{Equation 101}$$

and estimate its latent state $x_k^{(1)}$ while minimizing the behavior loss $L_z$ (Equation 98). The second optimization uses the extracted latent state $x_k^{(1)}$ from the RNN and fits the parameters $C_y^{(1)}$ in:

$$y_k = C_y^{(1)}(x_k^{(1)}, u_k) + e_k \qquad \text{Equation 102:}$$

while minimizing the neural loss $L_y$ (Equation 97). Equation 102 can be thought of as a regression model from $x_k^{(1)}$ and $u_k$ to neural activity $y_k$. This stage concludes extraction and modeling of behaviorally relevant latent states $x_k^{(1)}$.

In the optional second stage, the objective is to learn any additional dynamics in neural activity that were not learned in the first stage, i.e. $x_k^{(2)}$ and its associated parameters. To do so, the inventors learn the parameters $A_2'$, $C_y^{(2)}$, and $K^{(2)}$ of the following RNN:

$$\begin{cases} x_{k+1}^{(2)} = A_2'(x_k^{(2)}) + K^{(2)}(y_k, u_k, x_{k+1}^{(1)}) \\ y_k = C_y^{(2)}(x_k^{(2)}) + C_y^{(1)}(x_k^{(1)}, u_k) + e_k \end{cases} \qquad \text{Equation 103}$$

while minimizing the neural loss $L_y$ (Equation 97). Note that in this RNN, $y_k$, $u_k$ and $x_{k+1}^{(1)}$ jointly have the role of input and $y_k - C_y^{(1)}(x_k^{(1)}, u_k)$ (with the previously learned parameter $C_y^{(1)}$) is the output. If one assumes the second set of states $x_k^{(2)}$ do not contain any information about behavior (as in Equation 100), one could stop the modeling. However, in tests, the inventors found that the final model may be more accurate if one allows another numerical optimization to determine using the data whether and how $x_k^{(2)}$ should affect behavior prediction. Thus, a second optimization in the second stage uses the extracted latent state in both stages and fits $C_z$ in:

$$z_k = C_z(x_k^{(1)}, x_k^{(2)}, u_k) + \epsilon_k \qquad \text{Equation 104:}$$

while minimizing the behavior loss $L_z$ (Equation 98). This parameter will replace $C_z^{(1)}$ in Equation 100. This concludes the learning of all model parameters in Equation 100.

It should be noted that in Equation 103 from stage two, the effect of the states from the first stage were shown as additions to the output signal $y_k$. For general non-Gaussian $y_k$ (see subsequent sections), this addition should be done to the log likelihood, not the output itself. In other words, in the second stage parameters are learned to maximize the log likelihood of the neural signal, while considering the likelihood from the first stage (from Equation 102). In the case of Gaussian $y_k$, the first stage likelihood provides a prior on the mean of $y_k$, which can be implemented as addition to $y_k$ as in Equation 103.

Discussion now turns to nonlinear modeling of behaviorally relevant neural dynamics. By using a numerical optimization framework, RNN PSID is readily extendable to nonlinear models. Each parameter in the model represents an operation in the computation graph of RNN PSID (FIG. 37, b). Since the inventors solve the optimization via stochastic gradient descent, the numerical solution remains applicable for any modification of the computation graph that remains acyclic. Thus, the operation associated with each model parameter (e.g. A', $C_y$, $C_z$, and K), can be replaced with multi-layer neural networks with arbitrarily width and dept and the model should still be technically trainable. Of course, given that the training data is finite, the typical trade-off between model capacity and generalization error remains. Given that neural networks can approximate any continuous function (with a compact domain), replacing model parameters with neural networks should have the capacity to learn any nonlinear function in their place. In other words, the model architecture can be generalized to replacing each model parameter in Equation 95 with an arbitrary function. In the discussion regarding the results, unless otherwise noted, each nonlinear model parameter is modeled with a neural network with one hidden layer with 64 units and with a rectified linear unit (ReLU) activation. However, as mentioned earlier, the neural network for nonlinear parameters can in principle be any arbitrary multi-layer neural network.

Given that the model in Equation 95 is constructed in the predictor form, the model can readily be used to estimate the latent states $x_k$ given the neural observations $y_k$, and to decode behavior $z_k$. Although for any data, fitting the RNN PSID model readily provides a decoder, whether or not the decoder will be mathematically optimal for the data depends on the true underlying statistics of the data and whether it can be formulated in the form of Equation 95 or not. For example, any stationary and jointly Gaussian pair of random processes $y_k$ and $z_k$ can be written in the form of Equation 91 and thus in the form of Equation 95. For other general nonlinear random processes, this may not be clear, but as long as the optimal decoder for decoding the latent states $x_k$ or behavior $z_k$ using neural activity can be written in the form of Equation 95, the model should be capable of formulating the optimal decoder and can thus achieve optimal decoding given a large enough training data.

Discussion now will be directed to modeling intermittent neural or behavioral measurements. Using numerical optimization for learning the model parameters in RNN PSID has the benefit of gracefully handling missing observations in neural and/or behavioral signals. If out of the samples of training data $y_k$ and $z_k$ for k∈ {1, . . . , N}, some are unknown, with two adjustments RNN PSID can still learn the model parameters. First, the neural and behavioral loss functions $L_y$ and $L_z$ (Equations 97 and 98) should only be summed over data samples for which the true $y_k$ and $z_k$ are known, respectively. Second, for samples where $y_k$ is not available, in the RNN formulation implementing Equation 95, one may remove the K term. To make sure a Kalman filter is a special case of RNN PSID, for these samples one could further replace A' with a different parameter A" to be learned and also replace $K(y_k, u_k)$ with a different $K'(u_k)$ (or with zero if no external inputs are present). In the case of a linear model (Equation 94), this could allow the model to learn A as the parameter A"—in addition to learning A'=A−KC$_y$— and learn B as the parameter K', and use them in samples that lack neural observations (i.e. $y_k$ is not available) to capture the effect of setting the Kalman gain K to zero, indicating an infinite observation noise (i.e. unseen observation $y_k$).

Discussion now turns to modeling Poisson distributed neural spiking activity.

RNN PSID is also applicable to non-Gaussian neural observations such as Poisson distributed spike counts. To use RNN PSID with such neural signals, two adjustment are needed. First, one may reflect the distribution of the neural time series $y_k$ in the neural loss $L_y$ (Equation 97). For Poisson distributed $y_k$ the probability distribution of each dimension i (i.e. neuron i) can be written as:

$$P(y) = \frac{\lambda^y e^{-\lambda}}{y!} \quad \text{Equation 105}$$

where $y \triangleq y_k^{(i)} \in \mathbb{N}_0$ is the number of spikes from the neuron at time bin k and $\lambda \triangleq \hat{y}_k^{(i)} \in \mathbb{R}^+$ is the expected value of the spike counts during the time bin. Taking log from this distribution, multiplying by −1 and dropping terms that do not depend on λ results in:

$$L_y = \sum_k \sum_{i=0}^{n_y} \left( y_k^{(i)} \log \hat{y}_k^{(i)} + \hat{y}_k^{(i)} \right) \quad \text{Equation 106}$$

where k is an index over all available neural data samples. The inventors implement this Poisson log likelihood loss using the dedicated class in the tensorflow library (i.e. tf.keras.losses.Poisson). Second, the inventors use an exponential activation function for the output layer of $C_y$ to reflect that $\hat{y}_k^{(i)}$ needs to be strictly positive for the loss in Equation 106 to be well defined.

One standard method for modeling Poisson distributed spiking activity is to use a generalized linear state-space model with an exponentially linked Poisson distributed neural observation model as:

$$i0n : \begin{cases} x_{k+1} = A x_k + w_k \\ \lambda_k = \exp(C_y x_k + \beta) \\ y_k = \text{Poisson}(\lambda_k) \end{cases} \quad \text{Equation 107}$$

where $\beta \in \mathbb{R}^{n_y}$ is an additional model parameter and $\lambda_k \in \mathbb{R}^{n_y}$ is the parameter of the Poisson distribution that generates spike counts $y_k$ for time step k (i.e. the instantaneous mean spike count). Note that the size of the counting time bin (often shown as Δ) can be reflected via the other model parameters so it is not shown here. For such models, when the counting time bins are small such that spike counts are binary (i.e. almost no time bin has more than one spike), the estimation of latent states using the observed spike counts can be done using a point process filter. The specification will show here that a point process filter is approximately a special case of the RNN PSID model in Equation 95, with A' and $C_y$ being nonlinear. The point process filter can be written as the following recursive formulation:

$$\begin{cases} \hat{x}_{k|k} = \hat{x}_{k|k-1} + U_{k|k} C_y^T \left( y_k - \exp(C_y \hat{x}_{k|k-1} + \beta) \right) \\ \hat{x}_{k|k-1} = A \hat{x}_{k|k} \end{cases} \quad \text{Equation 108}$$

where $U_{k|k}$ is the estimated error covariance of $\hat{x}_{k|k}$. Assuming an approximate steady state value of U for $U_{k|k}$ and replacing $\hat{x}_{k|k}$ from the second line with its value from the first line of Equation 108, and defining $e_k$ as shown below gives:

$$\begin{cases} \hat{x}_{k+1|k} = A\hat{x}_{k|k-1} + AUC_y^T e_k(y_k - \exp(C_y \hat{x}_{k|k-1} + \beta)) \\ e_k \triangleq y_k - \exp(C_y \hat{x}_{k|k-1} + \beta) \end{cases}$$ Equation 109 which is analogous to the predictor form of the LSSM in Equation 93. Replacing $e_k$ in the first line with its value from the second line and defining $x_k \triangleq \hat{x}_{k|k-1}$ and $K \triangleq AUC_y^T$ gives:

$$\begin{cases} x_{k+1} = Ax_k - K\exp(C_y x_k + \beta) + Ky_k \\ y_k = \exp(C_y \hat{x}_{k|k-1} + \beta) + e_k \end{cases}$$ Equation 110 which is a special case of Equation 95, with nonlinear $A'(x_k) \triangleq Ax_k - K \exp(C_y x_k + \beta)$ and $C_y(x_k) \triangleq \exp(C_y \hat{x}_{k|k-1} + \beta)$ Thus, since nonlinearity in $A'$ and $C_y$ is required for the model in Equation 95 to be able to approximately capture a point process filter, one may always allow these two parameters to be nonlinear when modeling spiking activity.

Discussion now turns to modeling categorical behavioral measurements. RNN PSID is also applicable to categorical behavioral signals such as choice, epoch type, etc. For such signals, the distribution of the behavior signal $z_k$ follows a categorical distribution (also known as a generalized Bernoulli distribution), which is parameterized by the probability of each category. To reflect the behavior distribution in RNN PSID, three adjustments are needed. First, the behavior loss $L_z$ (Equation 98) should be set to the negative log likelihood of the behavior distribution, which the inventors implement using the dedicated class in the tensorflow library (i.e. tf.keras.losses.CategoricalCrossentropy). Second, the behavior mapping parameter $C_z$ needs to have an output dimension of $n_z \times n_c$, where $n_c$ denotes the number of behavior categories or classes. Third, $C_z$ needs to be followed by a Softmax operation to ensure the rows of the output of $C_z$ are valid probability mass functions and add up to 1. Softmax can be written as:

$$p_k^{(m,n)} = \frac{\exp(l_k^{(m,n)})}{\sum_{i=1}^{n_c} \exp(l_k^{(m,i)})}$$ Equation 111 where $l_k \in \mathbb{R}^{n_c \times n_c}$ is the output of $C_z$ at time k. With these modifications, RNN PSID is able to model categorical behavioral measurements.

Figure 38:
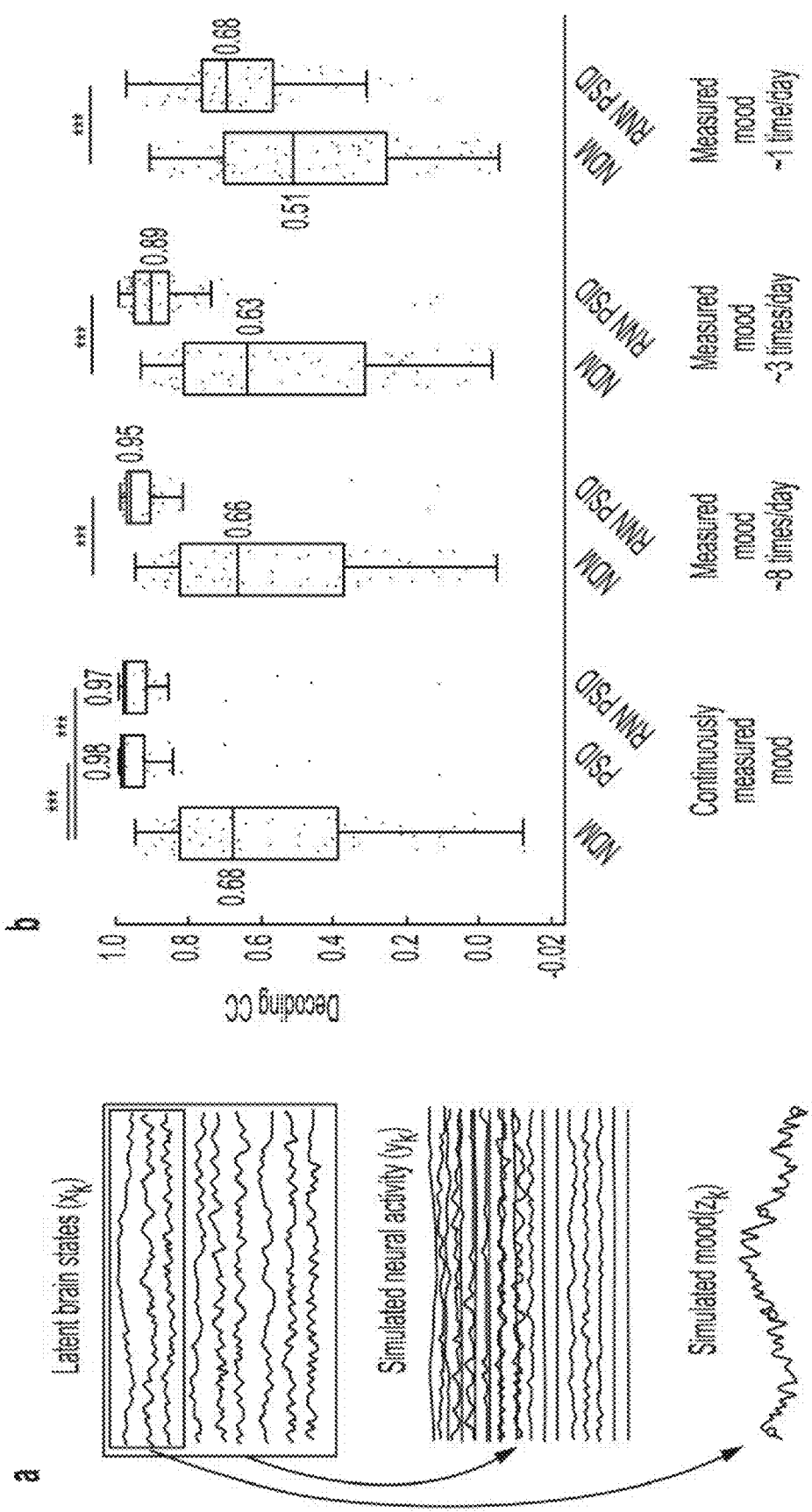
FIG. 38 illustrates that RNN PSID more accurately models and decodes intermittently sampled brain states such as mood states in simulated data according to an embodiment of the present invention.

Discussion now turns to results of PSID in analyses performed by the inventors, specifically to modeling intermittently sampled simulated mood measurements. To demonstrate the application of RNN PSID for modeling using intermittent behavioral measurements, the inventors simulated a mood decoding problem. The inventors took mood linear state-space encoding models fitted to prior real human neural signals and mood reports in prior work of the inventors. The inventors generated new simulated data realizations from these models. In each model, the simulated mood was generated from 3 dimensions of the latent state that also contributed to generating the simulated neural activity, while the other dimensions only contributed to generating the simulated neural activity (FIG. 38, a). The inventors first considered the hypothetical case where the simulated mood could be continuously measured. In this case, PSID is applicable and the inventors found that both PSID and RNN PSID were significantly more accurate than NDM (FIG. 38, b). The inventors next considered the case when only intermittent samples of simulated mood were available for modeling. RNN PSID was still applicable in this case and the inventors found that across various sampling rates for the intermittently sampled mood, RNN PSID was consistently significantly more accurate than NDM in decoding mood (FIG. 38, b).

FIG. 38 shows that RNN PSID more accurately models intermittently sampled mood in simulations. In particular, FIG. 38, a shows that in each model, the simulated mood is generated from 3 dimensions of the latent states, while all latent state dimensions contribute to generating the neural activity. FIG. 38, b shows cross-validated decoding correlation coefficient (CC) of simulated mood from neural activity, using NDM, PSID and RNN PSID, for models fitted using continues or intermittent mood samples.

Figure 39:
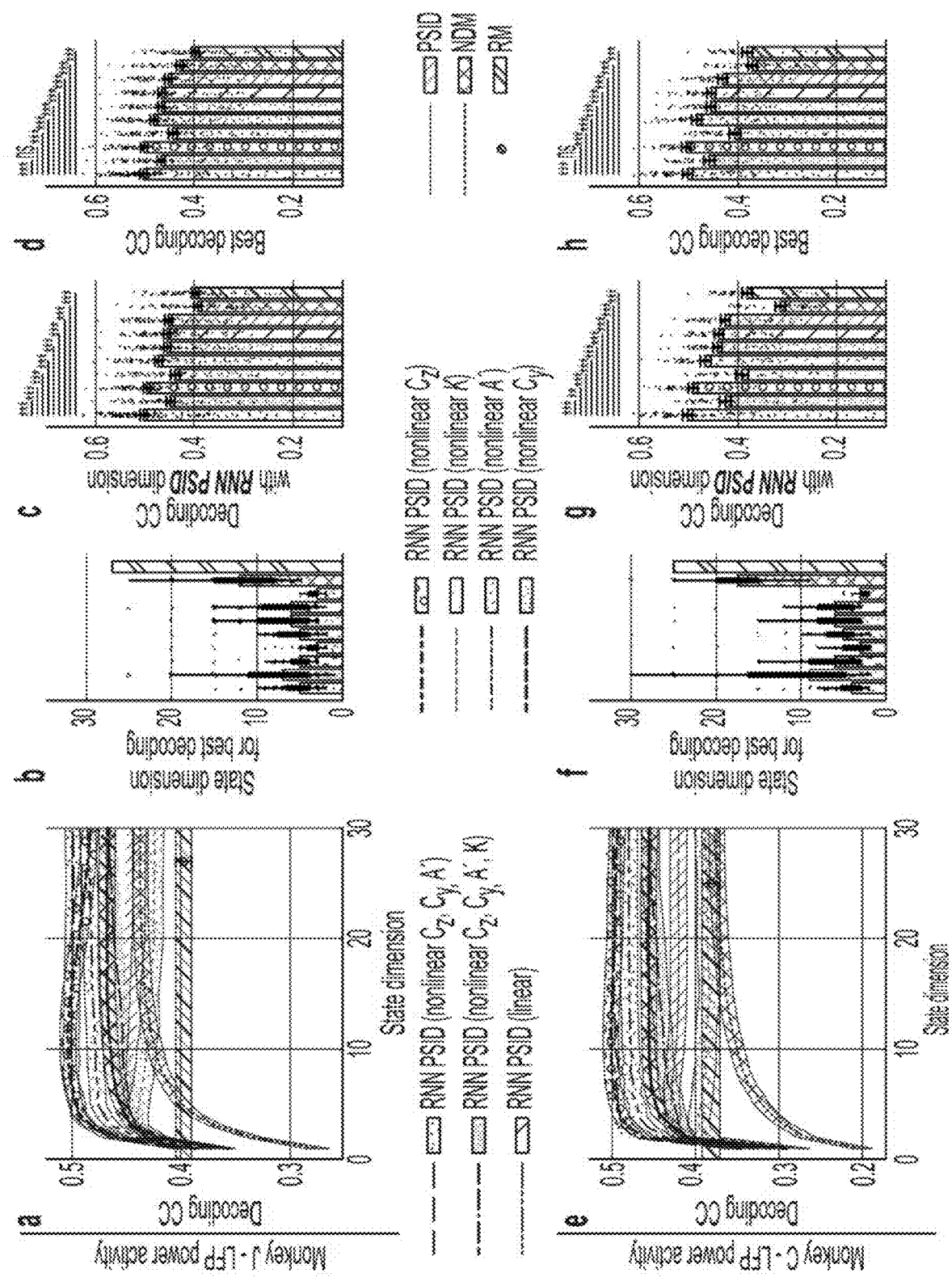
FIG. 39 illustrates that RNN PSID more accurately models behaviorally relevant neural dynamics by using nonlinearity and can help investigate the source of nonlinearity according to an embodiment of the present invention.

Next, discussion will turn to results of nonlinear modeling of behaviorally relevant neural dynamics. Given that RNN PSID can learn nonlinear models, the inventors used it to study nonlinearity in the behaviorally relevant neural dynamics in existing neural data from monkeys performing naturalistic 3D reach, grasp and returns while the joint angles in their arm, elbow, wrist, and fingers are tracked. First, the inventors found that nonlinear RNN PSID described behaviorally relevant neural dynamics significantly more accurately than the linear PSID (FIG. 39, a, e), suggesting that there is indeed nonlinearity in how behaviorally relevant dynamics are encoded in the data. Second, given the flexibility of RNN PSID in selectively allowing nonlinearity in each model parameter, the inventors used it to investigate the source of nonlinearity in the existing data. The inventors made individual model parameters nonlinear and found that only having a nonlinear behavior observation parameter C, is sufficient for achieving decoding that is as accurate as the best decoding obtained with multiple nonlinear parameters (FIG. 39). This suggests that in this data, the source of nonlinearity is not necessarily in neural dynamics themselves, but could be mostly confined to how these neural dynamics are mapped to behavior.

FIG. 39 specifically shows that RNN PSID more accurately models behaviorally relevant neural dynamics by using nonlinearity and can help investigate the source of nonlinearity. FIG. 39, a shows cross-validated decoding correlation coefficient (CC) using RNN PSID with nonlinearity in various sets of parameters as well as PSID, NDM and RM, averaged over joints. The solid lines show the average over datasets and the shaded areas show the s.e.m. FIG. 39, b shows the dimension of behaviorally relevant dynamics as estimated by each method, defined as the minimum state dimension that reaches within 1 s.e.m. of the peak decoding using that method. Dots show the dimension for individual datasets and boxes show the distribution, with the solid line showing the median, the box edges showing the 25th and 75th percentiles, and the whiskers showing the range of data minus outliers, which are defined as data points that are more than 1.5 times the box size away from the edge of the box. Asterisks show significance level for a one-sided Wilcoxon signed-rank test (*: P<0.05, : P<0.005, and *: P<0.0005). FIG. 39, c shows decoding obtained using each method when all methods use the dimension revealed by the first RNN PSID configuration in FIG. 39, b. Bars show the mean over datasets and whiskers show the s.e.m. Data points show the value for each dataset. FIG. 39, d shows the same as FIG. 39, c, when each method uses the dimension revealed by the same method in FIG. 39, b. FIG. 39, e-h show the same as FIG. 39, a-d for monkey C.

Figure 40:
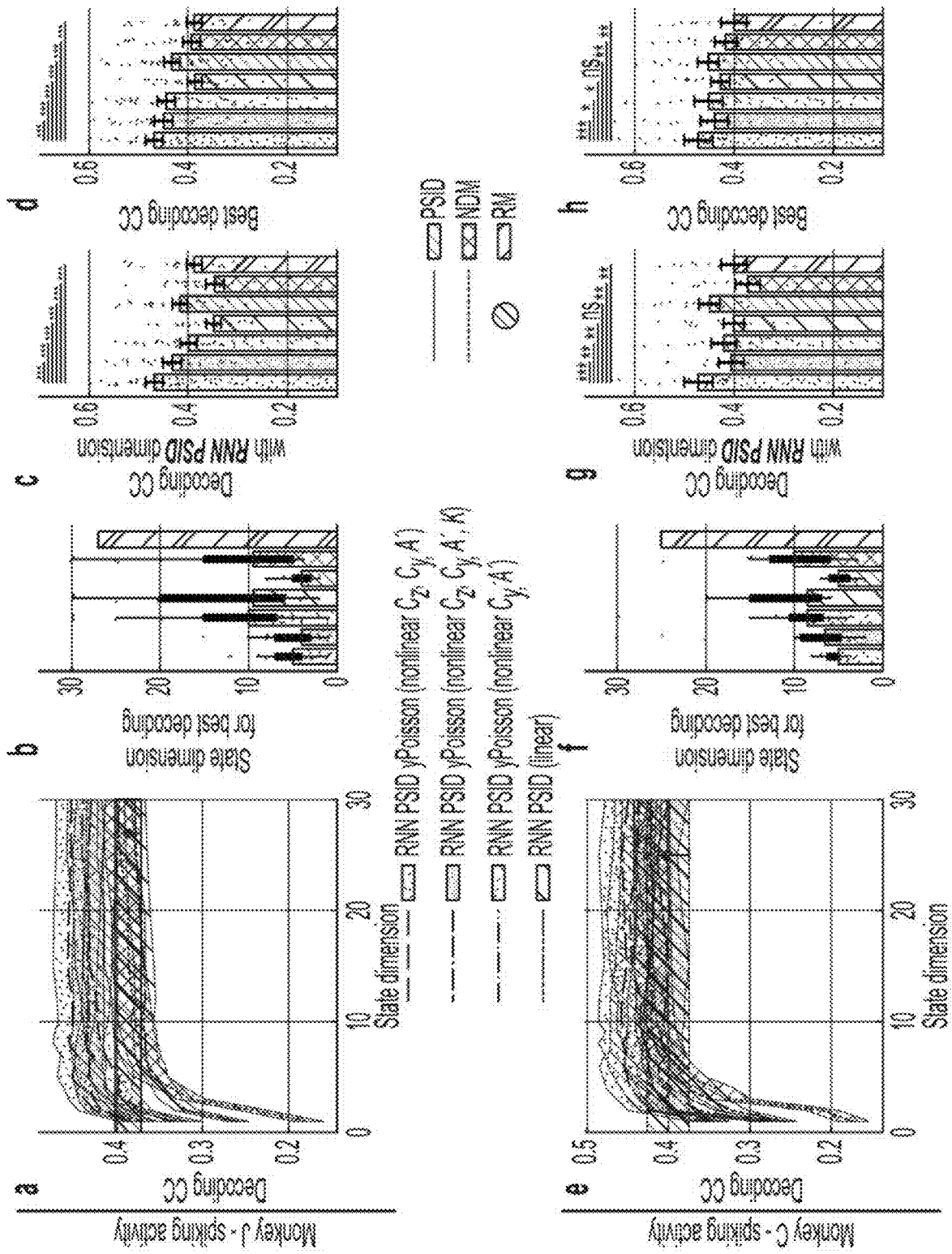
FIG. 40 illustrates that RNN PSID with a Poisson neural observation model more accurately models behaviorally relevant neural dynamics in spiking activity according to an embodiment of the present invention.

Discussion now turns to results obtained from modeling Poisson distributed neural spiking activity. With its flexible numerical optimization framework, RNN PSID is applicable to non-Gaussian neural observations such as Poisson distributed spike counts. The main difference from before is that the neural loss $L_y$ (Equation 97) is modified to reflect the log likelihood of the Poisson distribution (Equation 106). The inventors modeled the spike counts in their neural recordings from the naturalistic 3D reach, grasp and return task (see above). Given that RNN PSID is capable of accurately modeling Poisson distributed neural signals, the inventors did not perform any smoothing preprocessing on spike counts. The inventors found that in both subjects, modeling spike counts as Poisson distributed signals resulted in a more accurate model of behaviorally relevant neural dynamics (FIG. 40). Nonlinear RNN PSID with Poisson observations resulted in significantly more accurate decoding than other methods (FIG. 40, c-d, g-h).

Specifically, FIG. 40 shows that RNN PSID with a Poisson neural observation model more accurately models behaviorally relevant neural dynamics in spiking activity. The notation in FIG. 40 is the same as in FIG. 39. Only stage 1 is used for all PSID variants (i.e. $n_1 = n_x$). Results are shown for RNN PSID with a Poisson observation model for neural activity and for modeling spike counts in 50 ms bins, without any Gaussian smoothing applied as preprocessing. Note that the parameters A' and $C_y$ always need to be nonlinear when modeling Poisson neural observations. Thus, here for Poisson neural models the inventors only compared the effect of switching parameters $C_z$ and K between nonlinear and linear and found that nonlinearity in $C_z$ helps the decoding. Unlike the results for LFP activity (FIG. 39), for spike counts fitting a fully linear model numerically using RNN PSID with the mean-squared error (MSE) loss (Equation 97) is not as accurate as fitting the model using PSID. Since MSE only corresponds to the log likelihood for Gaussian distributions, this suggests that using the appropriate log likelihood functions as the neural loss that corresponds to the distribution of the neural observation could be critical in accurately modeling the data using RNN PSID.

Figure 41:
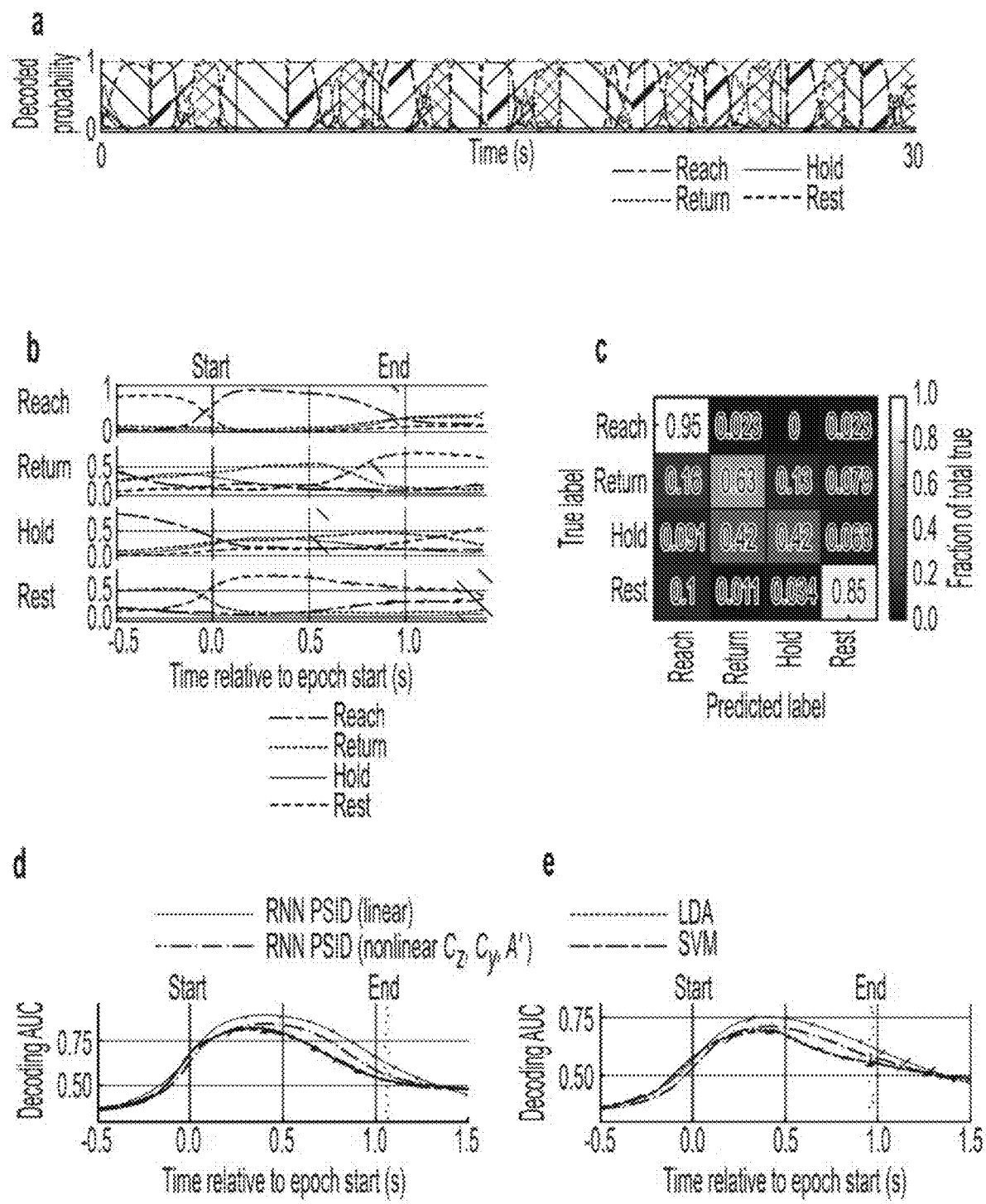
FIG. 41 illustrates that RNN PSID can model categorical behavioral signals according to an embodiment of the present invention.

Discussion will now turn to results from modeling categorical behavioral measurements. Given the flexible numerical optimization approach in RNN PSID, by appropriately adjusting the model output and behavior loss one can model categorical behavioral signals. To demonstrate this capability, the inventors applied RNN PSID to a naturalistic 3D movement data (see above), but here the inventors took the behavior signal $z_k$ to be a categorical signal with 4 possible values ($z_k \in \{1,2,3,4\}$) representing 4 types of epochs in the task: reach, hold, return, and rest epochs. The behavior prediction from RNN PSID in this configuration consists of a 4-dimensional time series with the probability of each epoch type given in one of the 4 dimensions, with the probabilities being between 0 and 1, and adding up to 1 (FIG. 41, a). The inventors found that as expected, soon after the beginning of each epoch, the predicted probability for that epoch type by RNN PSID increased to make that epoch type the most probable among all epoch types (FIG. 41, b). This resulted in highly accurate classification, with highest accuracy being achieved roughly 0.4s after the start of epochs (FIG. 41, c). The inventors quantified the overall classification performance using the multi-class generalization of the area under curve (AUC) measure and compared the overall accuracy for RNN PSID (linear and nonlinear), with standard linear discriminant analysis (LDA) and nonlinear support vector machine (SVM) classification (FIG. 41, d-e). The inventors found that linear RNN PSID resulted in more accurate decoding of epochs for all times after around 0.1s post epoch start time.

Here, nonlinear RNN PSID, perhaps due to increased model complexity, performed less accurately than linear RNN PSID, but still outperformed LDA and SVM for most time periods (FIG. 41, d-e). These results demonstrate the capability of modeling categorical behavior signals using RNN PSID. It is worth noting that a comprehensive search of all possible model architectures (e.g. using more hidden layers for nonlinearity, adding regularization, etc.) for RNN PSID, can potentially further improve the classification performance.

FIG. 41 shows that RNN PSID can model categorical behavioral signals. FIG. 41, a shows example cross-validated epoch decoding probabilities using RNN PSID during a continuous 30s segment of data with multiple epochs. Spiking activity smoother with a 50 ms s.d. Gaussian kernel was used for decoding. FIG. 41, b shows decoded probability of epochs, averaged within epochs of the same type, time-locked to the start time of the epoch. Shaded areas show the s.e.m. Start time of the epochs is indicated with a vertical line and the average end time of epochs, plus and minus the s.e.m., is shown with a shaded area. Ideally, the highest probability during an epoch should be the probability of that epoch (e.g. where one expects probability to be highest during in the first panel which is averaged over all reach epochs). FIG. 41, c shows an example confusion matrix for classifying epochs at time 0.4s relative to the start time of the epoch. The generalized multi-class area under curve (AUC) for the classification in this dataset, at +0.4s after start time of the epoch is 0.92. FIG. 41, d shows decoding AUC obtained for classifying epochs at different times relative to the start time of the epoch, averaged over all datasets. Notation is as in FIG. 41, b with the shaded areas showing the s.e.m. Results are shown for linear and nonlinear RNN PSID, as well as for standard LDA (linear) and nonlinear SVM classification, with $n_x = n_y = 30$ for all methods. FIG. 41, e shows the same as FIG. 41, d for monkey C.

Here, the inventors developed a variation of the PSID algorithm that adds support for multiple new applications. This variation, termed RNN PSID, not only can dissociate and model behaviorally relevant neural dynamics, it can also learn these dynamics (i) if they are nonlinear, (ii) if behavior or neural signals are intermittently sampled, (iii) if neural activity is non-Gaussian, for example Poisson distributed, and (iv) if behavioral signals are non-Gaussian, for example categorical. These additional capabilities can be useful for neuroscience and neurotechnology applications. First, from a neuroscience perspective, investigating the encoding of behaviorally measurable brain functions in neural activity is of broad interest, and it is likely that some of these dynamics may be nonlinear (FIG. 39), so the capability to model nonlinearity is beneficial. Second, in problems such as investigating the neural encoding of mood and decoding it, behavioral signals (e.g. mood reports) may only be intermittently available (FIG. 38), which is a major challenge for extracting and modeling the mood relevant neural dynamics. Third, some neural measurement such as spiking activity are more accurately described with non-Gaussian distributions, and here the inventors found the same for behaviorally relevant neural dynamics (FIG. 40). Fourth, in many experiments all or some behavioral signals of interest are categorical, such as a choice among some options, the condition of the trial, the type of epoch (FIG. 41), so it is of interest to be able to investigate behaviorally relevant neural dynamics in such scenarios. RNN PSID expands the applicability of PSID to these new domains and may allow more accurate learning of behaviorally relevant neural dynamics.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for preferential system identification (PSID) for modeling neural dynamics of a brain by a recurrent neural network (RNN), the method comprising:
    extracting, by the recurrent neural network, behaviorally relevant latent brain states via a projection of future behavior onto past neural activity, wherein the future behavior includes a movement kinematic and wherein the behaviorally relevant latent brain states are brain states associated with the movement kinematic; and
    identifying, by the recurrent neural network, based on the extracted latent brain states, model parameters for a linear state space dynamic model of neural activity.

2. The method of claim 1 wherein extracting the behaviorally relevant latent brain states includes:
    forming examples of the future behavior and associated examples of the past neural activity; and
    projecting the examples of the future behavior onto the associated past neural activity.

3. The method of claim 2 wherein extracting the behaviorally relevant latent brain states further includes computing a singular value decomposition (SVD) of the projection of the future behavior onto the past neural activity.

4. The method of claim 3 wherein identifying the model parameters includes identifying a full latent state consisting of the extracted behaviorally relevant latent brain states at each time-step.

5. The method of claim 1 further comprising extracting behaviorally irrelevant latent brain states via a projection of residual future neural activity onto the past neural activity, the residual future neural activity not being described by the behaviorally relevant latent brain states, wherein the behaviorally irrelevant latent brain states are brain states that are not the behaviorally relevant latent brain states.

6. The method of claim 5 wherein the method is further for dissociating neural dynamics that are behaviorally relevant from neural dynamics that are behaviorally irrelevant while prioritizing the neural dynamics that are behaviorally relevant.

7. The method of claim 5 wherein extracting the behaviorally irrelevant latent brain states further includes:
    computing a singular value decomposition (SVD) of the result of projecting the residual future neural activity onto the past neural activity; and
    computing the behaviorally irrelevant latent brain states based on the SVD.

8. The method of claim 7 wherein identifying the model parameters includes identifying a full latent state consisting of a concatenation of the extracted behaviorally relevant latent brain states and the behaviorally irrelevant latent brain states at each time-step.

9. The method of claim 8 wherein identifying the model parameters further includes identifying additional full latent states each having a shift of a single step in time.

10. The method of claim 9 wherein identifying the model parameters further includes computing a least squares solution for the model parameters using a pseudoinverse calculation.

11. The method of claim 10 wherein identifying the model parameters further includes computing a covariance of residuals in the least squares solution to get noise statistics.

12. The method of claim 11 wherein the model parameters are used to construct a Kalman filter to extract the behaviorally relevant latent brain states and the behaviorally irrelevant latent brain states from new neural data and to decode behavior from the extracted states.

13. The method of claim 1 wherein an effect of an external input to the brain can be accounted for by using oblique projections along an external input instead of orthogonal projections.

14. A method for preferential system identification (PSID) for modeling neural dynamics of a brain, the method comprising:
    extracting behaviorally relevant latent brain states, wherein the behaviorally relevant latent brain states are brain states associated with a movement kinematic; and
    identifying, based on the extracted latent brain states, model parameters for a state space dynamic model of neural activity,
    wherein the extracting and the identifying are performed using a numerical optimization of recurrent neural networks (RNN).

15. The method of claim 14 wherein extracting the behaviorally relevant latent brain states is performed using the RNN that minimizes an error of decoding behavior from the neural activity.

16. The method of claim 14 wherein behavior measurements include any known distribution including categorical distribution and the empirical optimization minimizes a negative log-likelihood of the behavior measurements given past neural activity.

17. The method of claim 14 further comprising extracting behaviorally irrelevant latent brain states using the RNN that minimizes a neural reconstruction loss, wherein the behaviorally irrelevant latent brain states are brain states that are not the behaviorally relevant latent brain states.

18. The method of claim 14 wherein neural measurements include any known distribution including a Poisson distribution and the optimization minimizes a negative log-likelihood of the neural activity given past neural activity.

19. The method of claim 14 wherein behavioral and neural measurements can be intermittently available in time rather than continuously available, and numerical optimization is solved only based on the intermittently available behavioral and neural measurements.

20. The method of claim 14 wherein the neural activity has nonlinear dynamics and a state-space dynamic model is made nonlinear by making components of the RNN be nonlinear multilayer neural networks.

21. A system for preferential system identification (PSID) for modeling neural dynamics of a brain, the system comprising:
    an input device configured to detect or receive at least one of past neural activity data or behavior; and
    a machine learning processor coupled to the input device and configured to:
        extract behaviorally relevant latent brain states via a projection of future behavior onto the at least one of the past neural activity data or the behavior, wherein the future behavior includes a movement kinematic and wherein behaviorally relevant latent brain states are brain states associated with the movement kinematic; and identify, based on the extracted latent brain states, model parameters for a liner state space dynamic model of neural activity, and wherein the machine learning processor utilizes recurrent neural networks (RNN) to extract the behaviorally relevant latent brain states and to identify the model parameters for the state space dynamic model of neural activity.

22. The system of claim 21 wherein the input device is configured to additionally detect or receive external inputs to the brain, and the machine learning processor is further configured to utilize oblique projections along the external input to extract the behaviorally relevant latent brain states.

* * * * *

UNITED STATES PATENT AND TRADEMARK OFFICE
CERTIFICATE OF CORRECTION

PATENT NO. : 11,832,953 B1
APPLICATION NO. : 17/069510
DATED : December 5, 2023
INVENTOR(S) : Maryam M. Shanechi and Omid Ghasem Sani It is certified that error appears in the above-identified patent and that said Letters Patent is hereby corrected as shown below:

In the Claims

Claim 21, Column 73, Line 5, delete "liner" and insert --linear--.

Signed and Sealed this
Twelfth Day of March, 2024

Katherine Kelly Vidal
*Director of the United States Patent and Trademark Office*